US010932826B2

(12) United States Patent
Hutton et al.

(10) Patent No.: US 10,932,826 B2
(45) Date of Patent: Mar. 2, 2021

(54) ROD INSERTER AND METHODS OF USE

(71) Applicant: Alphatec Spine, Inc., Carlsbad, CA (US)

(72) Inventors: Clark Hutton, Delmar, CA (US); Ketchen Smith, Escondito, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 921 days.

(21) Appl. No.: 15/378,626

(22) Filed: Dec. 14, 2016

(65) Prior Publication Data

US 2017/0095272 A1    Apr. 6, 2017

Related U.S. Application Data

(60) Division of application No. 13/828,573, filed on Mar. 14, 2013, now Pat. No. 9,545,271, which is a division of application No. 12/462,974, filed on Aug. 11, 2009, now Pat. No. 8,394,109, which is a continuation-in-part of application No. 12/290,035, filed on Oct. 23, 2008, now Pat. No. 8,469,960, and a continuation-in-part of application No. 12/290,035, filed on Oct. 23, 2008, now Pat. No. 8,469,960.

(Continued)

(51) Int. Cl.
  *A61B 17/70*    (2006.01)
  *A61B 17/88*    (2006.01)

(52) U.S. Cl.
  CPC ........ *A61B 17/708* (2013.01); *A61B 17/7032* (2013.01); *A61B 17/7082* (2013.01); *A61B 17/7083* (2013.01); *A61B 17/7085* (2013.01); *A61B 17/7086* (2013.01); *A61B 17/7091* (2013.01); *A61B 17/8861* (2013.01)

(58) Field of Classification Search
  CPC .............. A61B 17/032; A61B 17/1086; A61B 17/7091; A61B 17/8877; A61B 17/888; A61B 17/8883; A61B 17/8886
  See application file for complete search history.

(56) References Cited

U.S. PATENT DOCUMENTS 5,782,831 A    7/1998 Sherman et al.
6,090,113 A    7/2000 Le Couedic et al.
(Continued)

FOREIGN PATENT DOCUMENTS

WO    2006042188 A2    4/2006
WO    2006060430 A1    6/2006

*Primary Examiner* — Anu Ramana
(74) *Attorney, Agent, or Firm* — Robert Winn

(57) ABSTRACT

The tool and surgical kit are configured to facilitate in-situ reattachment of a screw extender to screw is provided. The surgical kit includes a screw extender, a screw assembly and a tool. The screw extender has a channel extending from a proximal end to a distal end of the screw extender. The screw assembly includes a screw and a set screw. The screw includes a threaded shaft and a head having a pair of sidewalls spaced apart from each. The interior surface of the sidewalls is threaded. The tool includes a first and a second removable shaft, the distal ends of which are configured to respectively engage the screw and the set screw. The tool includes a main shaft, a handle and a hollow housing. The main shaft is configured to fit through the channel, and the hollow housing is configured to receive the screw extender housing.

18 Claims, 102 Drawing Sheets

Related U.S. Application Data

(60) Provisional application No. 61/132,974, filed on Jun. 23, 2008, provisional application No. 61/000,263, filed on Oct. 23, 2007.

(56) References Cited

U.S. PATENT DOCUMENTS

| | | |
|---|---|---|
| 6,440,133 B1 | 8/2002 | Beale et al. |
| 6,530,929 B1 | 3/2003 | Justis et al. |
| 7,179,261 B2 * | 2/2007 | Sicvol ................ A61B 17/7032 606/86 A |
| 7,250,052 B2 * | 7/2007 | Landry .............. A61B 17/1604 606/86 A |
| 7,758,617 B2 * | 7/2010 | Iott ...................... A61B 17/701 606/246 |
| 7,963,433 B2 | 6/2011 | Whitman et al. |
| 2003/0200132 A1 | 10/2003 | Bryant |
| 2004/0138662 A1 | 7/2004 | Landry et al. |
| 2005/0131408 A1 | 6/2005 | Sicvol et al. |
| 2005/0131421 A1 | 6/2005 | Anderson et al. |
| 2006/0074418 A1 | 4/2006 | Jackson |
| 2006/0111715 A1 | 5/2006 | Jackson |
| 2006/0200132 A1 | 9/2006 | Chao et al. |
| 2006/0293693 A1 | 12/2006 | Farr et al. |
| 2007/0270842 A1 | 11/2007 | Bankoski et al. |

\* cited by examiner

FIG. 1A
FIG. 1B
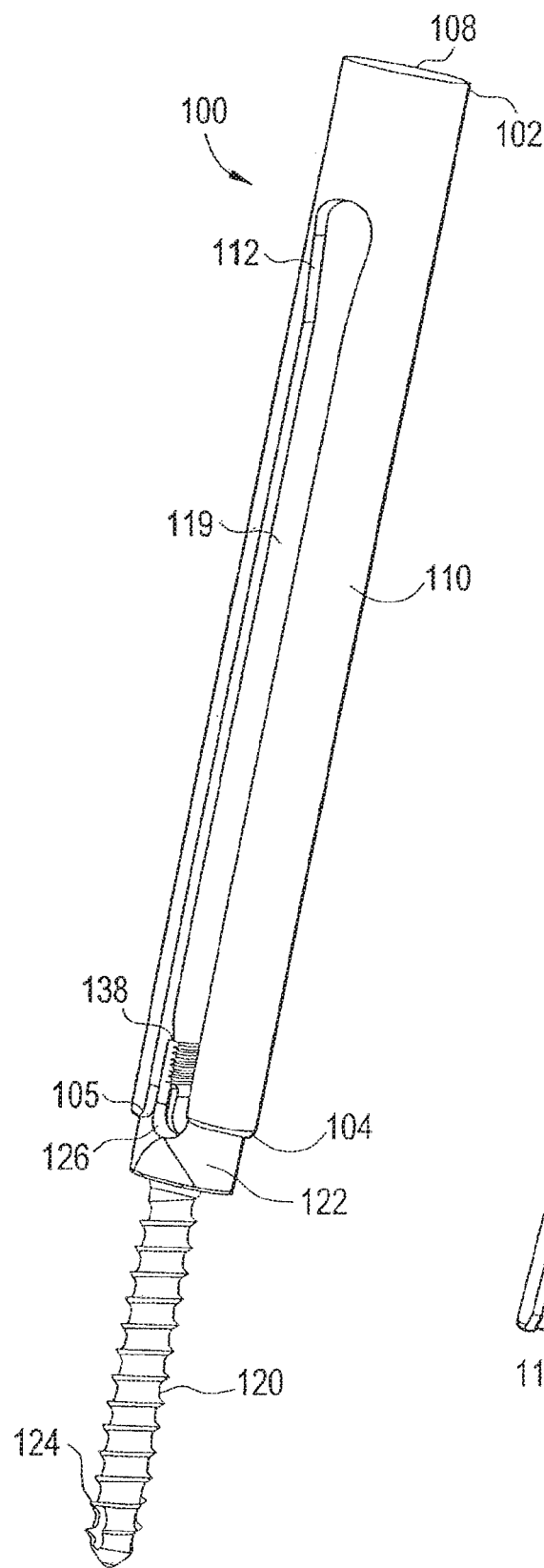
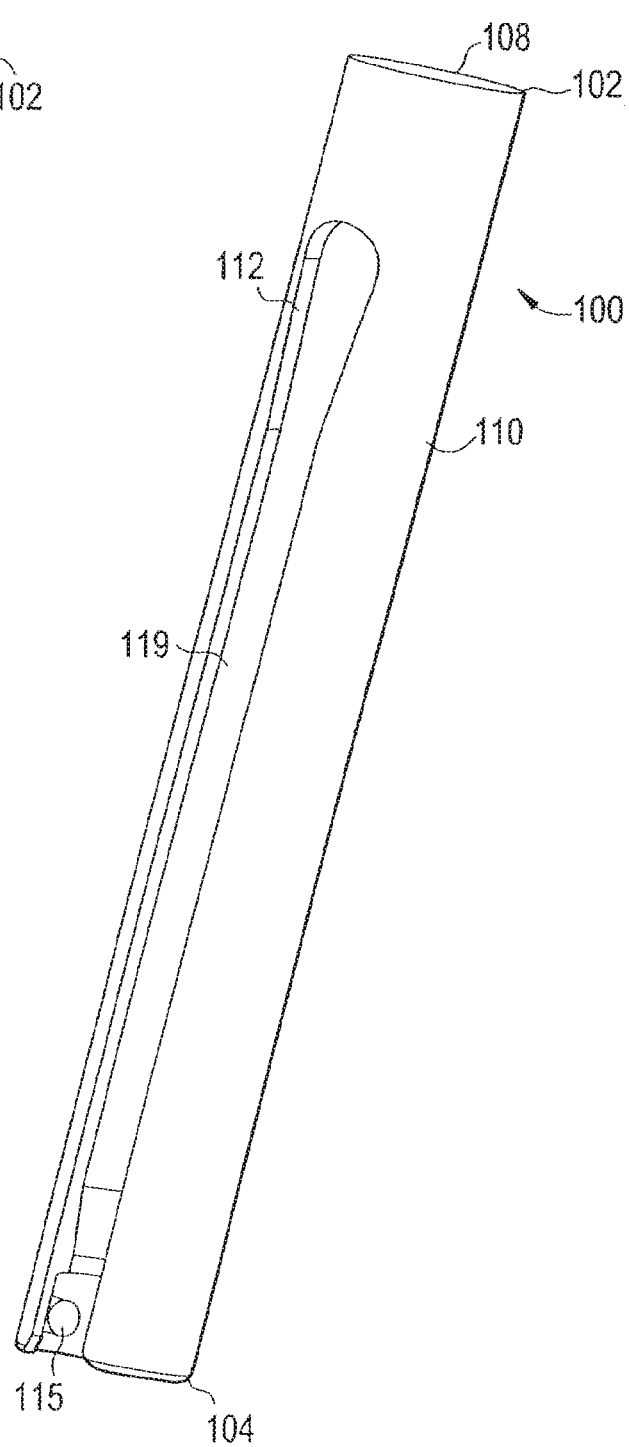

FIG. 9A
FIG. 9B
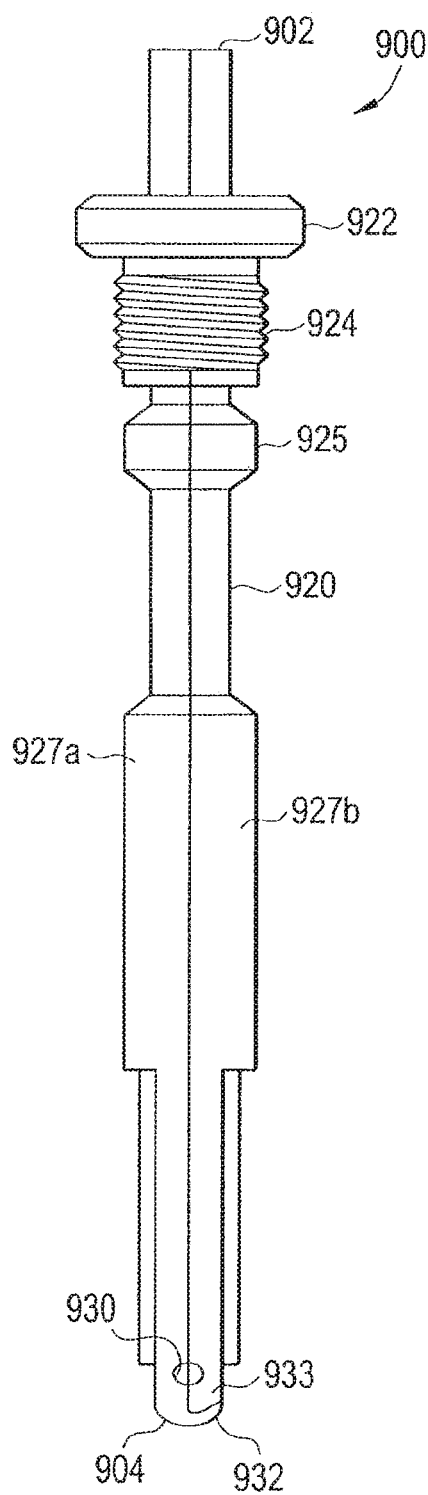
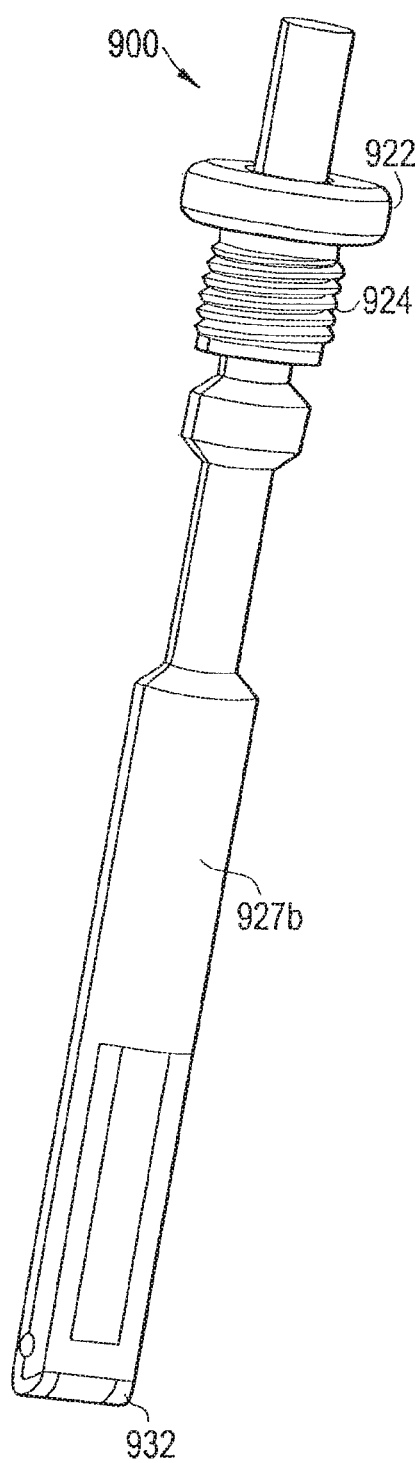

FIG. 9C
FIG. 9D
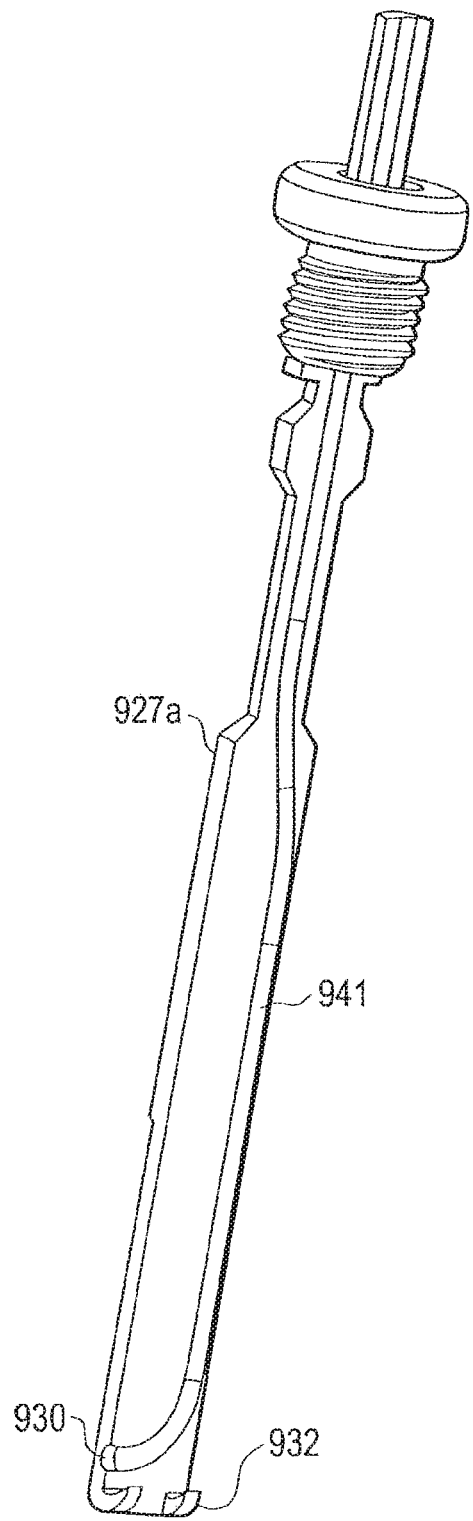
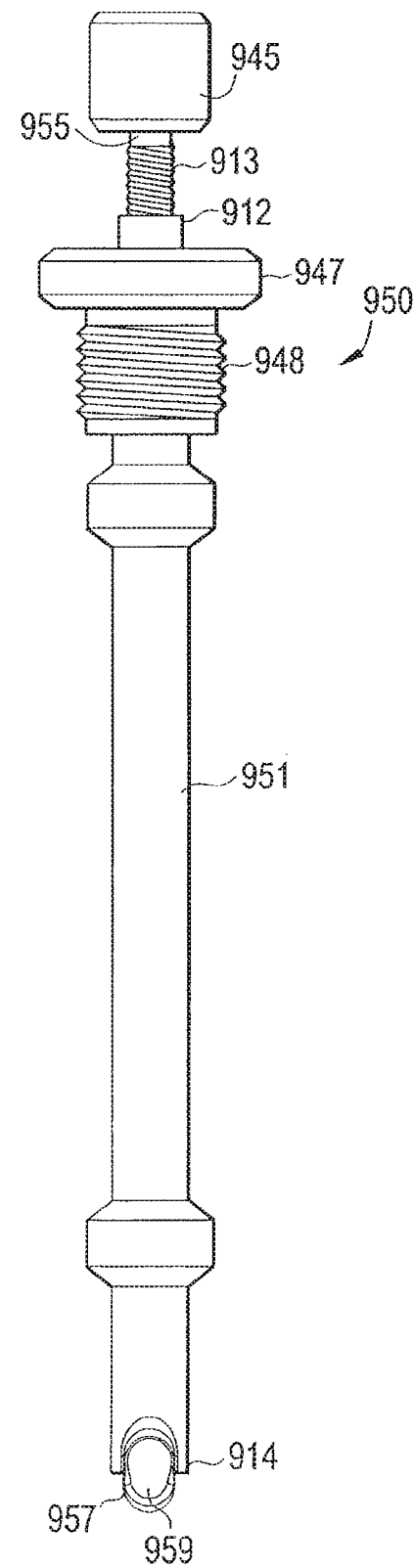

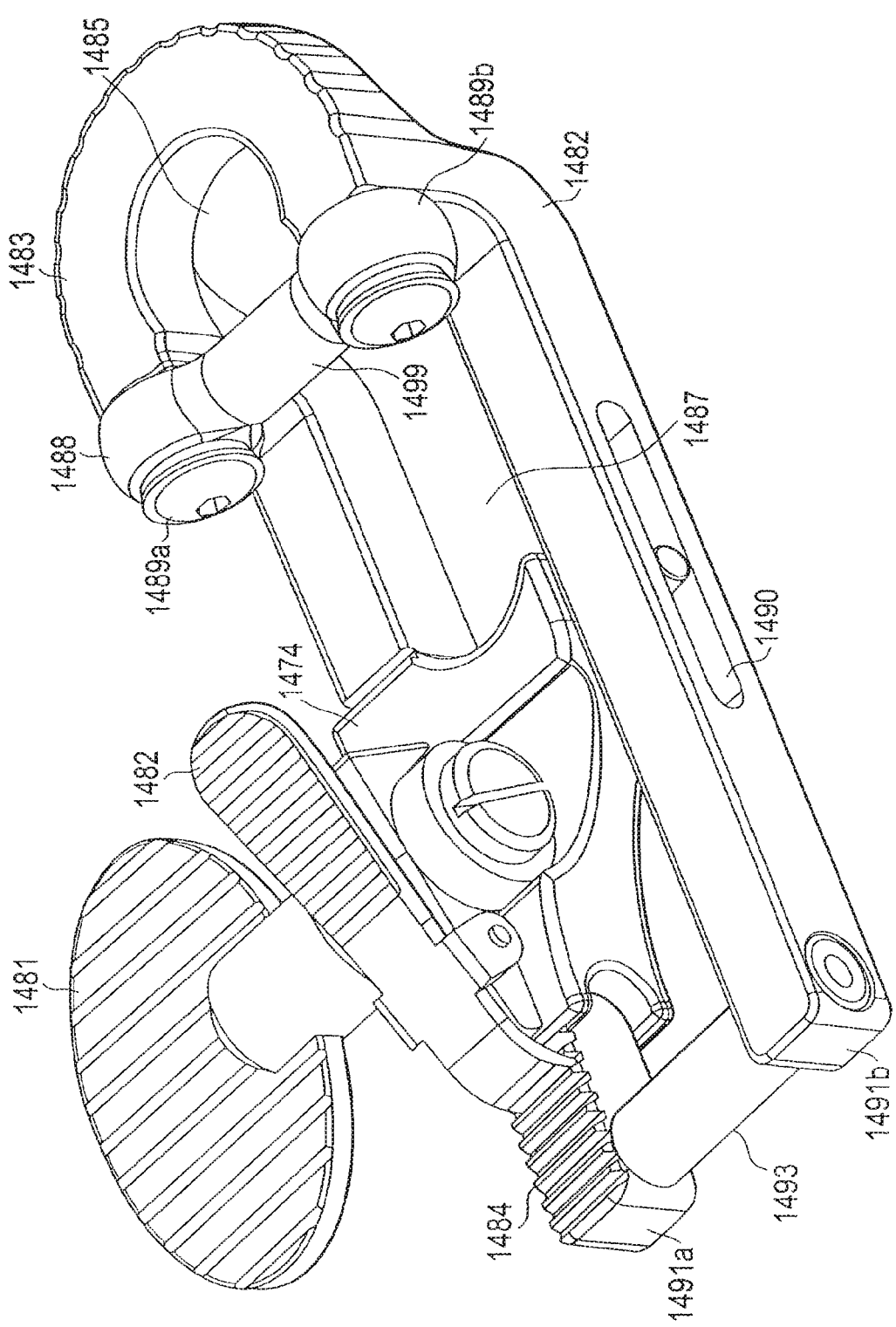

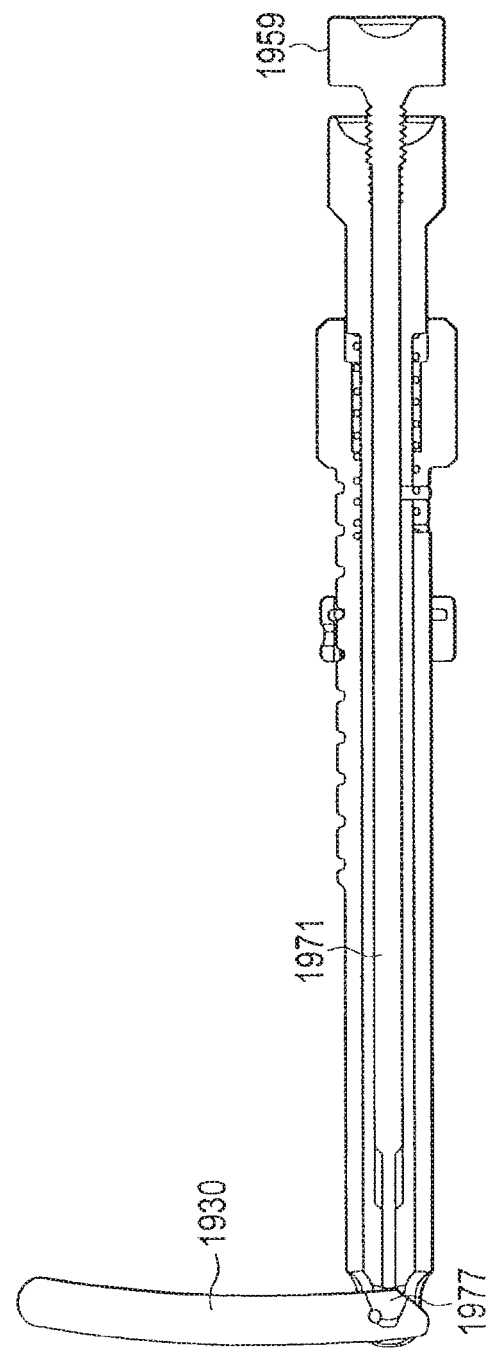

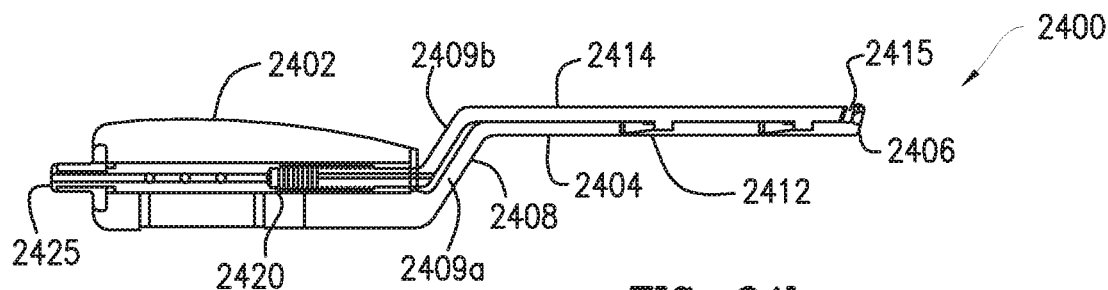
FIG. 24b
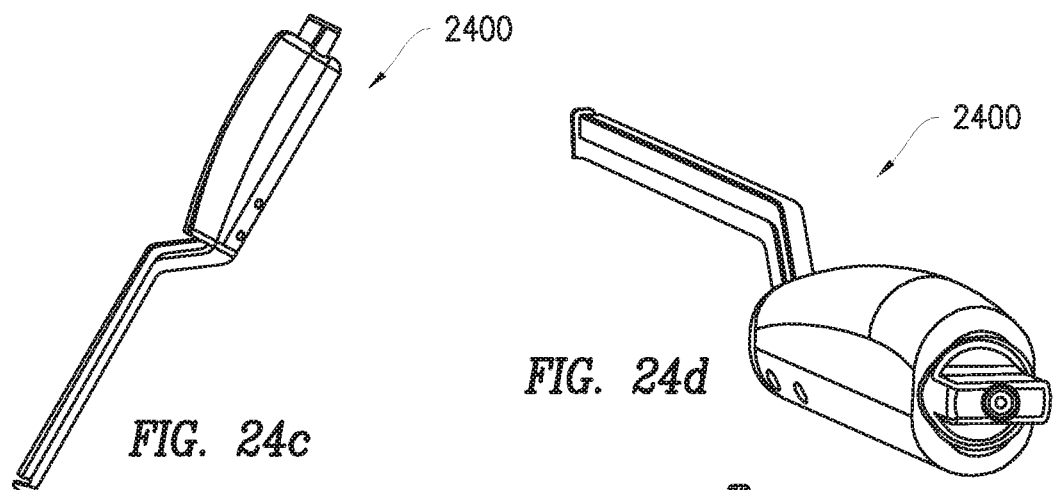
FIG. 24c
FIG. 24d
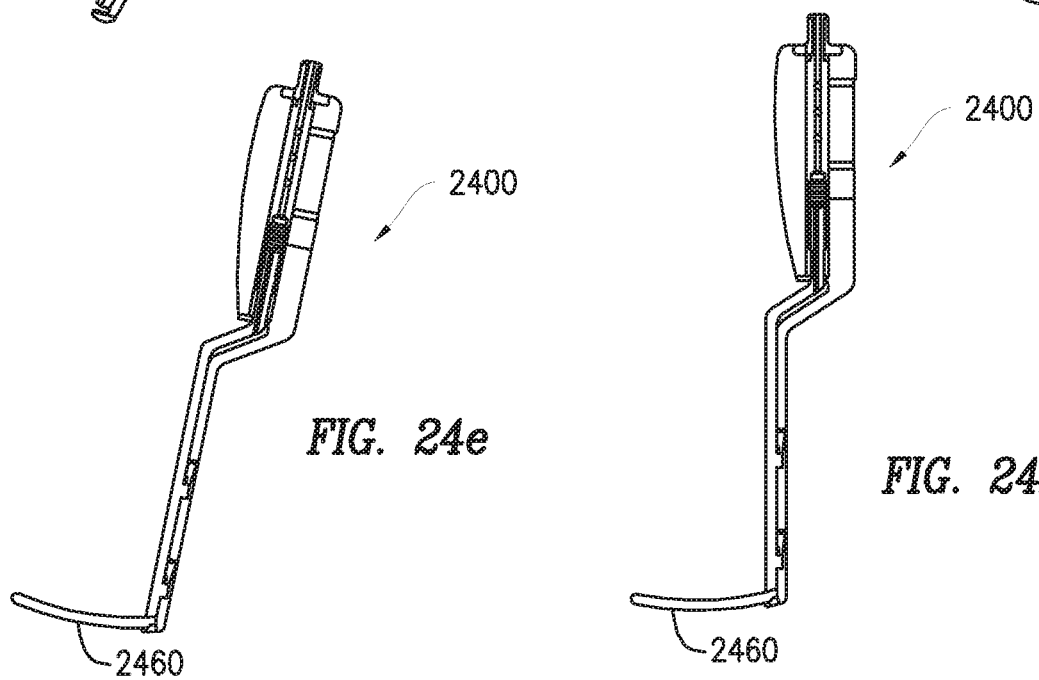
FIG. 24e
FIG. 24f

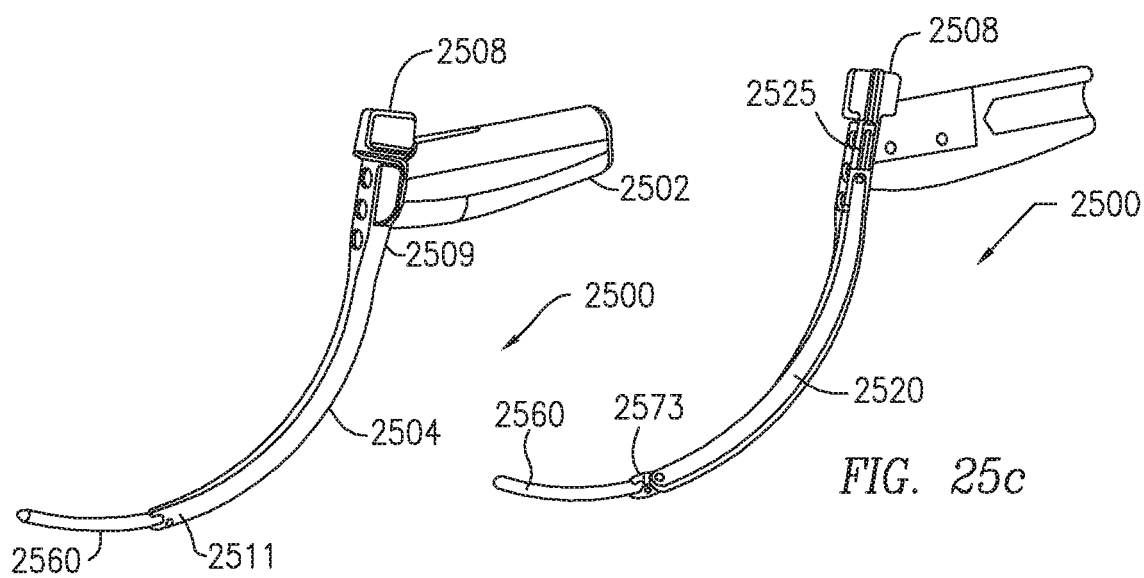
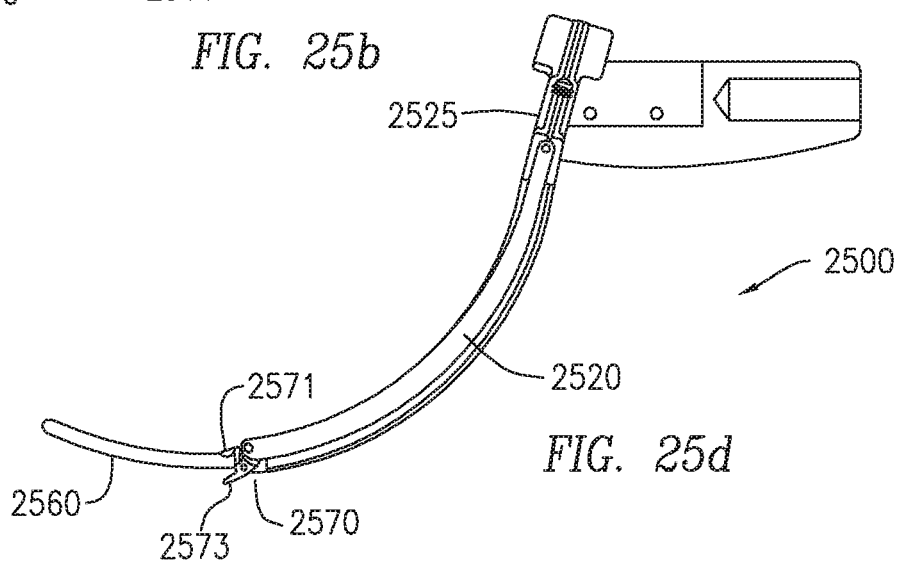
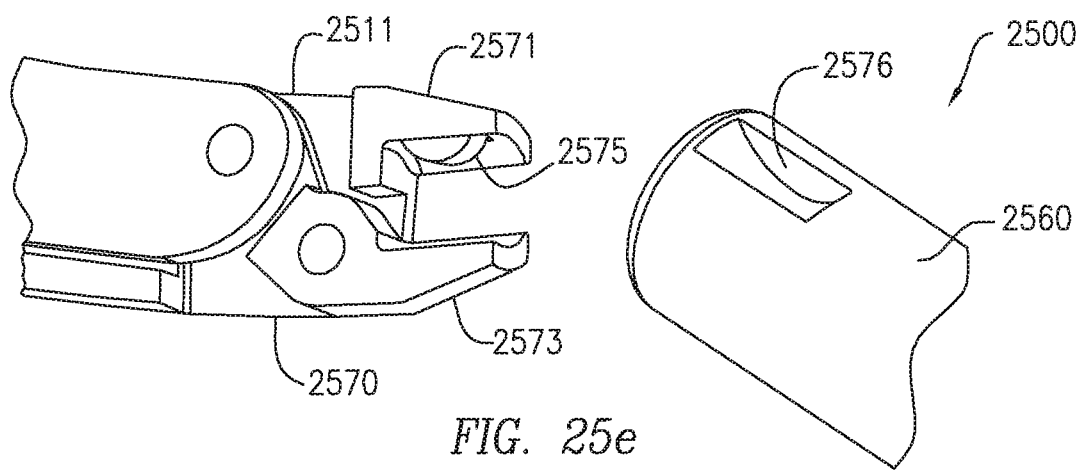

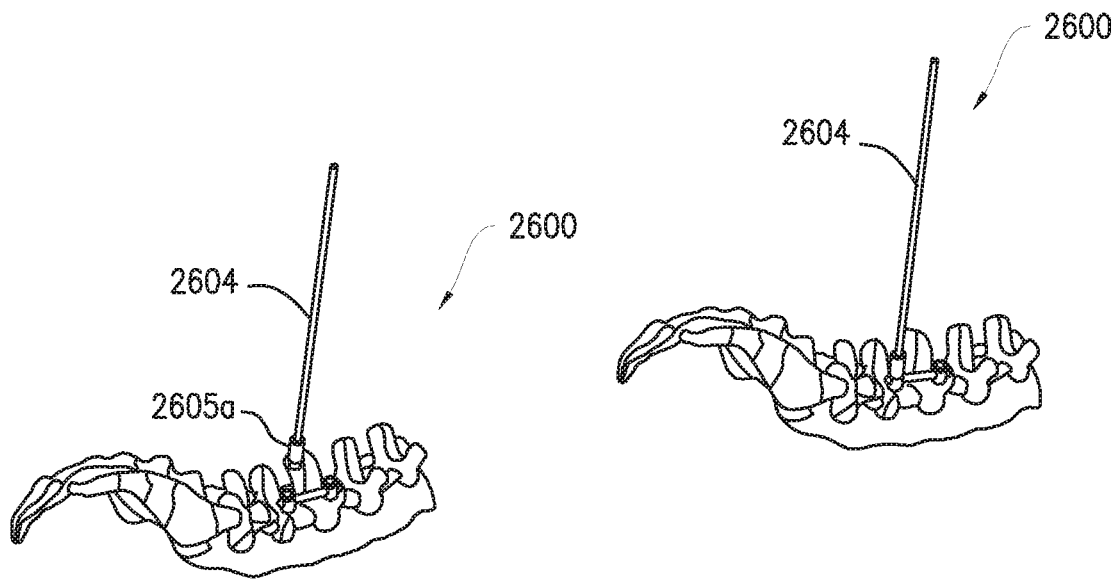
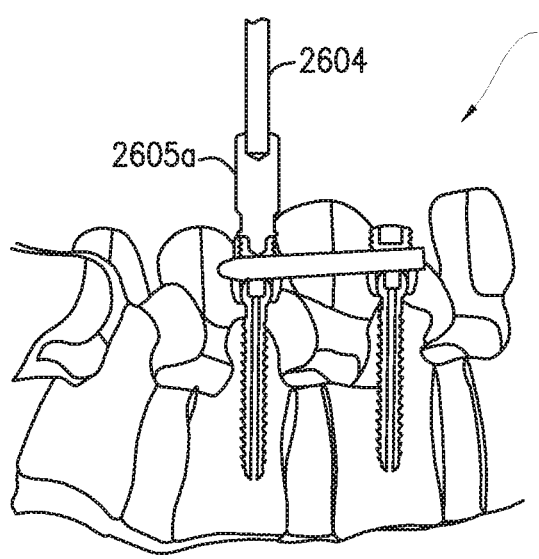
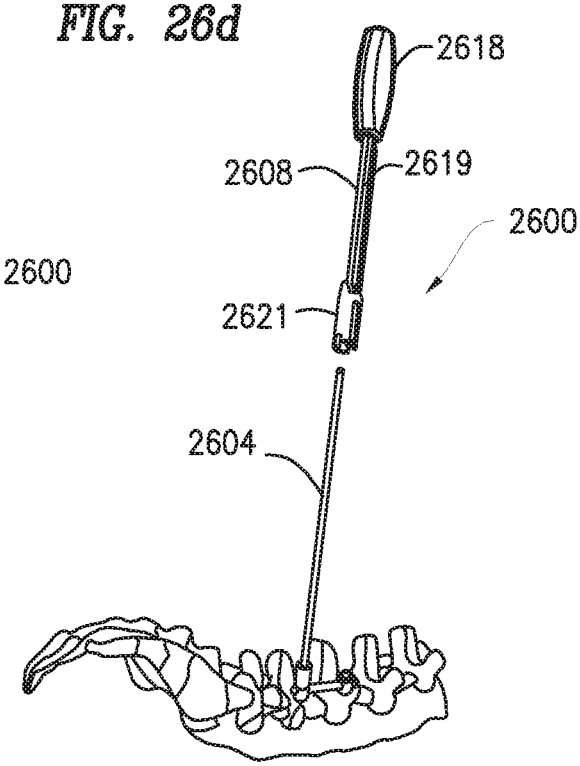
FIG. 26c
FIG. 26d
FIG. 26e
FIG. 26f

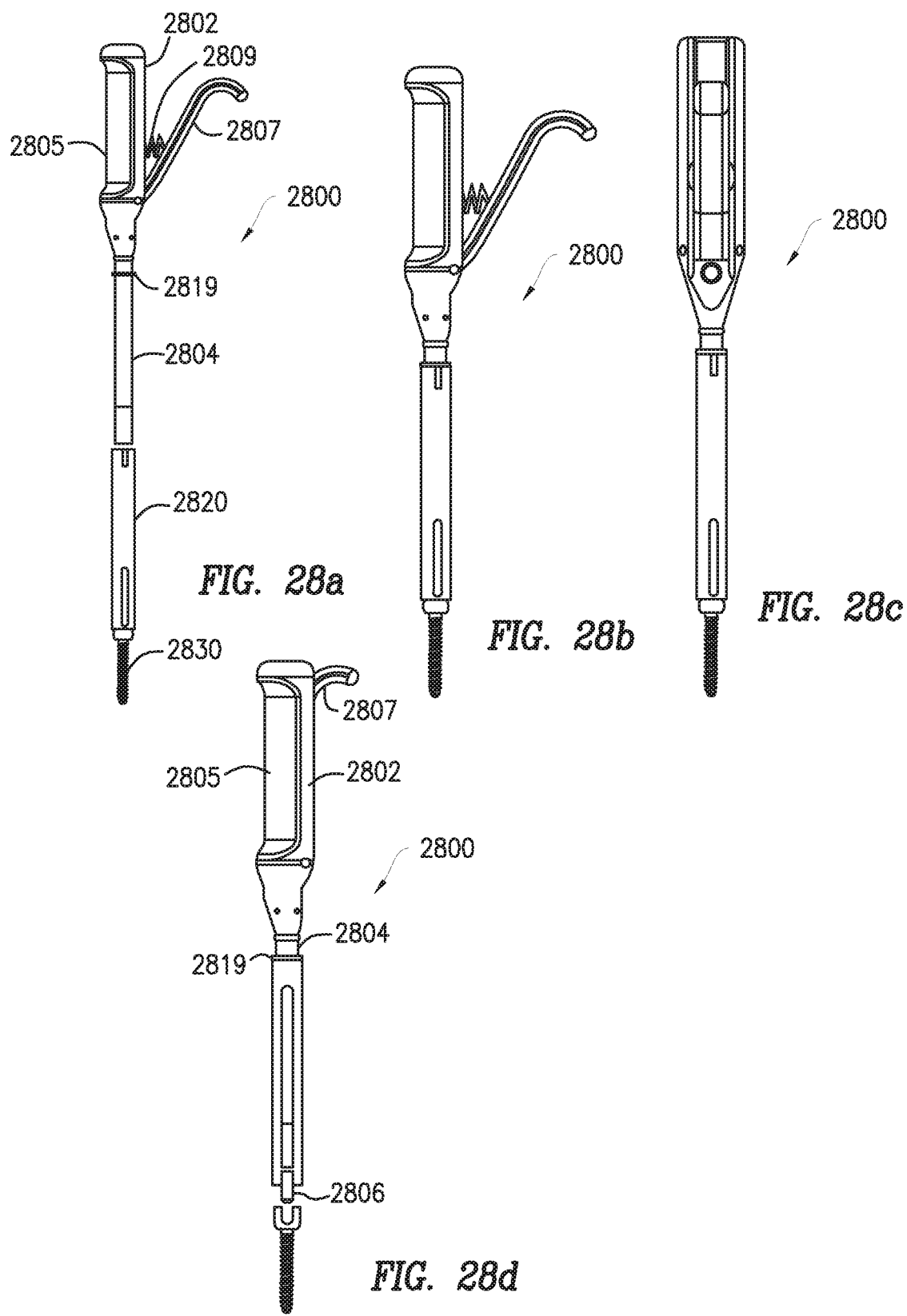

ROD INSERTER AND METHODS OF USE

CROSS-REFERENCE TO RELATED APPLICATIONS

The present application is a divisional application of U.S. patent application Ser. No. 13/828,573 filed on Mar. 14, 2013, which in turn is a divisional application of U.S. patent application Ser. No. 12/462,974 filed on Aug. 11, 2009 (now U.S. Pat. No. 8,394,109), which in turn is a continuation-in-part application of U.S. patent application Ser. No. 12/290,035 filed on Oct. 23, 2008 (now U.S. Pat. No. 8,469,960) which in turn claims priority to U.S. Provisional Patent Application No. 61/132,974 filed Jun. 23, 2008 and claims priority to U.S. Provisional Patent Application No. 61/000,263, filed Oct. 23, 2007, all of which are incorporated herein by reference in their entirety. The present application is a divisional application of U.S. patent application Ser. No. 13/828,573 filed on Mar. 14, 2013, which is also a continuation-in-part of U.S. patent application Ser. No. 12/290,035 filed Oct. 23, 2008, which is incorporate herein by reference in its entirety.

TECHNICAL FIELD

The present invention generally relates to the field of spinal surgery. In particular, the present invention relates to the field of surgical access to the spine.

BACKGROUND

Spinal fusion is a procedure that promotes fusing or growing together of two or more vertebrae in the spine. Spinal fusion can be performed to: straighten a spine deformed by scoliosis, neuromuscular disease, cerebral palsy, or other disorder; prevent further deformation; support a spine weakened by infection or tumor; reduce or prevent pain from pinched or injured nerves; compensate for injured vertebrae or disks.

One of the goals of spinal fusion procedure is to unite two or more vertebrae to prevent them from moving independently of each other. This may be done to improve posture, increase ability to ventilate the lungs, prevent pain, or treat spinal instability and reduce the risk of nerve damage. According to the American Academy of Orthopedic Surgeons, approximately a quarter-million spinal fusions are performed each year, half on the upper and half on the lower spine.

The spine is a series of individual bones called vertebrae, separated by cartilaginous disks. The spine includes seven cervical (neck) vertebrae, 12 thoracic (chest) vertebrae, five lumbar (lower back) vertebrae, and the fused vertebrae in the sacrum and coccyx that help to form the hip region. While the shapes of individual vertebrae differ among these regions, each is essentially a short hollow tube containing the bundle of nerves known as the spinal cord. Individual nerves, such as those carrying messages to the arms or legs, enter and exit the spinal cord through gaps between vertebrae. The spinal disks act as shock absorbers, cushioning the spine, and preventing individual bones from contacting each other. Disks also help to hold the vertebrae together. The weight of the upper body is transferred through the spine to the hips and the legs. The spine is held upright through the work of the back muscles, which are attached to the vertebrae. While the normal spine has no side-to-side curve, it does have a series of front-to-back curves, giving it a gentle "S" shape. The spine curves in at the lumbar region, back out at the thoracic region, and back in at the cervical region.

One of the types of spinal fusion procedures is a posterior spinal fusion surgery. This procedure is performed posteriorly, or from the back of patient, as opposed to anteriorly, or through the abdomen. There are three know posterior fusion techniques (all three are typically performed with pedicle screw fixation). The first is a posterolateral gutter fusion surgery. This type of spinal fusion involves placing bone graft in the posterolateral portion of the spine (a region just outside the back of the spine). The second is a posterior lumbar interbody fusion ("PLIF") surgery. A PLIF involves placing bone graft and/or spinal implant (e.g., cage) directly into the disc space in the front of the spine. The third is a transforaminal lumbar interbody fusion ("TLIF") surgery. A TLIF is essentially like an extended PLIF, as it also involves expanding the disc space by removing one entire facet joint (whereas a PLIF usually involves gaining access to the disc space by removing a portion of the facet joints on each side of the spine).

There have been various approaches and systems for performing posterior spinal surgery. Some conventional systems further include titanium construction that is compatible with current CT and MRI scanning technology, low profile implant systems, top-loading and top-tightening systems, and other parameters. Some systems also include cross-connectors that allow one-piece implant to be applied to a dual-rod construct for a top-loading approach.

The conventional devices and systems have a number of disadvantages. These devices do not provide flexibility when adjusting the devices either prior to, during, or after their placement into the patient. Thus, these devices force a surgeon to utilize a specific configuration, leaving very little room for adjustment in accordance with patient's physiological characteristics and needs.

In some embodiments, the present invention relates to a minimally invasive bone screw placement system that allows a surgeon to implant one or more bone screws into the spine and connect the screws with a wire or any other device, wherein the system does not require any incisions in excess of the bone screw incisions.

SUMMARY OF THE INVENTION

In some embodiments, the present invention is directed to a spinal stabilization system for stabilizing a spine using at least one a surgical screw implant configured to be implanted into the spine. The system includes a housing configured to accommodate placement of the surgical screw implant, the surgical screw implant is secured to the housing using a first mating feature in the surgical screw implant, a locking feature contained within the housing and configured to retain the surgical screw implant for implantation. The first mating feature is configured to control axial movement of the surgical screw implant.

In some embodiments, the present invention relates to a method of stabilizing spine of a patient including implanting a surgical screw implant having a housing configured to accommodate placement of a surgical screw implant, the surgical screw implant is secured to the housing using a first mating feature in the surgical screw implant, a locking feature contained within the housing and configured to retain the surgical screw implant for implantation, wherein the first mating feature is configured to control axial movement of the surgical screw implant. The method includes implanting the surgical screw implant coupled to the housing into a bone, manipulating the surgical screw implant and the housing to orient the housing in a predetermined manner, advancing a wire through the housing, and using the wire, connecting the surgical screw implant with another surgical screw implant.

In some embodiments, the present invention relates to a surgical stabilization system using at least one screw implanted into a bone of a patient, wherein the screw includes a head, wherein the head is configured to include a second mating feature that can be configured to include a plurality of openings and a plurality of recessed edges. The system includes a hollow housing having a wall surrounding an interior of the hollow housing, an open proximal end, and an open distal end, wherein the wall is disposed between the proximal end and the distal end. The distal end is secured to the surgical screw and the surgical screw is delivered via the proximal end. The housing includes a flexible portion having a first mating feature disposed along the wall of the housing and adjacent the distal end. The flexible indenting portion is configured to retain the surgical screw within the housing.

In some embodiments, the present invention relates to a surgical extender apparatus for implanting a surgical screw. The apparatus includes a housing having a distal end and a proximal end, a hollow interior passageway disposed between the distal end and the proximal end, a channel disposed along an exterior surface of the housing at least partially between the distal end and the proximal end and configured to at least partially expose the hollow interior passageway, an interior locking mechanism disposed on an interior surface of the housing and substantially adjacent the proximal end, wherein the interior locking mechanism is configured to allow attachment of at least one surgical tool, and at least one flexible member disposed substantially adjacent the distal end. The housing is configured to accommodate placement of a surgical screw implant. The surgical screw implant is secured to the housing using a mating feature in the surgical screw implant. The at least one flexible member is configured to retain the surgical screw implant. The mating feature is configured to control axial movement of the surgical screw implant.

In some embodiments, the present invention relates to a method of implanting a surgical screw implant into a bone of a patient using a an extender device having a housing configured to accommodate placement of a surgical screw implant, the surgical screw implant being secured to the housing using mating feature in the surgical screw implant, wherein the housing includes a flexible member contained within the housing and configured to retain the surgical screw implant. The method includes implanting the surgical screw implant into a bone of the patient, attaching the screw extender device to the surgical screw and, inserting a screw locking device along the long axis of the screw extender.

In some embodiments, the present invention relates to a surgical kit for stabilizing the spine of a patient. The kit includes a screw extender configured to be coupled to a surgical screw, wherein the screw extender includes a housing having a distal end and a proximal end, a hollow interior passageway disposed between the distal end and the proximal end, a channel disposed along an exterior surface of the housing at least partially between the distal end and the proximal end and configured to at least partially expose the hollow interior passageway, an interior locking mechanism disposed on an interior surface of the housing and substantially adjacent the proximal end, wherein the interior locking mechanism is configured to allow attachment of at least one surgical tool, and at least one flexible member disposed substantially adjacent the distal end. The housing is configured to accommodate placement of a surgical screw implant. The surgical screw implant is secured to the housing using a mating feature in the surgical screw implant. The flexible members are configured to retain the surgical screw implant. The mating feature is configured to control axial movement of the surgical screw implant.

In some embodiments, the present invention relates to a distraction/compression tool for use with a screw extender system having at least two hollow screw extender housings configured to be coupled to respective screw assemblies implanted into vertebrae. The tool includes a housing having a first screw extender holding portion, a second screw extender holding portion pivotally coupled to the first screw extender holding portion, each screw extender holding portion includes a base configured to hold a screw extender housing, a multi-directional threading mechanism configured to secure bases of the screw extender holding portion. Rotation of the threading mechanism in one direction causes distraction of the screw extender housings coupled to the bases and rotation of the threading mechanism in another direction causes compression of the screw extender housings.

In some embodiments, the present invention relates to a method for compressing/distracting screw extender system using the above distraction/compression tool, wherein the screw extender system includes at least two hollow screw extender housings configured to be coupled to respective screw assemblies implanted into vertebrae. The method includes rotating the threading mechanism to compress/distract screw extender housings.

In some embodiments, the present invention relates to a rod inserter tool for use with a hollow screw extender housing configured to be coupled to a screw assembly implanted into vertebrae. The tool includes a handle coupled to a curved shaft at a proximal end of the curved shaft. The shaft includes a static shaft portion configured to be permanently coupled to the handle, a sliding shaft portion configured to be slidably coupled inside the handle and further configured to slide along the static shaft portion, a rod holding mechanism formed by the static shaft portion and a sliding shaft portion and configured to be disposed at a distal end of the curved shaft. By translating the sliding shaft portion along the static shaft portion toward the distal end of the shaft, the rod holding mechanism is configured to secure a rod.

In some embodiments, the present invention relates to a method for inserting a rod using the above rod inserter tool in combination with a hollow screw extender housing configured to be coupled to a screw assembly implanted into vertebrae. The method includes securing the rod in the rod holding mechanism, and advancing the secured rod using the rod inserter tool through the screw extender housing and toward the corresponding screw assembly.

In some embodiments, the present invention relates to a re-attachment guide tool for re-attaching a hollow screw extender housing, having at least one open channel disposed in a wall of the screw extender housing, to a screw assembly implanted into a vertebrae. The tool includes at least one guide shaft configured to be coupled to a screw assembly, a main assembly having a handle coupled to a flat shaft at a proximal end of the flat shaft, a hollow housing coupled to the flat shaft at a distal end of the flat shaft and configured to accommodate insertion of the screw extender housing, and a hollow interior disposed inside the handle and the flat shaft and configured to accommodate insertion of the at least one guide shaft. The flat shaft is configured to have a predetermined thickness that allows coupling of the screw extender housing using the at least one open channel in the screw extender housing.

In some embodiments, the present invention relates to a method for re-attachment of a hollow screw extender housing to a screw assembly implanted into a vertebrae using the above re-attachment guide tool, wherein the hollow screw extender housing includes at least one open channel disposed in a wall of the screw extender housing. The method includes coupling the at least one guide shaft to the screw assembly, placing the main assembly over the at least one guide shaft, securing the main assembly to the screw assembly, coupling the screw extender housing to the flat shaft of the main assembly, translating the screw extender housing toward the distal end of the flat shaft, and, re-attaching the screw extender housing to the screw assembly.

In some embodiments, the present invention relates to a rod reducer tool for use with a screw extender housing secured to a screw assembly implanted into a vertebrae. The tool includes a hollow shaft having a proximal and a distal end and configured to accommodate insertion of the screw extender housing, a rotating handle coupled to the hollow shaft at the proximal end of the hollow shaft, a first threading mechanism disposed inside the handle, a second threading mechanism coupled to the handle and disposed inside the hollow shaft for coupling to the screw extender housing. The first threading mechanism is configured to allow independent rotation of the handle with respect to the hollow shaft. Rotation of the handle is configured to translate the hollow shaft along the screw extender housing that has been inserted into the hollow shaft through interaction of the second threading mechanism with a threading mechanism disposed on the screw extender housing.

In some embodiments, the present invention relates to a method for reducing a rod using the above rod reducer tool used in connection with a screw extender housing secured to a screw assembly implanted into a vertebrae. The method includes inserting the screw extender housing inside the hollow shaft, translating the rod reducer tool along the screw extender housing toward the screw assembly, and rotating the rotating handle to advance the rod reducer tool toward the screw assembly, thereby reducing the rod.

In some embodiments, the present invention relates to a screw extender removal tool for removing a screw extender housing having flexible portions disposed at a distal end of the screw extender housing, wherein the screw extender housing is coupled to a screw assembly. The tool includes an external shaft having a proximal end and a distal end, wherein a plurality of protrusions are disposed on an external surface at the distal end of the external shaft, the external shaft having an internal shaft disposed in a hollow interior of the external shaft, a handle coupled to the proximal end of the shaft, wherein the handle includes a spring-loaded mechanism pivotally coupled to the internal shaft. Upon actuation of the spring-loaded mechanism, the internal shaft is translated in the hollow interior of the external shaft to extend beyond the distal end of the external shaft. The external shaft is configured to be inserted into the screw extender housing coupled to the screw assembly. Then, using the handle, rotated to push apart the flexible portions of the screw extender housing. Upon actuation of the spring loaded mechanism, further configured to extend the internal shaft beyond the distal end of the external shaft in order to remove the screw extender housing from the screw assembly.

In some embodiments, the present invention relates to a method for removing a screw extender housing from a screw assembly using the above screw extender removal tool, wherein the screw extender housing includes flexible portions disposed at a distal end of the screw extender housing and the screw extender housing is coupled to a screw assembly. The method includes inserting the screw extender remover tool into the screw extender housing coupled to the screw assembly, using the handle, rotating the screw extender remover tool to push apart the flexible portions of the screw extender housing using the plurality of protrusions, and upon actuation of the spring loaded mechanism, extending the internal shaft beyond the distal end of the external shaft, and, removing the screw extender housing from the screw assembly.

In some embodiments, the present invention relates to a rod inserter tool for use with a hollow screw extender housing configured to be coupled to a screw assembly implanted into vertebrae. The tool includes a handle, a main housing configured to include a rod holding mechanism adjacent to a distal end of the main housing for holding a rod, wherein the handle is coupled to the main housing adjacent to a proximal end of the main housing, a secondary housing configured to be slidably disposed along the main housing and further configured to secure the rod to the distal end of the main housing, and a lateral housing configured to be slidably disposed along the main housing and further configured to change orientation of the rod upon being actuated by the handle.

In some embodiments, the present invention relates to a method of inserting a rod using a rod inserter tool described above in combination with a hollow screw extender housing configured to be coupled to a screw assembly implanted into vertebrae. The method includes coupling the rod to the distal end of the main housing of the rod inserter tool, advancing the rod toward the screw assembly implanted into vertebrae along the screw extender housing coupled to the screw assembly, securing to rod to the screw assembly, and releasing the rod from the rod inserter tool.

BRIEF DESCRIPTION OF THE DRAWINGS

The present invention is described with reference to the accompanying drawings. In the drawings, like reference numbers indicate identical or functionally similar elements.

FIGS. 1a-c illustrate an exemplary screw extender system, according to some embodiments of the present invention.

FIGS. 9*a*-*h* illustrate exemplary percutaneous wire inserters for use with screw extender system, according to some embodiments of the present invention.

FIGS. 14*a*-*e* illustrate another exemplary compressor/distractor tool, according to some embodiments of the present invention.

FIGS. 19*a*-*f* illustrate various exemplary rod inserter tools, according to some embodiments of the present invention.

FIGS. 24*a*-*l* illustrate an exemplary end-holding rod inserter tool, according to some embodiments of the present invention.

FIGS. 25*a*-*e* illustrate an exemplary percutaneous end-holding rod inserter tool, according to some embodiments of the present invention.

FIGS. 26*a*-*k* illustrate an exemplary in-situ re-attachment guide tool, according to some embodiments of the present invention.

FIGS. 28*a*-*e* illustrate an exemplary screw extender remover tool, according to some embodiments of the present invention.

DETAILED DESCRIPTION OF THE INVENTION

In some embodiments, the present invention allows a surgeon using conventional stab wounds to place bone screws. This is typically accomplished using a Jamshiti needle followed by progressive dilation. Once the bone has been prepared, the bone screw is implanted.

After implantation, the bone screw is manipulated for orientation by the extender. This "extender" extends out of the stab wound and allows the surgeon to control the implanted screw. Once two or more screws are implanted, the surgeon will place the wire inserters onto the screw extender. The wire components are designed to guide a wire down the axis of the screw extender. Once the desired depth is reached, the wire will exit out of the screw extender and puncture the muscle and create a path to join the adjacent bone screw.

Once the wire bridges the gap between the screws, an instrument that has been previously placed down the adjacent extender grabs the wire and pulls the distal portion of the wire to the surface. Attached to the proximal portion of the wire is a rod. By pulling on the distal portion of the wire, the rod is drawn down the extender and pulled across the gap between the screws. The "button" feature on the proximal portion of the rod prevents the rod from being overly pulled past the extender. In some embodiments, the extenders along with screws and the wire inserters are disposed at the surgical site prior to advancement of the wire.

Set screws can be placed, final tightened and the guide wire can be removed. This provides a minimally invasive placement of fusion hardware.

Figure 1C:
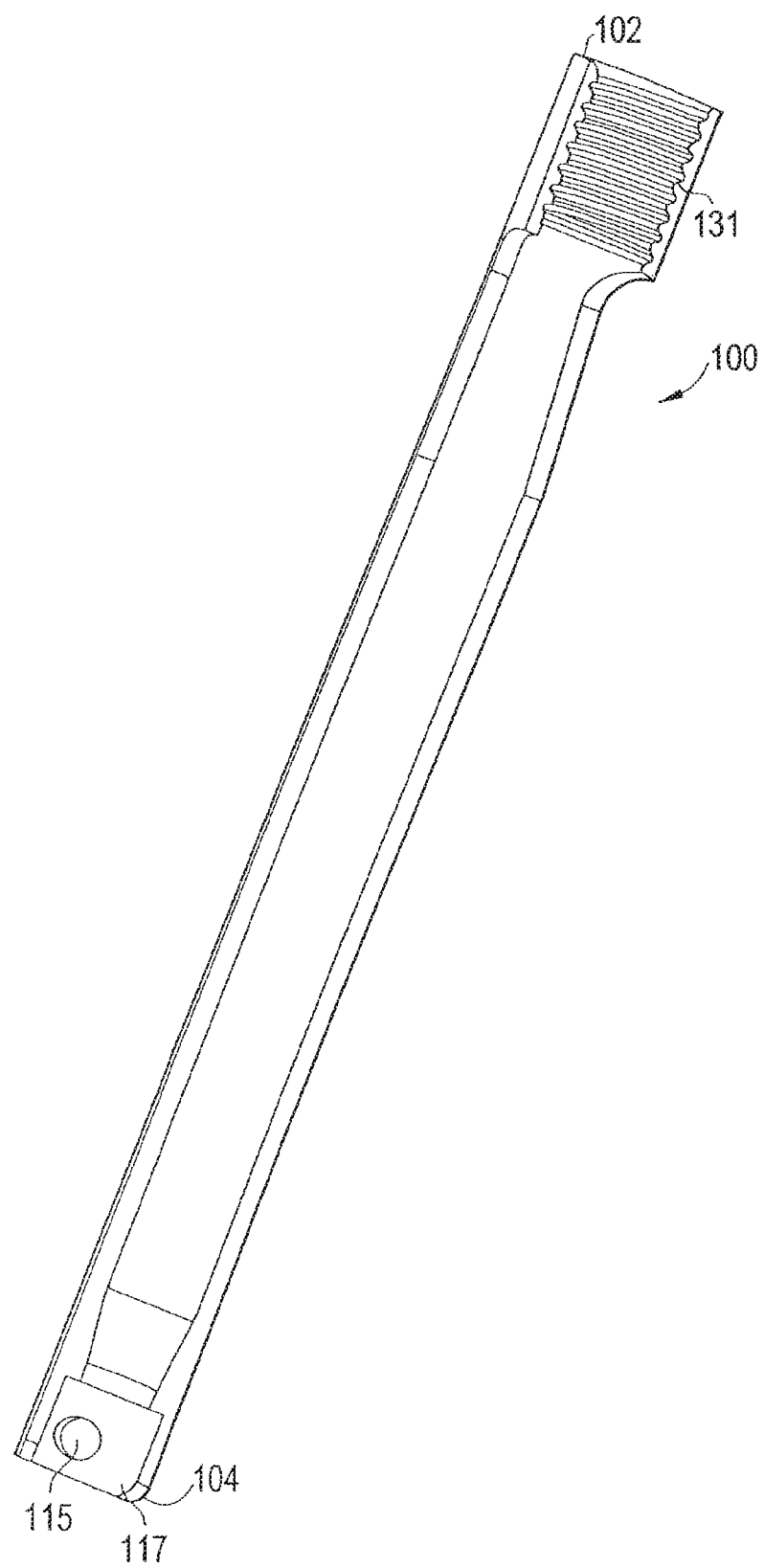

FIGS. 1*a*-*c* illustrate an exemplary embodiment of a screw extender device 100, according to some embodiments of the present invention. FIG. 1*a* illustrates the screw extender device 100 being coupled to a screw. FIG. 1*b* illustrate the screw extender device 100 by itself and FIG. 1*c* illustrates a cross-sectional cut out of the screw extender device shown in FIG. 1*b*. Screw extender device 100 includes a housing 110 that is coupled to a screw implant 120 using first mating features (or as shown in FIGS. 1*a*-*c*, the indented features) 105 disposed on the head of the screw 122. The indented features 105 are configured to control axial and torsional movement. The housing 110 has a proximal end 102 and a distal end 104. The housing 110 further includes a partially open channel 112, which permits insertion and passage of a rod toward from the proximal end 102 toward the distal end 104 of the housing 110. In some embodiments, as will be discussed below, the housing 110 can be configured to include a partially open channel 112 and/or a fully open channel, whereby the fully open channel is configured to stretch from the proximal end 102 to the distal end 104. The open channel is configured as a hollow interior or passageway 119 of the housing 110. The hollow interior 119 is configured to allow passage of instruments, rods, implants, etc. through the screw extender device during surgery. To allow such passage, the housing 110 includes an opening 108 disposed at the proximal end 102 and a similar opening disposed at the distal end 104. The sizes of the openings can be substantially similar to the size of the interior 119. The openings allow passages of instruments, tools, rods, implants, etc. during surgical procedures. In some embodiments, the screw extender housing 110 is configured to have a cylindrical shape. As can be understood by one skilled in the art, other shapes of the housing 110 are possible.

The distal end 104 of the housing 110 is configured to be coupled to the head of the screw 122. The distal end 104 includes second mating features (as shown in FIGS. 1a-c, protrusions) 115 (as shown in FIGS. 1b-c) that are configured to mate with the first (or indented) features (or openings) 105 disposed on the head of the screw 122. In the following description of FIGS. 1a-22b, the terms "protrusion(s)", "indentation(s)", "first mating feature(s)", "second mating feature(s)" will be used interchangeably, and thus, in some embodiments, the present invention can include a first mating feature that is a protrusion and a second mating feature that is an indentation configured to mate with the protrusions, whereas in some embodiments, a first mating feature can be an indentation and a second mating feature can be a protrusion with which the first mating feature mates. Hence, the terms "protrusion(s)" and "indentation(s)" are to mean "indentation(s) or protrusion(s)" are to be interpreted as such. Further, the terms "protrusion(s)" and "indentation(s)" are used in this description for illustrative non-limiting purposes only. The protrusions 115 are configured to flex as the screw 120 (a portion 117 of the screw is shown in FIGS. 1a-c) is coupled to the extender housing 110. In some embodiments, protrusions 115 are configured to be spring-loaded or otherwise be any locking feature, wherein upon insertion of the screw, the protrusions 115 are configured to retract toward the interior wall of the extender housing 110 and then protract toward the indented features 105 upon protrusions 115 being aligned with the features 105. Upon coupling, the protrusions 115 are configured to snap into indented features 105, thereby locking the screw to the screw extender housing 110 and creating a rigid structure. The interior walls of the housing 110 can further configured to include threading 131 disposed near the proximal end 104. The threading 131 is configured to allow securing of various tools to the extender housing 110 during surgical procedures. As can be further understood by one skilled in the art, the terms "threading" or "thread" are used in this description of FIGS. 1a-22c for exemplary non-limiting purposes and instead of threading components together, other means of compression and/or distraction and/or other ways of coupling can be used.

In some embodiments, the screw 120 can be a poly-axial screw that allows a surgeon to manipulate (rotate, tilt, etc.) the combination of the screw 120 coupled to the housing 110 once the screw is implanted into a bony matter (e.g., vertebrae) of the patient. The screw 120 further includes threading 124 on a threaded shaft of the screw that is configured to assist in insertion of the screw into a bony matter. The threaded shaft is coupled to the head of the screw 122. The head of the screw 122 includes a passageway 126 that is configured to be wide enough to accommodate placement and securing of a rod. The passageway 126 is configured to be aligned with the channel 112 so as to create a continuous channel between the screw and the screw extender. In some embodiments, the passageway 126 can be configured to include threading 138 disposed on passageway's interior surfaces. The threading 138 allows placement of set screws (not shown in FIGS. 1a-c) to secure a rod once it is installed into the screw.

Figure 2A:
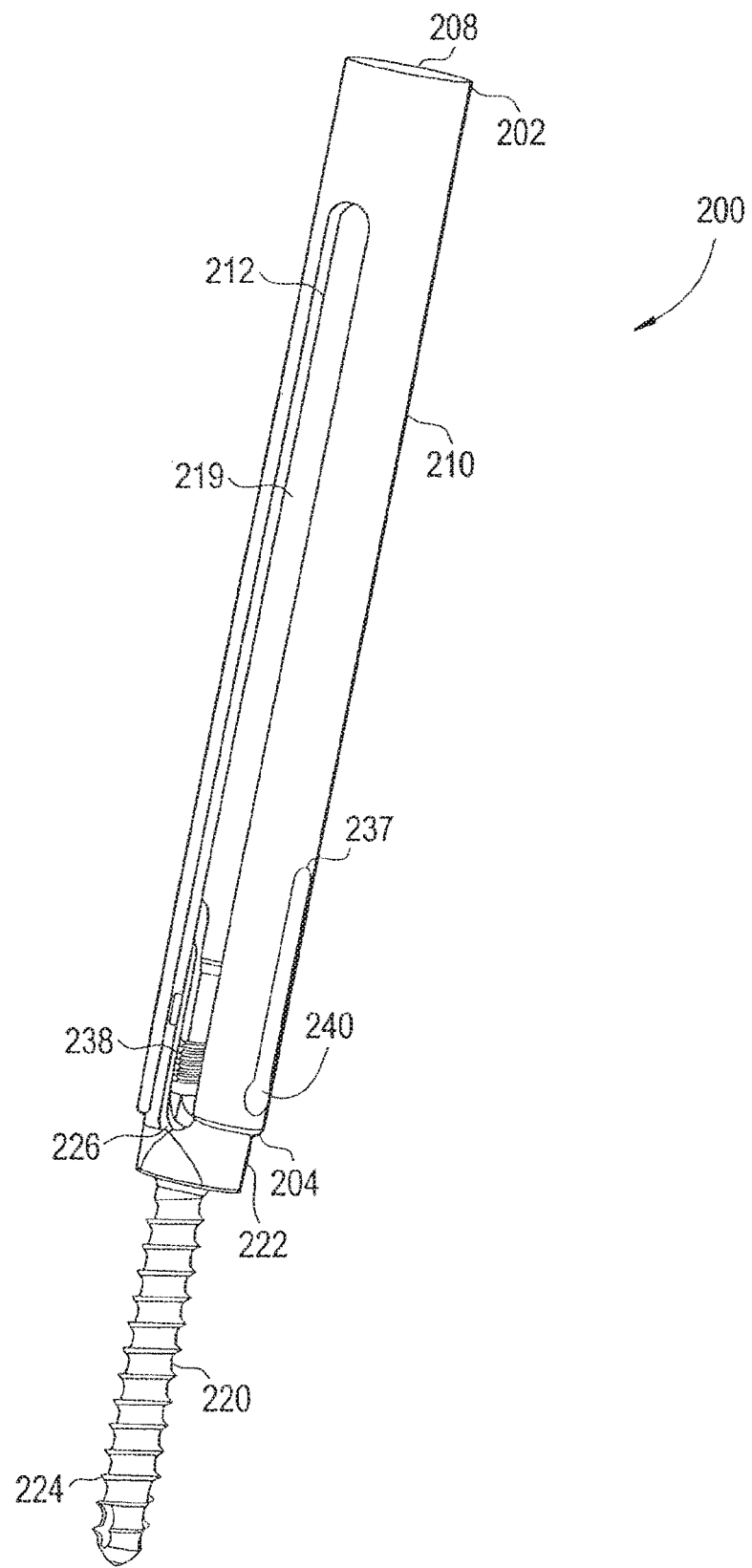
FIGS. 2a-b illustrate another exemplary screw extender system, according to some embodiments of the present invention.
Figure 2B:
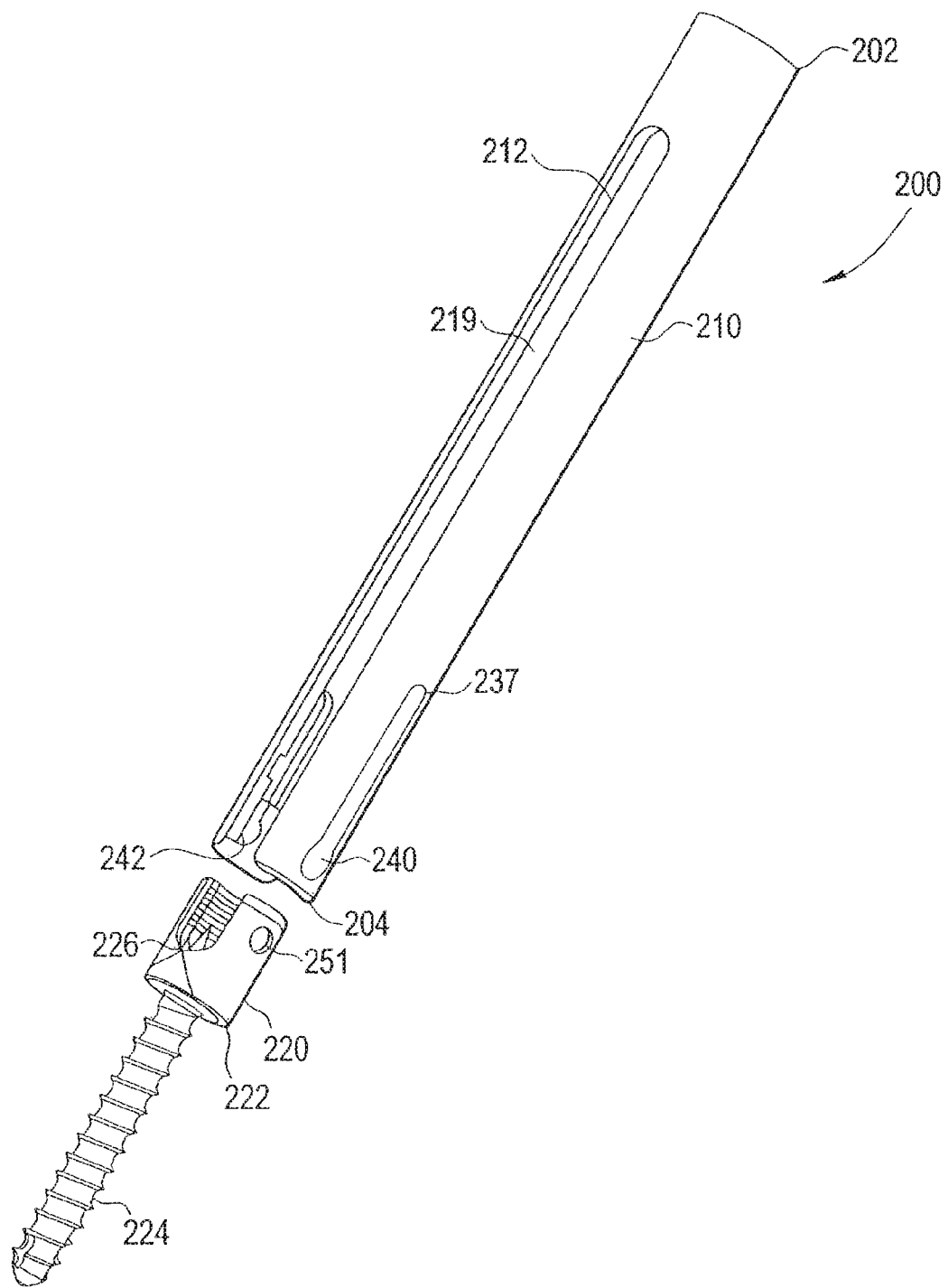

FIGS. 2a-b illustrate another exemplary screw extender system 200, according to some embodiments of the present invention. FIG. 2a illustrates the screw extender housing being coupled to the screw and FIG. 2b illustrates the screw extender housing being uncoupled from the screw. As shown in FIGS. 2a-b, a screw 220 is configured to be coupled to a screw extender housing 210. The screw extender housing 210 is configured to be an elongated tube that includes openings at both of its ends 202 (proximal), 204 (distal) for coupling to the screw 220 at one end 204 and for insertion of surgical instruments at the other end 202. The housing 210 further includes slots or channels 212 that extend along at least a portion of the housing 210 and are further configured to accommodate placements of rod(s). Additionally, the housing 210 further includes indentor portions or screw-locking features 240, which are configured to secure the screw 220 to the screw extender device housing 210. In some embodiments, the housing 210 includes two indentor portions 240 (second portion is not shown in FIG. 2a). The indentor portions 240 are configured to be fixed to the housing 210 at a location 237, which is disposed toward the screw-coupling end 204. In some embodiments, the indentor portions 240 are configured to be welded at a location 237. Once the screw 220 is loaded into the extender device (See, FIG. 2a), the indentor portions 240 are configured to engage the screw 220 using protrusions 242 that are disposed on an interior wall of the indentor portions 240 and are further configured to protrude into the interior of the housing 210. In some embodiments, the indentor portions 240 are configured to be flexible.

The indentor portions 240 are configured to engage an opening 251 in the head of the screw 220, as shown in FIG. 2b. Upon insertion of the screw 220 into the extender device housing 210, the indentor portions 240 are configured to spread apart from the center of the housing 210. In some embodiments, the indentor portions 240 are configured to be spring-like devices that pull apart upon application of external mechanical pressure. Once the screw 220 is inserted into the housing 210, the indentor portions 240 are configured to snap into openings 251 of the screw 220. Upon snapping into openings 251, the indentor portions 240 rigidly secure the screw 220 to the housing 210.

Similarly to the screw extender shown in FIGS. 1a-c, the screw extender housing 210 includes an interior passageway 219 that is configured to be exposed by the channel 212 (either fully or partially stretching along the length of the housing 210). The channel 212 is configured to be aligned with a passageway 226 disposed on the head of the screw 222 so as to create a continuous channel between the between the channel 212 and the passageway 226 for passing of tools, instruments, rods, etc.

Figure 3A:
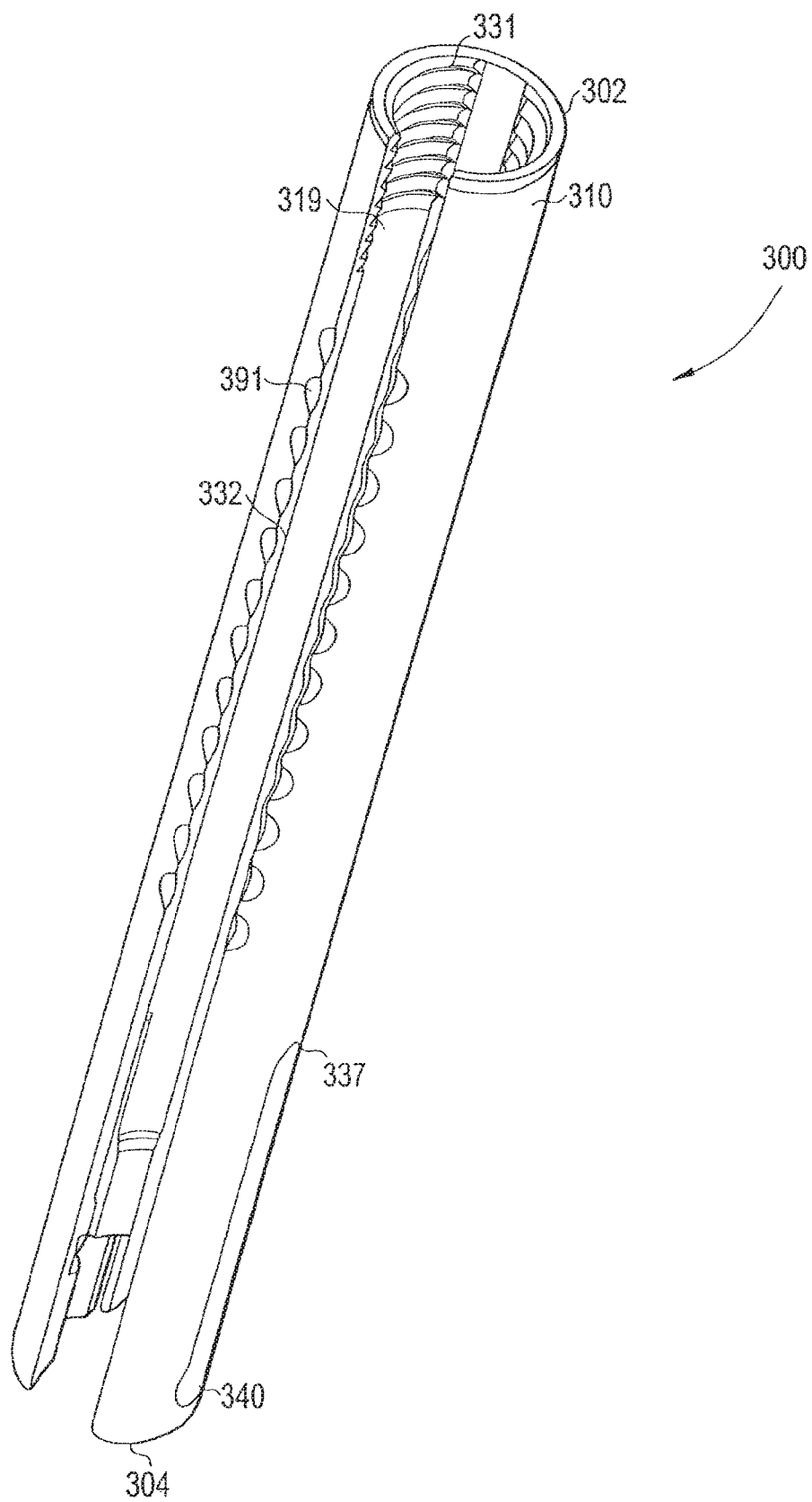
FIGS. 3a-d illustrate yet another exemplary screw extender system, according to some embodiments of the present invention.
Figure 3B:
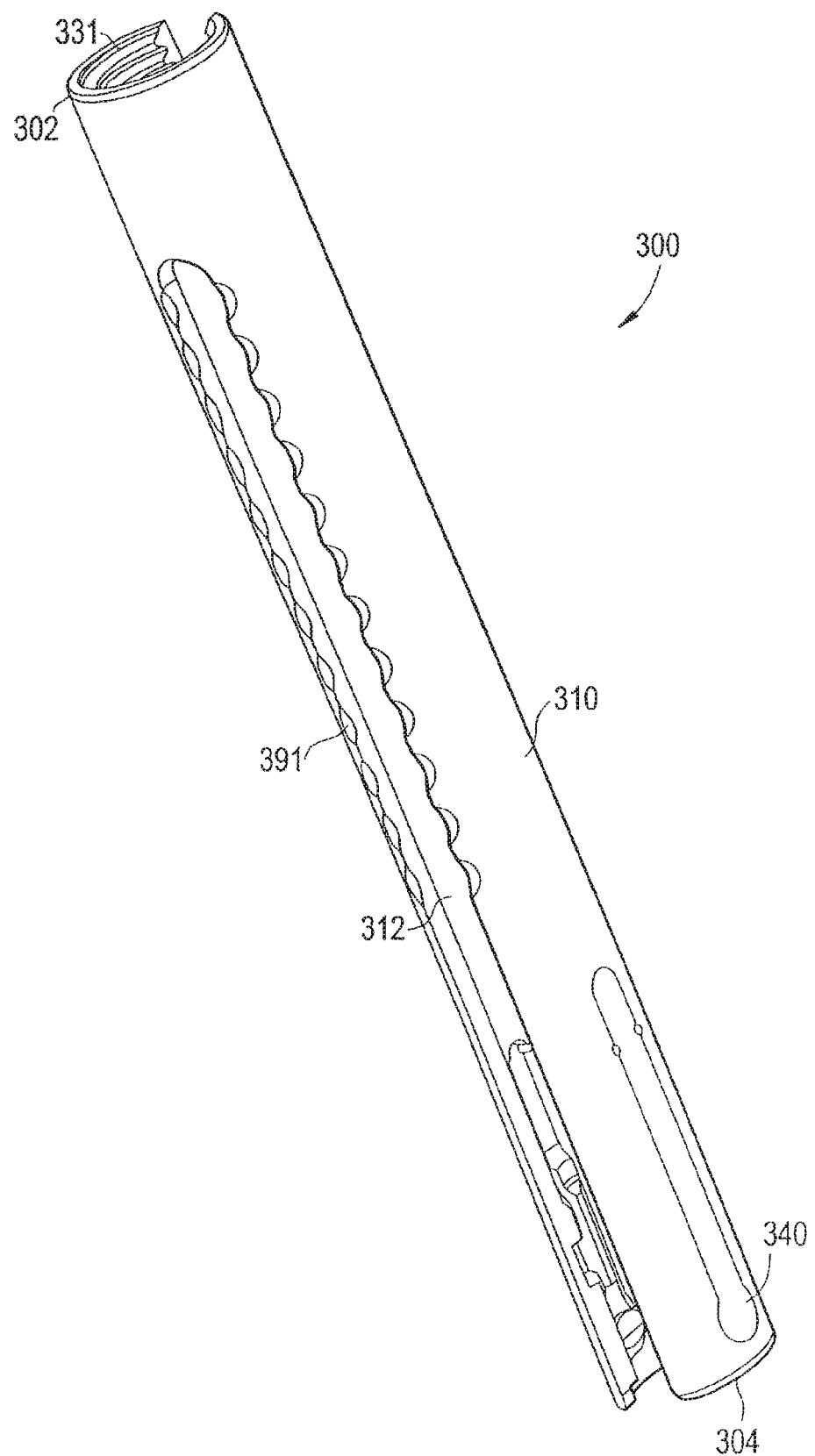
Figure 3C:
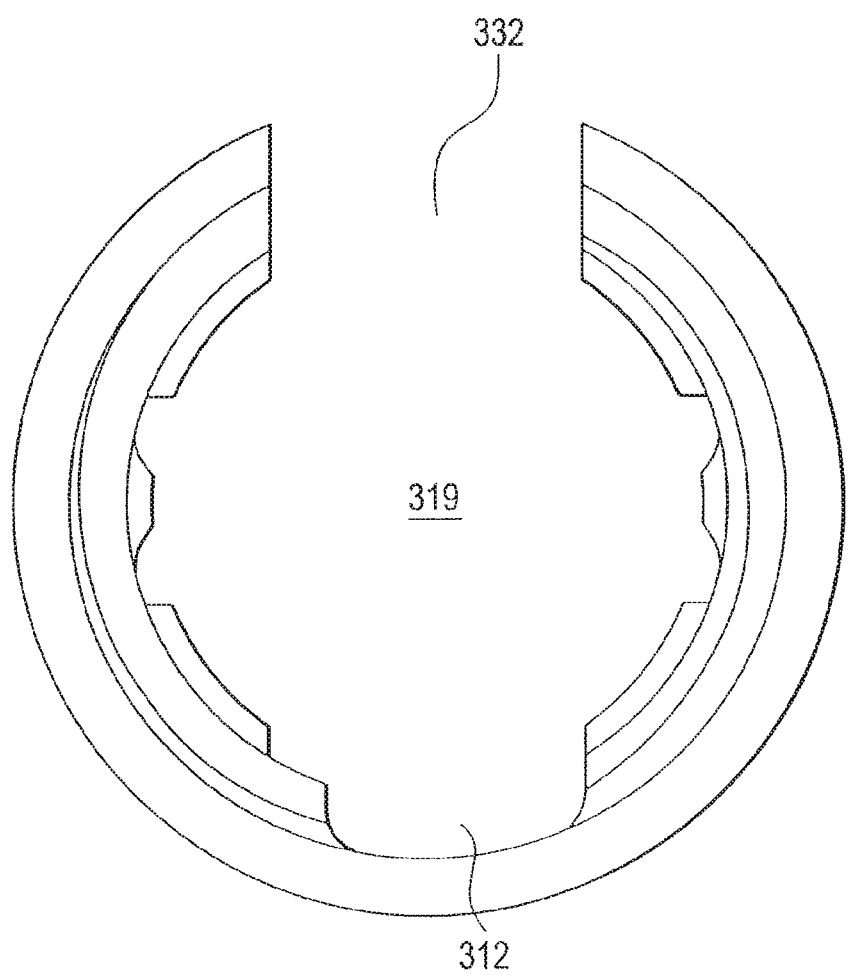

FIGS. 3a-c illustrate another exemplary screw extender housing 310, according to some embodiments of the present invention. The extender housing 310 includes two channels 312 and 332 that are configured to expose the interior 319 of the screw extender housing 310. The channel 312 is configured to be partially open (i.e., partially stretch out between proximal and distal ends) and channel 332 is configured to be fully open (i.e., connect the proximal and distal ends), as illustrated in FIGS. 3b and 3c, wherein FIG. 3c is a top cross-sectional view of the extender housing 310. The housing 310 further includes a gripping feature (or features) 391 that is configured to be disposed along edges of the channel 312 and/or channel 332, as shown in FIGS. 3a-b. The gripping feature 391 is configured to assist in providing additional support to the distractor/compressor device shown in FIGS. 14a-e and discussed below. In some embodiments, the gripping feature 391 is configured to form a small cavity disposed along edges of the channels. In some embodiments, the gripping features 391 can have a shape of a semi-circular cavity. The gripping features 391 can be configured to be disposed along the entire length of the channels 312 and/or 332 or along a portion of the channels.

Similarly to the screw extenders shown in FIGS. 1a-2b, the screw extender housing 300 can include interior threads 331 disposed adjacent the proximal end 302 of the screw extender housing 300. The screw extender housing 310 further includes a locking feature 340 disposed toward the distal end 304 for interlocking with a screw in a similar fashion as the screw extender shown in FIGS. 2a-b.

Figure 3D:
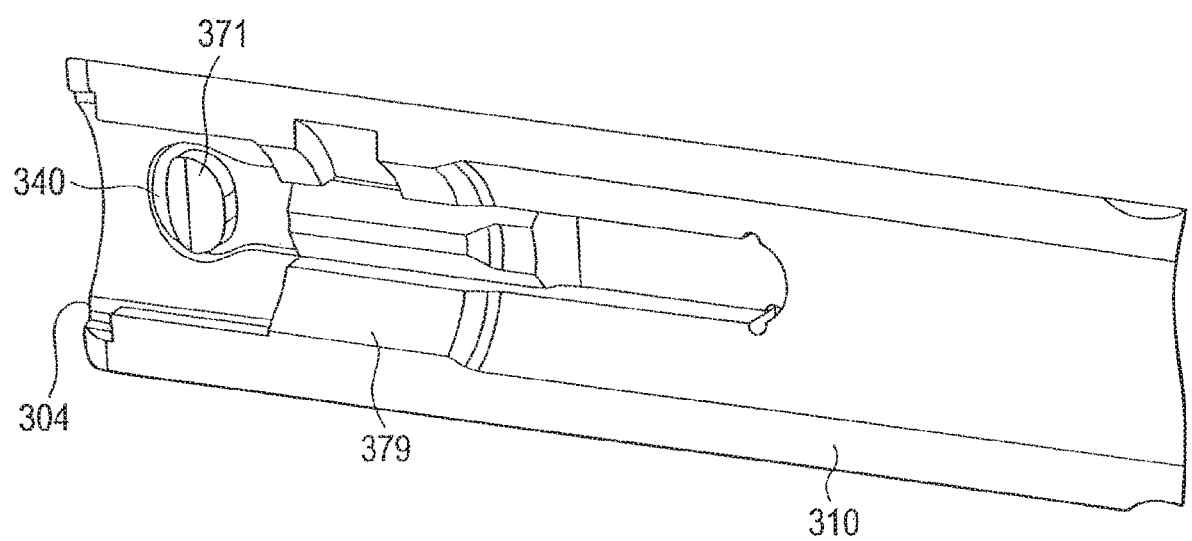

FIG. 3d is a cross-sectional view of a portion of the distal end 304 of the screw extender housing 310. FIG. 3d further illustrates in the locking feature 340 having a protrusion 371 that is configured to mate with an opening disposed on a head of the screw (not shown in FIG. 3d), similar to the feature 240 shown in FIGS. 2a-c. The locking feature 340 further includes a stopping mechanism 379 that is configured to prevent a screw extender removal tool (shown in FIGS. 8a-8d and discussed below) from over rotating once it is placed inside the screw extender housing's interior for the purposes of removing the screw extender housing from the screw. In some embodiments, the stopping mechanism 379 is configured to prevent rotation of the screw extender removal tool by more than 90 degrees. As can be understood by one skilled in the art, the stopping mechanism can prevent any angle of rotation.

As can be understood by one skilled in the art, the channels formed by the screw extender housing channels and the screw do not need to be continuous. For example, a channel on the extender housing can have multiple discontinuities disposed throughout the housing. As can be also understood by one skilled in the art, the screw extender housing can be configured to include one or more first mating features (or indentors, or indented features, or indentor portions, etc.) upon release of one of them, the extender housing can be configured to disengage from the screw.

Figure 4A:
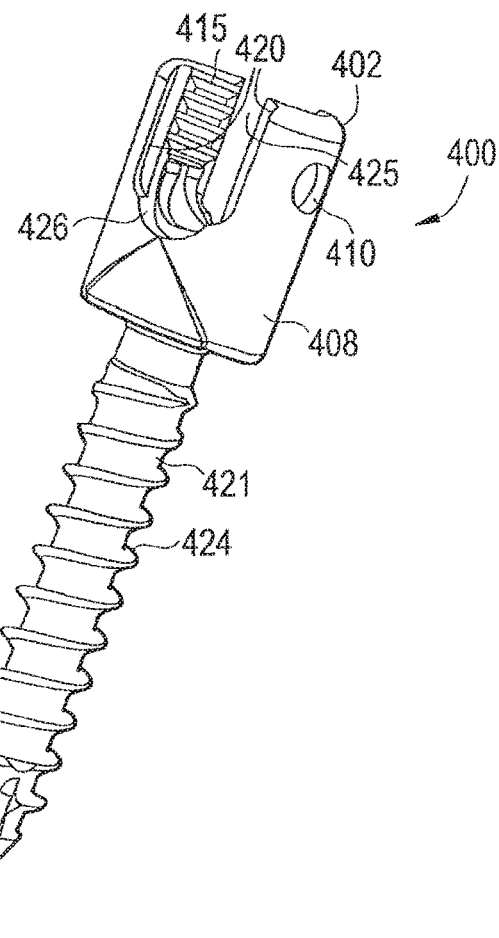
FIGS. 4a-b illustrate an exemplary screw for use with a screw extender system, according to some embodiments of the present invention.
Figure 4B:
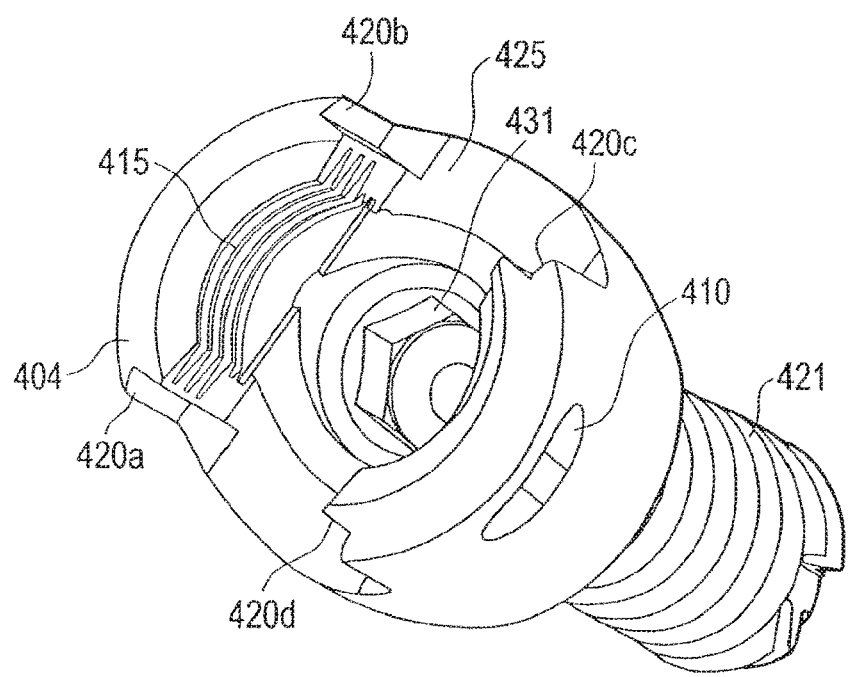

FIG. 4a-b illustrate an exemplary screw 400 configured to be used with screw extenders shown in FIGS. 1a-3d and discussed above, according to some embodiments of the present invention. The screw 400 includes a distal end 404, a proximal end 402, a shaft 421 having threads 424 disposed along its length, and a head of the screw 408 coupled to the shaft 421. The head of the screw includes a passageway 426 that is sized and configured to accommodate placement and securing of a rod. To secure the rod inside the screw head 408, the rod is placed into an interior space 425 created by the passageway 426 and then a set screw (not shown) is placed on top of the rod and secured using threads 415 disposed on the interior walls of the passageway 426. The passageway 426 can be configured to include recessed edges 420 (a, b, c, d) that are configured to accommodate placement of the screw extender housing (shown in FIG. 5). The head of the screw further includes openings 410 that are configured to receive protrusions of the locking features disposed on the screw extender housing (as shown in FIGS. 2a-3b).

Figure 5:
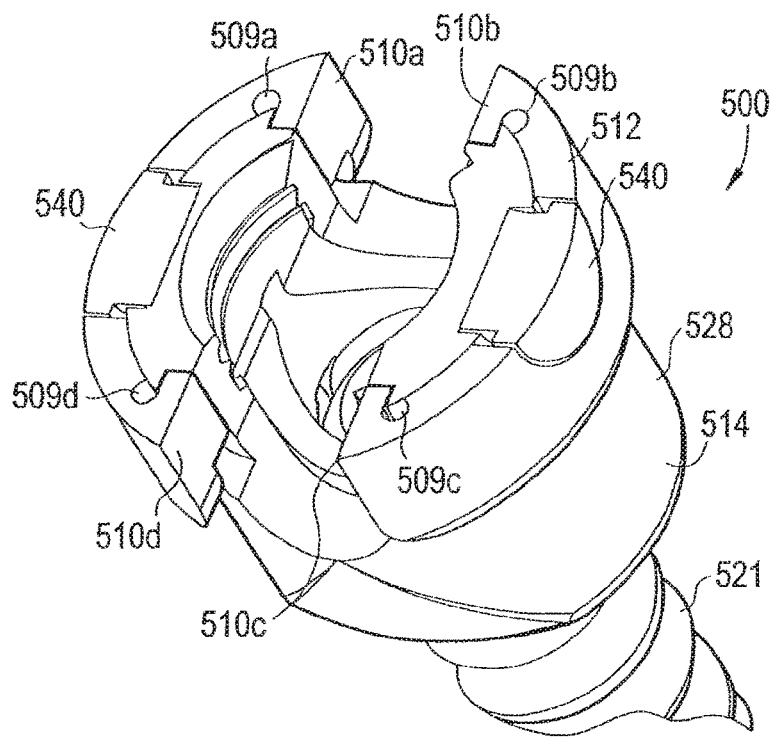
FIG. 5 illustrates exemplary coupling of the screw and the screw extender system, according to some embodiments of the present invention.

Referring to FIG. 5, to further secure the screw 500 (similar to the screw 400) to the extender device housing 512, the housing 512 includes a plurality of protrusions 510 (a, b, c, d). The protrusions 510 are configured to engage recessed edges 509 (a, b, c, d), respectively, of the head 528 of the screw 514. In some embodiments, the protrusions 510 are configured to wrap around the recessed edges 509. Such interaction of screw's recessed edges 509 and extender's protrusions 510 further secures the screw 514 to the extender housing 512 and prevents displacement of the screw 514 from the housing 512. This configuration also allows the surgeon (or any other medical professional) to controllably apply various forces to the screw (e.g., during placement of an implant, etc.), such translational, axial, torsional, or any other forces. As can be understood by one skilled in the art, the screw 514 and the housing 512 can have any number of recessed edges 509 and corresponding protrusions 510. Additionally, the screw 514 can have any number of openings (not shown in FIG. 5, but shown in FIGS. 4a-b) and the housing 512 can have any number of corresponding indentor portions 540 that interact with the openings.

As stated above, the screw extender aids in the placement of, for example, pedicle screws during spinal fusion procedures. In some embodiments, the surgeon (or other medical professional) attaches the screw extender to the pedicle screw and maintains control of the screw from an exterior (for example, from outside of the skin incision). The screw extender provides strong attachment so that axial, lateral, and torsional forces can be applied to the screw extender. The surgeon typically applies these forces to screw extenders to manipulate the vertebra to which pedicle screws are attached.

In some embodiments, the screw extender has a centerless tubular body. The extender includes various securing features, for example, flexible indenters, for holding the screw in an axial plane along the axis of the screw and the extender, where the securing features engage the recessed edges of the screw. In some embodiments, the screw extender indenters are flexible and are fixed to the main body of the screw extender at only one location (as shown in FIG. 3a). This allows the screw extender indenters to flex out of the way and allow the screw to be released from the screw extender. As stated above, extender's tubular body is also partially slotted to allow a rod to be placed in the typical fashion.

Figure 8A:
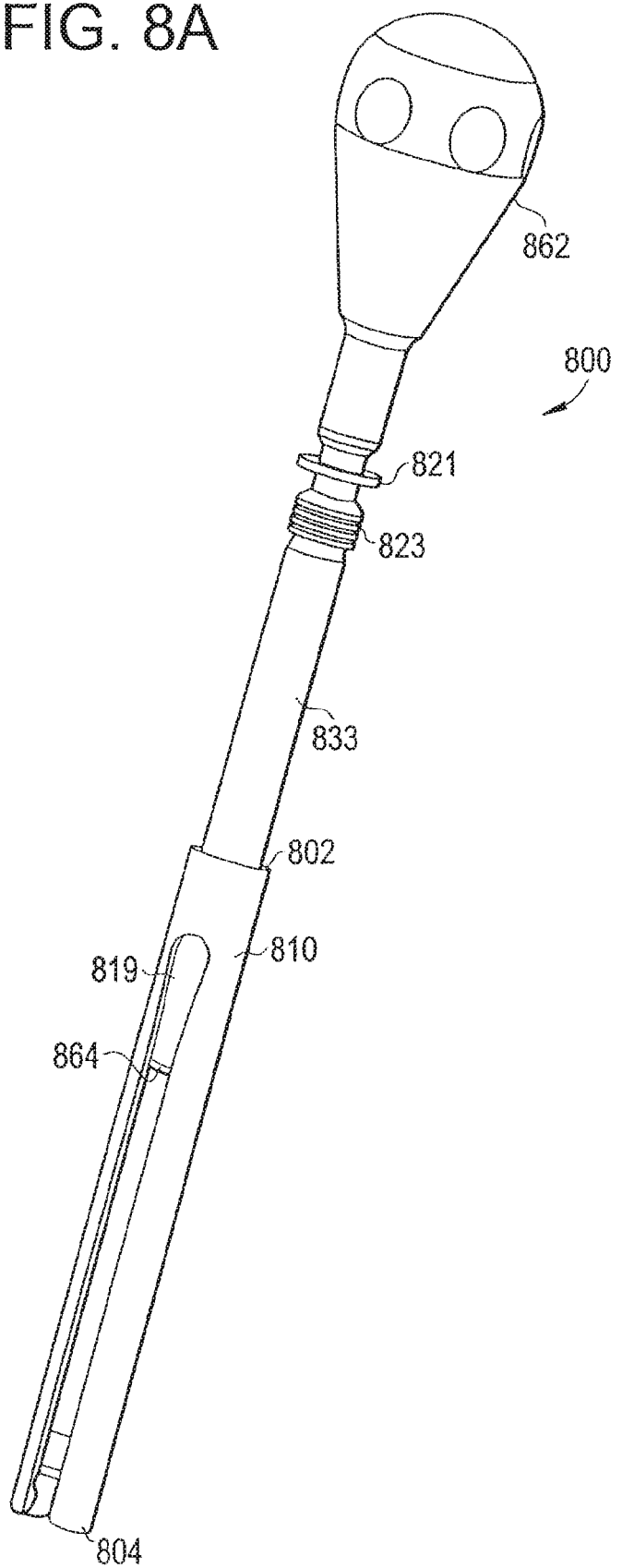
FIGS. 8*a*-*d* illustrate various exemplary screw extender remover tools, according to some embodiments of the present invention.
Figure 8B:
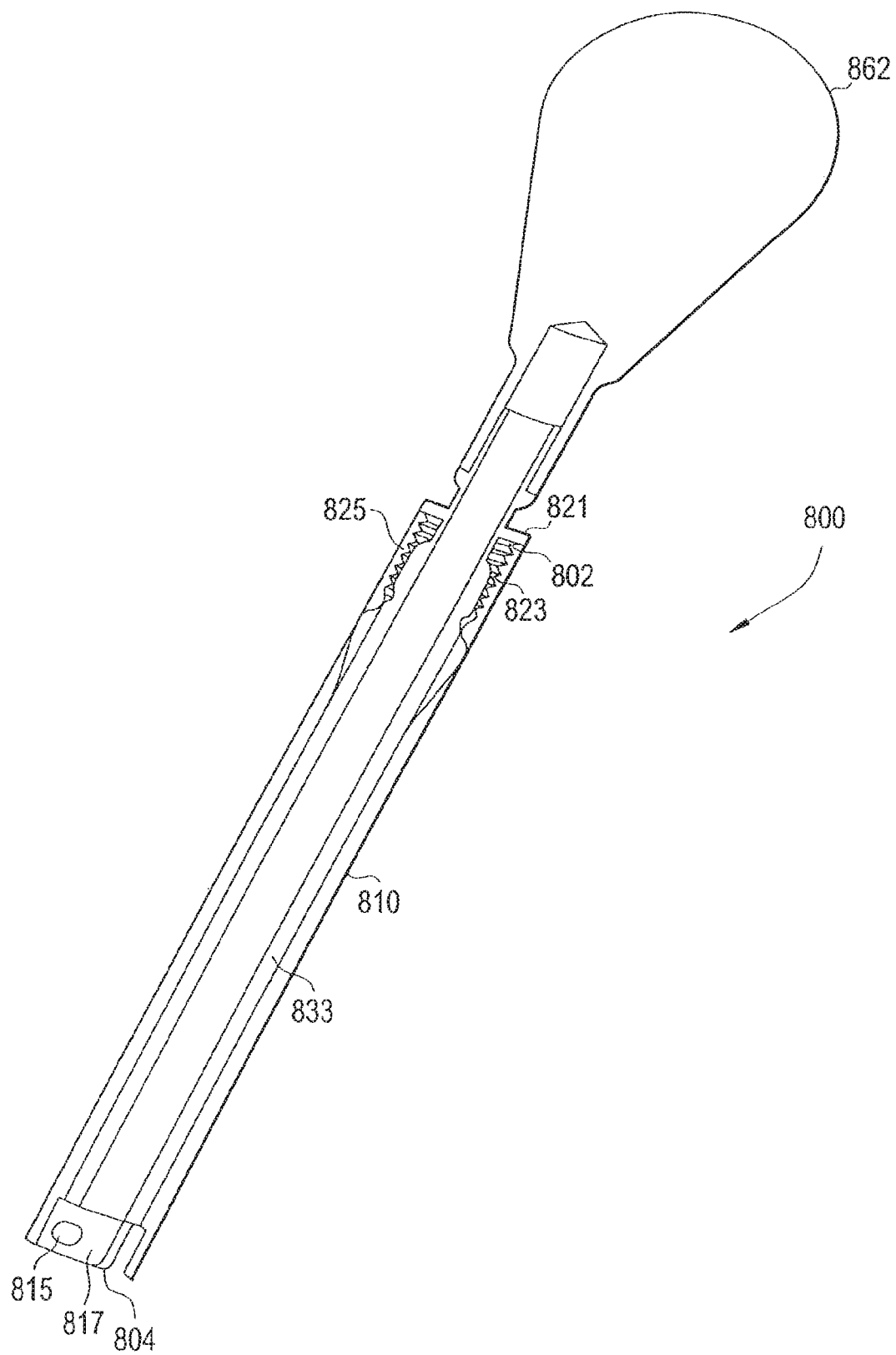
Figure 8C:
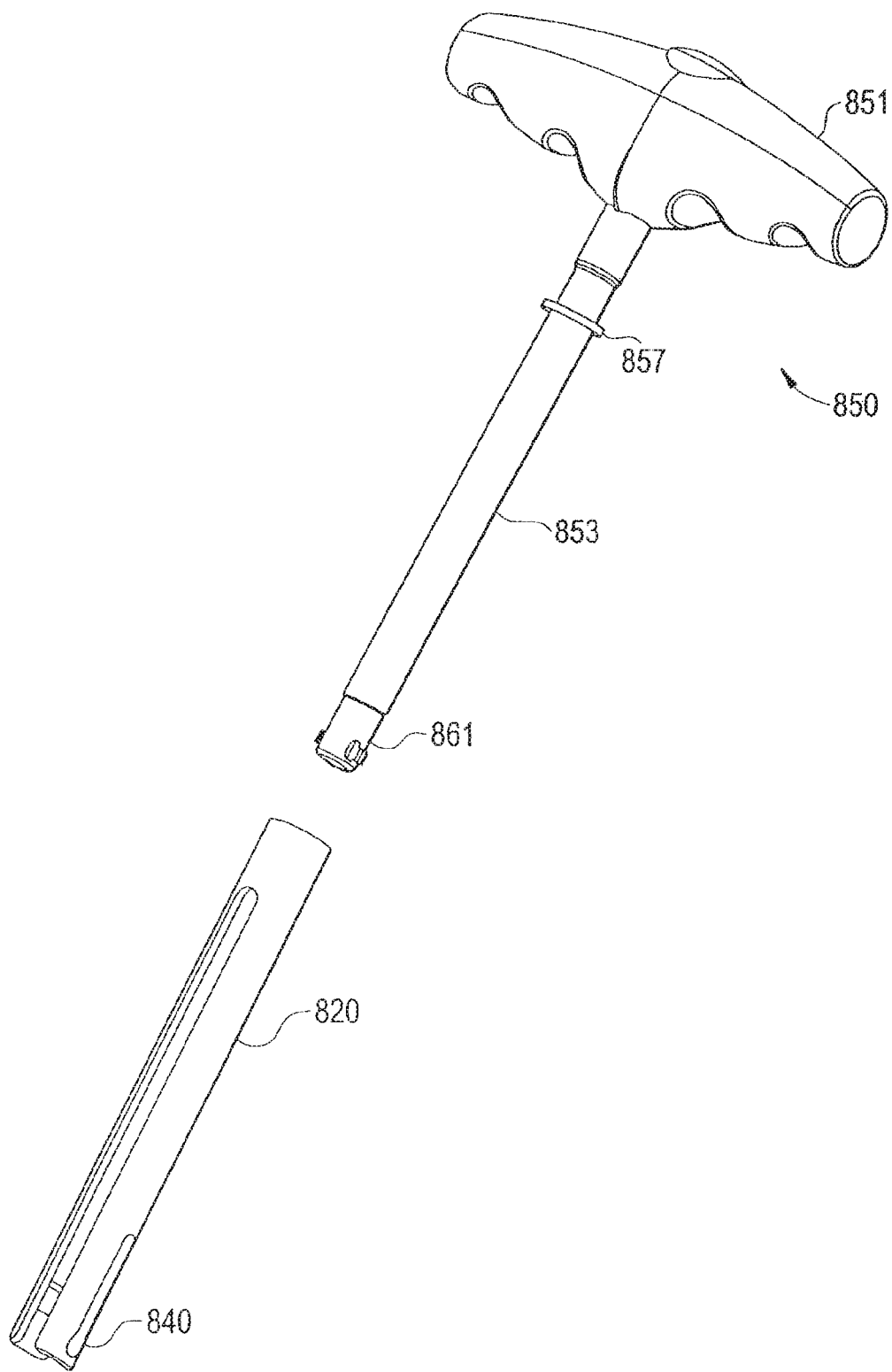
Figure 8D:
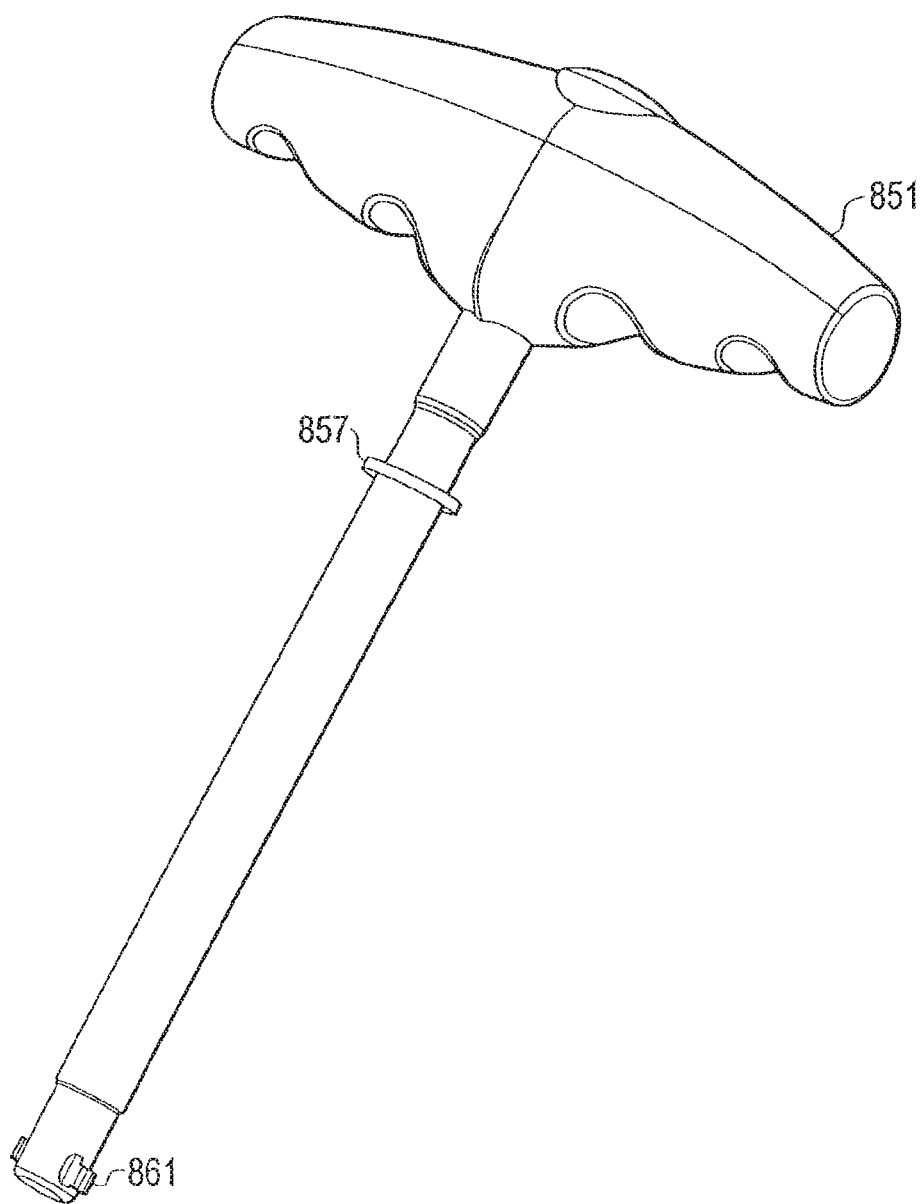

In other embodiments, the system includes a screw extender remover tool shown in FIGS. 8a-d. FIGS. 8a-b illustrate one embodiment of a screw extender remover tool 800 and FIGS. 8c-d illustrate another embodiment of a screw extender remover tool 850.

Referring to FIGS. 8a-b, the remover tool 800 includes a shaft 833 disposed between a distal end 864 and a handle 862. In some embodiments, the handle 862 is configured to have a rounded shape. As can be understood by one skilled in the art, the handle can be configured to have any desired shape. The shaft 833 further includes a threaded portion 823 disposed substantially adjacent to the handle 862 and a stopping mechanism 821 disposed between the handle and the threaded portion 823. The shaft 833 is configured to fit into the interior passageway 819 of the extender housing 810, as shown in FIG. 8a. The threaded portion 823 is configured to interact with an interior threaded portion 825 of the screw extender housing 810 upon insertion of remover tool 800 into the screw extender housing 810, as shown in FIG. 8b. Upon insertion of the remover tool 800, the threaded portions 823 and 825 are configured to interact with each other and a surgeon (or any other medical professional) begins to rotate the remover tool in a downward direction (e.g., clockwise direction) in order to advance the remover tool toward the screw. The remover tool is advanced until the stopping mechanism 821 prevents its further advancement toward the screw. In some embodiments, the length of the remover tool's shaft can be appropriately selected so that upon full insertion of the remover tool, its distal end 864 is configured to interact with flexible plates 817 containing protrusions 815 and to push the plates 817 apart, thereby causing disengagement of the screw extender housing 810 from the screw. The stopping mechanism 821 is further configured to prevent over-insertion of the remover tool and thus, damage to the screw.

Thus, to remove or disengage the extender housing 810 from the screw, a threaded shaft 833 is inserted down the long axis of the extender housing. This threaded shaft 833 engages the threads 825 of the extender housing and forces the distal indented ends of the extender apart. This mechanism releases the bone screw by releasing the tabs or flexible plates 817 in the screw extender from its mating hole in the screw.

Figure 18A:
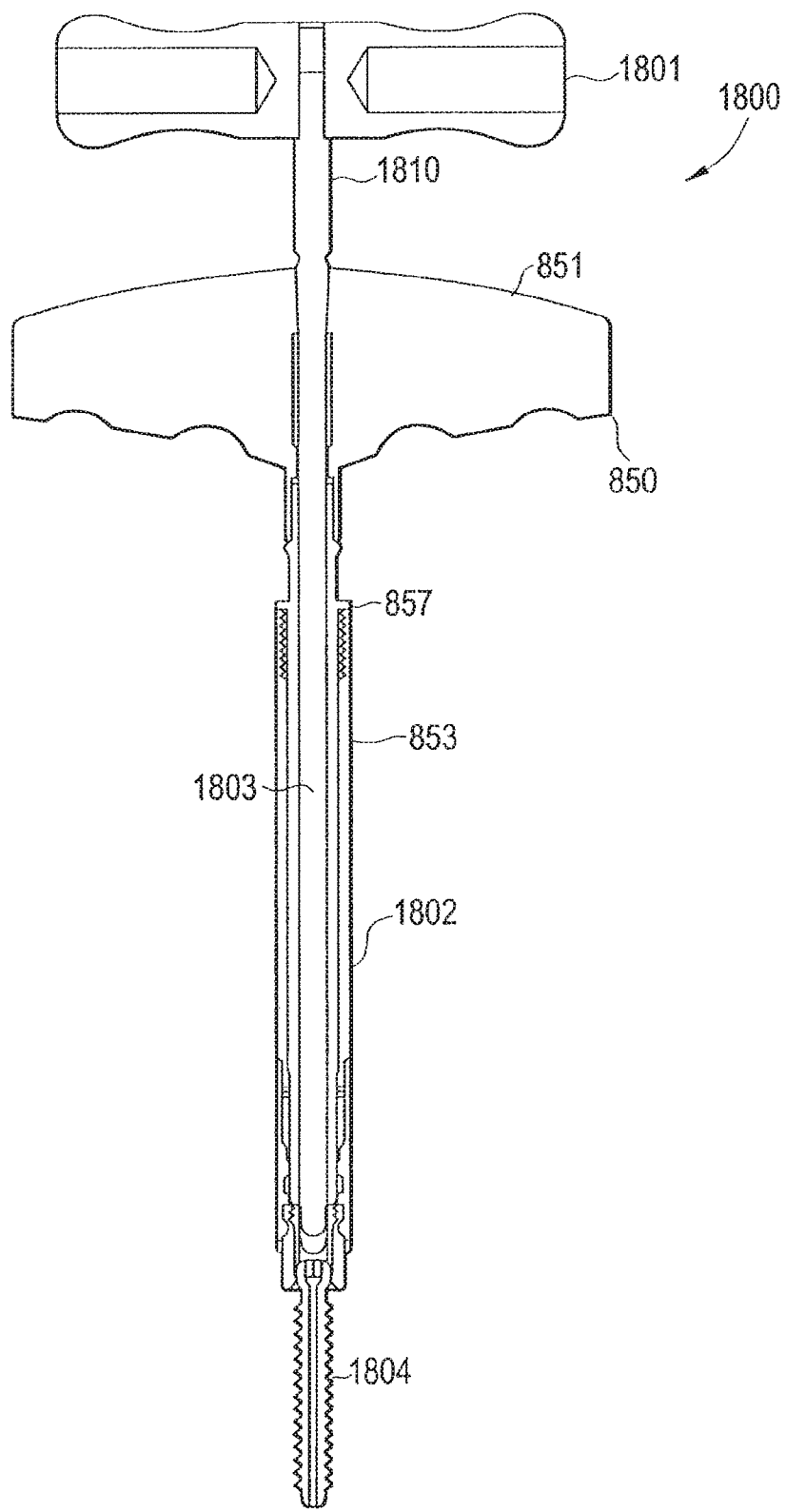
FIGS. 18*a*-*c* illustrate an exemplary supplemental screw extender remover tool, according to some embodiments of the present invention.
Figure 18B:
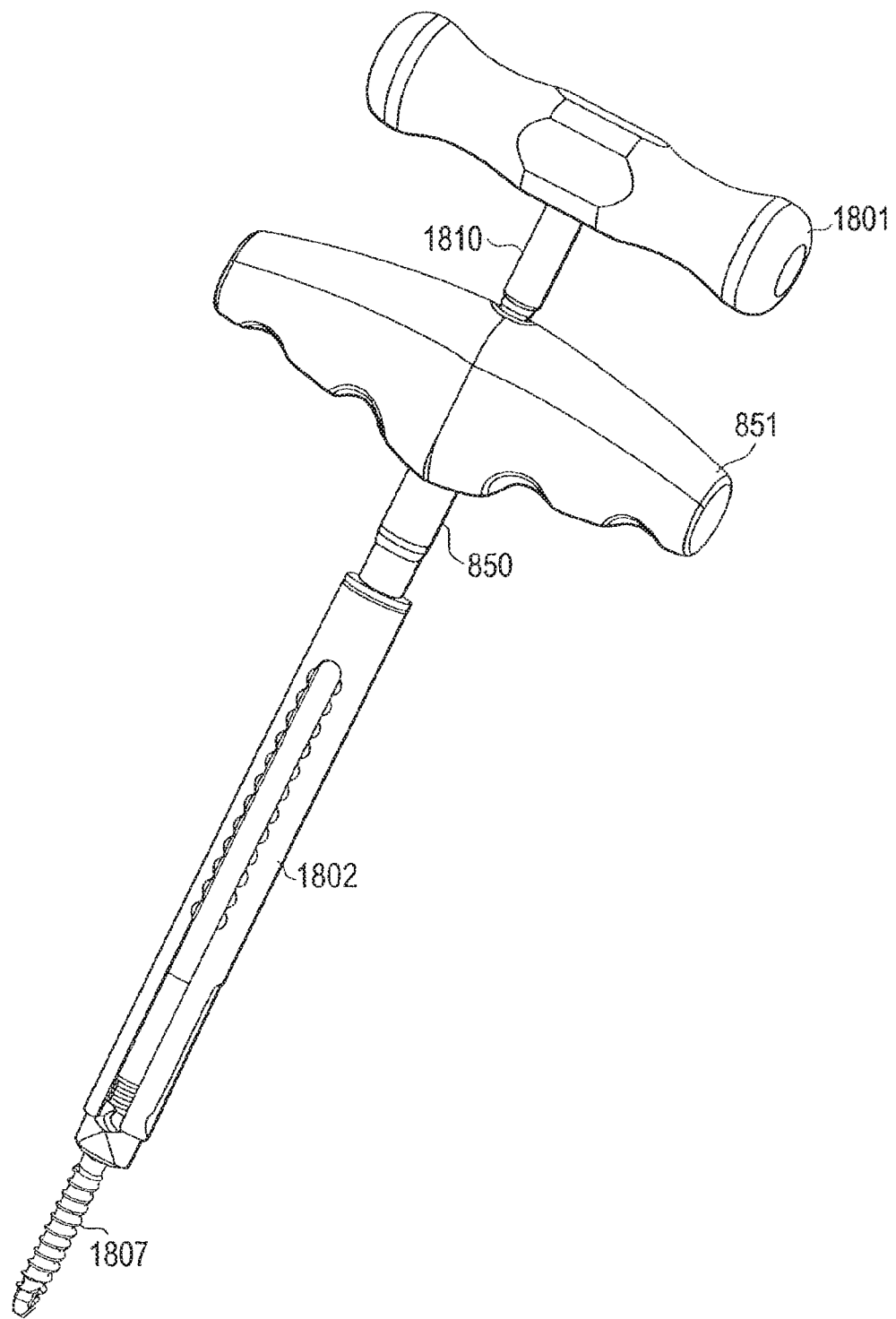
Figure 18C:
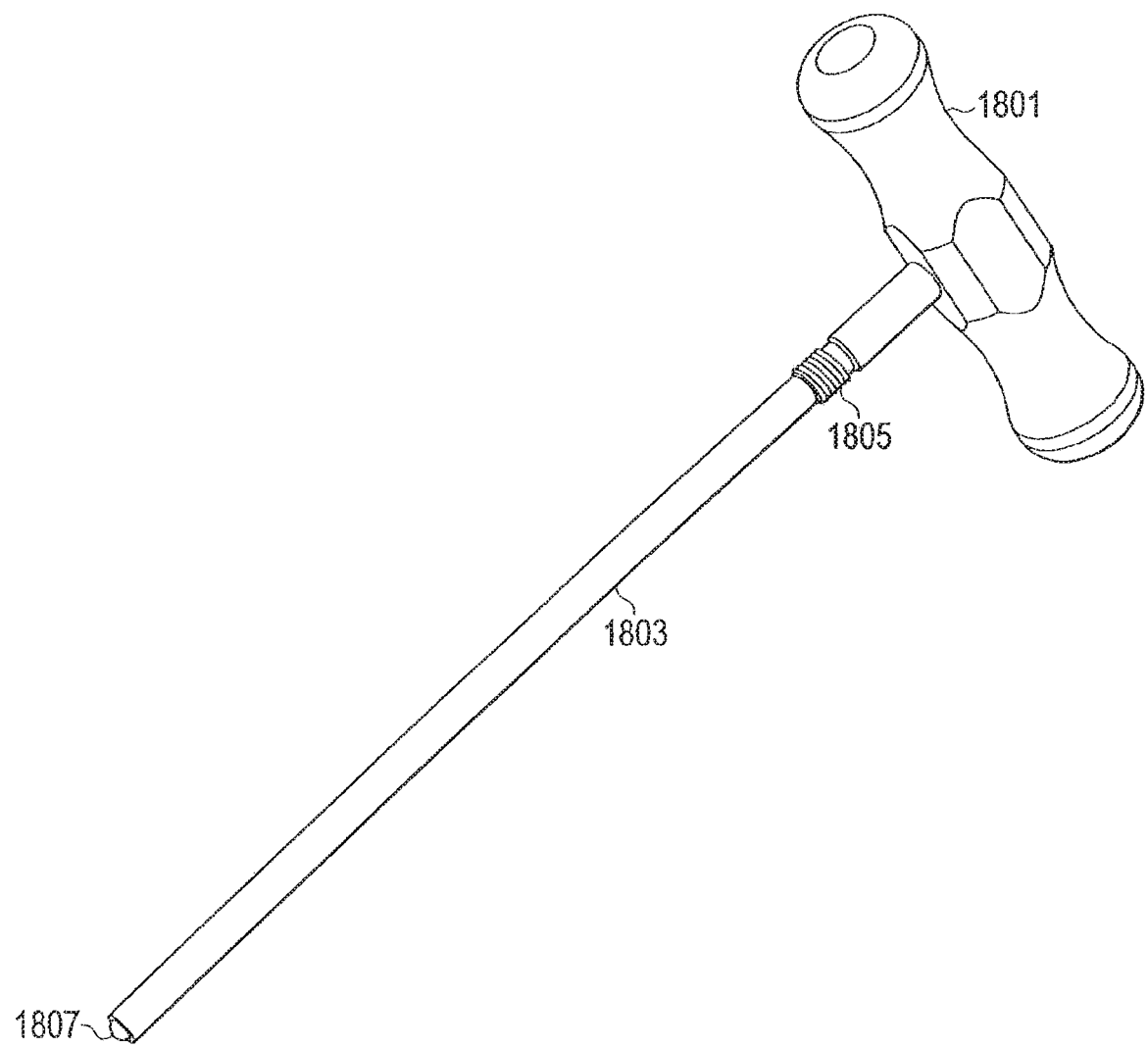

FIGS. 8c-d illustrate an alternate embodiment of the remover tool 850, according to some embodiments of the present invention. The remover tool 850 includes a shaft 853, a stopping mechanism 857, and a handle 851. In some embodiments, the handle 851 can be configured to be cannulated on the inside to allow passage of additional devices through it, as shown in FIGS. 18a-c. Such additional devices can be configured to be used to assist in removal of the screw extender from the screw in the event that the remover tool 850 is unable to disengage from the screw.

As shown in FIGS. 8c-d, the remover tool 850 is configured to fit inside the extender housing 820 and to be advanced toward the distal end of the housing upon application of a downward force by the surgeon (or any other medical professional). The stopping mechanism 857 is configured to prevent over-insertion of the remover tool 850 and thus, damage to the screw. The remover tool 850 further includes at least one protrusion 861 extending from an outer surface of the shaft 853 of the remover tool 850 substantially adjacent the distal end of the shaft 853 of the remover tool. The protrusions 861 are configured to interact with the flexible portions 840 of the extender housing 810 when the remover tool 850 is fully inserted into the screw extender housing (i.e., the stopping mechanism 857 is configured to interact with a proximal end of the screw extender housing) and rotated by the surgeon. Upon interaction of the protrusions and flexible locking features, the protrusions 861 are configured to push on the flexible locking features 840, thus pushing them away for the interior passageway of the screw extender and thereby unlocking the screw extender housing from the screw. In some embodiments, a stopping mechanism 379 shown in FIG. 3d prevents over-rotation of the remover tool once it is inserted into the housing of the screw extender. The stopping mechanism 379 can be a protrusion disposed on an inner surface of the extender housing substantially adjacent to the flexible indenters. The stopping mechanism 379 can be further disposed in the path of the rotating protrusions 861, thus, preventing rotation of the remover tool beyond a particular point. In some embodiments, the stopping mechanism 379 is configured to prevent rotation of the remover tool by more than 90 degrees. The stopping mechanism is configured to assist the surgeon in determining when the flexible members have been pushed apart and thus it is safe to remove the extender housing.

Figure 6:
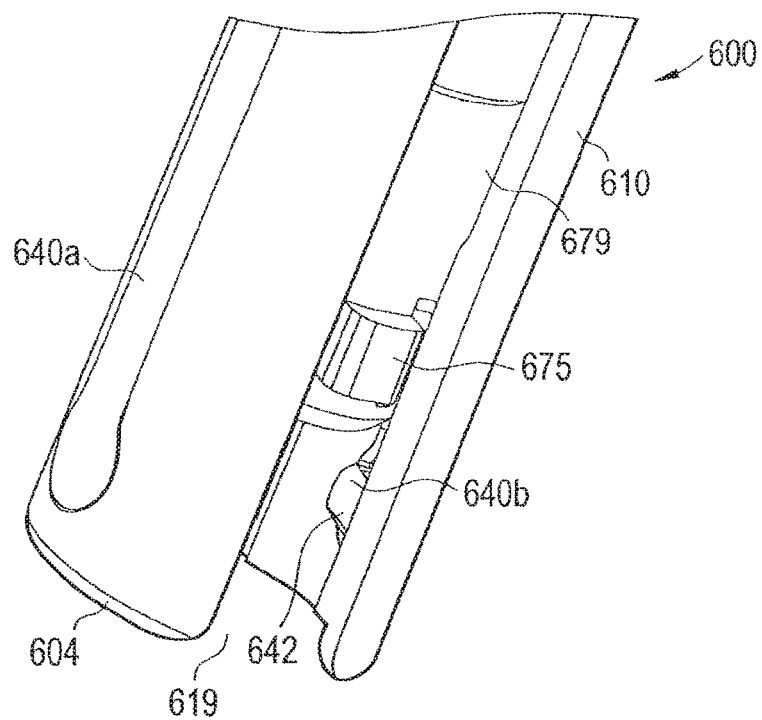
FIG. 6 illustrates a distal portion of the screw extender housing, according to some embodiments of the present invention.

FIG. 6 illustrates a closer view of the interaction of the distal end of the remover tool 679 (which is similar to the remover tool 850) with the extender housing 610. As shown, the distal end of the remover tool 679 includes protrusions 675 that are configured to extend away from the surface of the remover tool 679. The flexible portions 640 (a, b) (similar to those shown in FIGS. 2a-3c) include protrusions 642 (a, b), respectively, that are configured to be removed from the openings in the screw upon rotation of the remover tool and subsequent interaction of the protrusions 675 of the remover tool with the flexible portions 640.

Thus, for the surgeon to remove the screw extender 610 from the screw (which is typically done after completion of a procedure), the screw extender remover device 679 is used. In addition to the components shown in FIGS. 8c-d, the remover device 679 includes a tip having protrusions or ramps 675. The ramps 675 are configured to be disposed around the perimeter of the tip. The shaft and the tip of the remover device can be cylindrical in order to match the cylindrical housing 610 of the extender device 600. As can be understood by one skilled in the art, the shaft and the tip have any other shape and can correspond to the shape of the housing 610.

In some embodiments, the tip can be smaller than the shaft (e.g., the diameter of the tip is smaller the diameter of the shaft). The shaft is also sized to fit inside the housing 610 of the extender device 600. The stopping mechanism or a stopper rim 823 (see, FIGS. 8c-d) that acts as a stopper and limits the depth at which the remover device 679 can be placed into the housing 610, thereby controlling the depth that the ramps 675 can engage the screw extender's indentor portions 640 (shown in FIG. 6).

Figure 7A:
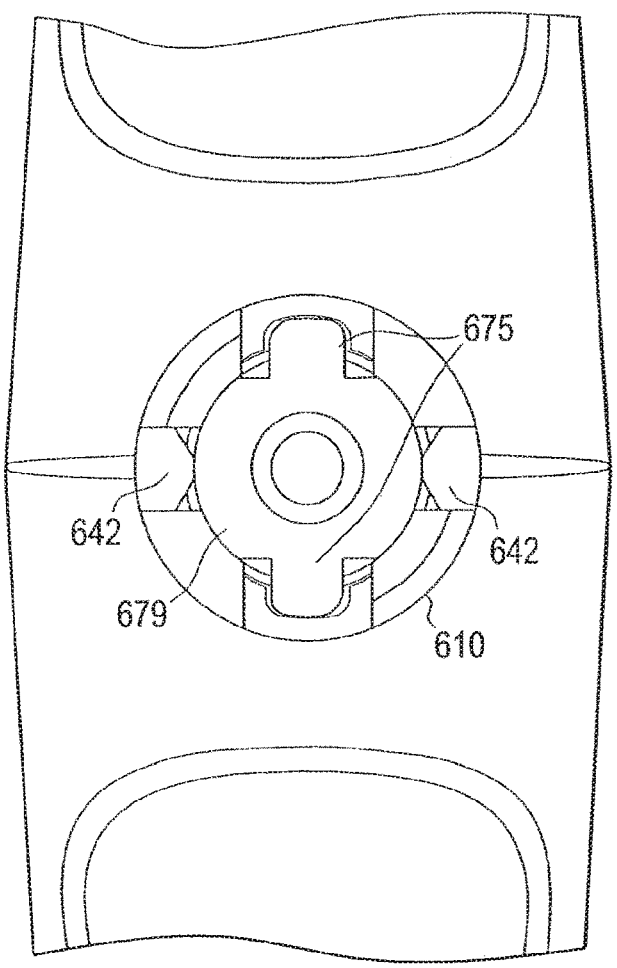
FIGS. 7a-b are bottom views of the screw extender housing having an exemplary screw remover device configured to remove the housing from the implanted screw, according to some embodiments of the present invention.
Figure 7B:
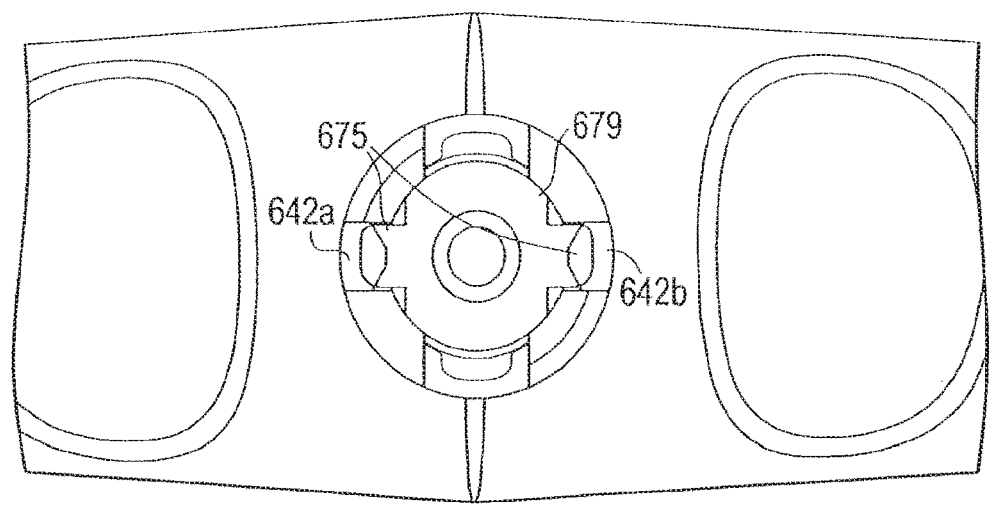

The ramps 675 are configured to protrude away from the surface of the tip. The ramps 675 interact with the indentor portions 640 of the housing 610, as illustrated in FIGS. 6-7b, wherein FIGS. 7a-b illustrate a bottom view of the remover tool interacting with the indentor portions. To remove the extender device 600 from the screw, the remover device 679 is inserted into the hollow housing 610 via its proximal end (not shown in FIGS. 6-7b). In some embodiments, the ramps 675 of the remover device 679 can be aligned with the channels 619 during insertion of the remover device 679 into the housing 610. As such, during insertion, the ramps 675 slide down the channels 619 (as shown in FIG. 6). The insertion of the device 679 continues until the stopper rim of the remover device (not shown in FIG. 6) comes in contact with the proximal end of the extender housing. At this point, the device 679 is rotated about 90 degrees (in any direction) by gripping the handle of the remover device (shown in FIG. 8c-d) and twisting it in an appropriate direction. By rotating the handle, the ramps 675 come in contact with the indentor portions 640. Due to flexible nature of the indentor portions 640, the ramps 675 are configured to push the indentor portions 640 towards exterior portion of the housing 610 of the extender device 600. As the portions 640 are pushed apart, the indentor protrusions 642 disengage from the openings of the screw. Once the protrusions 642 are removed from the openings in the head of the screw, the extender device 600 becomes loose and can be removed from the screw. In some embodiments, the extender device 600 and the remover device 610 can be removed at the same time. As can be understood by one skilled in the art, other ways of removing the screw extender housing from the screw are possible.

FIGS. 18a-c illustrate an exemplary supplemental screw extender remover device 1810, according to some embodiments of the present invention. In the event that a surgeon is unable to disengage the screw extender device from the screw, the device 1810 can assist the surgeon in pushing the screw extender away from the screw. As shown in FIGS. 18a-c, the supplemental remover device 1810 includes a shaft 1803 disposed between the distal tip 1807 and a handle 1801. The supplemental remover device 1810 is configured to have a smaller diameter than that of the remover tool 850. The shaft 1803 of the device 1810 is configured to be longer than that of the remover tool 850. The remover tool 850 includes an interior cannulated portion (not shown in FIGS. 18a-c) that is disposed within the remover tool 850 and that further accommodates insertion of the device 1810, as shown in FIGS. 18a-b. The device 1810 further includes a threaded portion 1805 configured to be disposed substantially adjacent the handle 1801. The threaded portion 1805 is configured to interact with a threaded portion disposed inside the handle 851 of the device 850.

Thus, in the event that the surgeon cannot remove the screw extender device 1802 from the screw 1807 using just the remover tool 850, the surgeon inserts the device 1810 through an opening in the handle 851 of the remover device 850 and pushes the device 1810 along the interior channel (i.e., cannulated portion) of the remover device 850, until threaded portion 1805 comes in contact with an interior threaded portion of the remover device 850. At this time, the surgeon begins to rotate the device 1810 along the threaded portion, thereby protruding the tip 1807 of the device 1810 beyond the distal tip of the remover device 850. Thus, the tip 1807 comes in contact with the screw 1804 and effectively pushes the screw extender 1802 along with remover tool 1810 away from the screw, thus, allowing the surgeon to remove the screw extender.

In some embodiments, the screw extender system of the present invention can be utilized for delivery of a percutaneous wire, which can then be utilized for advancement of a rod. Initially, to perform a spinal surgery using the screw extender device of the present invention, the surgeon initially makes an incision at a location where a first screw along with a first screw extender device is to be implanted. Another incision can be made at another location where a second screw along with a second screw extender are to be implanted. As can be understood by one skilled in the art, the surgeon can make as many incisions as are necessary for creating a spinal stabilization system according to the present invention. Once, the incisions are made, the surgeon can couple the screw extenders with the screws and advance this combination toward the bony matter (e.g., vertebrae) for subsequent insertion. Once the screw-extender-and-screw combination are inserted, the surgeon is able to manipulate to the screw extenders and the screws for insertion of percutaneous wires and/or rods and/or other tools and device. In some embodiments, the screws can be poly-axial screws that allow the surgeon to manipulate the screw extenders in any direction while the screw extenders are rigidly attached to the screws.

FIGS. 9a-9h illustrate exemplary percutaneous wire insertion devices 900 and 950, according to some embodiments of the present invention. The devices 900 and 950 are configured to be inserted into the screw extender's hollow interiors for guiding a percutaneous wire along and between the screw extenders. Referring to FIGS. 9a-c and 9h, a first percutaneous wire insertion device 900 is illustrated. The device 900 includes a shaft 920 disposed between a proximal end 902 and a distal end 904. The device 900 is configured to be cannulated and thus includes an interior channel 941 configured to be disposed between an opening at the proximal end 902 and an opening 930 disposed at the distal end 904 of the device 900. In some embodiments, the opening 930 is configured to be placed on the side of the device 900 so as to accommodate advancement of the wire toward another screw extender.

In some embodiments, the device 900 further includes two parts 927a and 927b that are configured to be coupled using a nut or any other locking mechanism 922 that is configured to be placed adjacent the proximal end 902 of the device 900. The two-part configuration is provided for ease of removal of the device 900 from the screw extender. The two parts 927 are configured to be coupled using hook features 932 and 933 disposed at the distal end 902 of the device and the nut 922 disposed adjacent the proximal end 904 of the device 900. The nut 922 further includes threading 924 that is configured to interact with the threading disposed at a proximal end of the screw extender on the screw extender's inner surface.

To secure the device 900 inside a screw extender device, the surgeon inserts the assembled device 900 with the distal end 904 into the screw extender's proximal end and slides the device 900 along the interior passageway of the screw extender until the threads 924 of the device 900 begin to interact with the screw extender's interior threads disposed at the proximal end of the screw extender. At this point, the surgeon begins rotation of the nut 922, thereby screwing the nut 922 into the screw extender without rotation of the shaft 920 of the device 900. Upon insertion of the device 900 into the screw extender, the distal end 904 of the device 900 is configured to fit within the passageway of the head of the screw. This allows proper alignment of the opening 932 toward another screw extender. In some embodiments, upon placement of the screws and respective screw extenders, the surgeon can manipulate the screw extenders (coupled to the screws) so that the channels disposed on the extenders' exterior surfaces are aligned toward each other. The device 900 can be inserted with the opening 930 pointed toward the second screw extender that has been already installed into patient's vertebrae. During insertion of the wire through the device 900, the wire is advanced along the interior channel 941, out of the opening 930 and toward the second extender through patient's muscle tissue.

As stated above, the device 900 is configured to be separated into to portions 927a and 927b. In some embodiments, the portion 927a is configured to include the channel 941 for advancing the wire along the device 900. The channel 941 is configured to begin at the proximal end of the device 900 and protract through the entire length of the portion 927a toward the opening 930 disposed on the side of the device 900. In some embodiments, the channel 941 is configured to be curved to accommodate bending of the wire during advancement.

In some embodiments, the device 900 can include a balancing feature 925 configured to extend away from the surface of the shaft 920. The feature 925 is configured to prevent the device 900 from wobbling once it is inserted into the interior passageway of the screw extender.

Figure 9E:
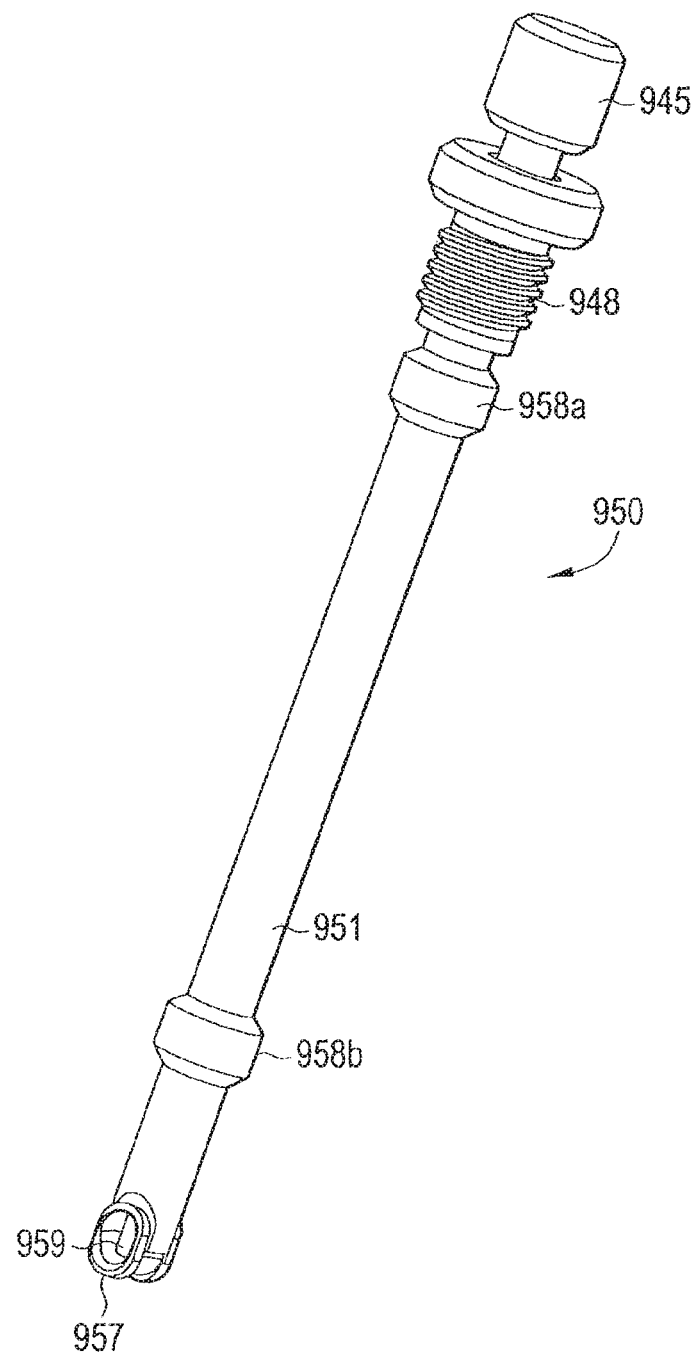
Figure 9F:
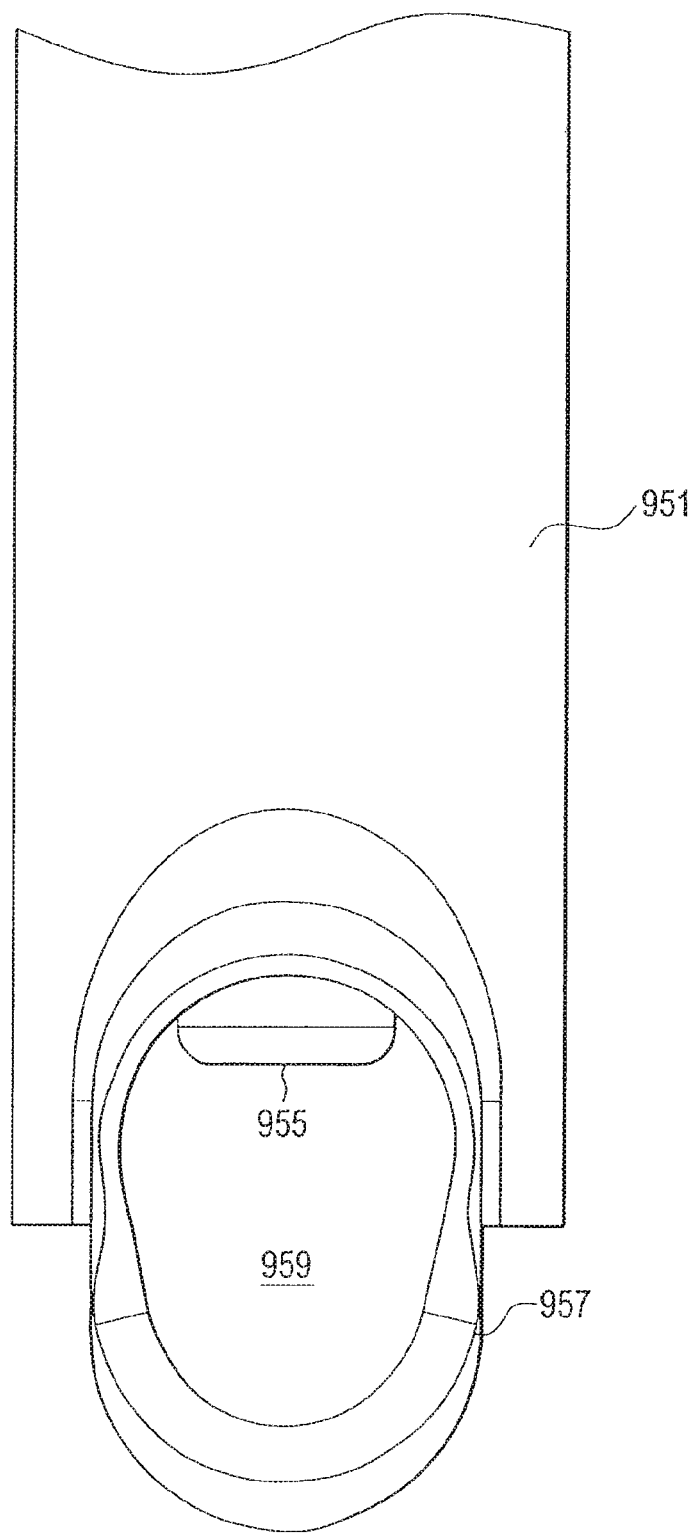
Figure 9G:
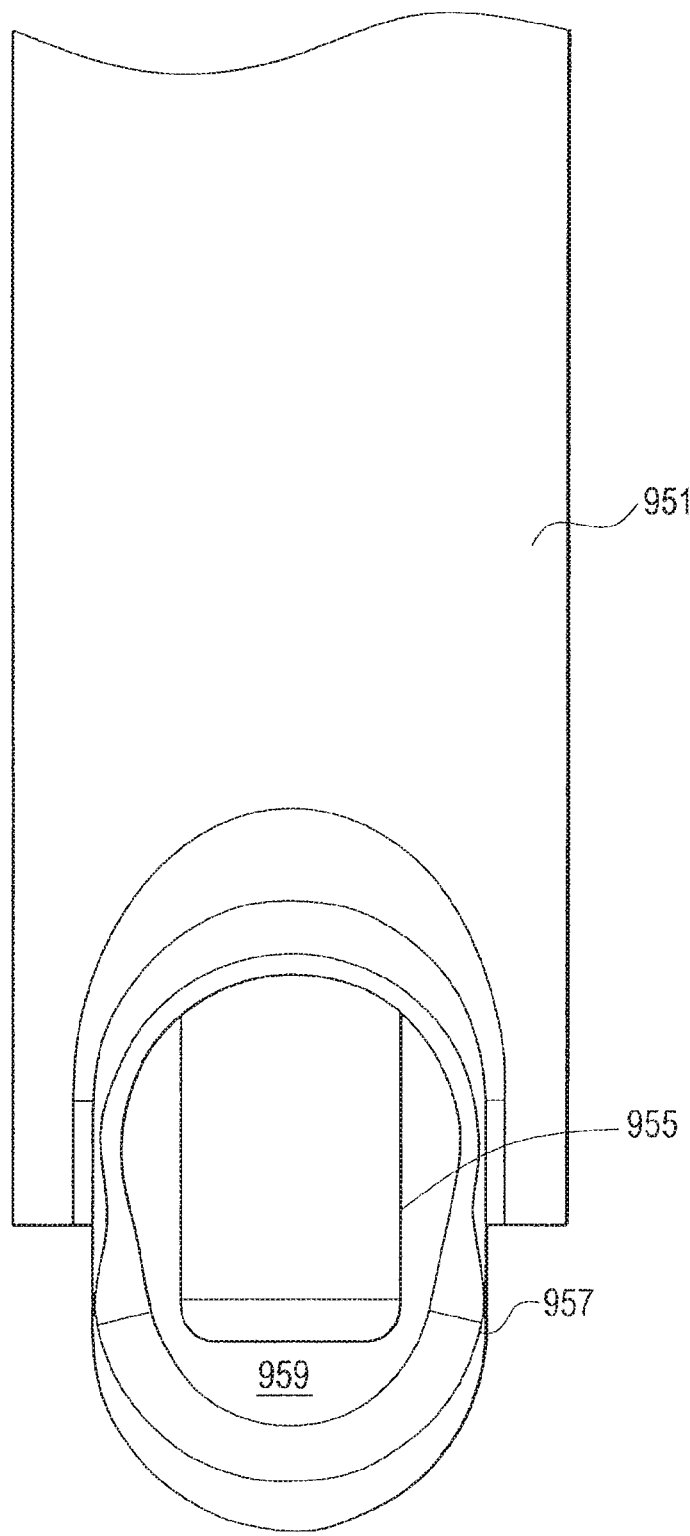
Figure 9H:
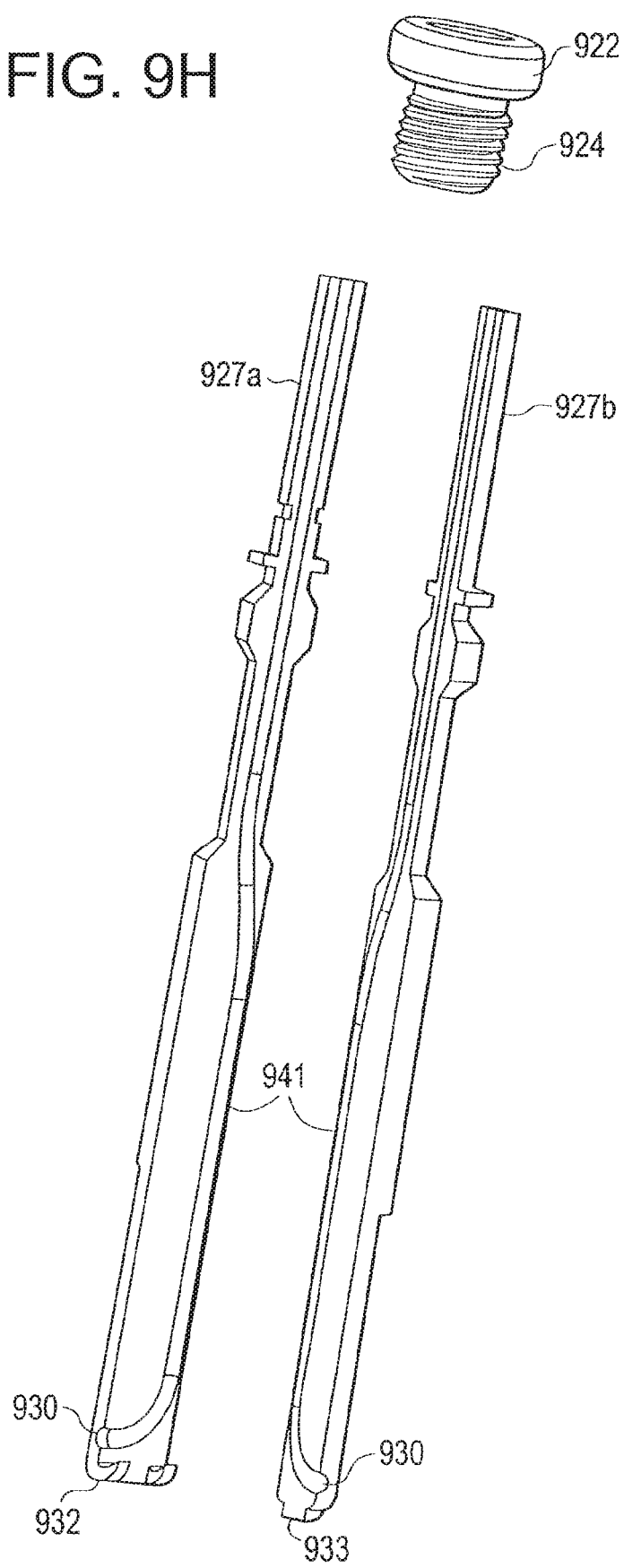

The second device 950, shown in FIGS. 9d-g, is configured to include a shaft 951 disposed between a distal end 914 and a proximal end 912. In some embodiments, the shaft can be configured to have a unitary structure as opposed to a two-part structure of the device 900. The device 950 further includes a nut or any other locking mechanism 947 disposed substantially adjacent the proximal end of the device 950. The nut 947 further includes threading 948 configured to interact with the threading disposed at a proximal end of the screw extender on its interior wall. The nut is configured to be coupled to the shaft 951 at the proximal end 912. The device 950 further includes a wire-pinching or a wire-holding mechanism 957 disposed at the distal end 914 of the device 950 and that is configured to pinch or secure the wire once the wire is advanced from the first screw extender (containing device 900) through patient's muscle tissue. The wire-pinching mechanism 957 includes an opening 959. Upon advancement of the wire from the first screw extender and through the muscle tissue, the opening 959 is configured to receive the wire, which is then secured by the wire-pinching mechanism 957. The wire-pinching mechanism 957 is controlled by a knob or any other locking feature 945 disposed at the proximal end 912 of the device 950. The knob 945 is configured to be coupled to a shaft 955 that is inserted through the interior of the shaft 951 of the device 950. The shaft 955 is configured to have a smaller diameter than the diameter of the shaft 951. The shaft 955 further includes a threading 913 that is configured to mate with a threading disposed on an interior surface of shaft 951 (not shown). Upon such mating, the surgeon can begin rotating the knob 945, thereby advancing the shaft 955 through the opening 959, as illustrated in FIGS. 9f-g. Upon advancement of the shaft 955, the shaft 955 is configured to decrease available space within opening 959, thereby pinning the wire to one of the walls of the opening 959.

Figure 12:
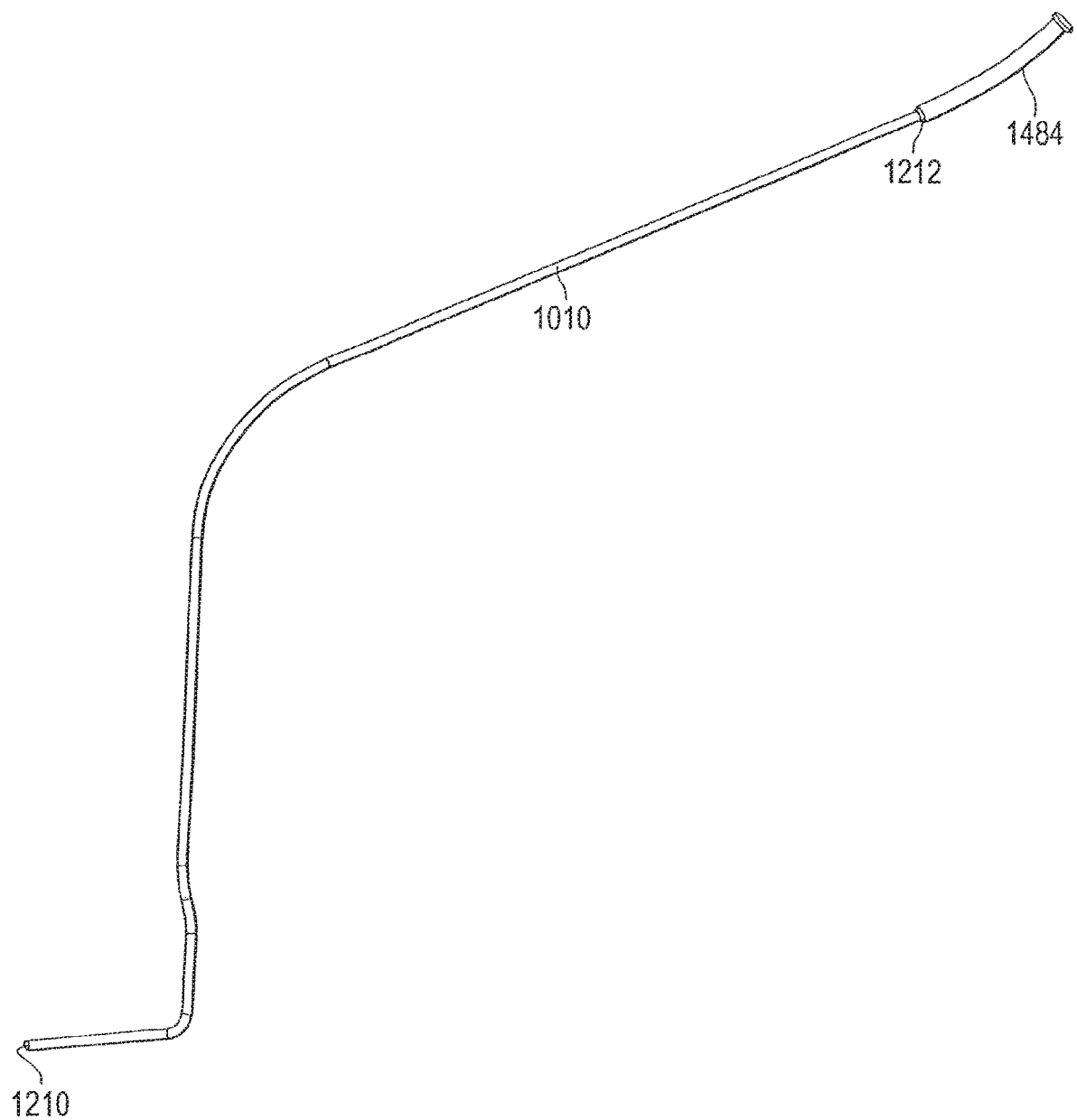
FIG. 12 illustrates an exemplary wire, according to some embodiments of the present invention.

FIG. 12 illustrates an exemplary wire 1010, according to some embodiments of the present invention. The wire 1010 includes a distal tip 1210 that is configured to lead the wire through the first extender (and the device 900), through the patient's muscle tissue, and into the second extender (and the device 950). The wire 1010 also includes a proximal end 1212 to which a rod 1984 is attached. The rod 1984 contains a hole where the wire interlocks with the rod. This attachment can have a thread or a mechanical attachment mechanism. The rod also contains a feature on the far proximal portion of the rod, (the end not attached to the wire). This prevents the rod from being pulled through the screw extender. As can be understood by one skilled in the art, any other ways of coupling the wire to the rod are possible, e.g., any mechanical coupling of the wire and the rod are possible. In some embodiments, such coupling can be configured to allow for a quick release of the rod from the wire.

Figure 11A:
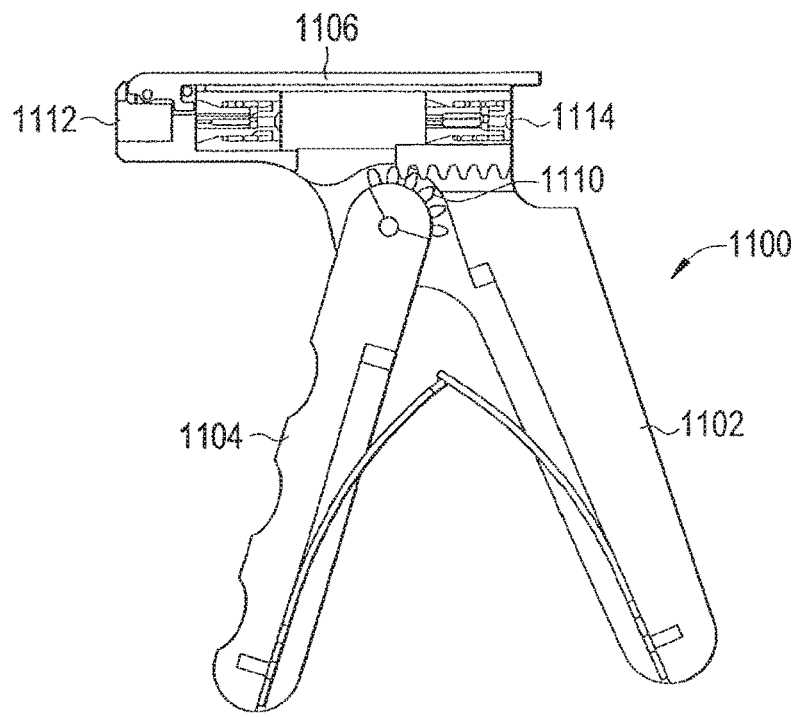
FIGS. 11*a*-*b* illustrate an exemplary wire advancement mechanism, according to some embodiments of the present invention.
Figure 11B:
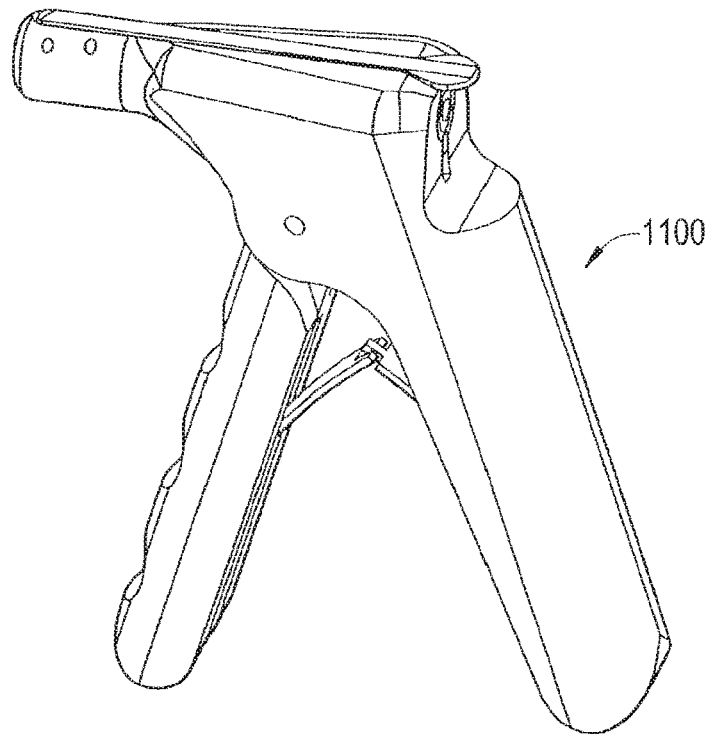

In some embodiments, the wire 1010 can be configured to be advanced using a wire-advancement device or a wire advancement gun 1100, as shown in FIGS. 11a-b. FIG. 11a illustrates a cross-sectional view of the gun 1100 and FIG. 11b illustrates a perspective view of the gun 1100. In some embodiments, the gun 1100 includes a fixed handle 1102, an actuating handle 1104, and a barrel 1106 coupled to the handles 1102 and 1104. The barrel 1106 is configured to include a loading opening 1114 disposed at a proximal end of the barrel 1106 and a discharge opening 1112 disposed at a distal end of the barrel 1106. The wire 1010 (not shown) is configured to be loaded into the loading opening 1114 and discharged through the discharge opening 1112 by advancing the wire through the barrel 1106. The actuating handle 1104 is configured to be spring-resistance-loaded with respect to the fixed handle 1102, i.e., upon squeezing the actuating handle 1104 toward the fixed handle 1102, a ratcheting mechanism 1110 is configured to cause advancement of the wire 1010 through the barrel 1106 and then forcing the handle 1104 to spring back to its original position. In some embodiments, the surgeon, upon squeezing the handle 1104 multiple times, can advance the wire 1010 to any desired length. As can be understood by one skilled in the art, other methods and/or instruments of advancing the wire 1010 are possible and are not limited to the wire advancement device 1100 shown in FIGS. 11a-b.

FIGS. 10a-e illustrate an exemplary procedure for advancement of wire 1010 through screw extenders 1002 and 1004. As stated above, prior to advancement of wire 1010, a surgeon (or any other medical professional) makes an incision above the location of implantation of a spinal stabilization system (represented by a screws, wires, rods, or any other devices), where the incision is configured to correspond to the location where a first combination of a screw and a screw extender (i.e., screw 1006, screw extender 1002) are to be implanted into patient's vertebrae. The surgeon can make another incision corresponding to the location where a second combination of a screw and a screw extender (i.e., screw 1008, screw extender 1004) are to be implanted into patient's vertebrae. Then, the surgeon implants first and second combination. The screw extenders are subsequently aligned so that the channels disposed on their housings (i.e., channels 1012 disposed on the first screw extender 1002 and channels 1014 disposed on the second screw extender 1004; wherein channels can be partially open or fully open, as discussed above) are facing each other. Along with the channels, the passageways in the heads of the screws (i.e., passageway 1016 in the head of the screw 1006 and passageway 1018 in the head of the screw 1008) are also aligned, thus creating a virtual corridor between the passageways and the channels.

Figure 10A:
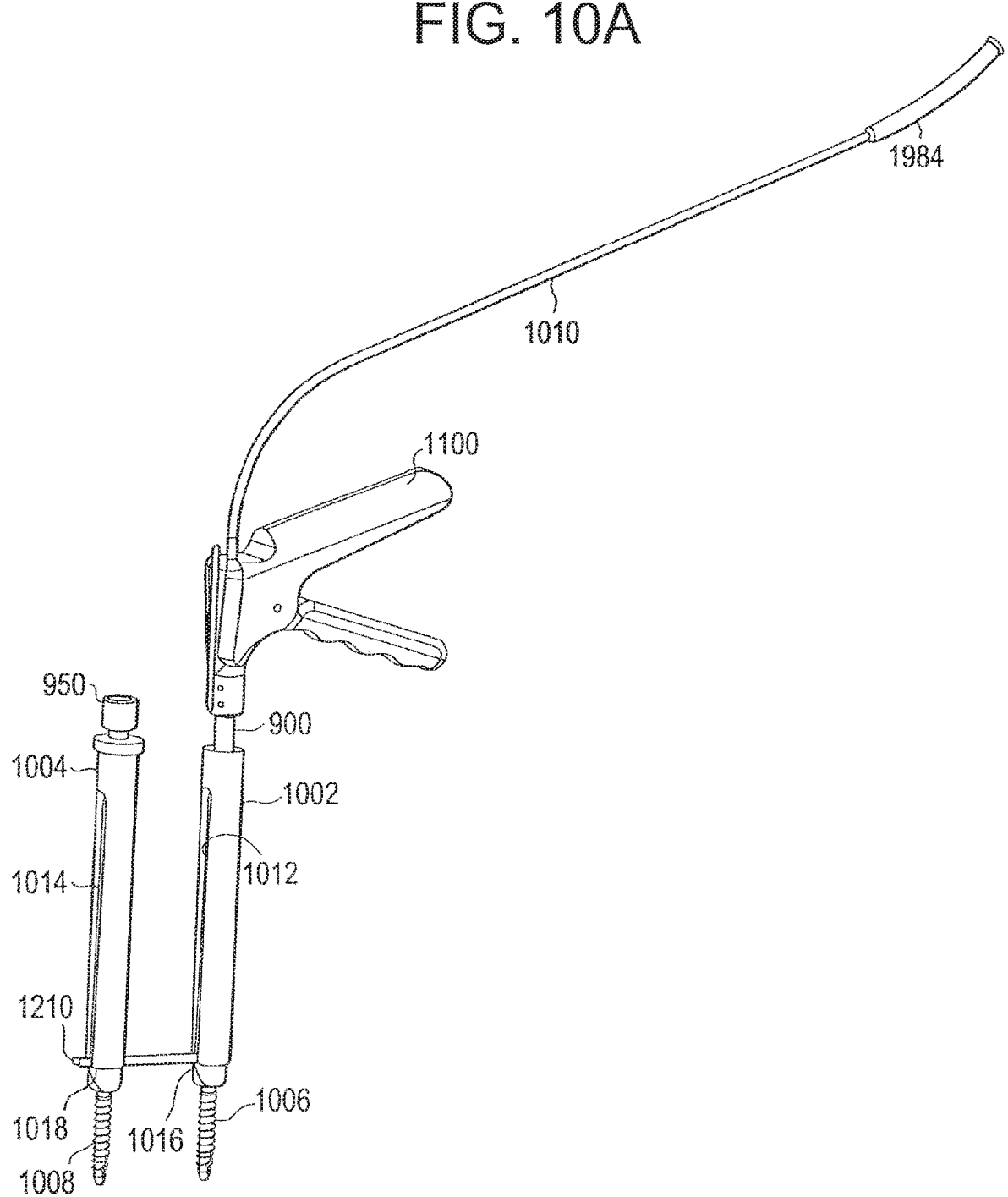
FIGS. 10*a*-*h* illustrate an exemplary step-by-step procedure for percutaneously inserting a wire using a screw extender system, according to some embodiments of the present invention.

Subsequent to the alignment procedure, devices 900 and 950 are inserted into the interior portions of the housings of screw extenders 1002 and 1004, respectively. The devices 900 and 950 are then secured using appropriate knobs and threaded portions, as discussed in connection with FIGS. 9a-h. During insertion, the surgeon also aligns devices 900 and 950 so that the opening 930 on the device 900 is aligned with the opening 959 of the device 950 (not shown in FIG. 10a). The wire advancement device 1100 is loaded with the wire 1010 and is then coupled to the device 900, as shown in FIG. 10a. Upon coupling of the device 1100, the opening 1112 in the barrel of the device 1100 is aligned with the opening on the device 900 disposed at a proximal end of the device 900 so that the wire 1010 can safely pass through the interior channel 941 of the device 900 (not shown in FIG. 10a).

As the surgeon advances the wire 1010 using the device 1100, the wire 1010 begins to travel along the channel 941 of the device 900 and is configured to advance out of the opening 930 of the device 900. Then, the wire 1010 begins to travel through the muscle tissue toward the second screw extender 1004. In some embodiments, the wire 1010 can be configured to have a sharpened tip in order to pierce through the muscle tissue. As the wire 1010 is advanced further, it reaches and is passed through the opening 959 of the device 950 disposed within the second screw extender 1004. As the sufficient length of wire has passed through the opening 959, the surgeon actuates the pinching mechanism of the device 950, which compresses the wire 1010 in the device 950. The surgeon can observe wire advancement using X-ray.

Figure 10B:
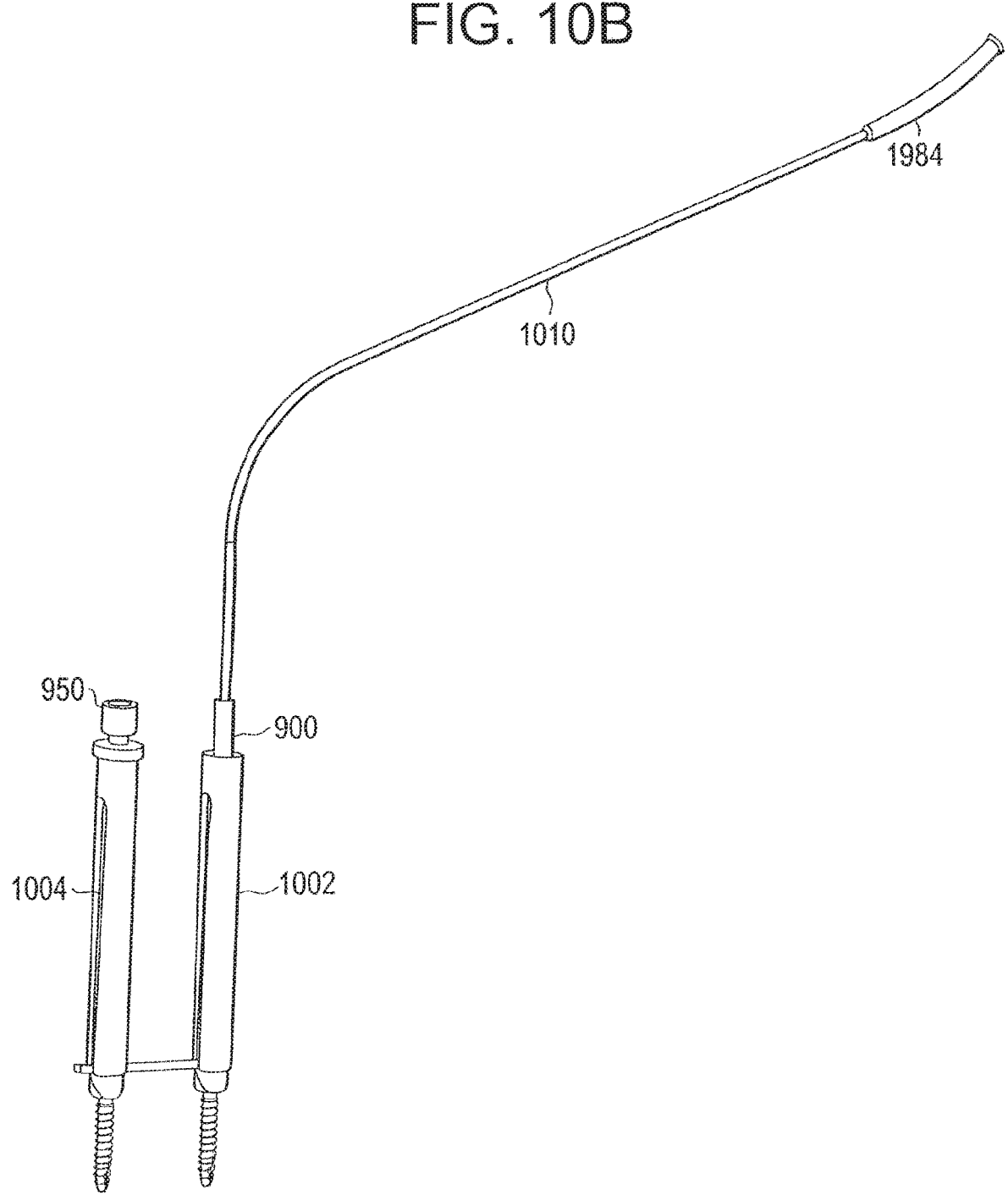
Figure 10C:
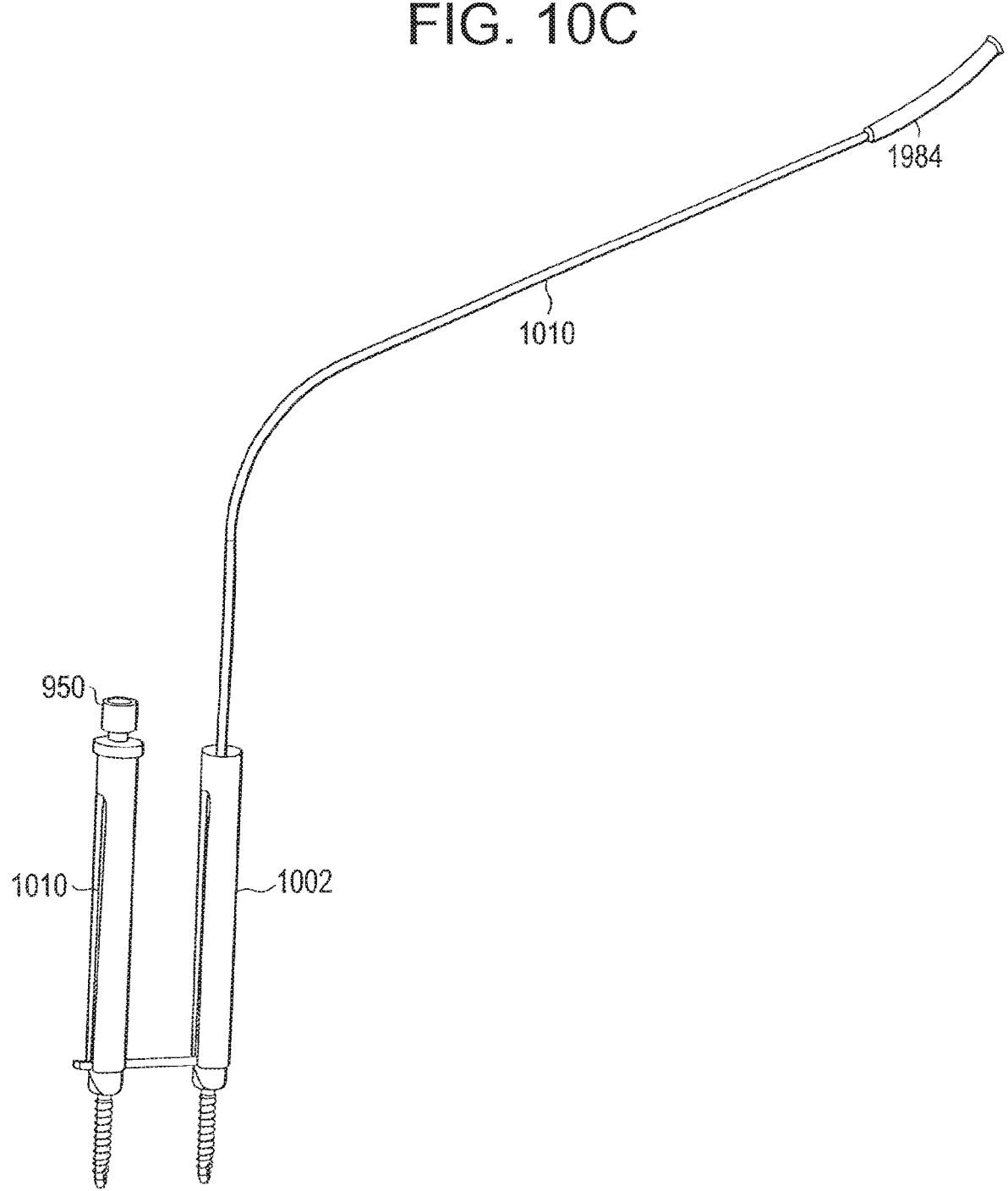
Figure 10D:
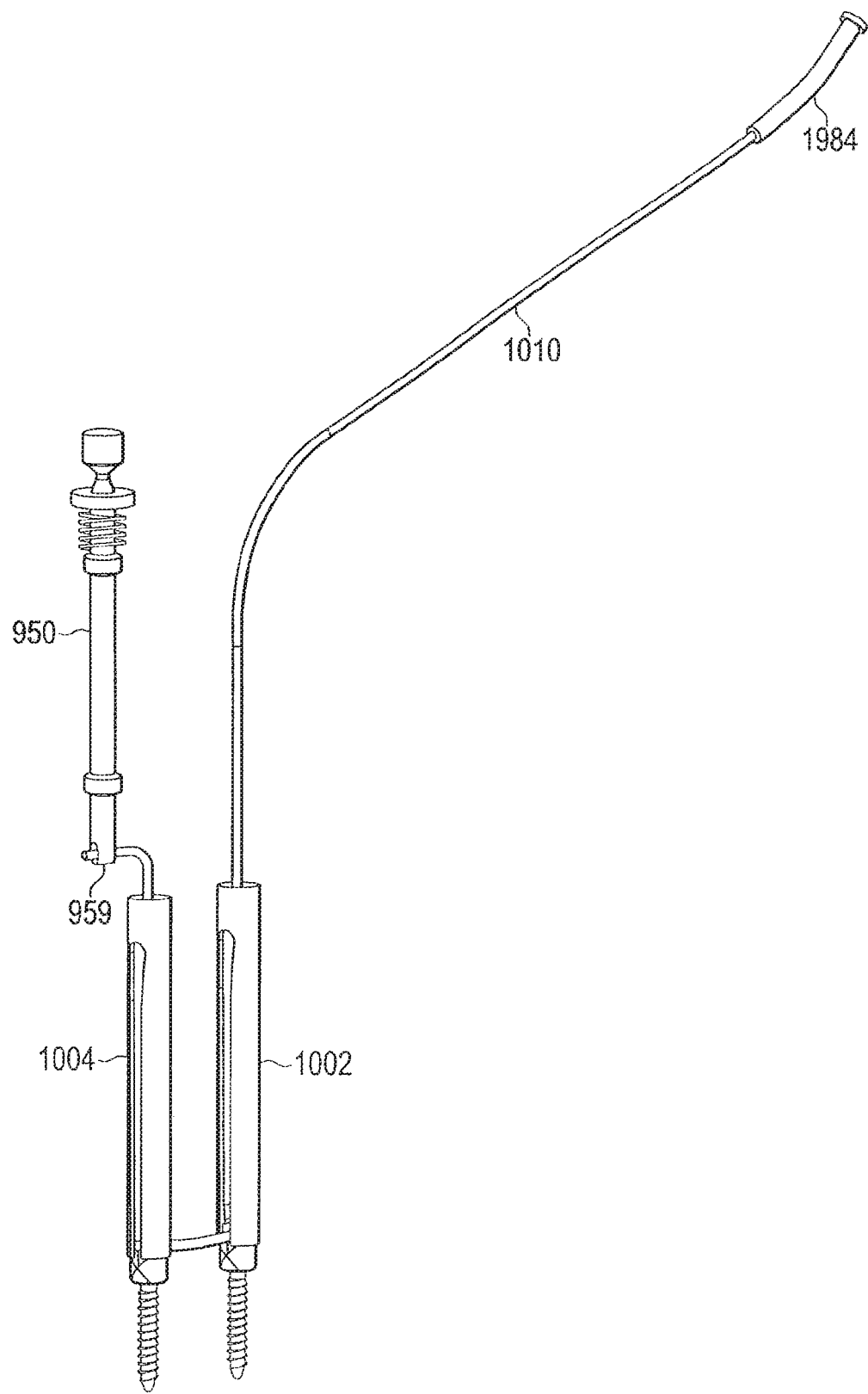
Figure 10E:
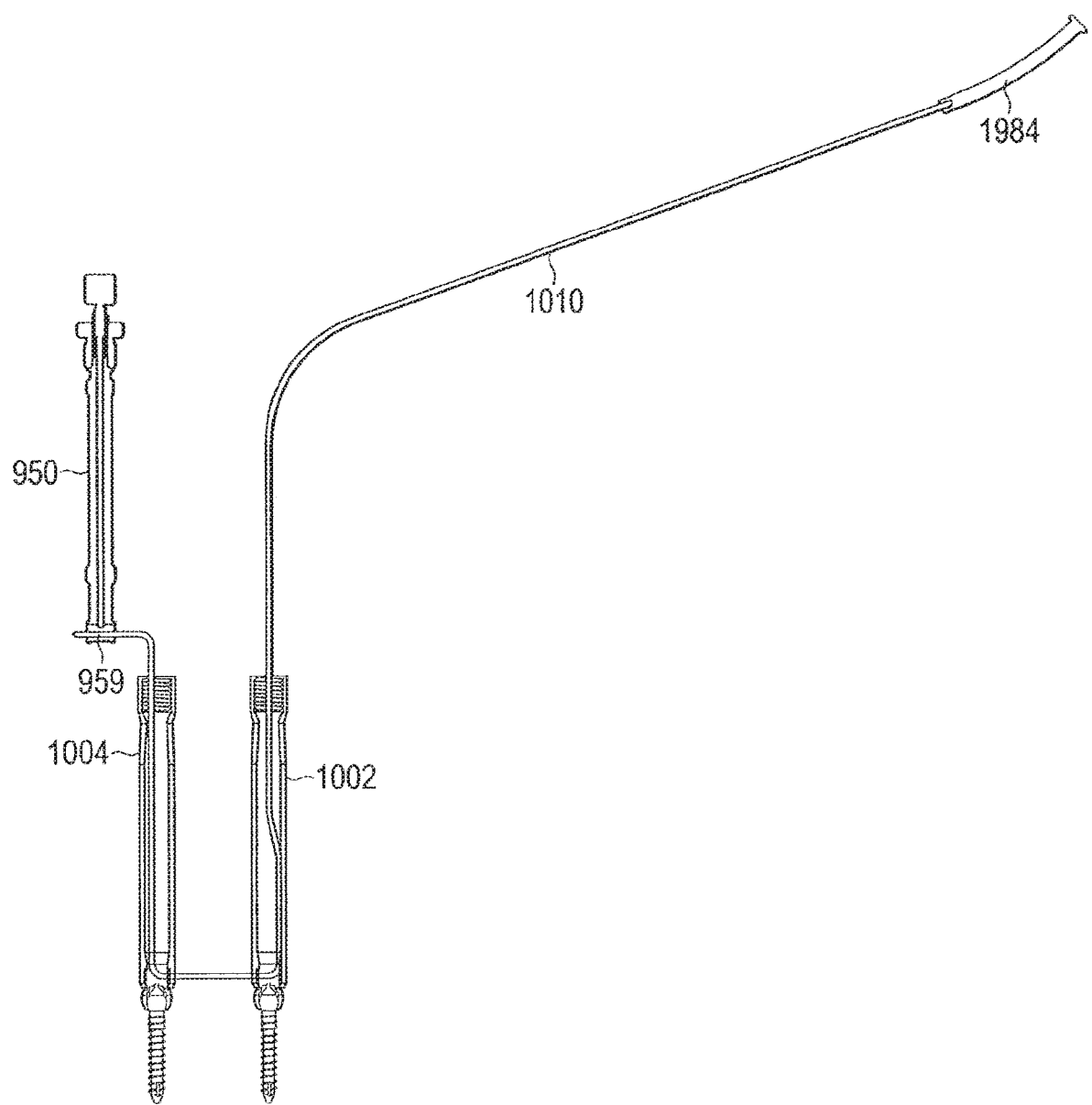

Once the wire 1010 is secured in the device 950, the surgeon removes the wire-advancement device 1100, as illustrated in FIG. 10b. In some embodiments, the device 1100 can be simply slid off the wire 1010. Thus, at this stage, the wire remains secured by the device 950 and both devices 900 and 950 are secured within their respective screw extenders 1002 and 1004. Then, the surgeon removes the nut 922 by unthreading it along the threads 924 (as shown in FIGS. 9a-b) and removes the portion 927b followed by removal portion 927a of the device 900 from the screw extender 1002, as shown in FIG. 10c. The device 950 still remains in the second screw extender 1004. Referring to FIGS. 10d-e, the surgeon removes the device 950 by unscrewing it from the housing of the extender 1004. The device 950 is removed while the wire is being held by the pinching mechanism 957. Upon removal of the device 950, the wire 1010 is configured to protract through the first extender 1002, through the muscle tissue of the patient disposed between extenders 1002 and 1004, and the second extender 1004 while being coupled to the removed device 950.

Figure 10F:
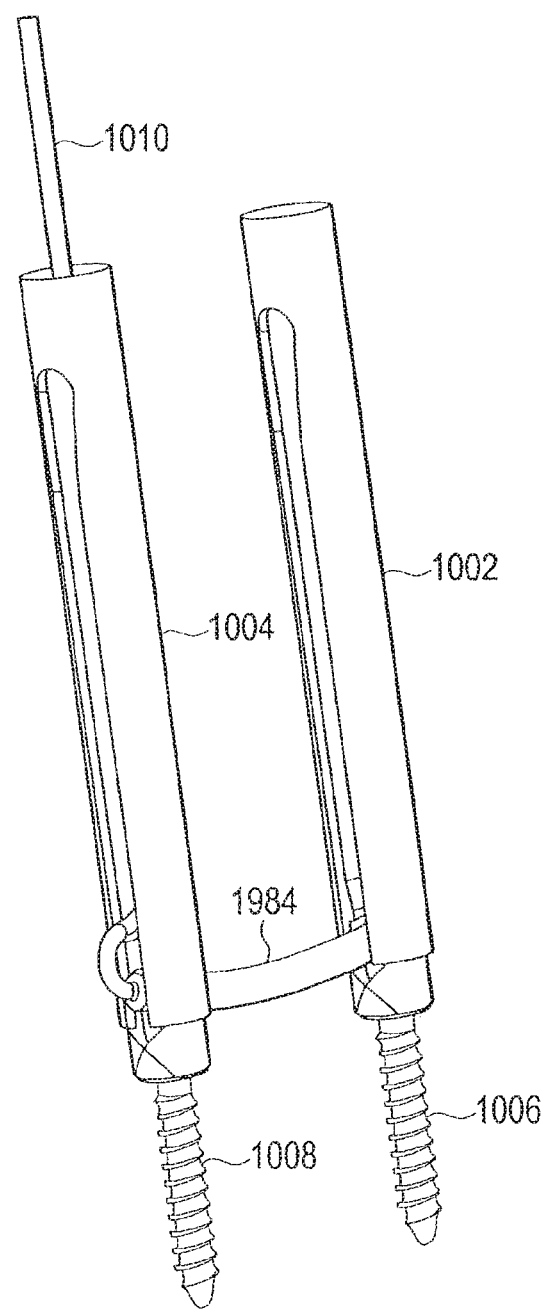
Figure 10G:
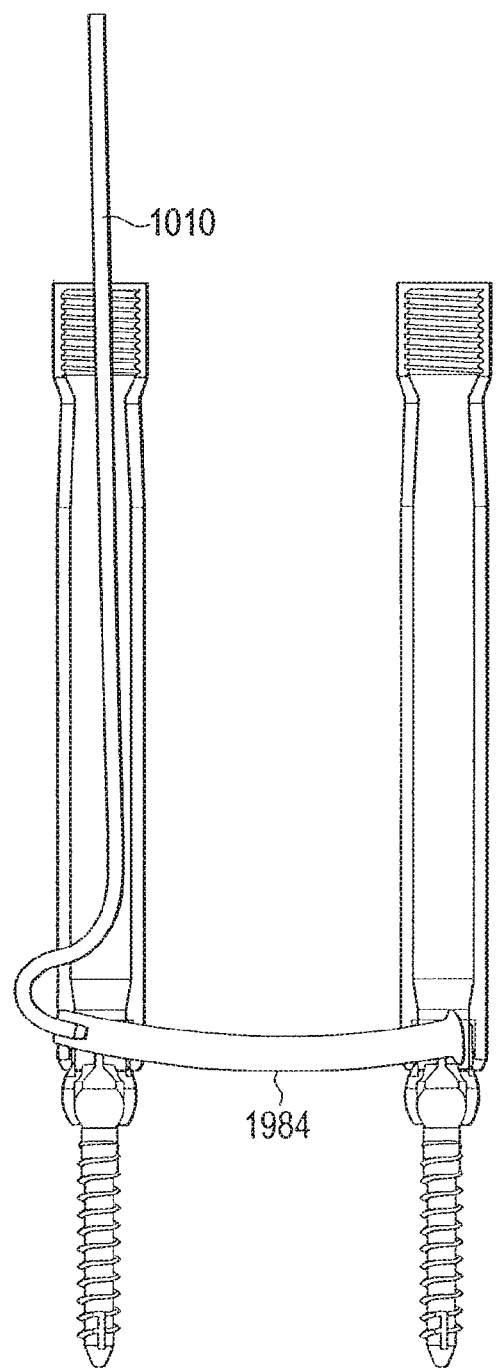
Figure 10H:
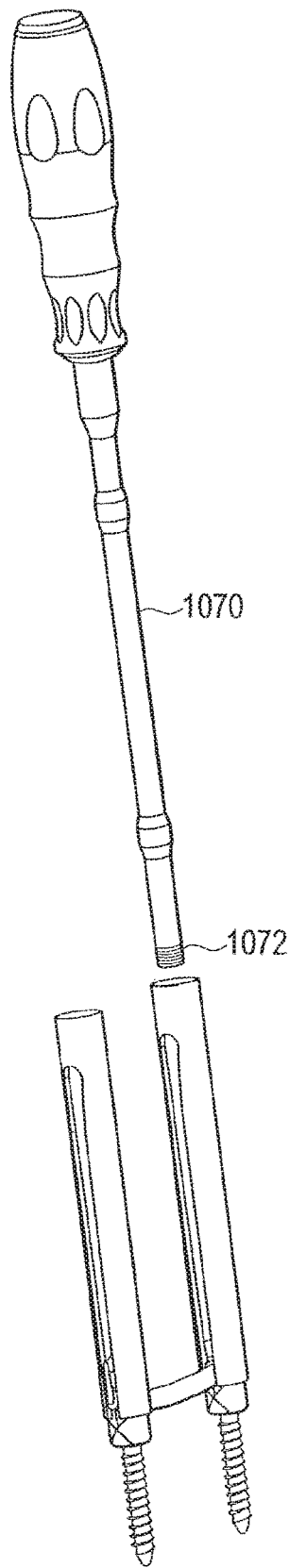

In some embodiments, the rod 1984 (shown in FIG. 104) can be configured to be advanced along with the wire 1010 (or follow the wire through the screw extender 1002 and then along the virtual corridor in the muscle tissue created by the wire) for installation between two screws. FIGS. 10f-g illustrate advancement of the rod 1984 along the wire 1010, where FIG. 10f is a perspective view of the installed rod and FIG. 10g is a cross-sectional view. The rod 1984 can be configured to include an advancing tip 1952 disposed at a distal end of the rod 1050 and a proximal end 1954 of the rod 1984 that in some embodiments can be configured to be coupled to a rod inserter (discussed below in detail). The rod's advancing tip 1952 is configured to travel from the first screw extender 1002 along the passageway created by the wire 1010 in the muscle tissue of the patient to reach the second screw extender 1004. Once the rod 1984 is disposed in the passageways of screws 1006 and 1008 that are coupled to the respective screw extenders 1002 and 1004, the rod 1984 can be secured using setscrews 1072 that can be advanced through the interior of the screw extenders using a setscrew setting device 1070, as shown in FIG. 10h. The setscrew setting device 1070 can be configured to carry a setscrew at its distal tip and then upon insertion into the passageway in the head of the implanted screw begin rotating the setscrew (having appropriate threads) along the threads disposed on the interior of the passageway of the implanted screw. Upon setting the setscrew, the device 1070 can be released from the setscrew 1072 and removed from the interior of the screw extender. Upon removal of the setscrew setting device 1070, the screw extenders can be removed using the remover tools discussed above.

During installation of the spinal stabilization system of the present invention, the surgeon may wish to compress or distract the screw extenders that are coupled to the screws, which are implanted into patient's bony matter. FIGS. 13a-13f and 14a-e illustrate various embodiments of compressor/distractor tools. In some embodiments, the compression motion can be characterized by pushing the distal ends of the screw extenders closer to each other and by pulling the proximal ends of the screw extenders away from each other. The distraction motion can be characterized by pushing the proximal ends of the screw extenders closer to each other and by pulling the distal ends of the screw extenders away from each other (i.e., a reverse of the compression motion).

FIGS. 13a-f illustrate an exemplary compression/distractor tool 1300, according to some embodiments of the present invention. The tool 1300 includes a housing 1310, compression/distraction arms 1304 (a, b), ratchet handle 1302, fulcrum 1312, and a release handle 1320. The arms 1304 are configured to be coupled to the housing 1310 using respective shoulders 1315 (a, b). The arms 1304 are configured to substantially perpendicularly protrude away from the housing 1310 in the same direction. The ratchet handle 1302 is configured to be disposed on the side of the housing 1310 that is opposite to the side where the arms 1304 are disposed. The ratchet handle 1302 is configured to cause movement of the arms 1304 to and from each other. The ratchet handle 1302 can be configured to use any conventional ratcheting mechanism for activating such translational movement of the arms 1304. In some embodiments, the ratchet handle 1302 can be configured to have a gripping portion to allow for better gripping of the handle 1302. The arms 1304 further include respective inner cavities 1308 (a, b) that are configured to accommodate placement of the screw extenders between the arms 1304 and the fulcrum 1312. The fulcrum 1312 can be configured to have a rhombus shape (as can be understood by one skilled in the art, other shapes are possible) that creates pivot points for the screw extenders being secured between the arms 1304 and the fulcrum 1312. The pivot points are configured to allow tilting of the of the screw extenders either during compression or distraction motions. In some embodiments, the fulcrum 1312 can be configured to be rotated to allow for variable angle distraction/compression of extenders. In some embodiments, the arms 1304 can be configured to include respective openings 1306 (a, b) configured to accommodate insertion of pins 1353(a, b), which serve for attachment of an anti-torque device 1370 (shown in FIG. 130.

Figure 13A:
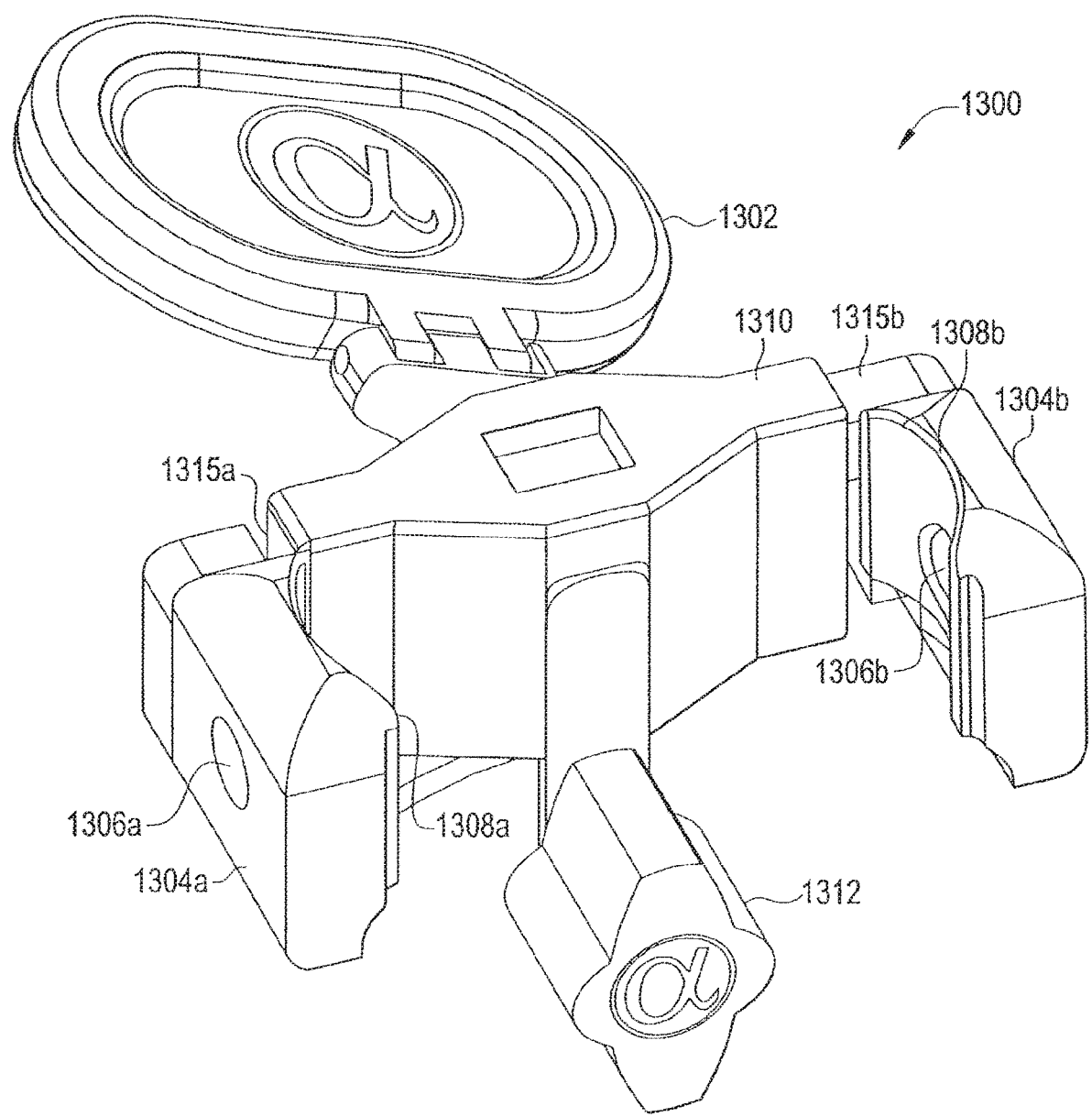
FIGS. 13*a*-*f* illustrate an exemplary compressor/distractor tool, according to some embodiments of the present invention.
Figure 13B:
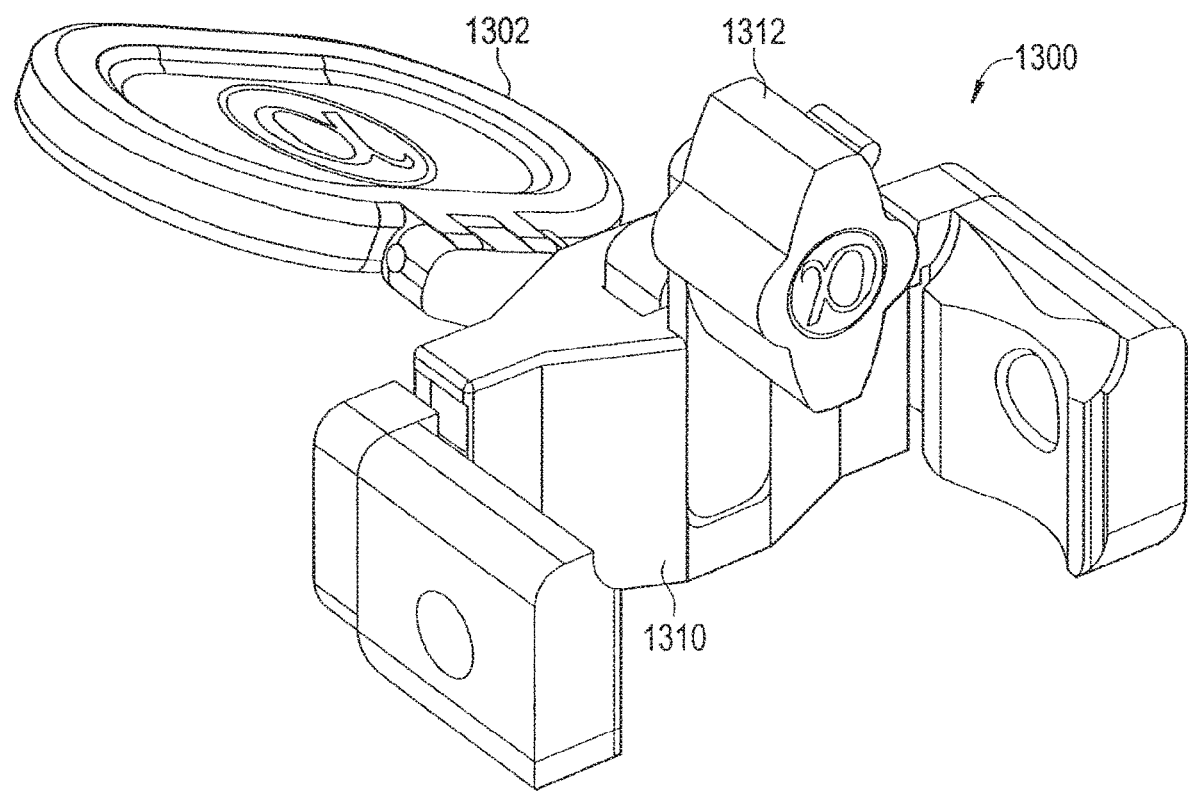
Figure 13C:
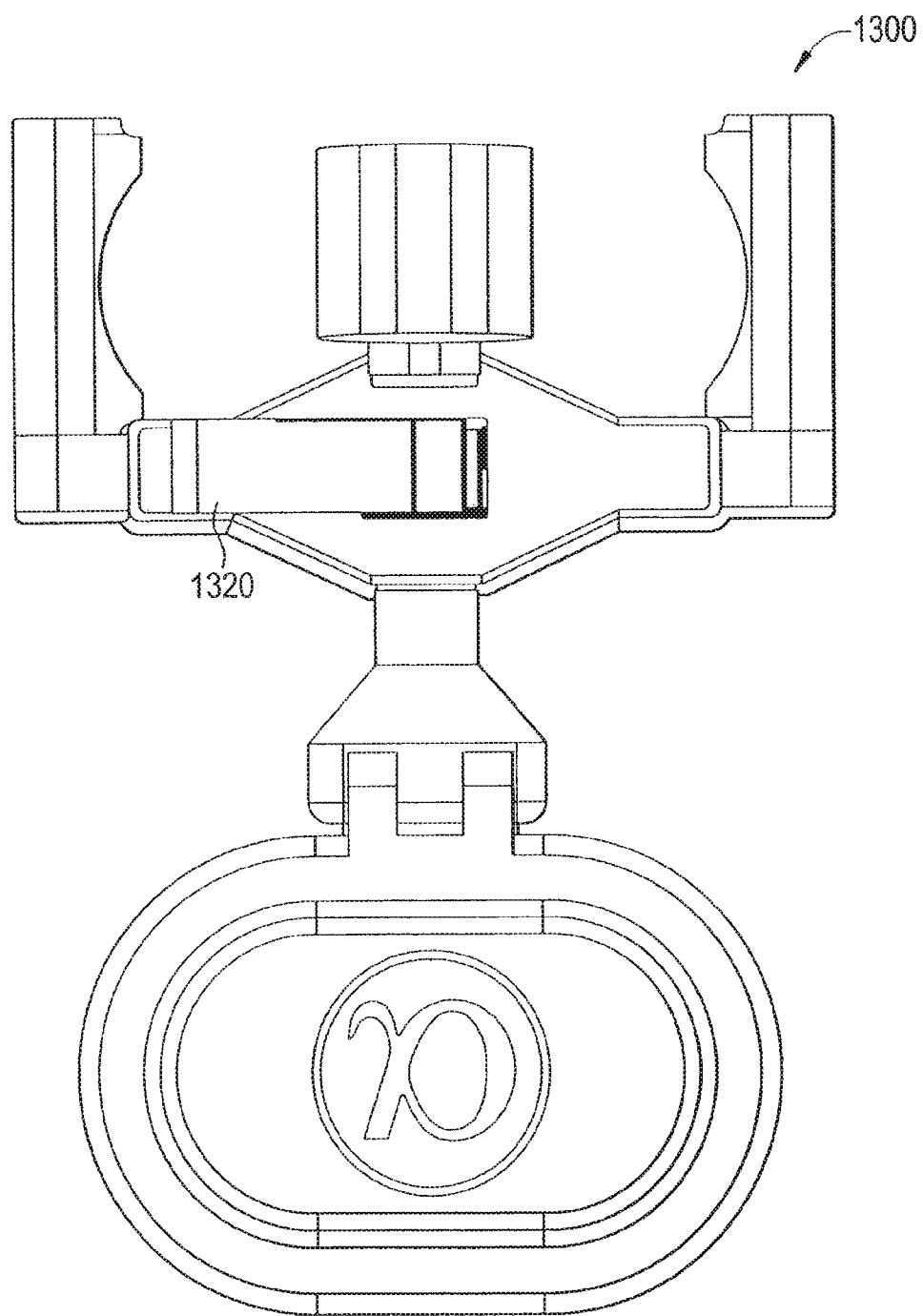
Figure 13D:
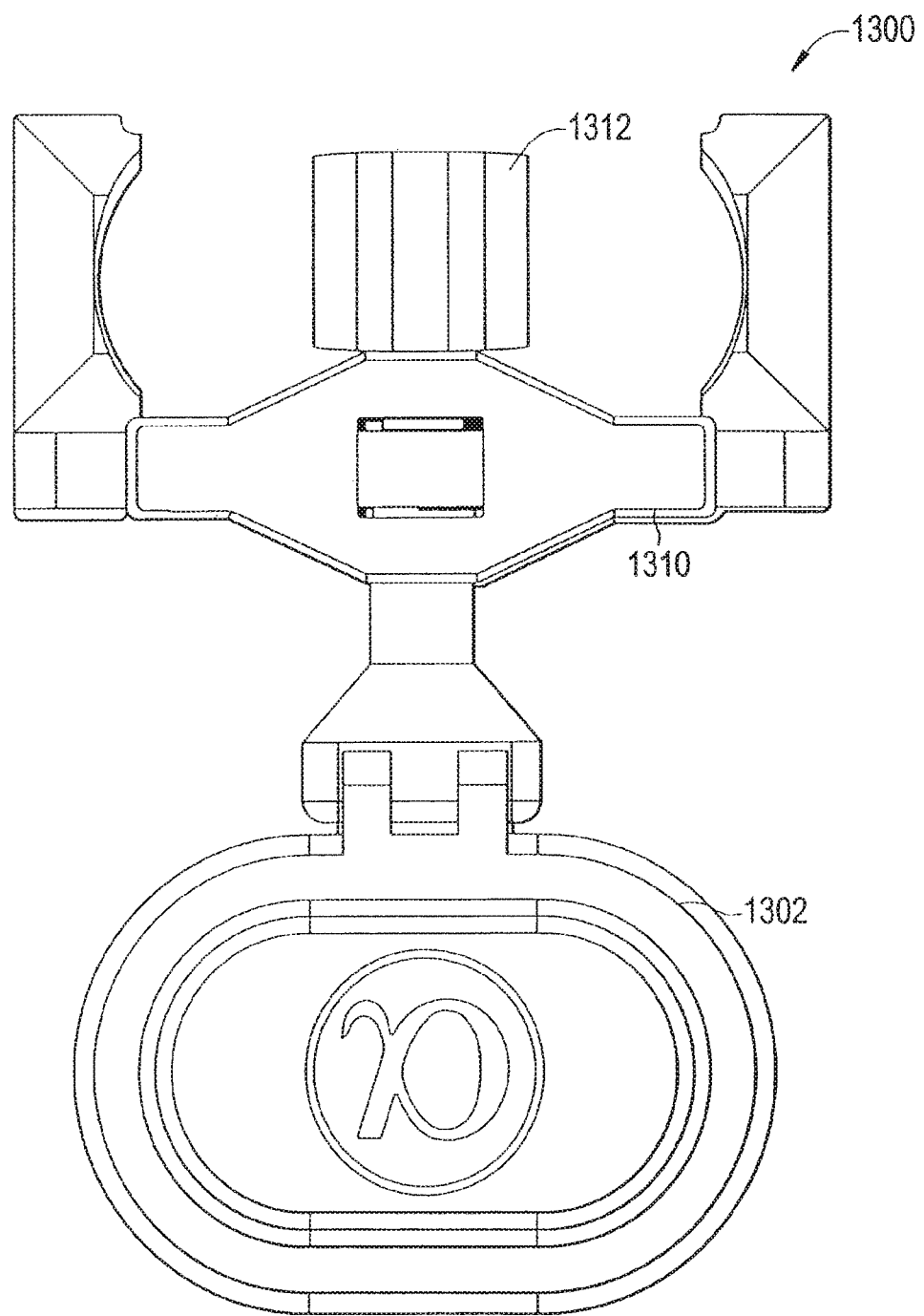
Figure 13E:
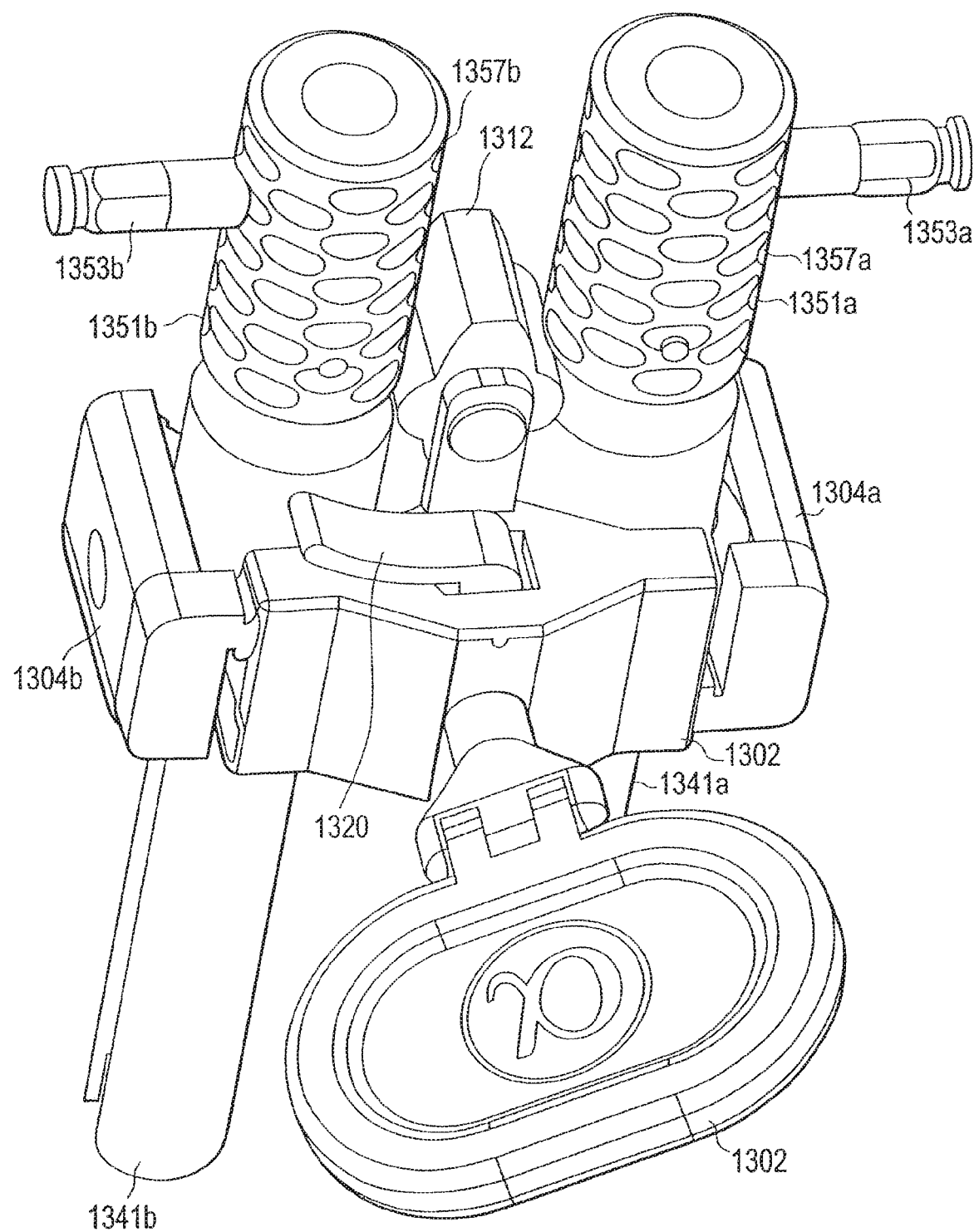
Figure 13F:
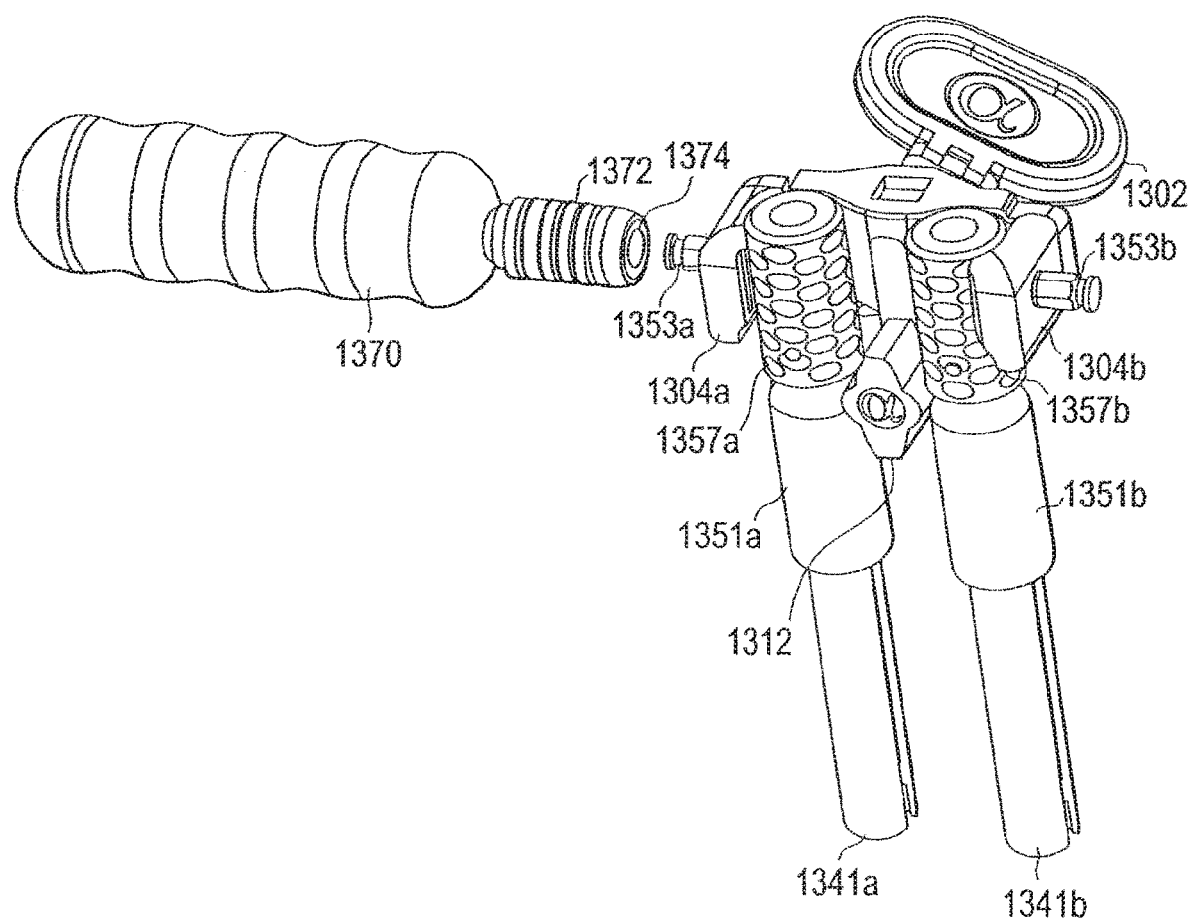

In order to prevent slippage of the screw extenders, an anti-splay device 1351 (shown in FIG. 15) can be placed over each of the proximal ends of the extender housings prior to performing any distraction/compression. In some embodiments, the anti-splay device can also be anti-torque device. As can be understood by one skilled in the art, the terms "anti-splay" and "anti-torque" are used interchangeably in this description and an anti-splaying device can be configured to have anti-torque capabilities and vise versa. The anti-splay device 1351 includes a body portion 1504 coupled to an anti-splay portion 1357. The body portion 1504 is configured to be coupled to the housing of the screw extender using any known methods (e.g., hook-and-slide (shown in FIG. 15), snap-fit, or any other ways). The anti-splay portion 1357 is configured to interact with the arms of the 1304 or any other parts (e.g., fulcrum 1312) of the device 1300, as shown in FIGS. 13e-f. Upon coupling, the anti-splay device 1351 and the screw extender housing create a unitary structure that can withstand the forces being applied to it during compression/distraction motions. The anti-splay portions 1357 can be configured to have mesh-like surface that is configured to create friction between components of the device 1300 and the anti-splay devices 1351.

Referring to FIG. 13e, the screw extenders 1341 (a, b) are configured to be arranged in the device 1300 for the purposes of compression, i.e., pulling of the proximal ends of the screw extenders apart from each other. For compressing the screw extenders, the anti-splay devices 1351 (a, b) are coupled to proximal ends of the respective screw extenders 1341(a, b). The device 1300 is configured to be arranged so that the fulcrum 1312 is disposed above the arms 1304 (a, b) in relation to the proximal ends of the screw extenders. The screw extenders 1341 are configured to be arranged between the respective arms 1304 and the fulcrum 1312, as shown in FIG. 13e. Once the screw extenders 1341 along with anti-splay device 1351 are secured between the respective arms 1304 and the fulcrum 1312, the handle 1302 is further rotated to tilt the screw extenders 1341 about side edges of the fulcrum 1312, thereby causing the distal ends of the extenders 1341 to be pushed together, whereas the proximal ends of the extenders 1341 are pulled apart. In some embodiments, an anti-torque device 1370 can be coupled to the pins 1353 to prevent slippage or any other movement of the extenders while performing compression. To increase the angle of inclination of the extenders 1341, the surgeon can continue rotating the handle 1302. To release the handle 1302 after compression, the handle 1320 is depressed.

FIG. 13f illustrates a reverse motion of distraction. To perform this motion, the device 1300 is turned upside down in relation to the motion of compression situation, whereby the fulcrum 1312 is arranged below the arms 1304, as shown in FIG. 13f. During distraction, the arms 1304 are configured to interact with the anti-splay portions 1357 of the anti-splay devices 1351. By rotating the handle 1302, the device 1300 is configured to push the proximal ends of the extenders closer together while pulling the distal ends of the extenders apart. The anti-torque device 1370 can also be attached to the pins 1353 to prevent slippage of the device.

In some embodiments, the arms 1304 can be "powered" by a rack and pinion or a mechanical link system. In some embodiments, the anti-splay device 1351 further prevents the extenders from splaying, bending, or undergoing flex during activities such as distraction, compression, torsion, and axial loads common in manipulating vertebra during spine surgery.

Figure 14B:
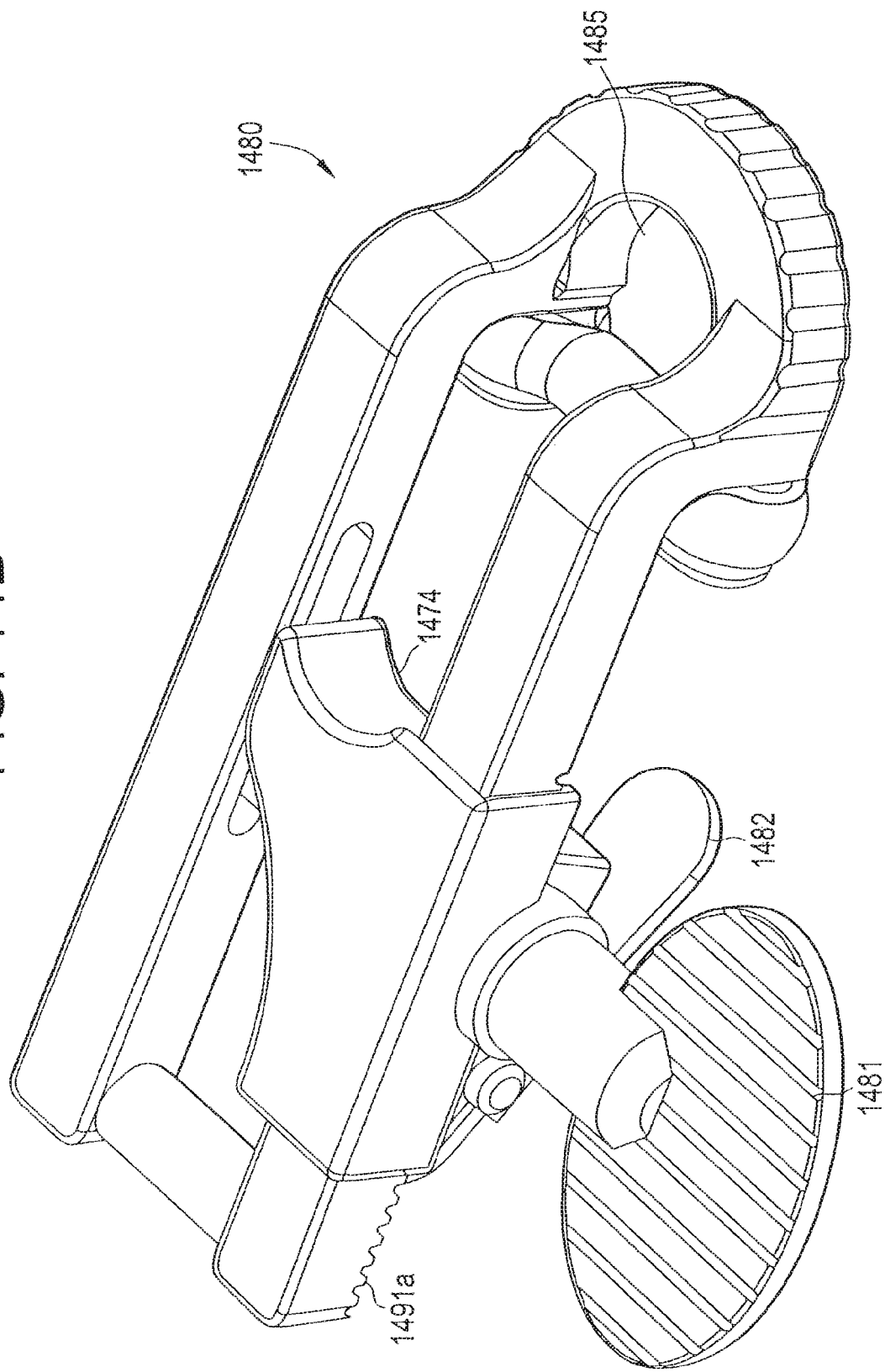
Figure 14C:
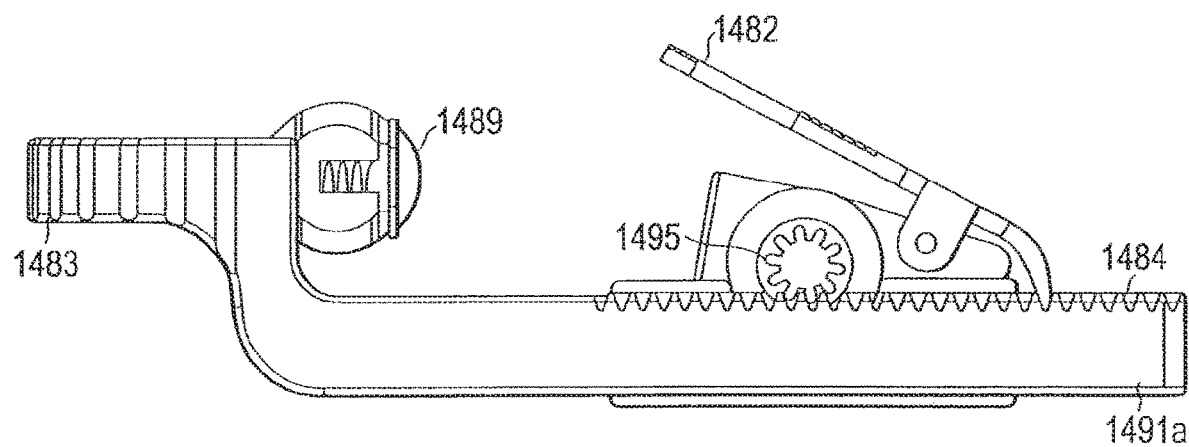

FIGS. 14a-e illustrate another exemplary compressor/distractor device 1480, according to some embodiments of the present invention. The device 1480 includes a housing 1482 that includes an elongated opening between two rails 1491 (a, b) running in parallel to each. The rails 1491 are configured to be connected at one end using an elevated rounded section 1483 and at the other end using a connection rod 1493. The device 1480 further includes a crank-and-ratchet mechanism 1474 that is configured to slide along the rails 1491 using a sliding mechanism 1490 disposed within each rail. The rail 1491a further includes a plurality of ratchet teeth 1484 with which a ratchet wheel 1495 of the mechanism 1474 is configured to interact, as shown in FIG. 14c. The mechanism 1474 further includes a handle 1481 that is coupled to the ratchet wheel 1495 and configured to cause rotation of the ratchet wheel 1495. The mechanism 1474 further includes a release handle 1482 that is configured to allow movement of the mechanism toward the elevated portion 1483 and prevent a reverse motion of the mechanism 1474. Upon depressing of the release handle 1482, the mechanism 1474 is released and is allowed movement (i.e., translation) away from the elevated portion 1483.

Figure 14D:
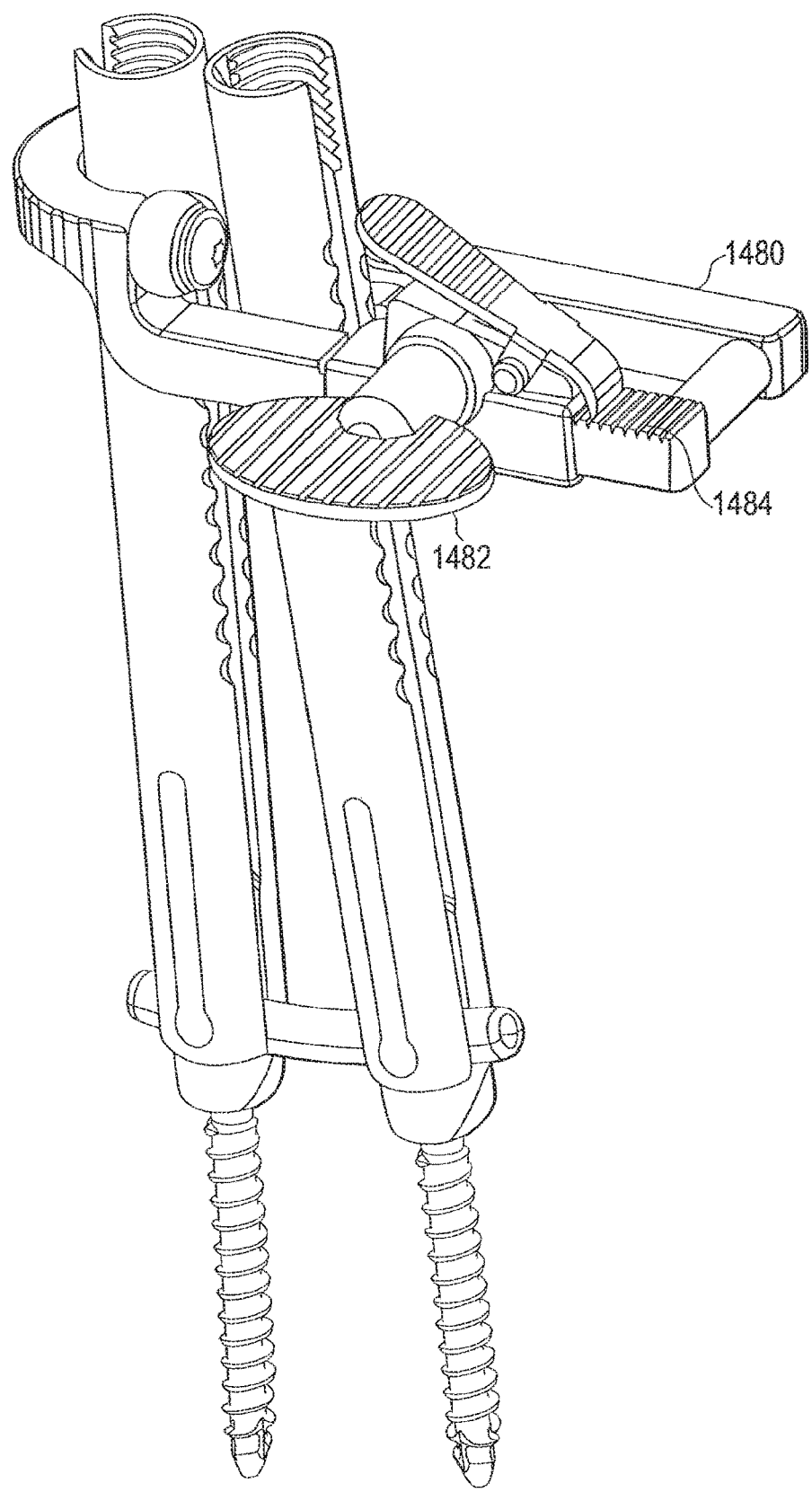
Figure 14E:
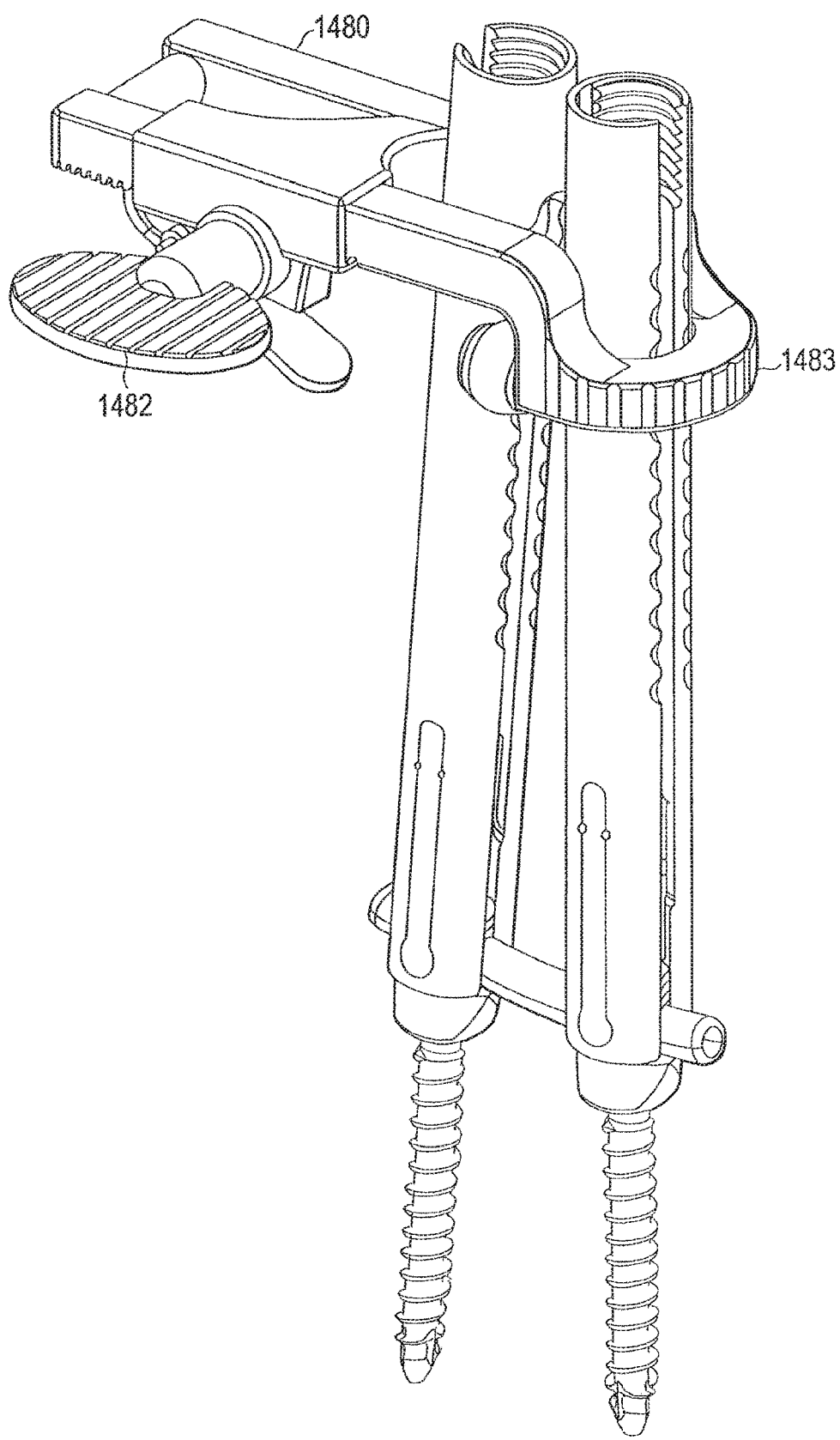
Figure 15:
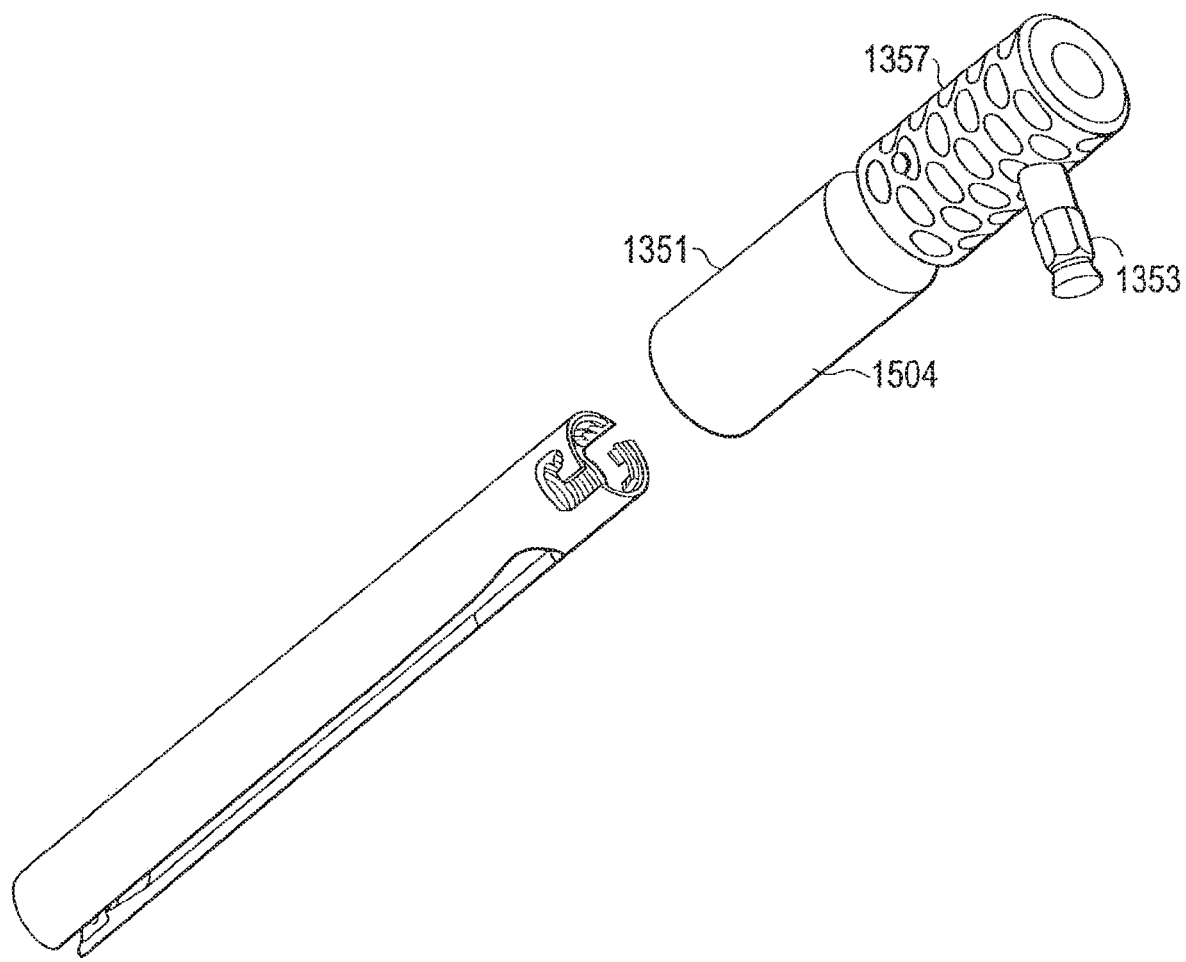
FIG. 15 illustrates an exemplary anti-splay device, according to some embodiments of the present invention.

The elevated portion 1483 of the device 1480 includes a spring-loaded locking feature 1488 having two spring-loaded locking pins 1489 (a, b) connected by a rod 1499. The rod 1499 and the elevated portion 1483 are configured to create an opening 1485 for insertion of a screw extender device, as shown in FIGS. 14d-e. In some embodiments, the screw extender device housing's features 391 shown in FIGS. 3a-b are configured to interact with the rod 1499 and prevent movement of the screw extender device inside the opening 1485. A second screw extender device can be inserted into an opening created between the rails 1491, the rod 1499 and the mechanism 1474. The second screw extender can be secured by translating mechanism 1474 along the rails 1491, until the second screw extender is secured between the rod 1499 and the mechanism 1474. In some embodiments, each of the openings 1485 and 1487 are configured to be sized to allow insertion and securing of the screw extenders. The spring-loaded features 1489 are configured to be locked in using a screwdriver or any other tool. Referring to FIG. 14d, a motion of distraction is shown, whereby the distal ends of the screw extenders are pulled apart. During this motion, the device 1480 is configured to be secured so that the ratchet teeth 1484 are facing upwards. FIG. 14e illustrates a motion of compression, whereby the proximal ends of the screw extenders are pulled apart. In this case, the ratchet teeth 1484 are configured to face downwards. The device shown in FIGS. 14a-e is advantageous as no anti-splay or anti-torque devices are required to maintain stability of the screw extenders during distraction/compression motions.

Figure 16A:
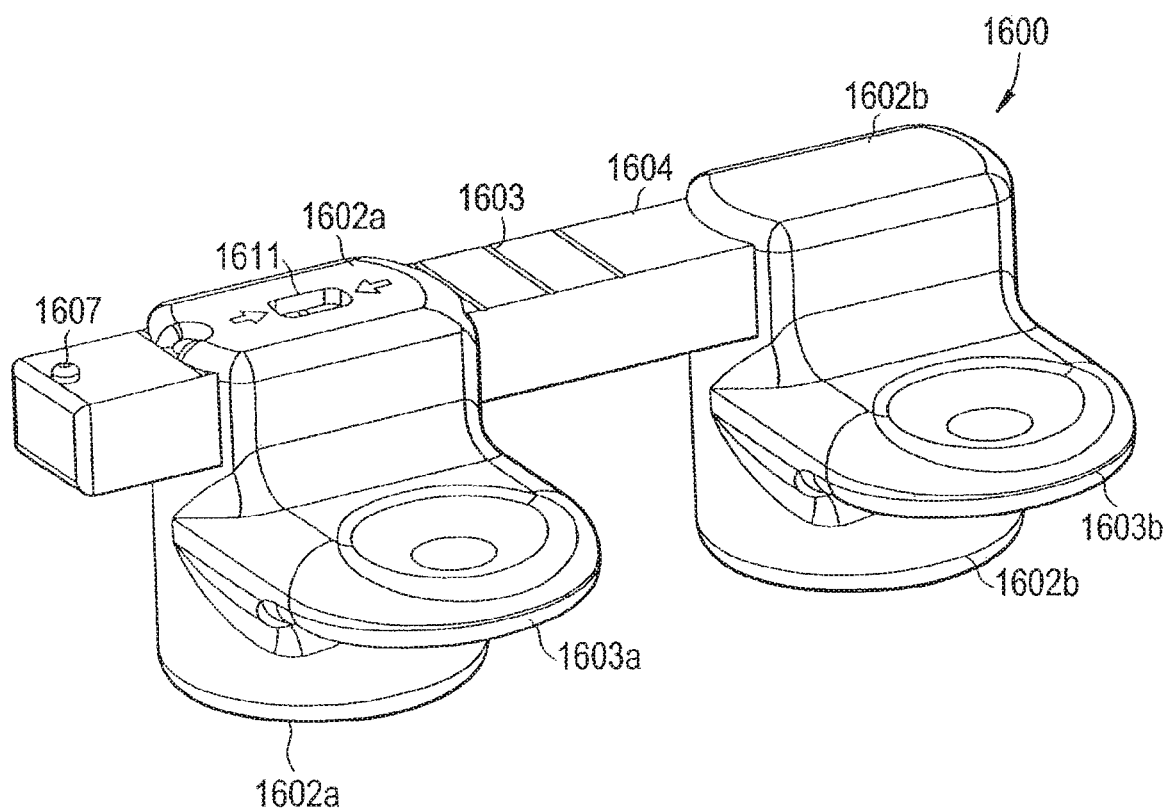
FIGS. 16*a*-*c* illustrate an exemplary caliper tool, according to some embodiments of the present invention.
Figure 16B:
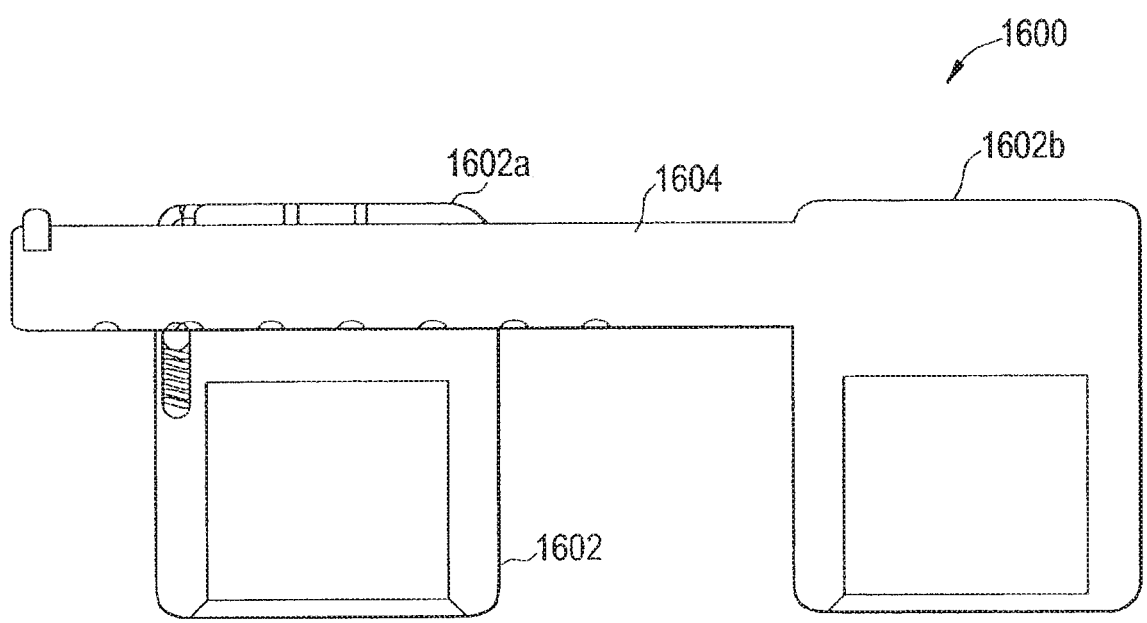
Figure 16C:
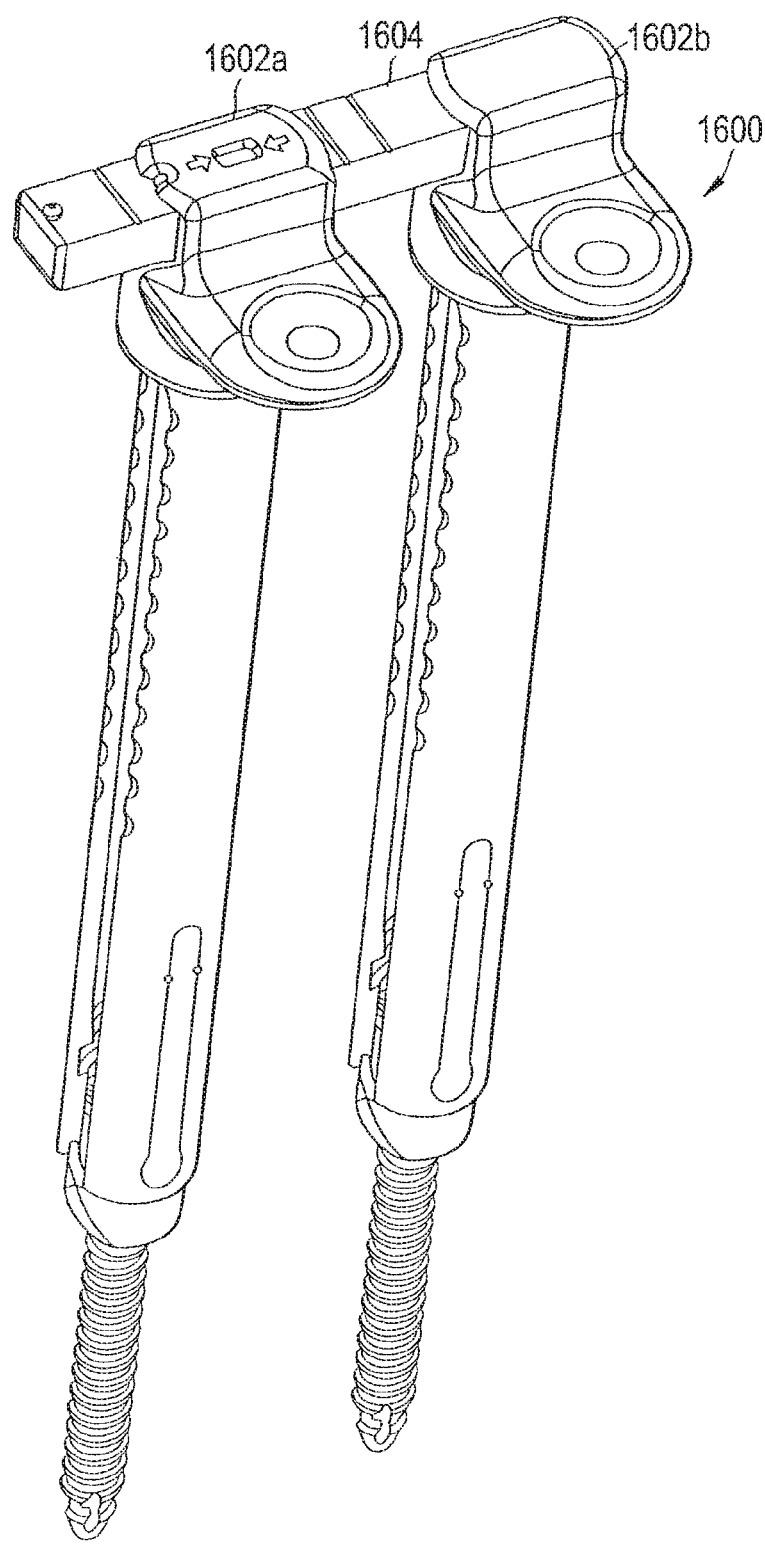

FIGS. 16a-c illustrate an exemplary caliper tool 1600 having screw extender attachment barrels 1602 (a, b) that are coupled to a measuring ruler 1604, whereby the measuring ruler 1604 is configured to be slidably coupled to the barrel 1602a (for example) and fixed to the barrel 1602b. In some embodiments, the barrels 1602 are also coupled to respective handles 1603(a, b) that are configured to allow a surgeon to easily translate the barrels 1602. The barrels 1602 are configured to be hollow inside and are appropriately sized to accommodate placement of the screw extenders. The caliper tool 1600 assists the surgeon in determining the length of a rod that is needed to for a particular surgery.

Upon installation of the screw extenders into the vertebrae, the surgeon places the barrels 1602 over the proximal ends of the screw extenders (as shown in FIG. 16c) and slides one of the barrels 1602a along the ruler 1604. The ruler 1604 is configured to have markings 1608 indicating an appropriate size of the rod needed for surgery. In some embodiments, the ruler 1604 can be configured to have a stopping mechanism 1607 that prevents slippage of the barrels 1602 from the ruler 1604. Once the size of the implant is noted on the rule 1604, the caliper tool 1600 can be removed from the extenders. In some embodiments, the moving barrel 1602b can also include a locking feature 1611 that the surgeon can use to lock the device upon determining the appropriate size of the rod.

Figure 17A:
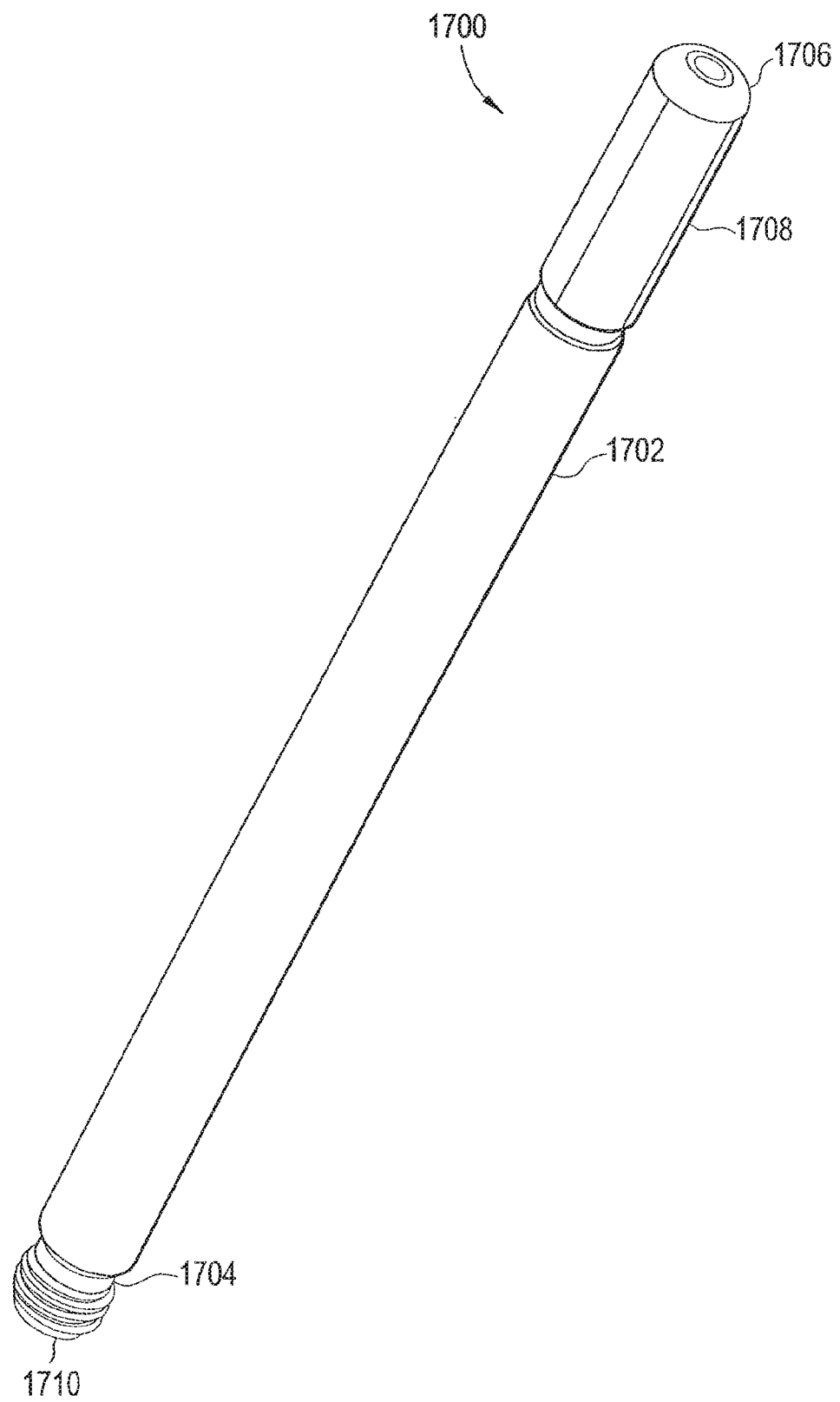
FIGS. 17*a*-*c* illustrate an exemplary screw extender guide tool, according to some embodiments of the present invention.
Figure 17B:
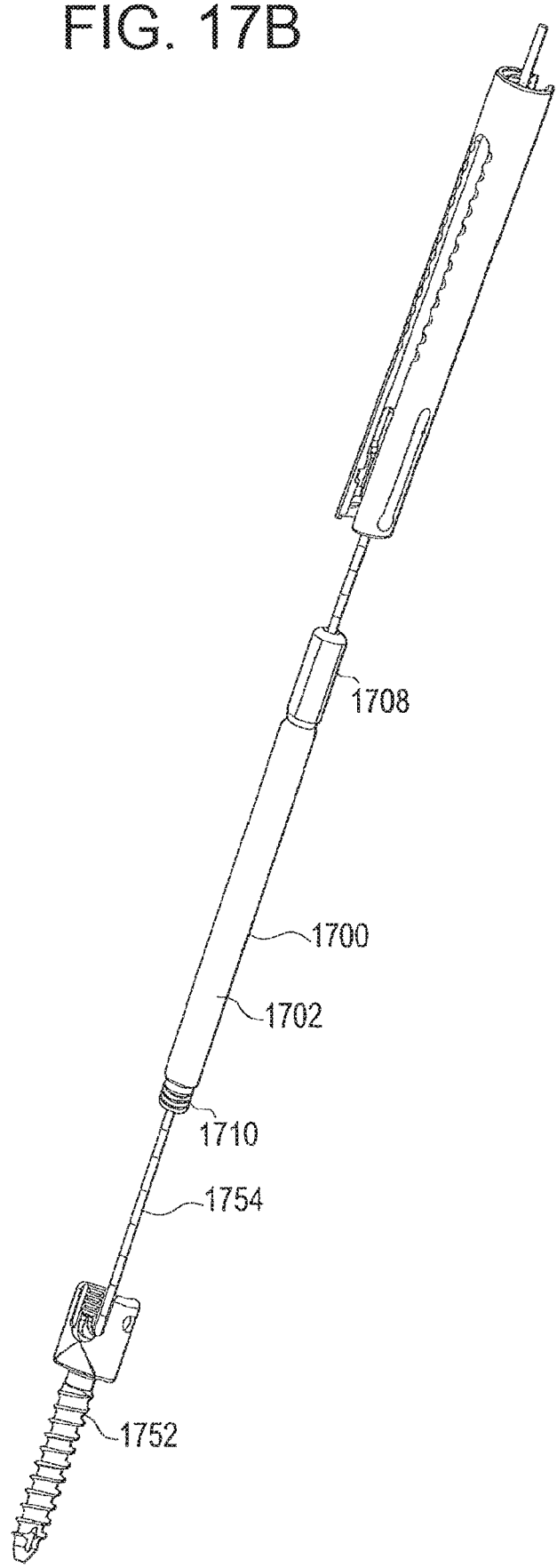
Figure 17C:
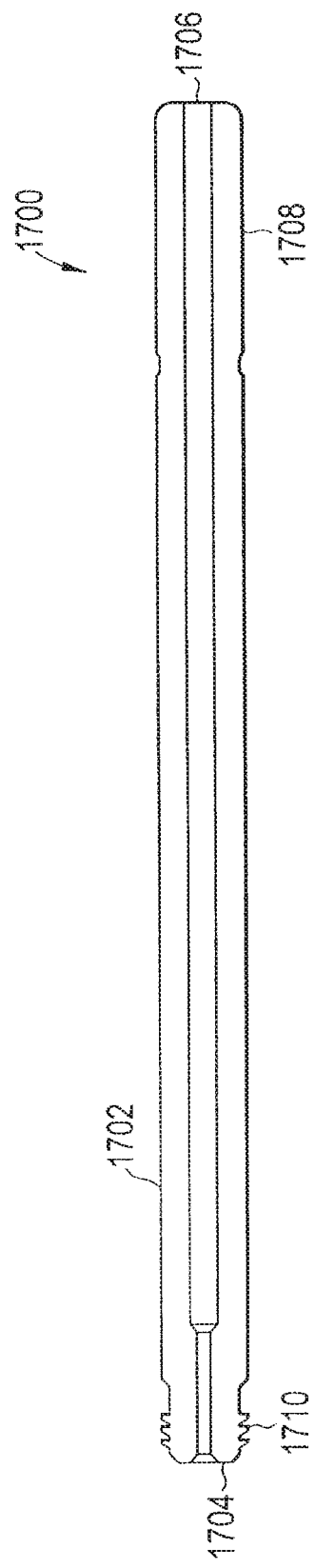

FIGS. 17a-c illustrate an exemplary screw extender guide tool 1700 for reinstalling the screw extender, according to some embodiments of the present invention. The tool 1700 can be used in the event that a screw extender is removed from (or for example, accidentally slips off) the installed screw and needs to be re-installed to the screw. The tool 1700 can be used during any re-installation procedures.

The tool 1700 includes a hollow housing 1702 disposed between a distal end 1704 and a proximal end 1706. The proximal end 1706 is configured to include a handle 1708 that controls rotation of a threaded portion 1710 disposed at a distal end 1704. The threaded portion 1710 is configured to interact with the threaded portion inside the head of the screw (not shown in FIG. 17a). Thus, in the event that the screw extender 1750 is removed from the screw 1752 (either accidentally or not) and needs to be reinstalled, the tool 1700 is placed over the wire 1754 and slid downwards along the wire 1754 and toward the screw 1752. Upon reaching the screw 1752, the tool 1700 is screwed into the head of the screw 1752 and thus, secured to the screw 1752. Once the tool 1700 is secured to the screw, the extender 1750 can be advanced along the tool 1700 for coupling to the screw in a similar fashion as described above. After coupling of the extender 1750, the tool 1700 is unscrewed from the head of the screw 1752 and removed along the wire 1754. In some embodiments, the wire 1754 can be a guide-wire placed to outline a perimeter of the surgical procedure and guide the surgeon during procedure.

Figure 19A:
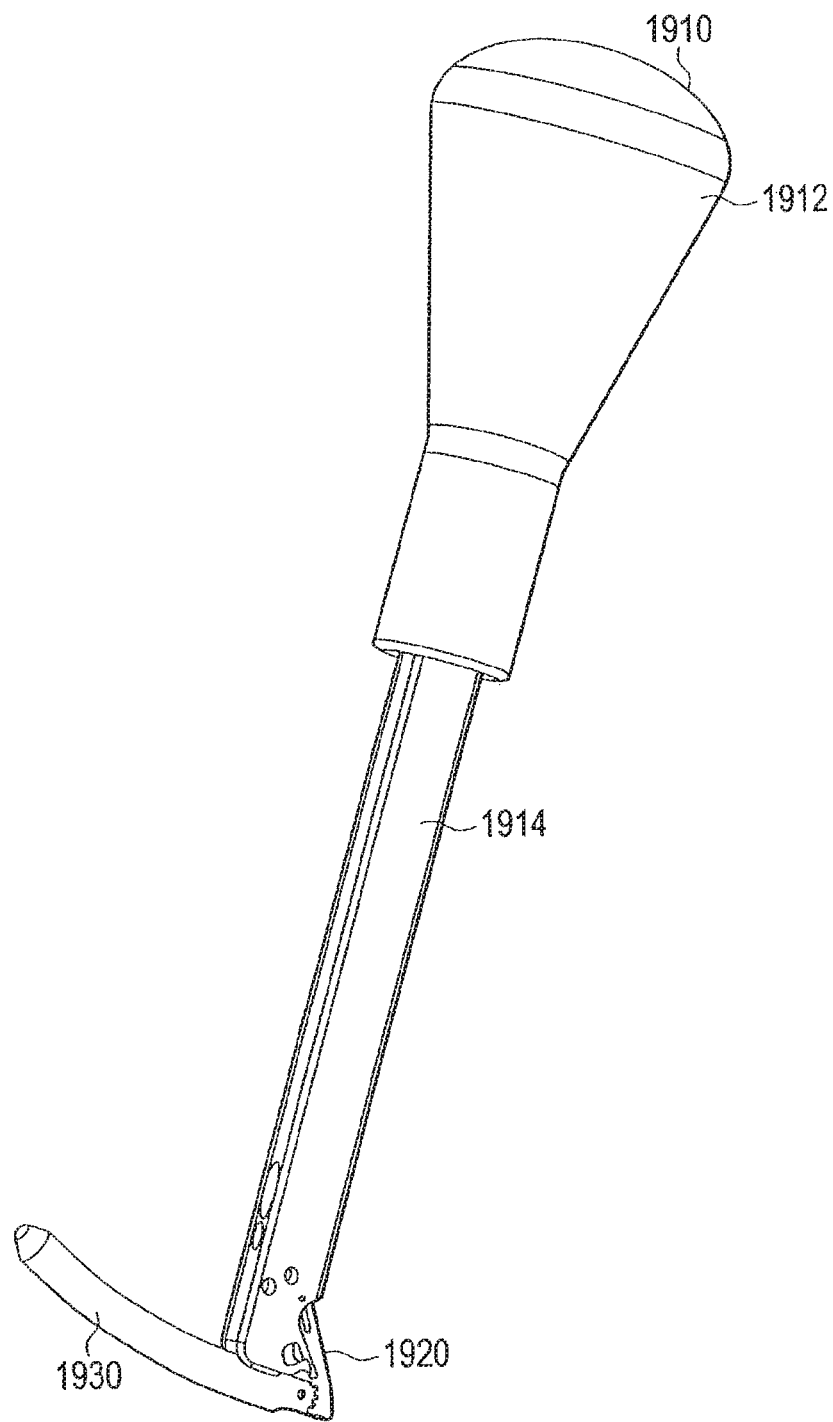
Figure 19B:
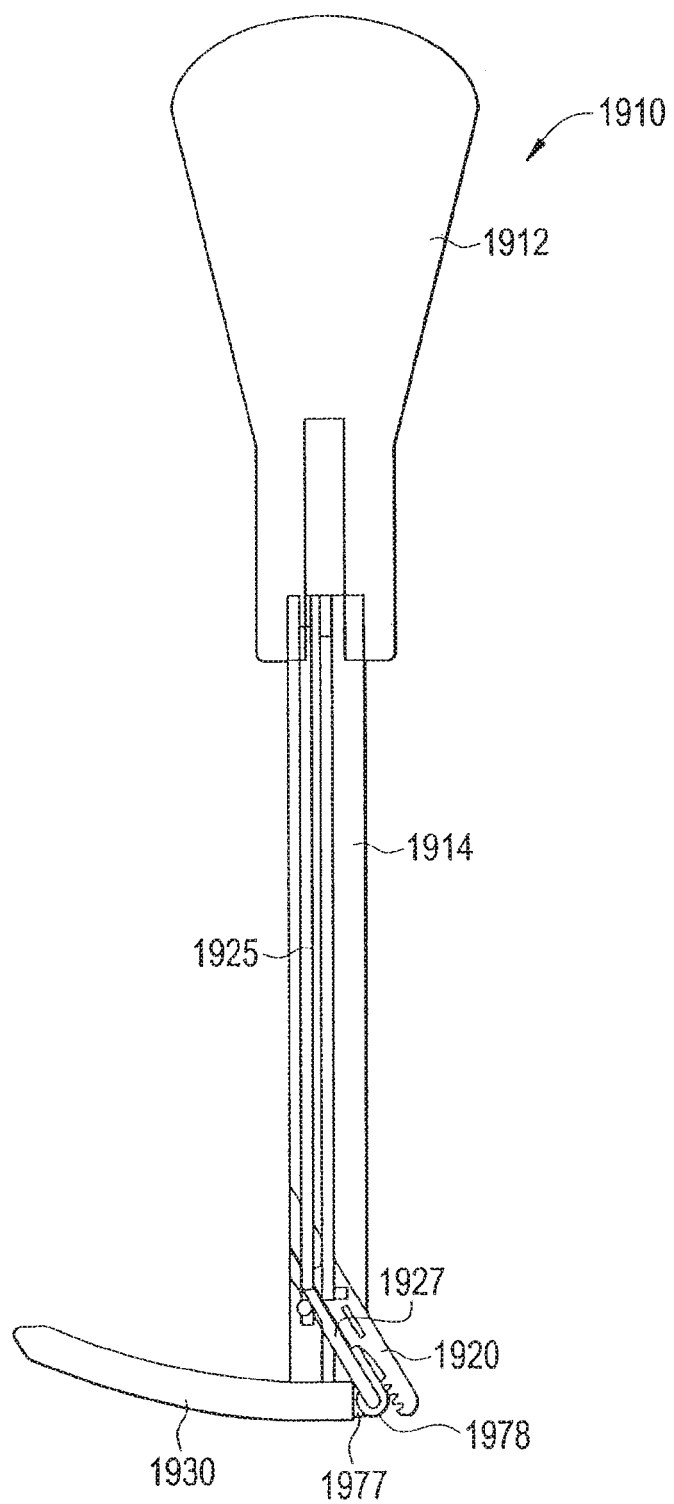

FIGS. 19a-e illustrate various embodiments of a rod inserter device, according to some embodiments of the present invention. FIGS. 19a-b illustrate an exemplary a rod inserter tool 1910. The rod inserter tool 1910 includes a handle 1912 disposed at a proximal end of the tool 1910 and a shaft 1914 coupled to the handle 1912. At a distal end of the shaft 1914, the shaft includes a rack-and-pinion mechanism 1920 that is configured to slide out of the shaft 1914 and to rotate a rod 1930 (that was previously coupled to the mechanism 1920) by approximately 90 degrees. As can be understood by one skilled in the art, other angles of rotation are possible. In some embodiments, such rotation is accomplished through rotation of the handle 1912 that is coupled to rods 1925 disposed within the shaft 1914. Rotation of the handle 1912 causes the rods 1925 to push down the rods 1927 of the rack-and-pinion mechanism 1920, thereby causing the rotational motion of the rod 1930. Reverse rotation of the handle 1912 causes reverse rotation of the rod 1930.

In some embodiments, the rod 1930 (which is similar to the rod 1984 shown in FIG. 19o includes an opening 1979 disposed at its distal end and configured to be coupled to an insertion pin of the rack-and-pinion mechanism 1920. This allows the rod 1930 to be held in place by the rod inserter tool 1910, while the rod is being inserted into the screw extenders. The rod further includes ratchet teeth 1978 (shown in FIG. 190 that are configured to be disposed at the distal end of the rod and further configured to interact with ratchet teeth 1922 of the mechanism 1920. The ratcheting interaction of the rod 1930 and the mechanism 1920 provides a controlled rotation of the rod 1930.

Figure 19C:
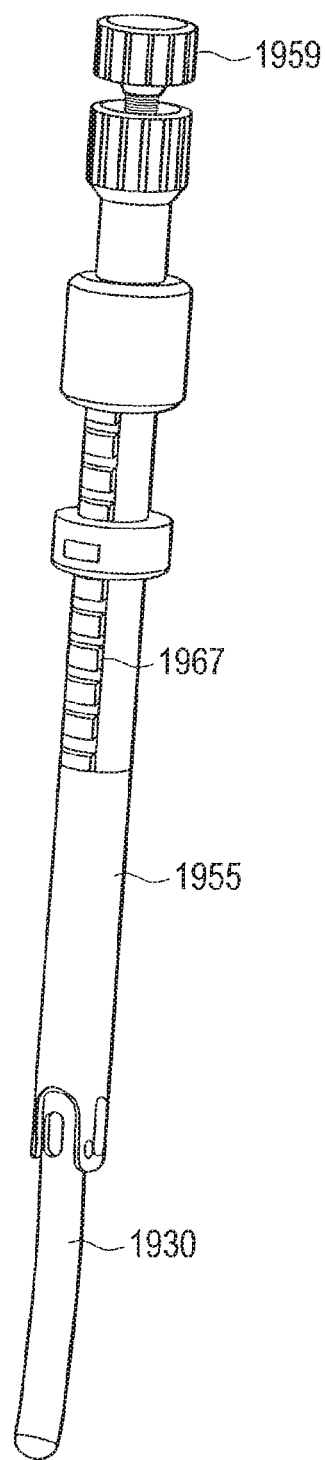
Figure 19D:
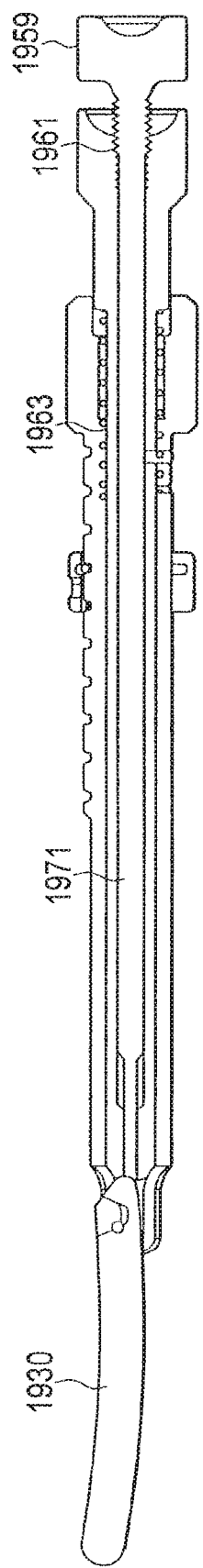
Figure 19F:
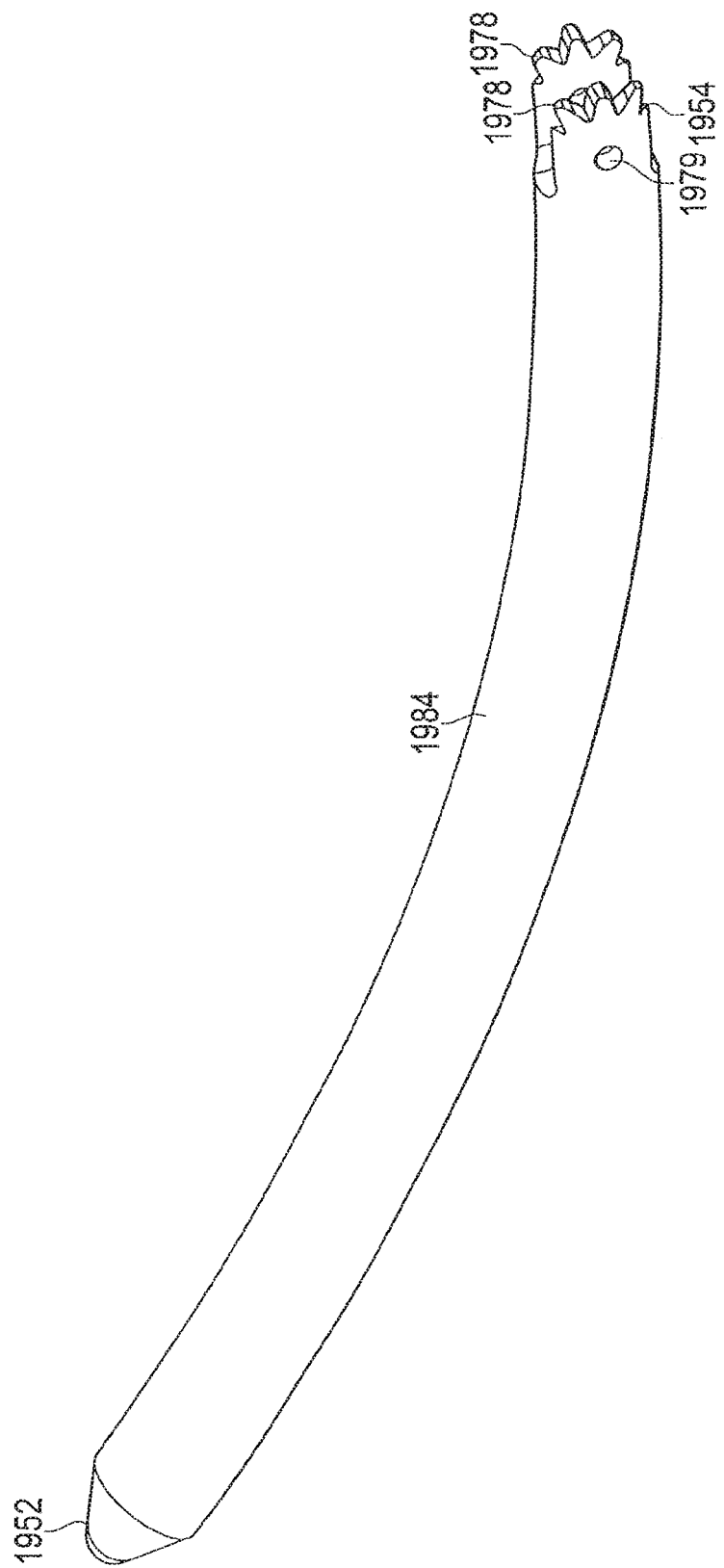

FIGS. 19*c-e* illustrate another exemplary rod insertion tool 1950, according to some embodiments of the present invention. The tool 1950 includes a shaft 1955 disposed between a distal end 1957 configured to be coupled to a rod 1930 (in a similar fashion as with the tool 1910 in FIGS. 19*a-b*) and a control handle 1959. The control handle 1959 is configured to be threadedly secured inside the shaft 1955 using threads 1961. The control handle 1959 is further secured to an interior rod 1971 that is disposed inside the shaft 1955 and is configured to slide inside the shaft 1955. The rod 1930 is rotatably coupled to the interior rod 1971. Upon rotation of the control handle 1959, the interior rod 1971 begins to push on the pivoted connection between rod 1930 and interior rod 1971, thereby causing the rod 1930 to rotate, as shown in FIGS. 19*d-e*. In some embodiments, the interior rod 1971 can be configured to be spring loaded inside the shaft 1955 using springs 1963, which cause the handle 1959 to spring back upon completion of rotation of the rod 1930. In some embodiments, the rod 1930 can be configured to include a pivot hole 1977 that is configured to disengage from the interior rod 1971 upon rotation of the rod 1930. Thus, this allows for a release of the rod 1930 from the interior rod 1971.

In some embodiments, the shaft 1955 further includes a measuring scale 1967 disposed along a portion of the length of the shaft 1955. The scale 1967 is configured to determine the proper depth of insertion of the inserter tool 1950 into the screw extender housing.

Figure 20A:
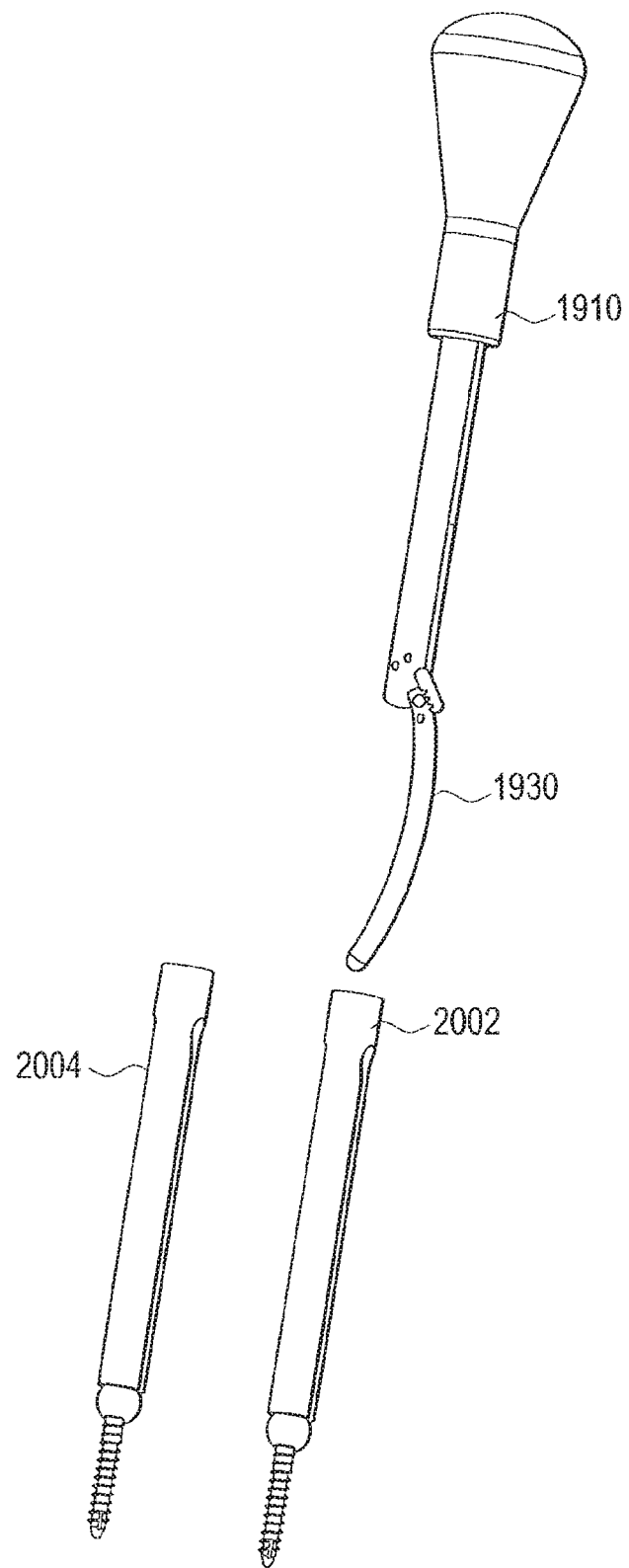
FIGS. 20*a*-*o* illustrate exemplary step-by-step procedures for insertion of a rod using rod inserter tools, according to some embodiments of the present invention.
Figure 20B:
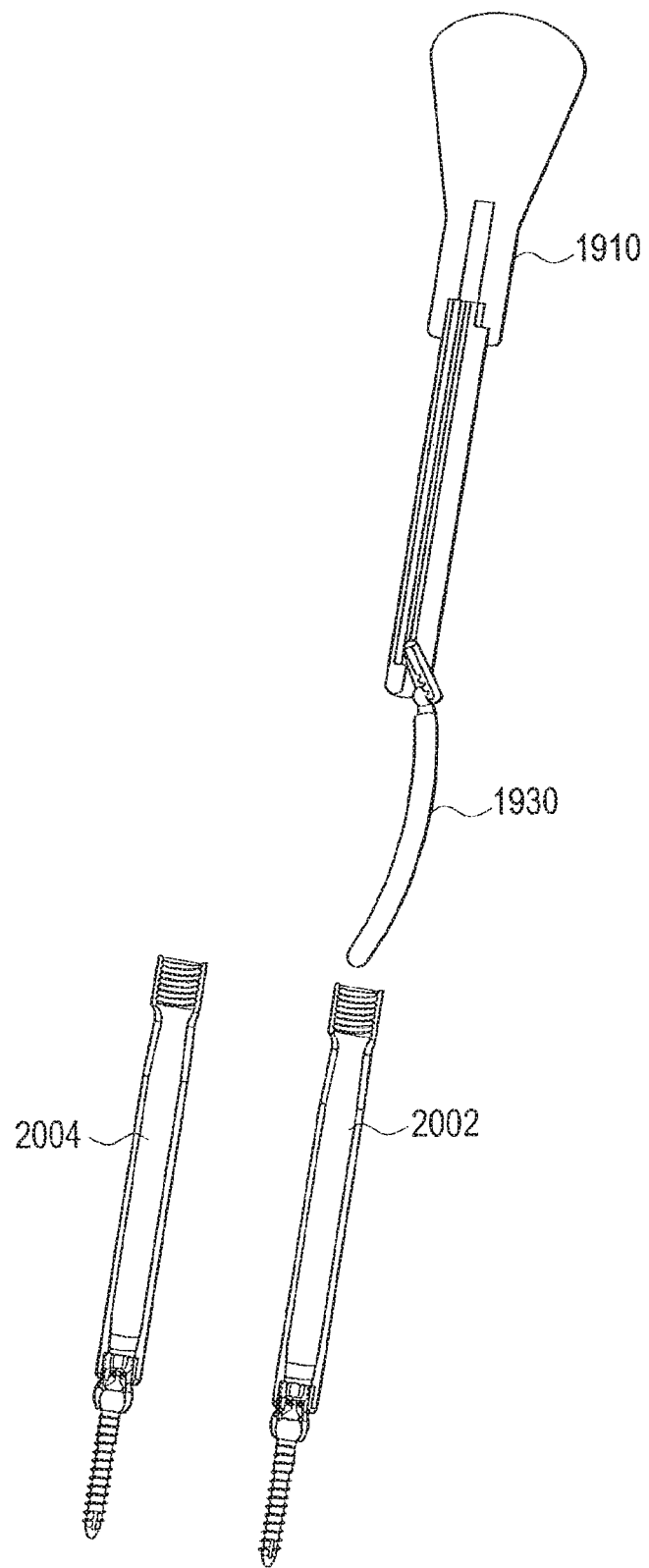
Figure 20C:
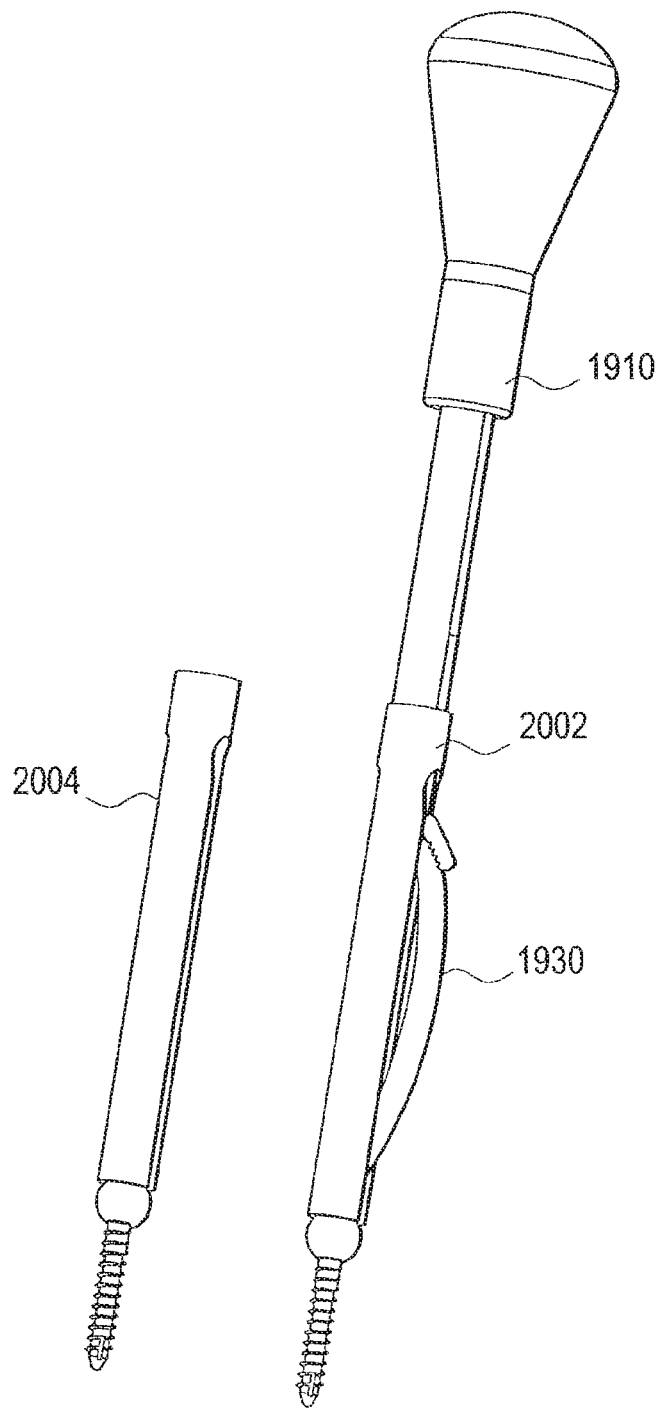
Figure 20D:
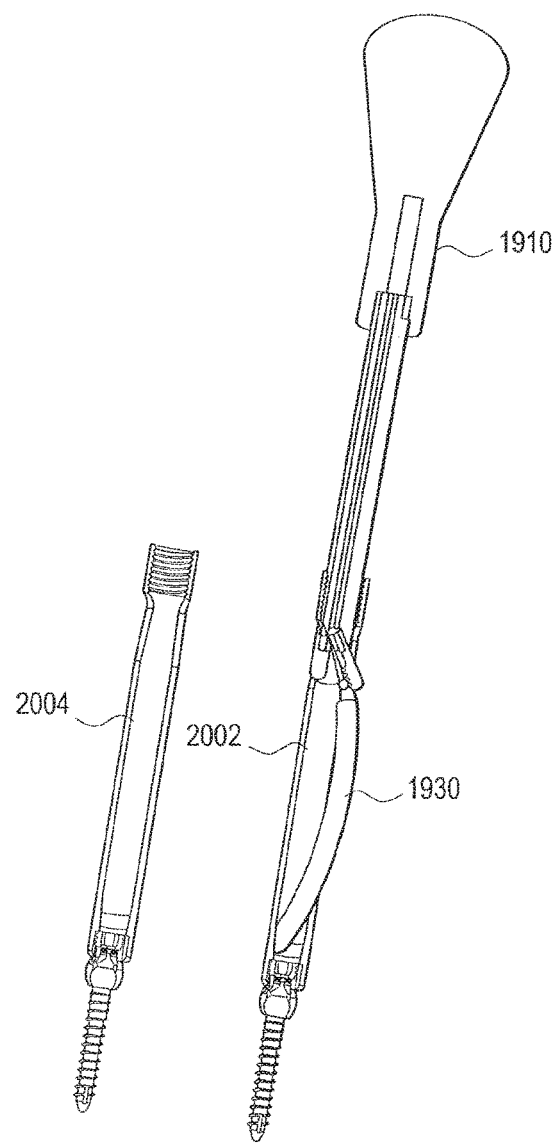
Figure 20E:
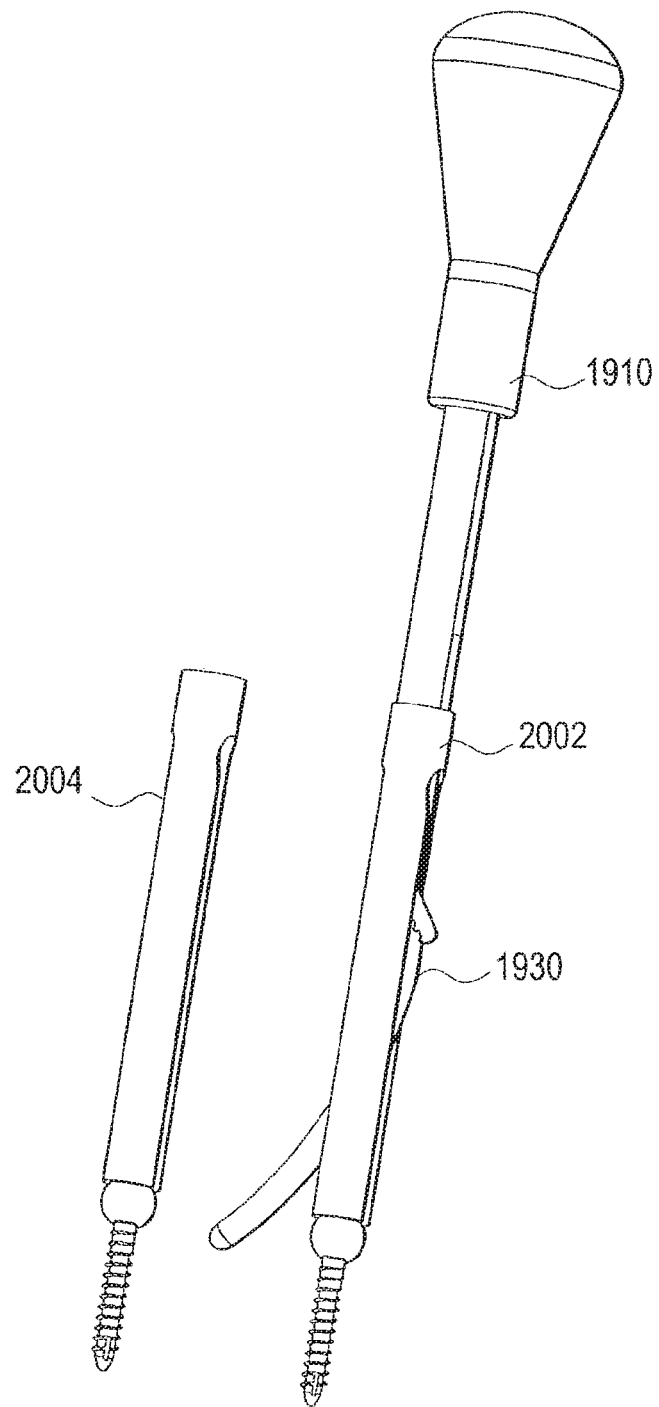
Figure 20F:
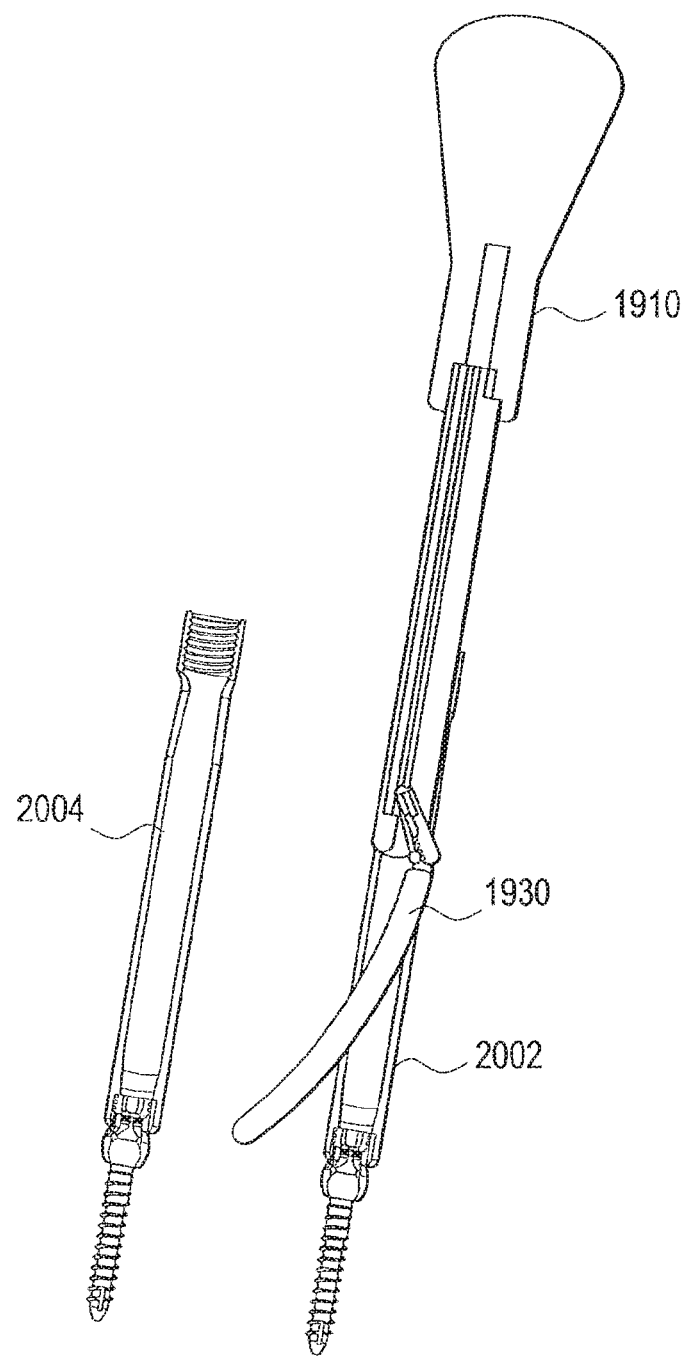
Figure 20G:
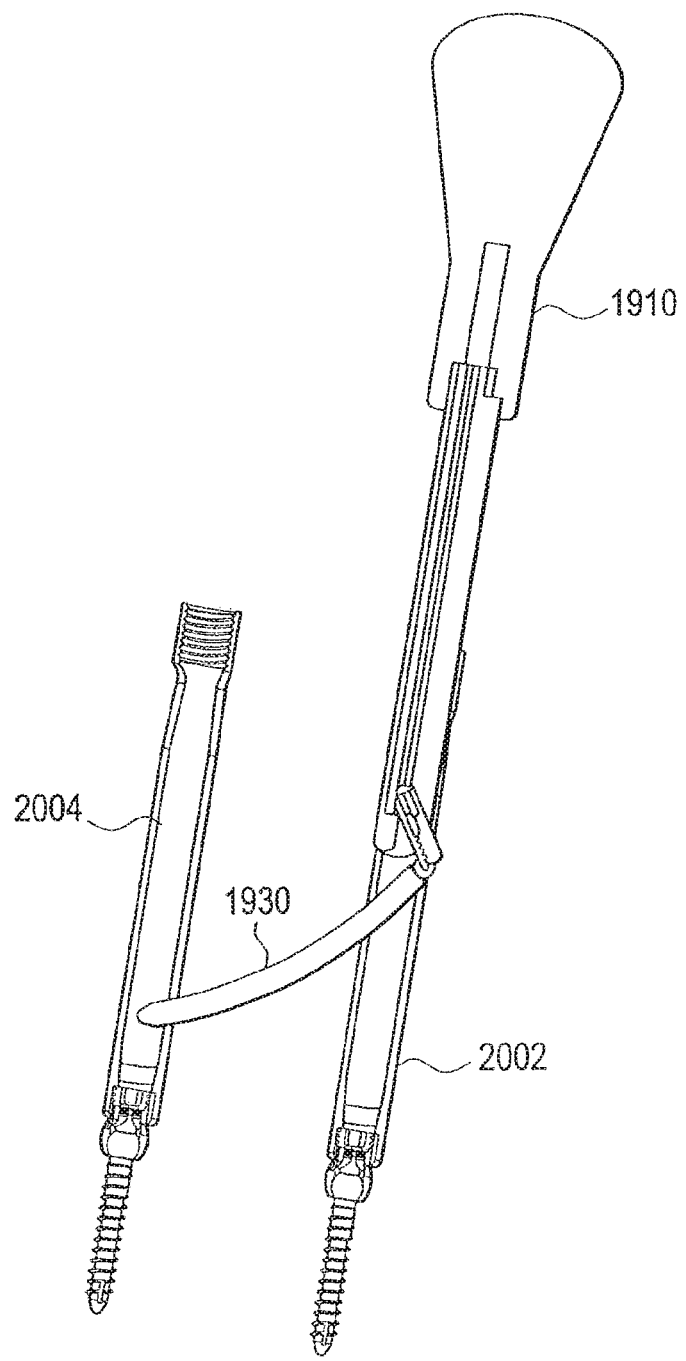
Figure 20H:
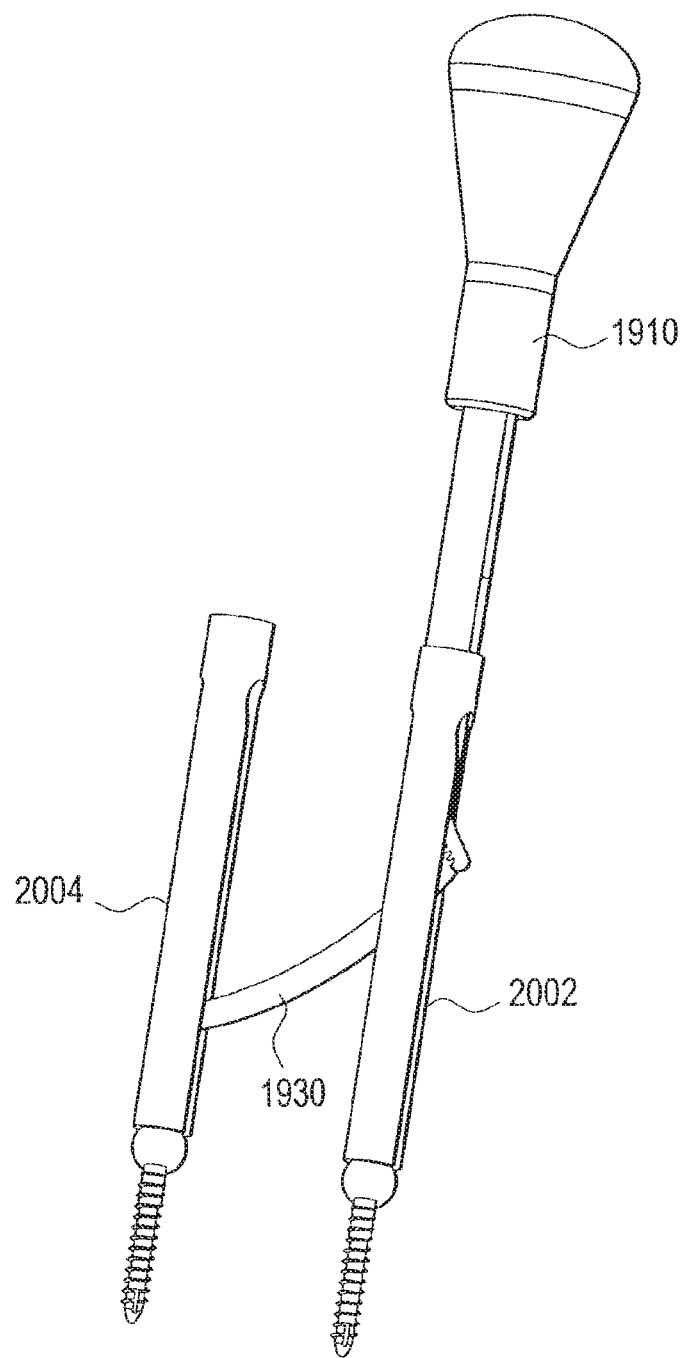
Figure 20I:
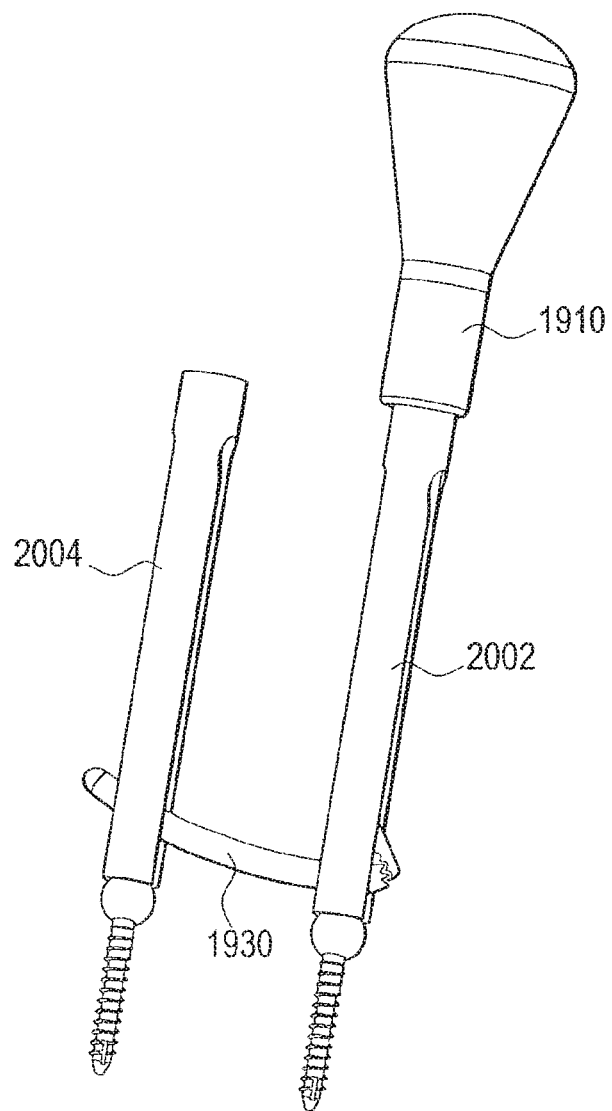
Figure 20J:
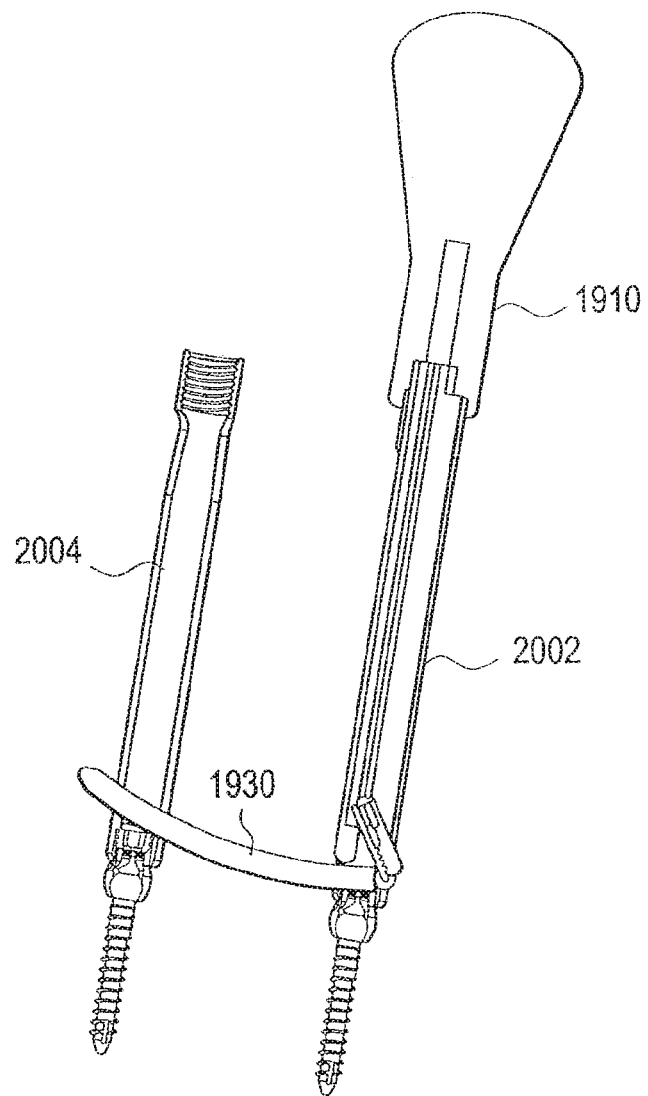
Figure 20K:
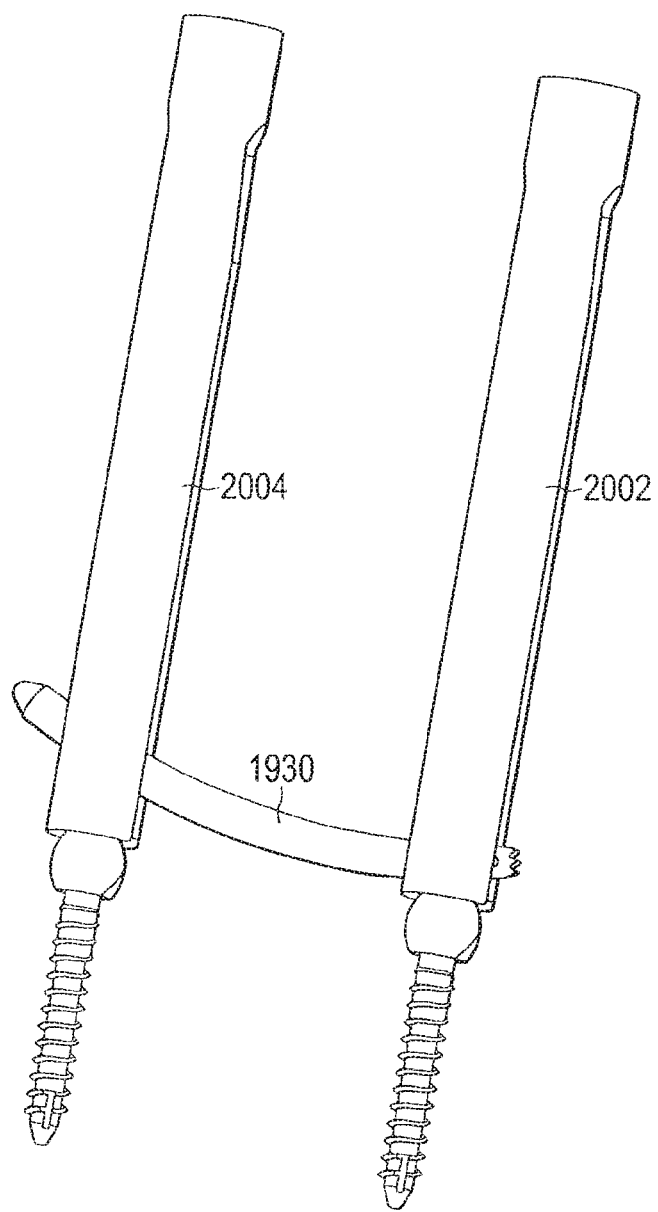
Figure 20L:
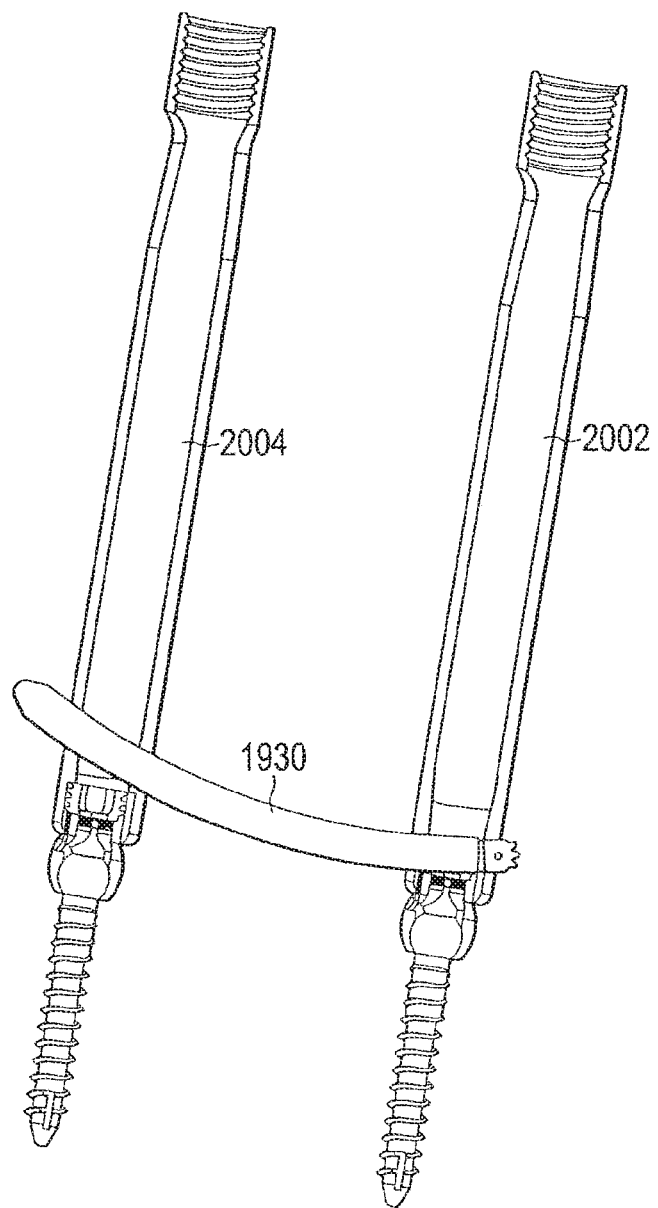
Figure 20M:
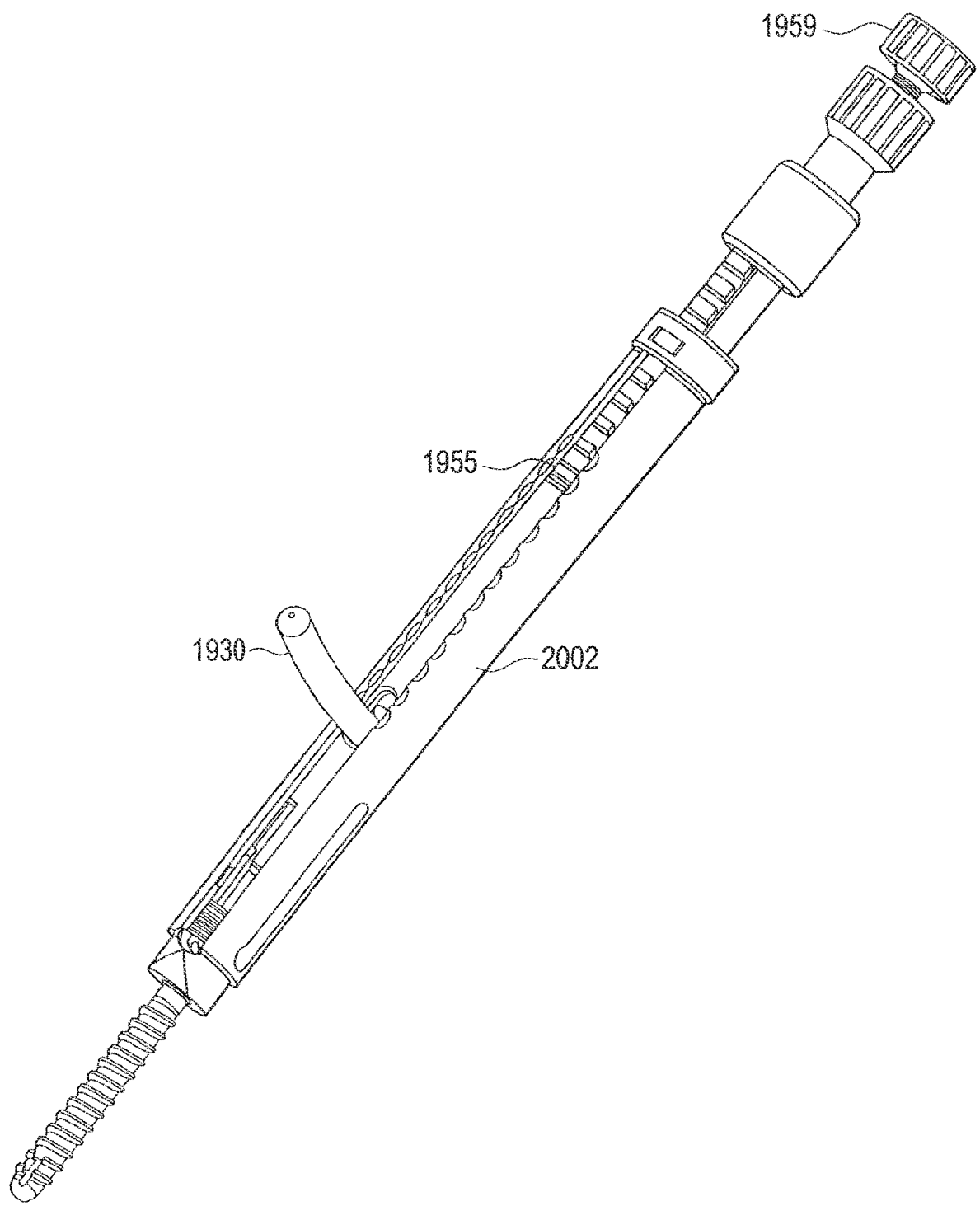
Figure 20N:
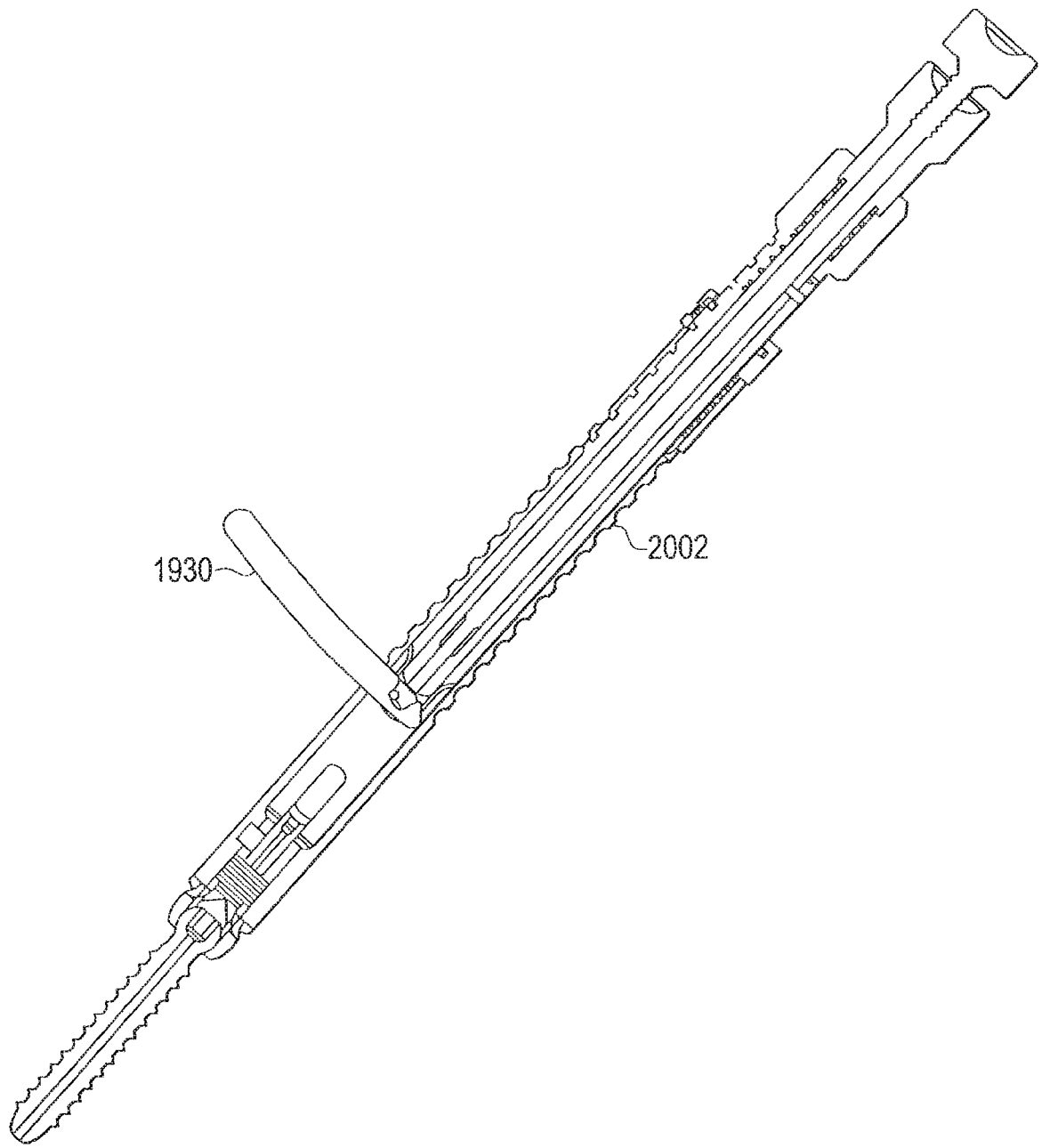
Figure 20O:
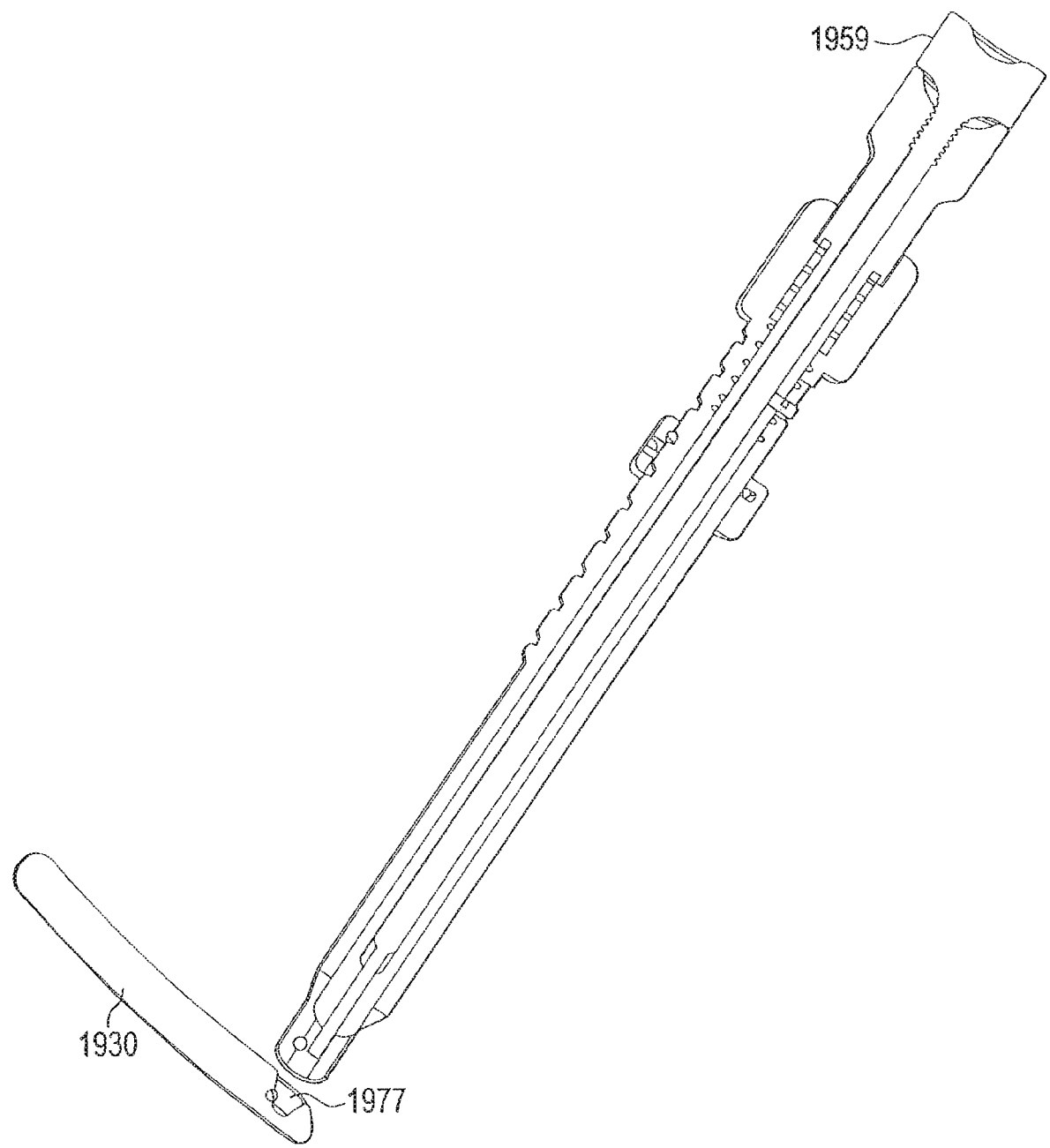

FIGS. 20*a-l* illustrate a procedure for rod insertion using a tool 1910 shown in FIGS. 19*a-b*. Referring to FIGS. 20*a-d*, the rod inserter tool 1910 coupled to the rod 1930 (pointing towards the screw extender) is inserter into the first screw extender 2002. Upon insertion, the rod 1930 is rotated to being protruding outside the exterior channels of the first screw extender 2002 and to begin pointing toward the second screw extender 2004, as shown in FIGS. 20*e-f*. Then, the rod 1930 is advanced into one of the exterior channels of the second screw extender 2004, as shown in FIGS. 20*g-j*. Upon being inserted into the channels of the first and second screw extenders 2002 and 2004, the inserter tool 1910 is disengaged, as shown in FIGS. 20*k-l*. FIGS. 20*m-o* illustrate insertion of the rod 1930 using the tool 1950 shown in FIGS. 19*c-e*.

Figure 21A:
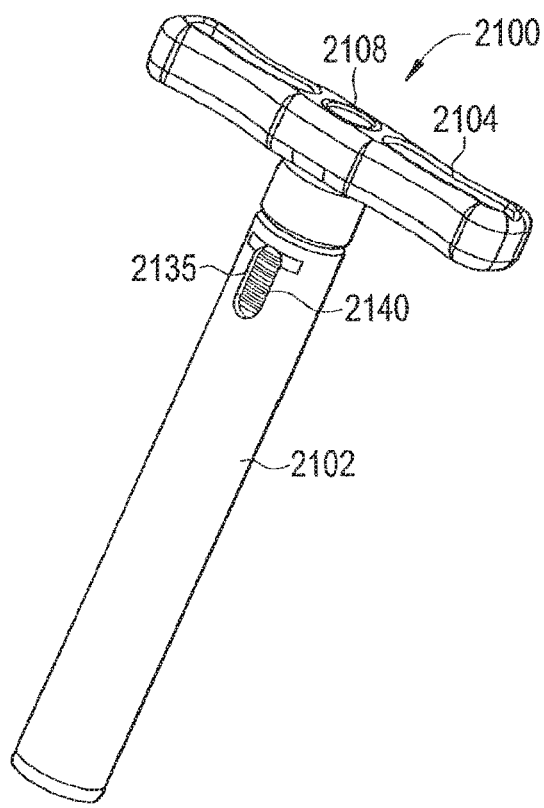
FIGS. 21*a*-*e* illustrate an exemplary rod reducer tool, according to some embodiments of the present invention.
Figure 21B:
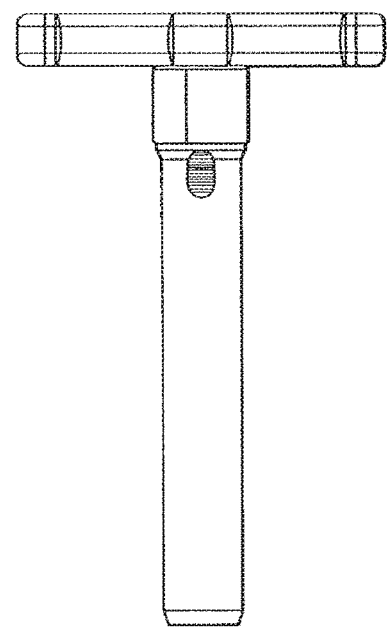
Figure 21C:
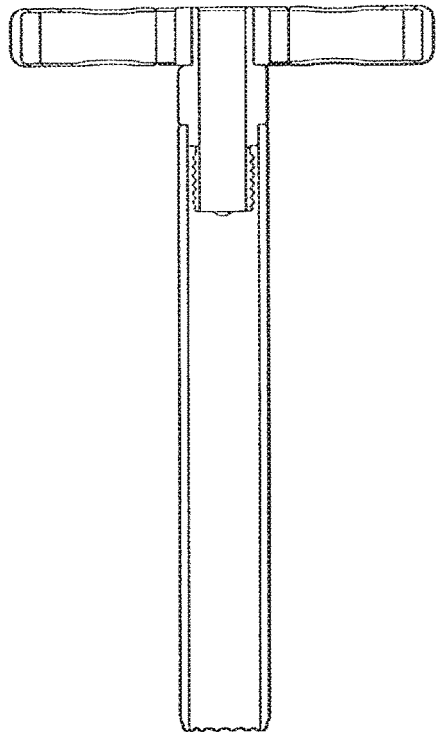
Figure 21D:
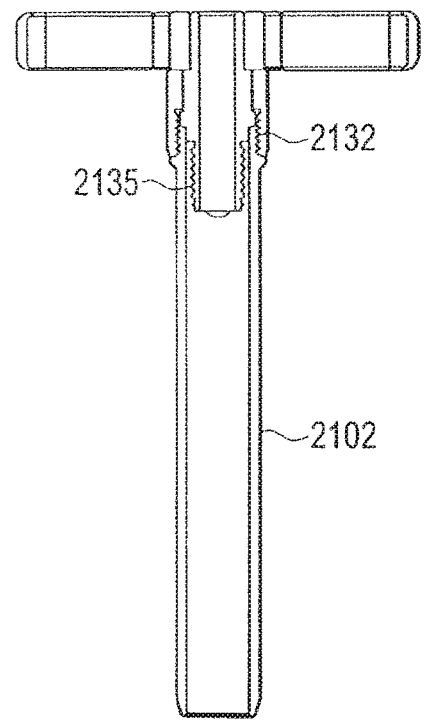
Figure 21E:
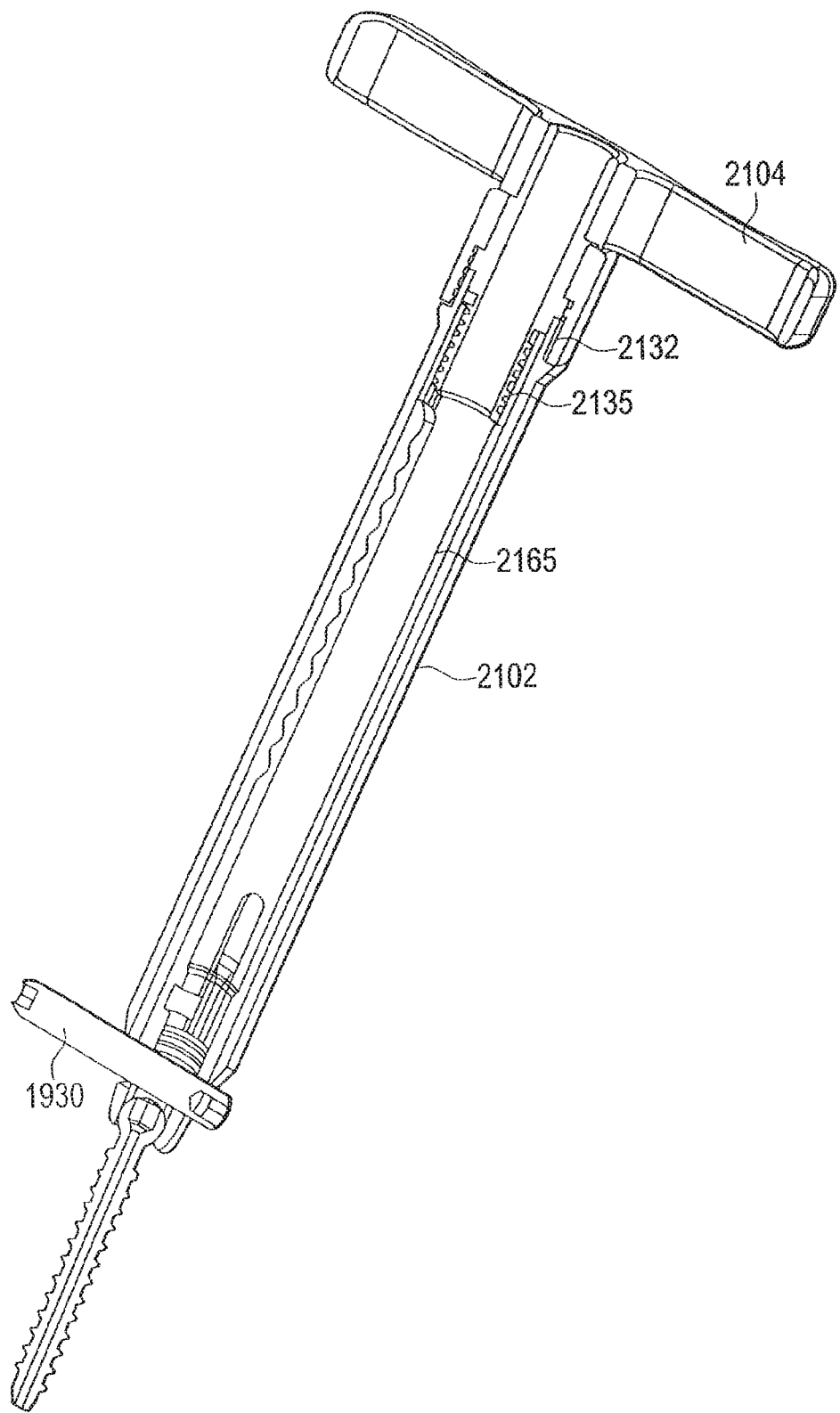

FIGS. 21*a-e* illustrate an exemplary rod reducer tool 2100 for reducing the rod 1930 toward the implanted screw, according to some embodiments of the present invention. The rod reducer 2100 includes a rod reducer shaft 2102 coupled to a handle 2104. The handle 2104 is configured to be rotatably coupled to the shaft 2102. The shaft 2102 is configured to include an interior passage 2120 for insertion over a screw extender. The reducer further includes handle threads 2132 and extender threads 2135. The extender threads 2135 are configured to interact with the threads disposed on an interior surface of the screw extender housing 2165 (as shown in FIG. 21*a*) and thus are configured to secure the tool 2100 to the screw extender housing. The handle threads 2132 are configured to allow rotation of the handle 2104 once the reducer tool 2100 is secured to the extender housing 2165. In some embodiments, the reducer tool 2100 includes a window 2140 disposed on the shaft 2102 that allows a surgeon to get a visual confirmation that the extender housing 2165 has been secured to the reducer tool 2100.

In some embodiments, the handle 2104 of the tool 2100 includes an opening 2108 that is configured to allow insertion of setscrews or other tools, once the reducer tool 2100 has aligned the rod 1930 and it is time to secure to the implanted screw.

Figure 22A:
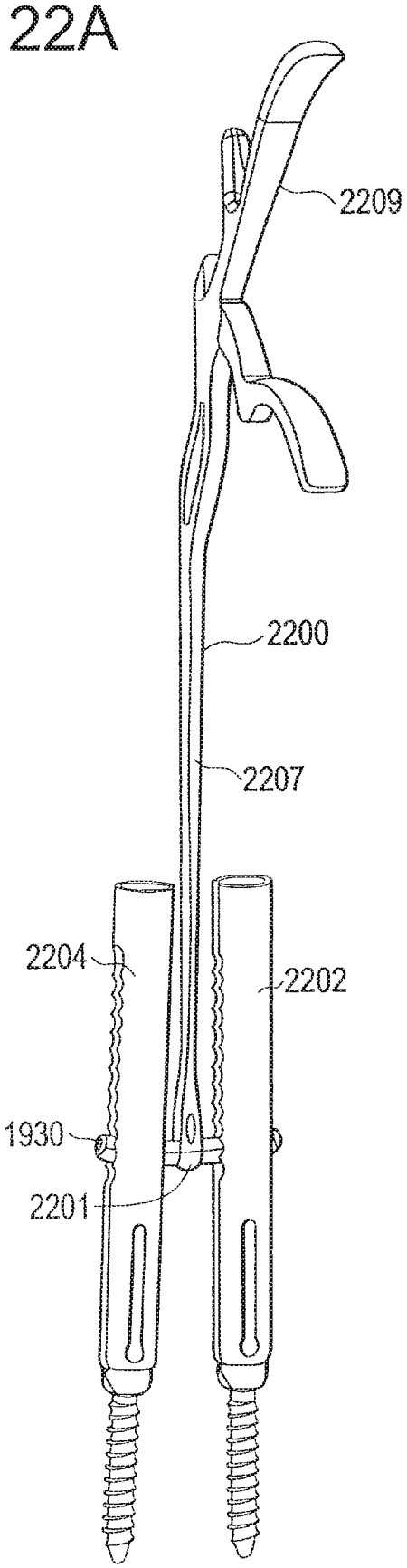
FIGS. 22*a*-*b* illustrate an exemplary rod inserter tool, according to some embodiments of the present invention.
Figure 22B:
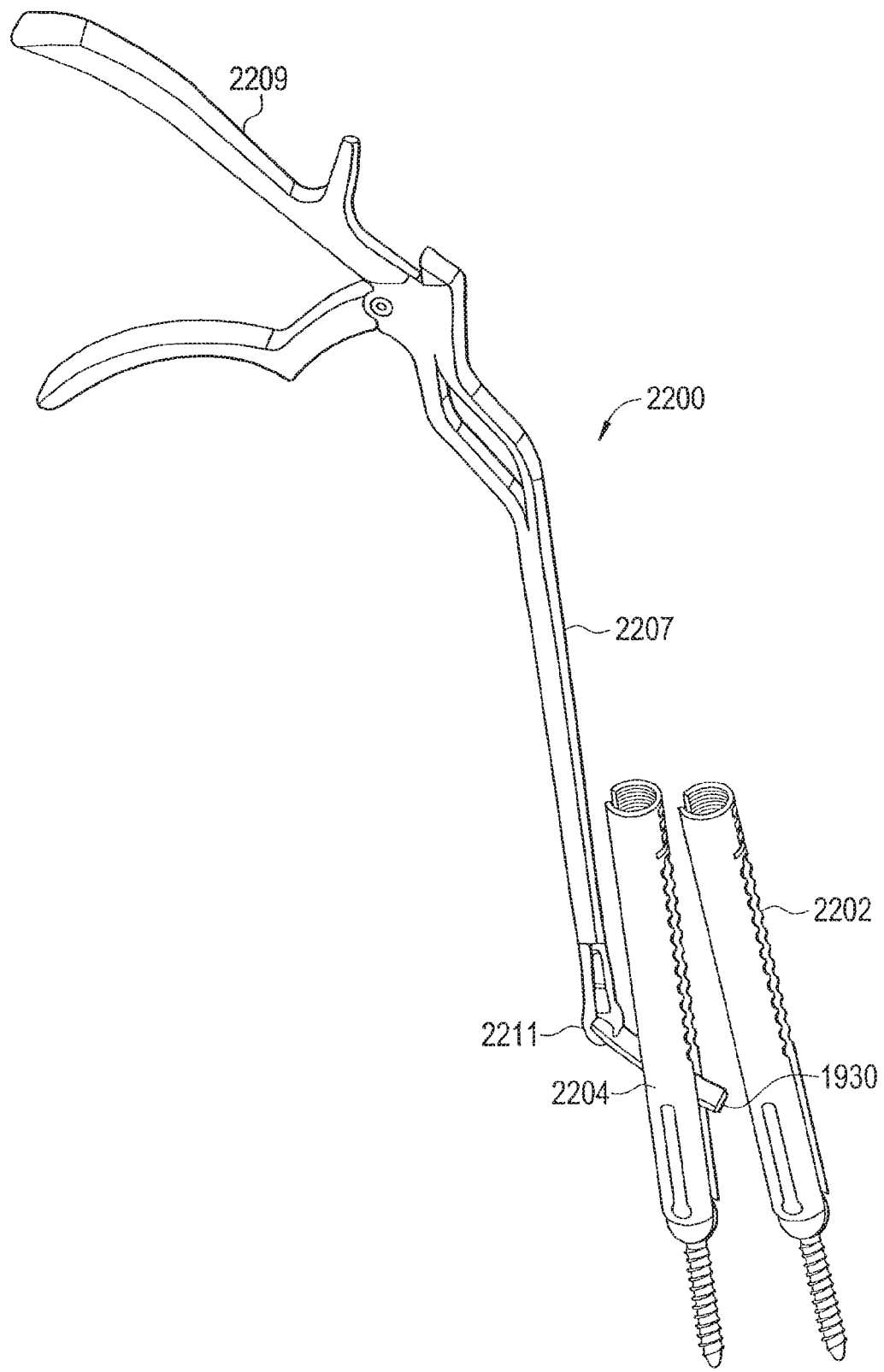

FIGS. 22*a-b* illustrate an exemplary rod inserter tool 2200, according to some embodiments of the present invention. The tool 2200 is configured to allow pushing of the rod 1930 disposed in the channels between two extenders 2202 and 2204 toward the implanted screws. The tool 220 can push the rod 1930 from a side of one of the extenders (as shown in FIG. 22*b*) or between two extenders (as shown in FIG. 22*a*). The scenarios shown in FIGS. 22*a-b* may require different types of incisions made. For example, the scenario shown in FIG. 22*a* may require a surgeon making an incision that connects the two incisions created for the two extenders. In some embodiments, the tool 2200 includes an elongated shaft 2207 coupled to scissor-like handles 2209 at a proximal end and gripping jaws 2211 at a distal end. The gripping jaws 2211 are configured to grip the rod 1930 upon actuation of the handles 2209. Once the jaws 2211 have gripped the rod 1930, the surgeon can begin pushing the rod toward the implanted screws.

In some embodiments, components of the present invention can be manufactured from Nitinol or any other suitable materials.

In some embodiments, the above referenced extender devices can be used by a surgeon (or any other medical professional) in a variety of applications. The extender devices can be used subsequent to preparation of a bone for screw-implantation. Screw is implanted using a bone biopsy needle, such as a Jamshidi needle, manufactured by Cardinal Health Inc., Dublin, Ohio, USA, which can be followed by progressive dilation. Once the bone has been prepared, the bone screw is implanted. After implantation, the bone screw can be manipulated for orientation using the extender device. This "extender" extends out of the stab wound and allows the surgeon to control the implanted screw.

The following description illustrates some additional tools that can be used with the screw extender devices that have been discussed above and shown in FIGS. 1-22*b*.

Figure 23A:
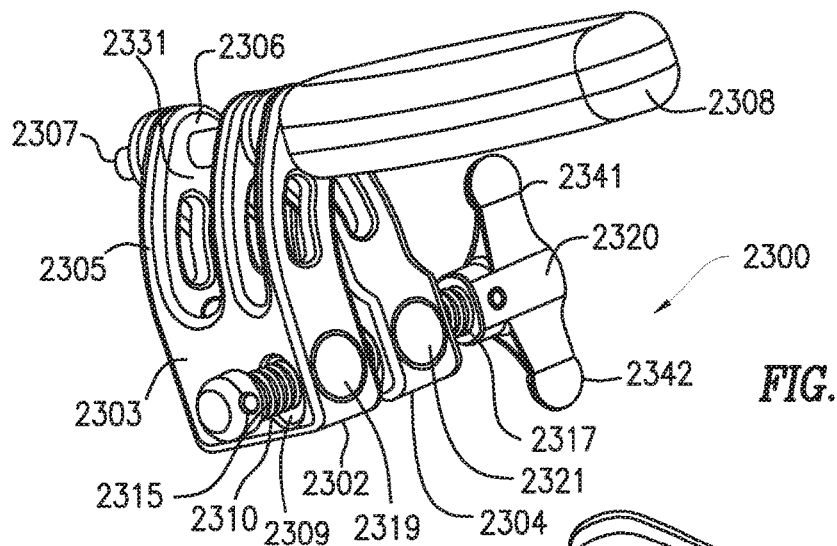
FIGS. 23*a*-*i* illustrate an exemplary compression-distraction tool, according to some embodiments of the present invention.
Figure 23B:
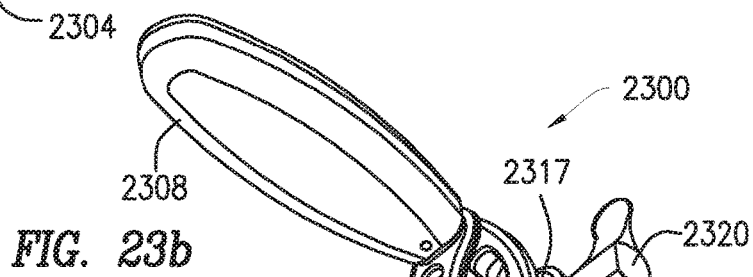
Figure 23C:
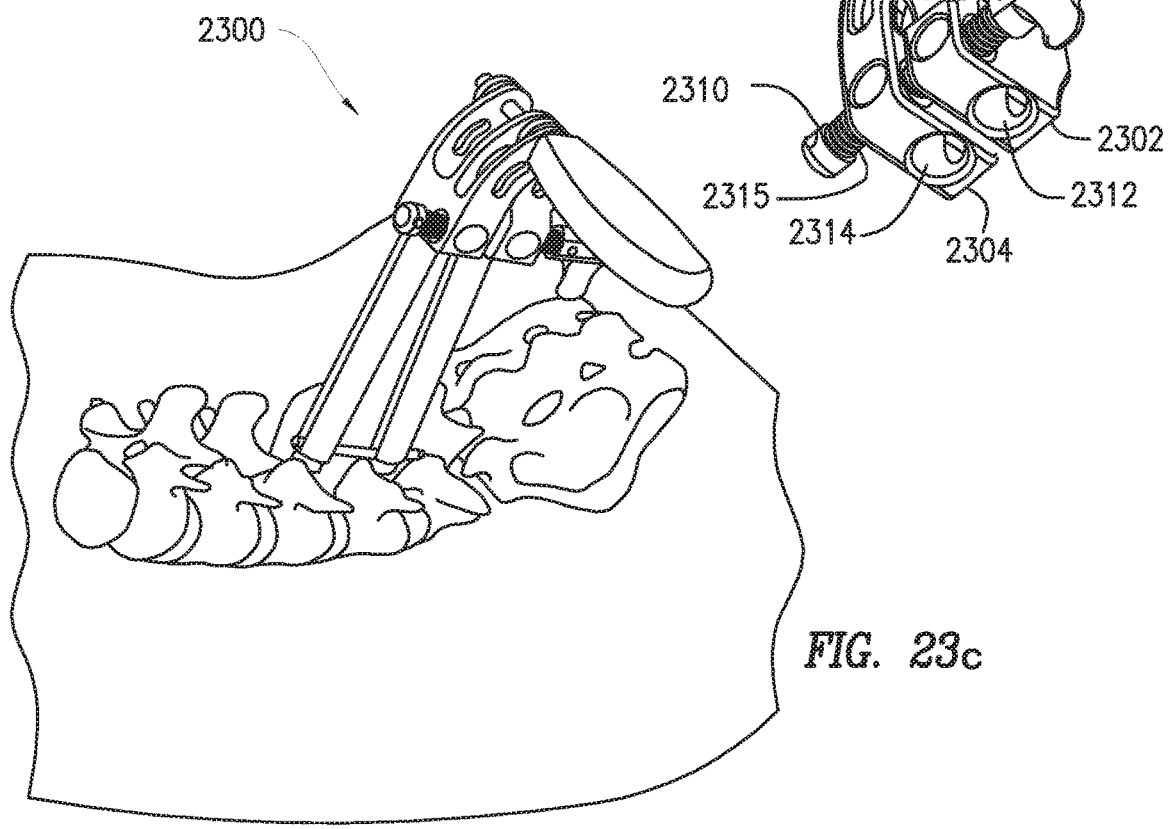
Figure 23D:
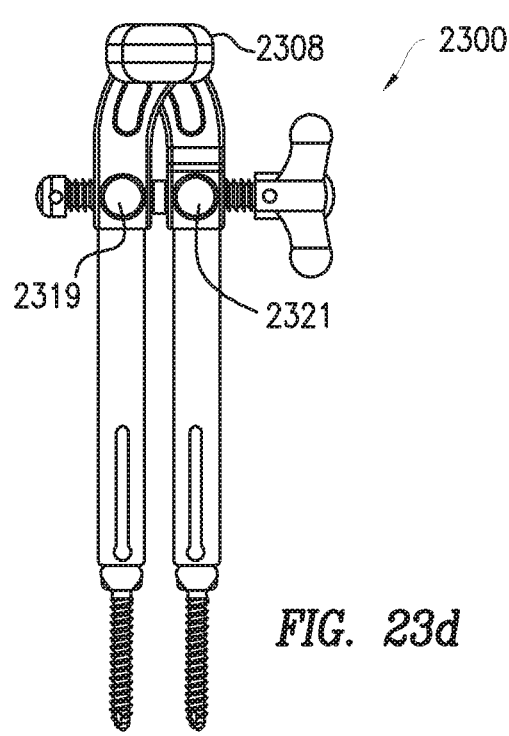
Figure 23E:
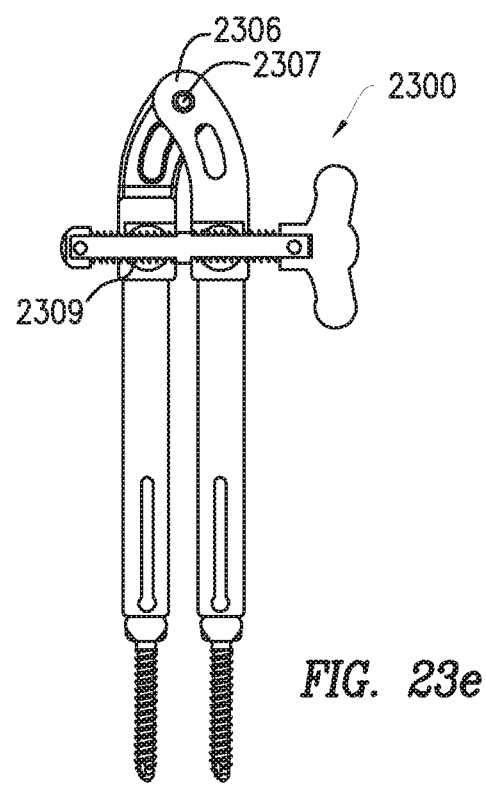
Figure 23F:
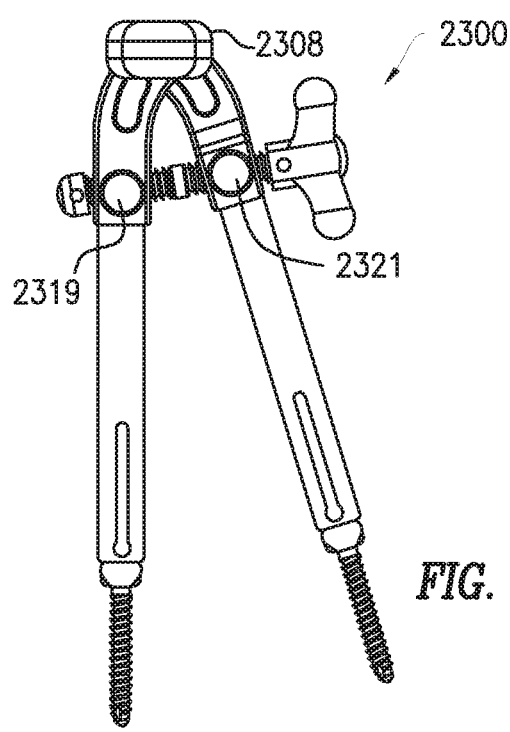
Figure 23G:
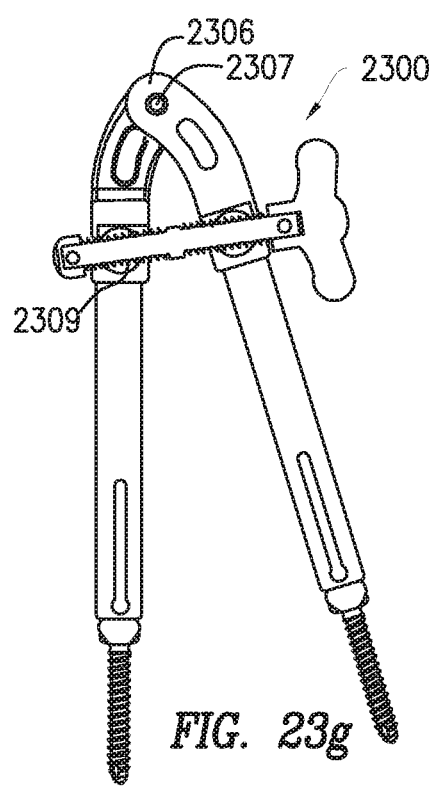
Figure 23H:
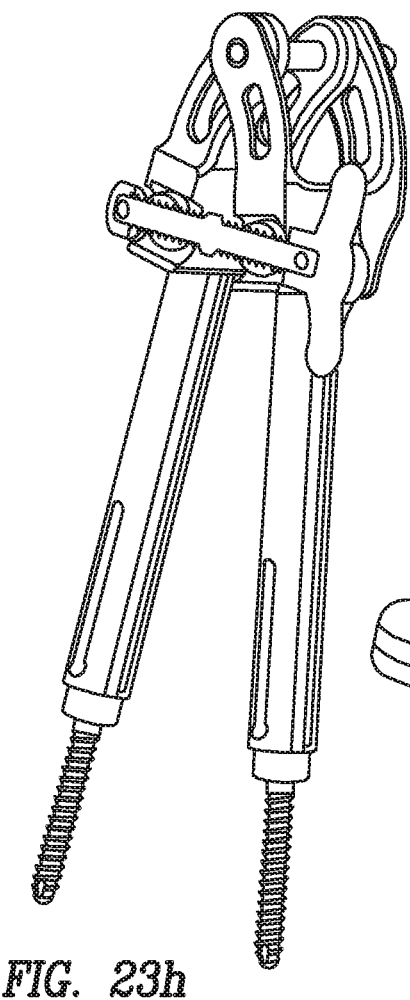
Figure 23I:
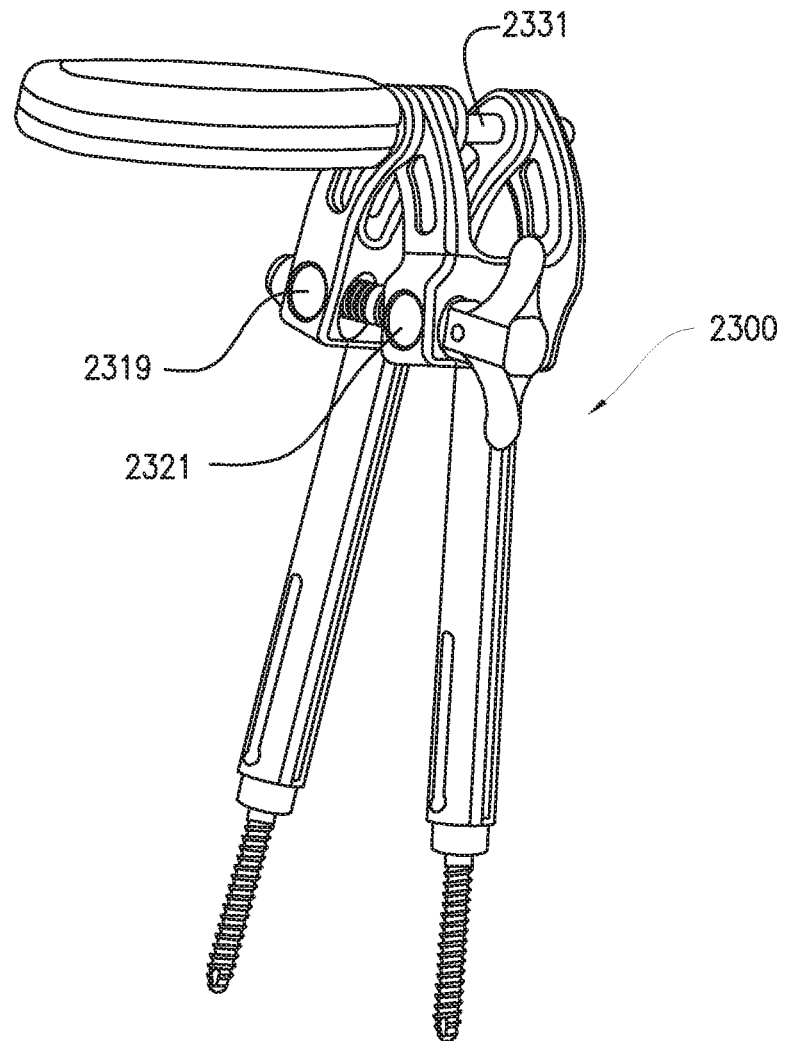

FIGS. 23*a-i* illustrate an exemplary compressor-distractor tool 2300, according to some embodiments of the present invention. FIGS. 23*a-b* illustrate perspective views of the tool 2300; FIG. 23*c* illustrates the tool 2300 being coupled to screw extenders that are attached to respective screws implanted into a vertebrae; FIGS. 23*d-e* illustrate the tool 2300 being in a compressed state (FIG. 23*d* is a perspective view and FIG. 23*e* is a cross-sectional view); FIGS. 23*f-g* illustrate the tool 2300 being a distracted state (FIG. 23*f* is a perspective view and FIG. 23*g* is a cross-sectional view); FIGS. 23*h-i* are perspective views of the tool 2300 being attached to screw extenders along with respective screw assemblies.

Referring to FIGS. 23*a-i*, the tool 2300 is configured to apply compressive and/or distractive forces to screw extenders and, ultimately, screw assemblies that have been implanted into vertebra and coupled to the screw extenders. In some embodiments, the tool 2300 is placed over top portions of two screw extenders that can be adjacent to one another and then, by turning a handle or a knob, the screw extender assemblies can be compressed together or distracted from each other, as shown in FIG. 23*c-g*.

In some embodiments, the tool 2300 includes a first screw extender holding portion 2302 and a second screw extender holding portion 2304, as shown in FIGS. 23a-b. Each portion 2302, 2304 can be configured to have a respective base part 2303 coupled to a respective top part 2305. The base part 2303 is configured to be coupled to a screw extender (not shown in FIGS. 23a-b). The top part 2305 is configured to protrude away from the base part 2303 and, in some embodiments, can be further configured to have a curvature. The top parts of the portions 2302 and 2304 can be configured to curve toward each other, where portions 2302 and 2304 are pivotally coupled to each other at their respective tops, as shown in FIGS. 23a-b.

The portions 2302 and 2304 are pivotally coupled to each other using a pivoted connection 2306. In some embodiments, a removable handle 2308 coupled to a rod 2307 can be inserted through openings at the top of the portions 2302 and 2304 to allow pivoting of the portions 2302, 2304 about the rod 2307.

The base parts 2303 of each portion 2302 and 2304 include respective screw extender openings 2312 and 2314 disposed at the bottom of the respective base parts. The openings 2312 and 2314 are configured to receive upper portions of screw extenders, i.e., tool 2300 is placed on top of the extenders using the openings 2312 and 2314, as shown in FIGS. 23c-i.

The tool 2300 further includes a multi-threaded screw 2310 that is configured to further connect the portions 2302 and 2304 at their base parts 2303. The screw 2310 is configured to be inserted through openings 2309, where the openings 2309 are configured to be disposed substantially perpendicularly to the openings 2312 and 2314. The screw 2310 is configured to include multi-directional threading 2315 and 2317 that is disposed at opposite ends of the screw. The base parts 2303 of each portion 2302, 2304 include respective threading mechanisms 2319, 2321. The mechanism 2319 is configured to interact with threading 2315 of the screw 2310 and mechanism 2321 is configured to interact with threading 2317 of the screw 2310. The screw 2310 can be further configured to include a handle 2320 for rotating the screw once it is inserted through the openings 2309. Since threading 2315 and 2317 have oppositely disposed threads, rotation of the handle 2320 and the screw 2310 in one direction (e.g., clockwise direction 2341) causes base parts 2303 of portions 2302 and 2304 to come closer to each other (i.e., compression). Similarly, rotation of the handle 2320 and the screw 2310 in an opposite direction (e.g., counterclockwise direction 2342) causes base parts 2303 of portions 2302 and 2304 to spread apart from each other (i.e., distraction). Such movement of the base parts 2303 translates into compression/distraction movement of the screw extender towers inserted into the respective openings 2312 and 2314. Compressed extenders are illustrated in FIGS. 23d-e. Distracted extenders are illustrated in FIGS. 23f-i. Because the screw 2310 rotates at the same angular velocity, equal rotational force is applied to the portions 2302 and 2304 that allows the portions to translate along the length of the screw 2310 equally in their respective directions (which depends on compression or distraction).

In some embodiments, the fulcrum handle 2308 can be configured to be removable and can be further configured to accommodate right-handed or left-handed usage. This is advantageous in the event that the portions 2302 and 2304 may need to be separated.

As shown in FIG. 23a, the respective top parts 2305 of the portions 2302 and 2304 can be configured to include openings 2331 that allow access to the screw extender towers that are inserted into the respective openings 2312 and 2314. The surgeon (or other medical professional) can insert instruments or any other tools through the top parts 2305 and respective openings 2331 of the tool 2300 and into the screw extender towers. The openings 2331 can be also configured to provide a visual indicator of the placement of the screws through the screw extender towers/housings.

As can be understood by one skilled in the art, the tool 2300 can be configured to compress/distract at least two screw extender towers.

FIGS. 24a-l illustrate an exemplary end-holding rod inserter tool 2400, according to some embodiments of the present invention. The tool 2400 is used during rod insertion procedures and is configured to grip the rod at a distal end by squeezing onto the rod.

Referring to FIGS. 24a-l, the tool 2400 includes a handle 2402 coupled to a curved shaft 2404. The shaft 2404 includes a distal end 2406 configured to secure a rod and a proximal end 2408 that is coupled to the handle 2404. In some embodiments, the rod can be held at an approximately 75 degrees (or any other angle) with respect to the shaft 2404. The proximal end 2408 is configured to have a curved portion 2409, which allows the user of the tool 2400 to conveniently secure and manipulate the rod inside the screw extenders coupled to respective implanted screw assemblies.

The shaft 2404 is configured to have a stationary or static portion 2412 and a sliding portion 2414. The sliding portion 2414 is configured to slide on top of the stationary portion 2412. The stationary portion 2412 is configured to be permanently secured to the handle (or inside the handle) 2402. Both portions 2412 and 2414 have curved proximal ends 2409 (a, b). The distal end of the stationary portion 2412 further includes an L-shaped receiving groove 2415 that, in combination with the distal end of the sliding portion 2414, is configured to secure the rod. In some embodiments, as illustrated in FIG. 24l, the distal end of the stationary portion 2412 can have a male mating feature 2451 that is configured to interact with a female mating feature 2453a disposed on the rod 2460. The rod 2460 can be configured to have another mating feature 2453b disposed oppositely to the mating feature 2453a and configured to interact with the distal end of the sliding portion 2414 (not shown in FIG. 24l). The rod 2460 is configured to be securely "squeezed" between the mating feature of the stationary portion 2412 and the sliding portion 2414, when the rod is placed into the L-shaped receiving groove 2415.

Figure 24A:
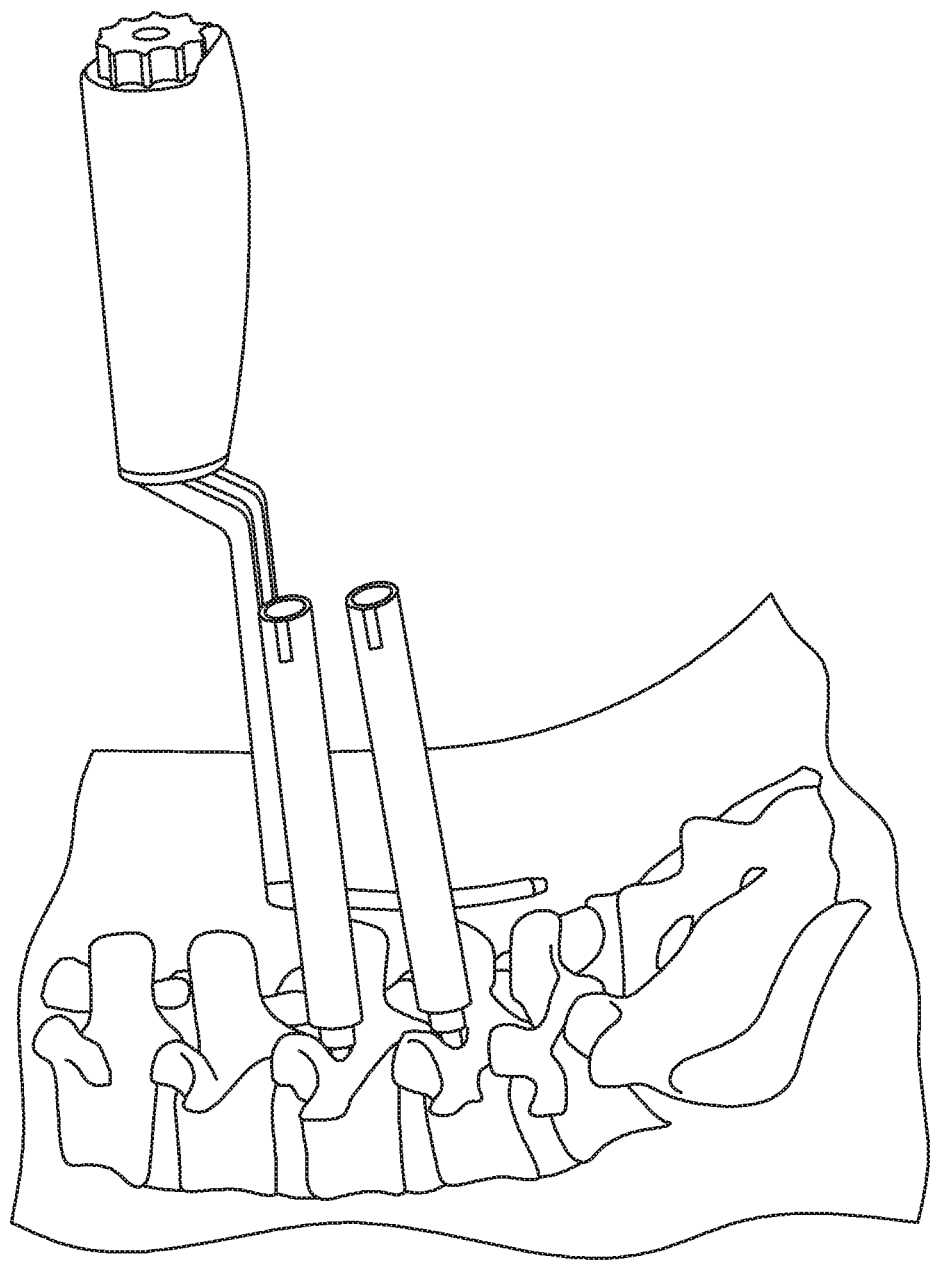
Figure 24G:
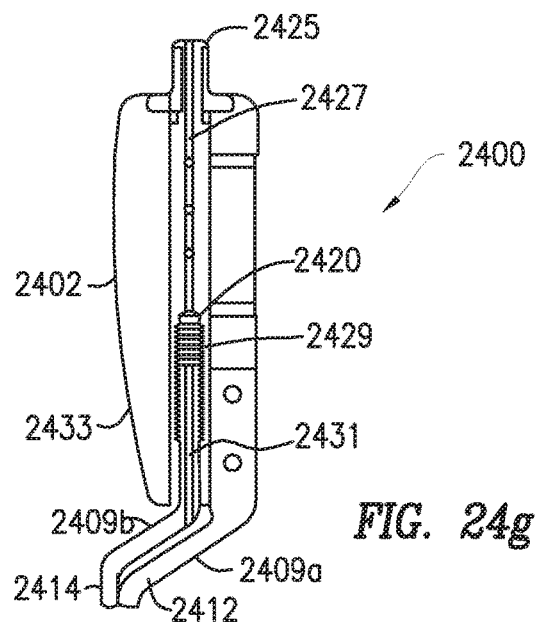
Figure 24H:
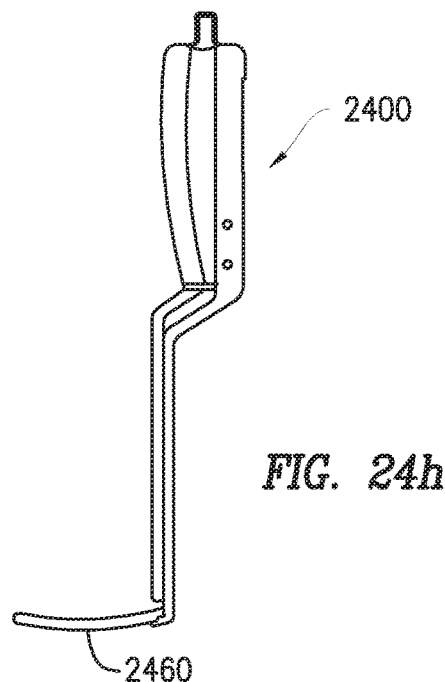
Figure 24I:
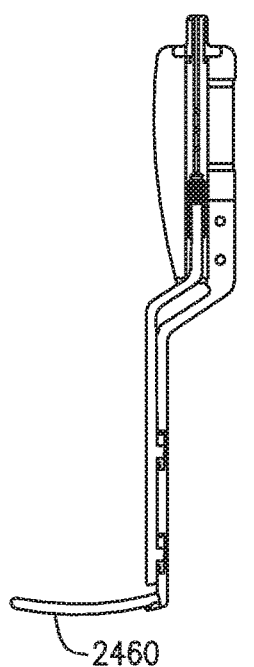
Figure 24J:
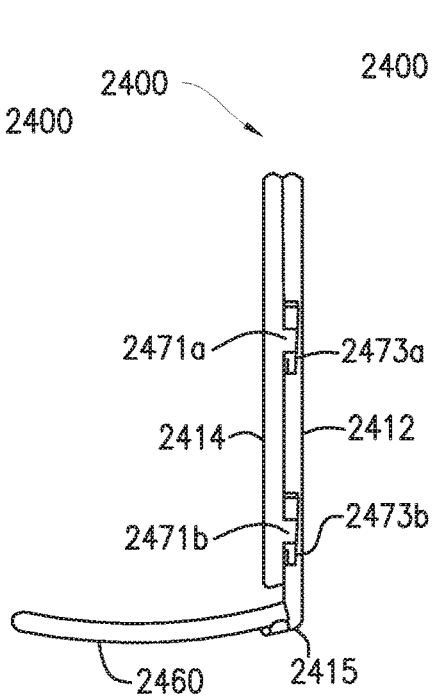
Figure 24K:
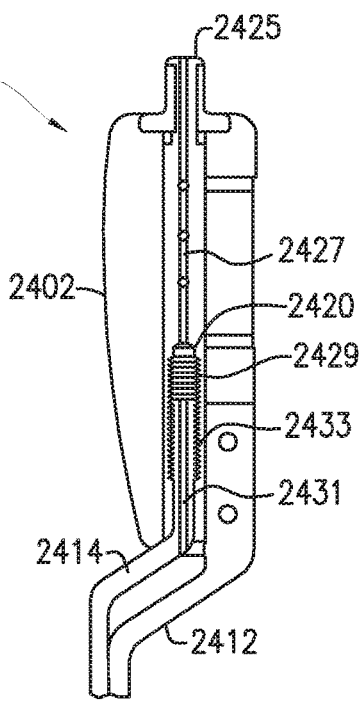
Figure 241:
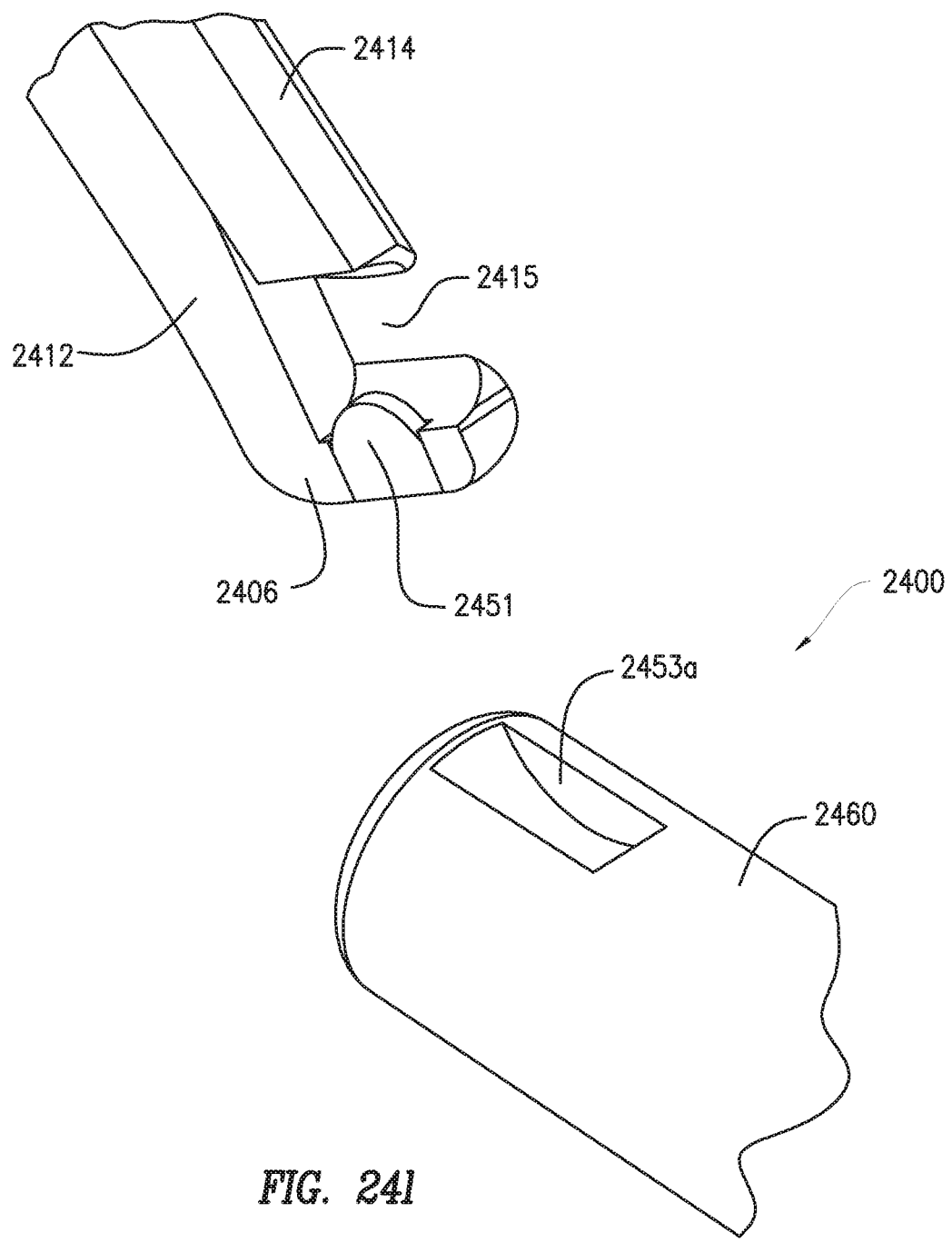
Figure 25A:
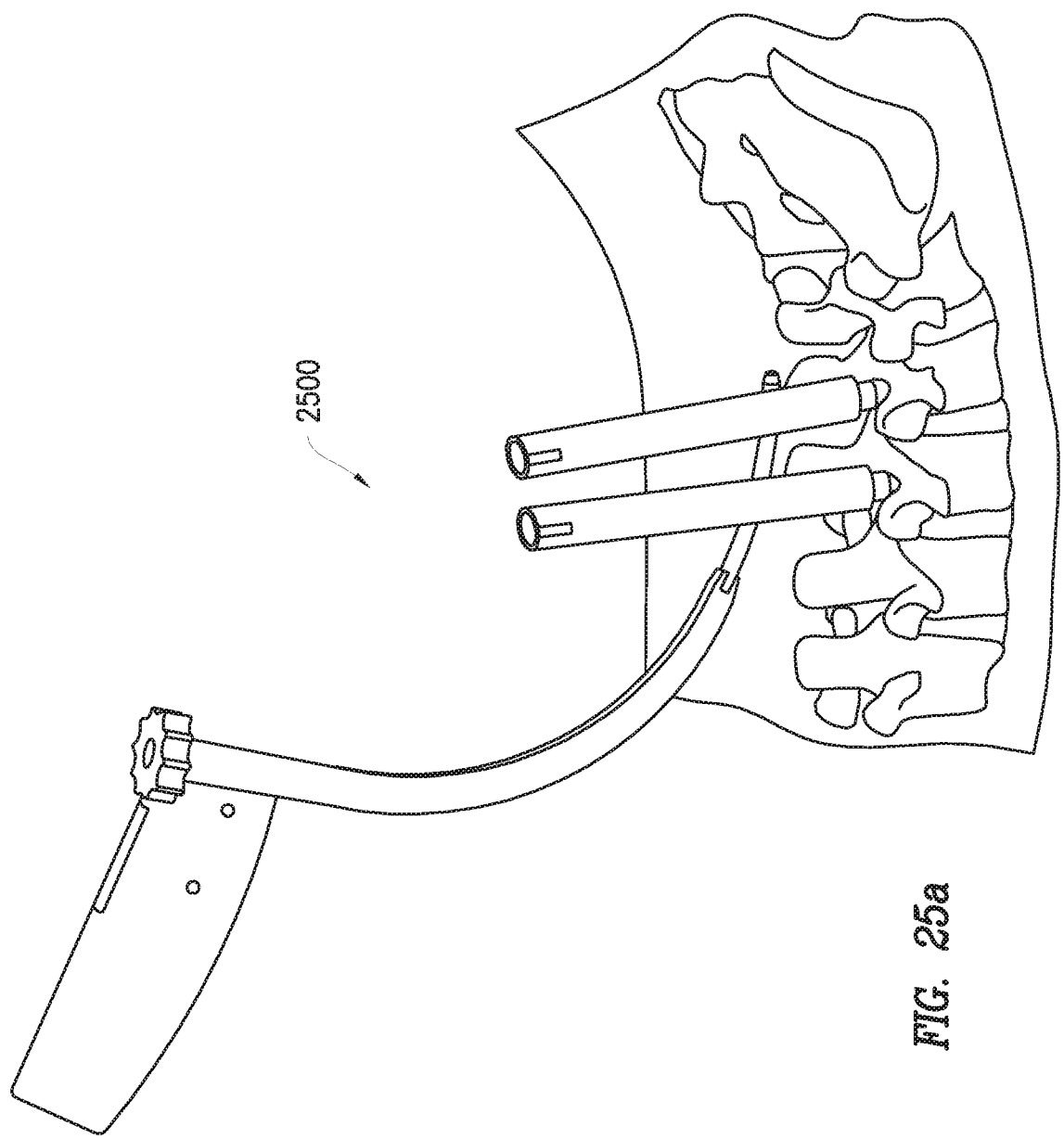

The sliding portion 2414 is configured to be coupled to a rotary mechanism 2420 disposed inside the handle 2402. The rotary mechanism 2420 is further coupled to a control knob 2425. The rotary mechanism 2420 further includes a first rod 2427 that is disposed between and coupled to the knob 2425 and a threaded nut 2429 and a second rod 2431 that is coupled to the threaded nut 2429 and an interior portion of the curved proximal end of the sliding portion 2412. The threaded nut 2429 is configured to rotate inside and along a threaded portion 2433, as shown in FIGS. 24g, 24i, and 24k. The threaded portion 2433 is coupled to the sliding portion 2414 and depending on the movement of the threaded nut 2429 either pulls or pushes the sliding portion 2414 along the stationary portion 2412, as shown in FIGS. 24g and 24k. Rotation and translation of the threaded nut 2429 along the threaded portion 2433 is controlled by the control knob 2425, whose rotational motion causes the first rod 2427 to rotate, thereby rotating the threaded nut 2429 and thus, either pulling towards or pushing away from the control knob 2425.

In some embodiments, the stationary portion 2412 can be configured to have grooved stopper portions 2471 (a, b) disposed in its shaft, and the sliding portion 2414 can be configured to have corresponding protrusions 2473 (a, b) that slide inside the stopper portions 2471 when sliding portion 2414 is translated along the stationary portion 2412. The stoppers prevent the sliding portion 2414 from overextending and thus, damaging the rod 2460 or the tool 2400.

Thus, to secure the rod 2460 to the tool 2400, the control knob 2425 is rotated in one direction (e.g., counterclockwise) to open the L-shaped receiving groove 2415 at the distal end of the shaft of the tool 2400. Thus, such rotation translates the sliding portion 2414 along the stationary portion 2412 toward the handle 2408, thereby spreading apart the distal ends of the portions 2412, 2414 and forming a gap between the proximal curved ends of the stationary and sliding portions, as shown in FIG. 24k. The rod is then placed into the opened L-shaped receiving groove 2415. Optionally, mating features 2451 and 2453a on the stationary portion 2412 and the rod 2460, respectively, can be engaged to further secure the rod. Once the rod 2460 is in place, the knob 2425 is rotated in an opposite direction (e.g., clockwise) and the sliding portion 2414 is translated away from the handle 2408 and toward the distal end of the stationary portion 2412 that is holding the rod 2460. The sliding portion 2414 contacts the rod 2460 and secures it inside the L-shaped receiving groove 2415. Optionally, mating features of the sliding portion and the rod can be engaged to provide further stability to the secured rod. In some embodiments, the tool 2400 can be configured to include a locking mechanism to prevent unintentional translation of the sliding portion 2414. The rod 2460 can be released by performing the above steps in reverse. The mating features are also configured to prevent axial and torsion forces during rod-insertion procedures.

FIGS. 25a-e illustrate an exemplary percutaneous end-holding rod inserter tool 2500, according to some embodiments of the present invention. The tool 2500 is in some respects similar to the tool 2400 as it allows rod holding during insertion of the rod through the screw extender system. The tool 2500 includes a handle 2502 and a curved shaft 2504. The shaft 2504 has a proximal end 2509 to which a control knob 2508 is attached and a distal end 2511 that is configured to secure a rod 2560. The proximal end 2509 is further configured to be permanently coupled to the handle 2502. The handle 2502 is configured to assist the user of the tool 2500 during rod-insertion procedures. The distal end 2511 includes a rod-holding mechanism 2570. The mechanism 2570 is configured to clamp the rod 2560 in a pliers-type fashion. The mechanism 2570 may include an upper immovable lip 2571 that is permanently coupled to the distal end of the shaft 2504 and a pivoting lip 2573 that is rotatably coupled to the distal end of the shaft 2504.

As illustrated in FIG. 25e, in some embodiments, the immovable lip 2571 can be configured to include a male mating feature 2575 that is configured to interact with a corresponding female mating feature 2576 disposed on the rod 2560. In some embodiments, the pivoting lip 2573 can be also configured to include similar mating features that can interact with corresponding mating features disposed on the rod 2560 (not shown in FIG. 25e). Similarly to the tool 2400, the mating features allow better gripping of the rod 2560, when the rod 2560 is placed between the immovable lip 2571 and the pivoting lip 2573. The mating features are also configured to prevent axial and torsion forces during rod-insertion procedures.

The curved shaft 2504 further includes a slidable rod 2520 disposed in an interior portion of the shaft 2504. The slidable rod 2520 is coupled to a threaded mechanism 2525 disposed at the proximal end of the shaft 2504. The slidable rod 2520 is further rotatably coupled to the pivoting lip 2573.

To secure the rod 2560 to the tool 2500, the knob 2508 is rotated in one direction (e.g., counterclockwise), causing the rod 2520 to be pushed away from the handle 2502, and thereby rotating the pivoting lip 2573 in a downward direction away from the immovable lip 2571. The rod 2560 is inserted into an opening created by the two lips 2571, 2573. In some embodiments, the mating features on the rod 2560 and the lip 2571 can interact with each other. Once the rod 2560 is inserted, the knob 2508 is rotated in an opposite direction (e.g., clockwise), thus causing the slidable rod 2520 to retract toward the handle, and thereby rotating the pivoting lip 2573 in an upward direction toward the immovable lip 2571 and the rod 2560. In some embodiments, the mating features of the rod 2560 and the pivoting lip 2573 can be configured to interact to further secure the rod 2560 inside the mechanism 2570. In some embodiments, the tool 2500 can be configured to have a stopper mechanism that can be configured to prevent accidental unwinding of the knob 2508, which can release the rod 2560. As can be understood by one skilled in the art, the tool 2500 can have both lips 2571, 2573 rotate to secure the rod.

FIGS. 26a-k illustrate an exemplary in-situ re-attachment guide tool 2600, according to some embodiments of the present invention. In some embodiments, the tool 2600 is configured to facilitate re-attaching a screw extender 2601 to a screw assembly while the latter one is already implanted into vertebrae. This tool can also be useful in the following scenarios: (1) when screw assembly is by itself; (2) when the screw assembly already includes a rod that has been inserted; and (3) when the screw assembly already includes a rod that has been inserted and secured by a setscrew.

Figure 26A:
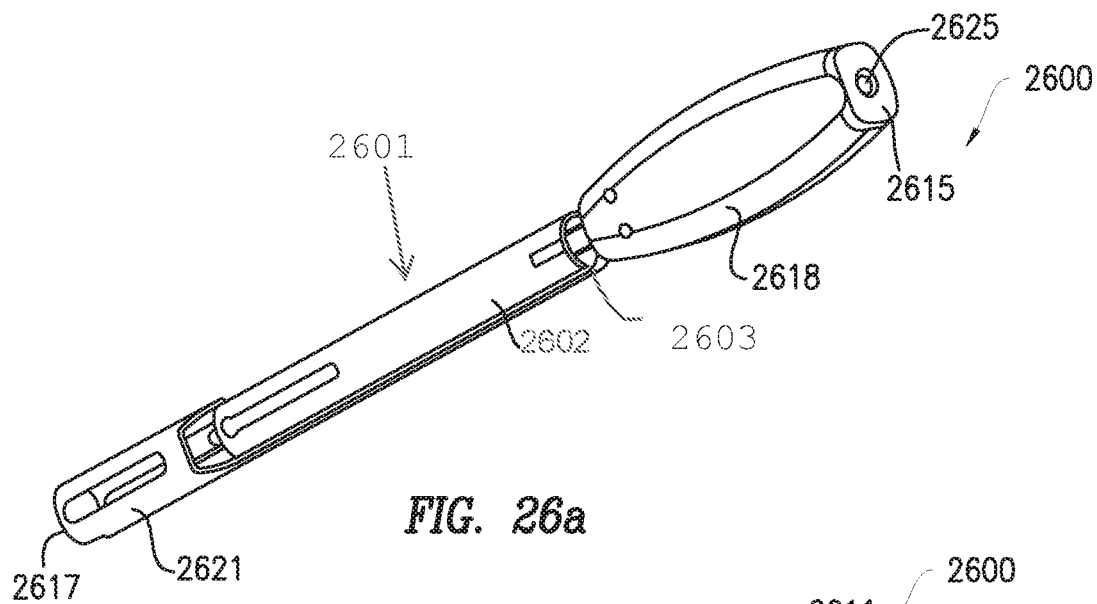
Figure 26B:
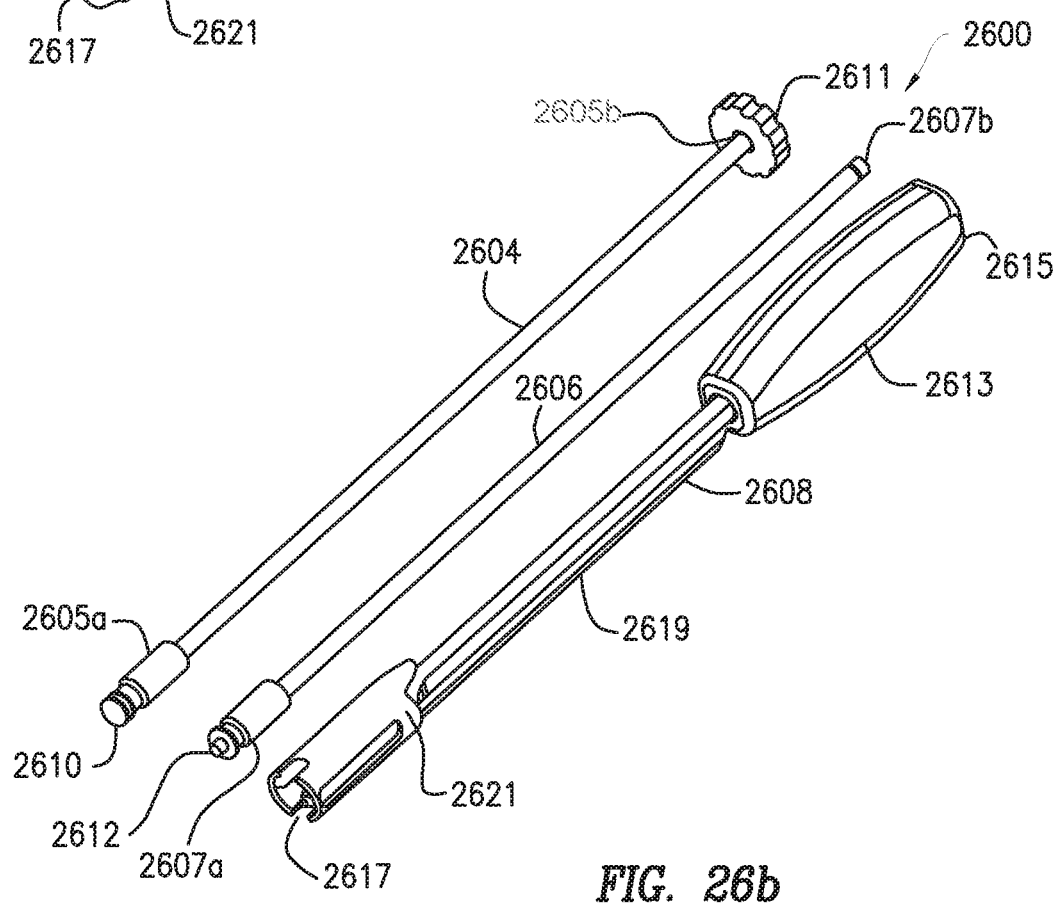
Figure 26G:
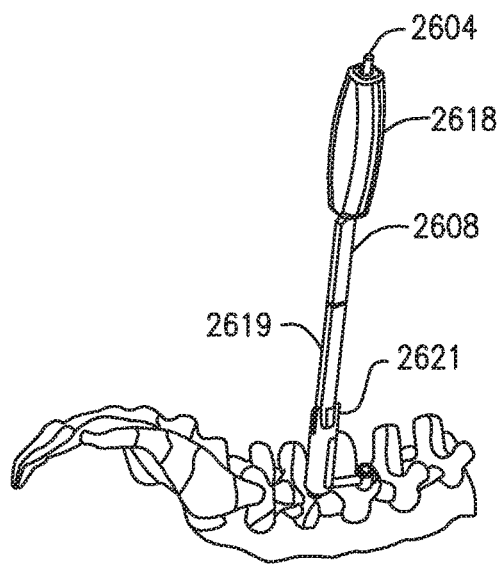

FIG. 26a illustrates the tool 2600 being coupled to a screw extender 2601 having a housing 2602 with a fully open channel 2603. Screw extenders 2601 have been previously discussed above with regard to FIGS. 1-22b. As shown in FIG. 26b, the tool 2600 can be configured to include two removable shafts 2604 and 2606 along with a main assembly 2608. The shaft 2604 is configured to be used when a setscrew has not been attached to a screw assembly being implanted into vertebrae (i.e., scenarios nos. (1) and (2)). The shaft 2604 has a distal end 2605a and a proximal end 2605b. The distal end 2605a includes a threaded tip 2610 that allows screwing the shaft 2604 into the head of the screw assembly when the setscrew is not installed. The proximal end 2605b accommodates placement of a removable knob 2611 that is configured to rotate the shaft 2604 during installation into and removal from the screw assembly.

Alternatively, if the setscrew has been already installed into the screw assembly (i.e., scenario no. (3)), the shaft 2606 can be used. The shaft 2606 includes a distal end 2607a and a proximal end 2607b. The distal end 2607a includes a peg 2612 that is configured to be inserted into the setscrew and that secures the shaft 2606 to the setscrew. The proximal ends 2607b and 2605b are similar to one another. The knob 2611 can be configured to be secured to the proximal end 2607b of the shaft 2606 in the same way as with respect to the shaft 2604.

Once one of the shafts 2604, 2606 is installed into the screw assembly, as shown in FIGS. 26c-d, the main assembly 2608 is the placed over the installed shaft. The main assembly 2608 includes a proximal end 2615 and a distal end 2617 and a shaft 2619 disposed between the proximal end 2615 and the distal end 2617. The proximal end 2615 includes a handle 2618. The distal end 2617 includes a hollow housing 2621 that is configured to be placed over a head of an installed screw and further accommodate placement of a screw extender housing. The shaft 2619 and the handle 2618 include an interior channel 2625, which is used to place the assembly 2608 over the shaft 2604 or 2606. In some embodiments, the length of the shaft 2619 or, alternatively, the distance between the distal end of the handle 2618 and the proximal end hollow housing 2621 is greater than the length of the screw extender 2601 that is to be re-attached to the screw.

The hollow housing 2621 has a diameter that is larger than the diameter of a screw extender 2601 that is to be re-attached to the screw assembly. In some embodiments, the housing 2621 can be further configured to have grooved portions 2622 disposed at its distal end, where the grooved portions 2622 are configured to be placed over the rod that has been previously secured to the screw assembly (if such rod has been installed).

Figure 26H:
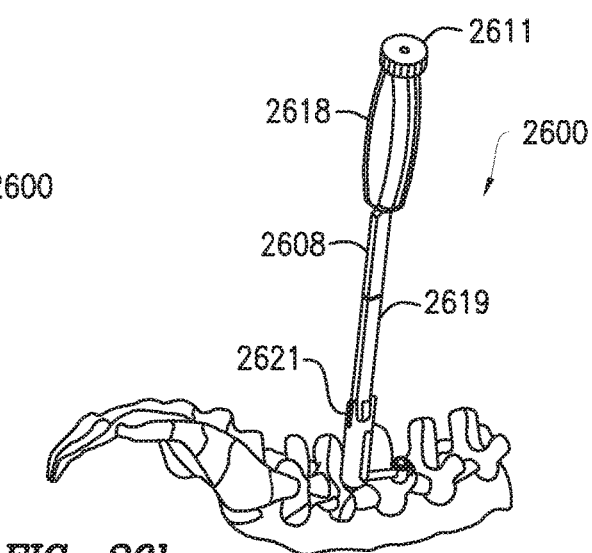
Figure 26I:
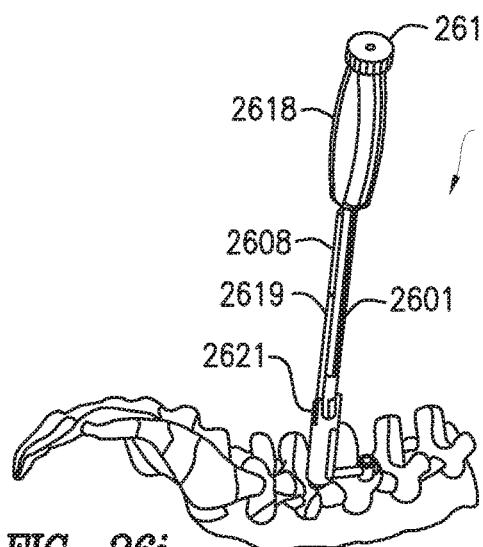
Figure 26J:
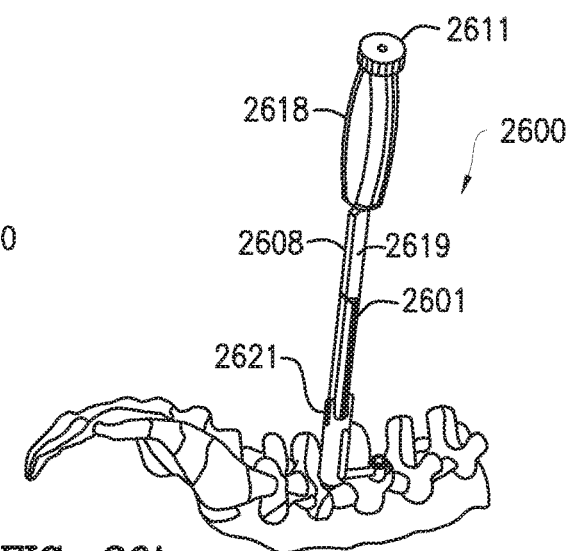
Figure 26K:
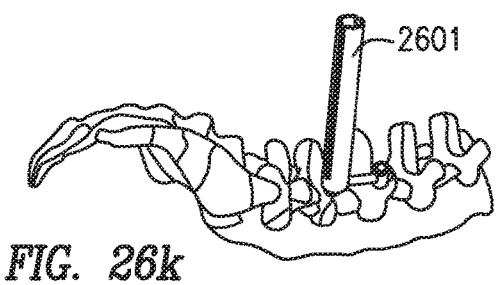

Once the shaft 2604 or 2606 and the assembly 2608 are installed to the screw assembly, the knob 2611 secures the combination of the shaft 2604 (or 2606) and the assembly 2608 to the screw, as shown in FIG. 26h. Then, the screw extender 2601 having an open channel (as illustrated in FIGS. 3a-c) is configured to be slid over the flat shaft 2619 via its open channel. The thickness of the flat shaft 2619 can be configured to be less than the width of the screw extender's 2601 open channel. Once the screw extender 2601 is placed over the shaft 2619 (as shown in FIG. 26i), the screw extender 2601 is translated toward the screw assembly (e.g., in a downward fashion) along the shaft 2619, thereby inserting the screw extender 2601 into the hollow housing 2621, as shown in FIG. 26j. Upon insertion, the screw extender 2601 is secured to the screw assembly, as discussed above with regard to FIGS. 1-22b. Once the screw extender 2601 is secured to the screw assembly, the tool 2600 is removed. The tool 2600 can be unscrewed from the screw assembly, if the setscrew is not installed; alternatively, it can be removed from the screw assembly by removal of the assembly 2608 and the shaft 2606, if the setscrew is installed. Once, the tool 2600 is removed from the screw assembly, the screw extender 2601 is configured to remain attached to the screw assembly, as shown in FIG. 26k.

FIGS. 27a-g illustrate an exemplary rod reducer tool 2700, according to some embodiments of the present invention. In some respects, the rod reducer 2700 is similar to the rod reducer 2100 shown in FIGS. 21a-e with the following differences. In some embodiments, the rod reducer 2700 includes a threaded reduction mechanism and allows its outer shaft portion to be independent of the spinning or rotating forces. The handle of the rod reducer 2700 is configured to be attached to an internal thread that engages a screw extender tower. The rod reducer 2700 includes a collar that is attached to the main shaft and is configured to float within the handle assembly. As such, the rotational threading of the rod reducer 2700 causes the rod to be forced downward along the screw extender, however, the collar and/or the main shaft of the rod reducer are configured to remain in place. The rod reducer 2700 is configured to provide counter-rotational forces on the rod and to further provide a better translation of downward forces from the rod reducer to the rod.

Figure 27A:
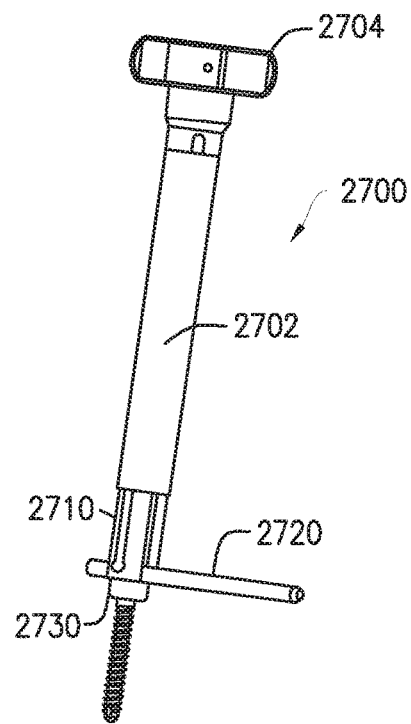
FIGS. 27*a*-*i* illustrate an exemplary rod reducer tool, according to some embodiments of the present invention.
Figure 27B:
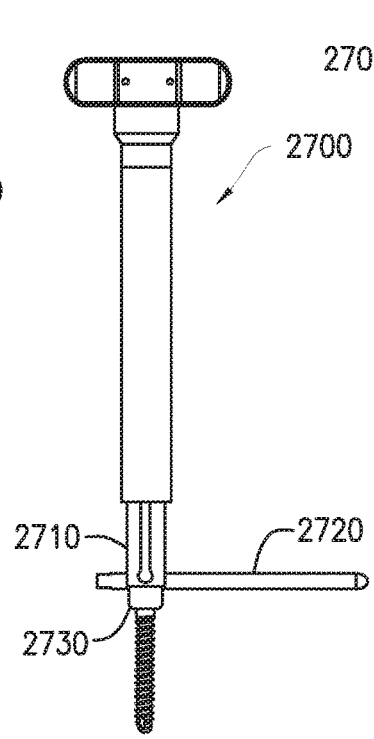
Figure 27C:
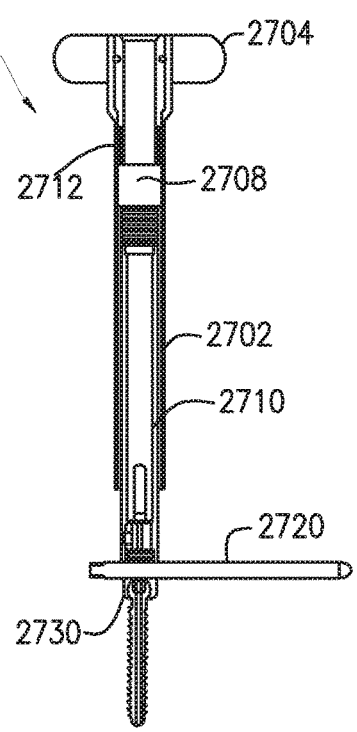
Figure 27D:
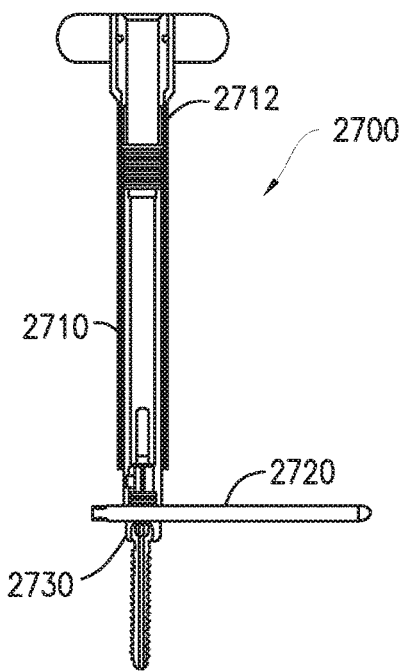
Figure 27E:
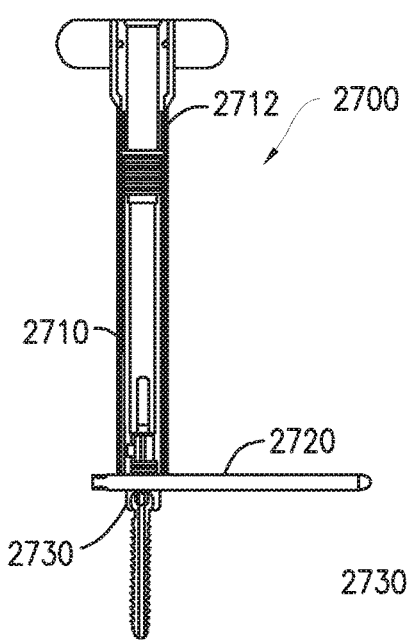
Figure 27F:
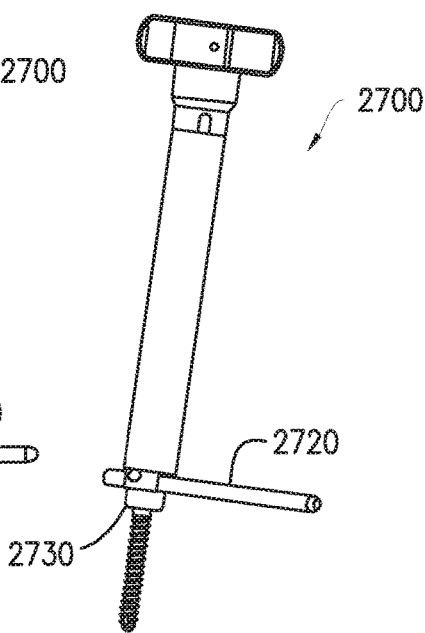
Figure 27G:
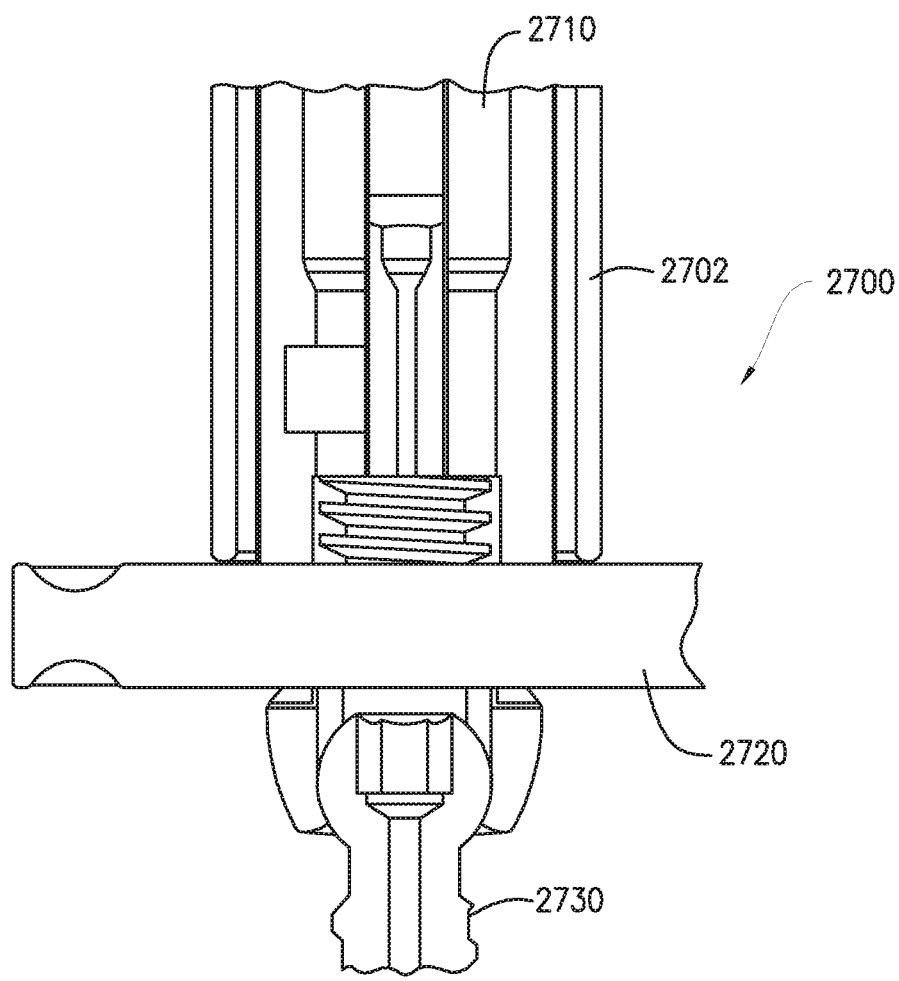

Referring to FIG. 27a-f, assuming that a screw extender tower/housing 2710 is already coupled to the screw assembly 2730 that has been implanted into the vertebrae and a rod 2720 has been placed inside the screw extender 2710 substantially adjacent to the screw assembly, the rod reducer tool 2700 can be placed over the screw extender tower/housing 2710 for further securing the rod 2730 in place. In some embodiments, the rod reducer 2700 includes a main shaft 2702 coupled to a handle 2704. As shown in FIG. 27c, a cross-sectional view of the rod reducer 2700, the rod reducer includes a hollow interior 2708 that is configured to accommodate placement of the screw extender housing/tower 2710 (See, FIGS. 27d-e). The handle 2704 is configured to include an interior threading mechanism 2712 that is further configured to engage the screw extender housing 2710, as shown in FIGS. 27d-e. Upon engaging the screw extender tower, the threading mechanism 2712 is rotated in a downward fashion using the handle 2704, thereby translating the rod reducer 2700 also in a downward direction toward the screw assembly and the rod. The handle is configured to rotate together with the main shaft 2702. In some embodiments, the handle is configured to rotate independently of the main shaft 2702, where the main shaft 2702 does not rotate. Such translation of the rod reducer 2700 pushes the rod toward the screw assembly, as shown in FIGS. 27e-g. After pushing the rod to the screw assembly, the rod reducer tool 2700 is removed.

Figures 27H, 27I:
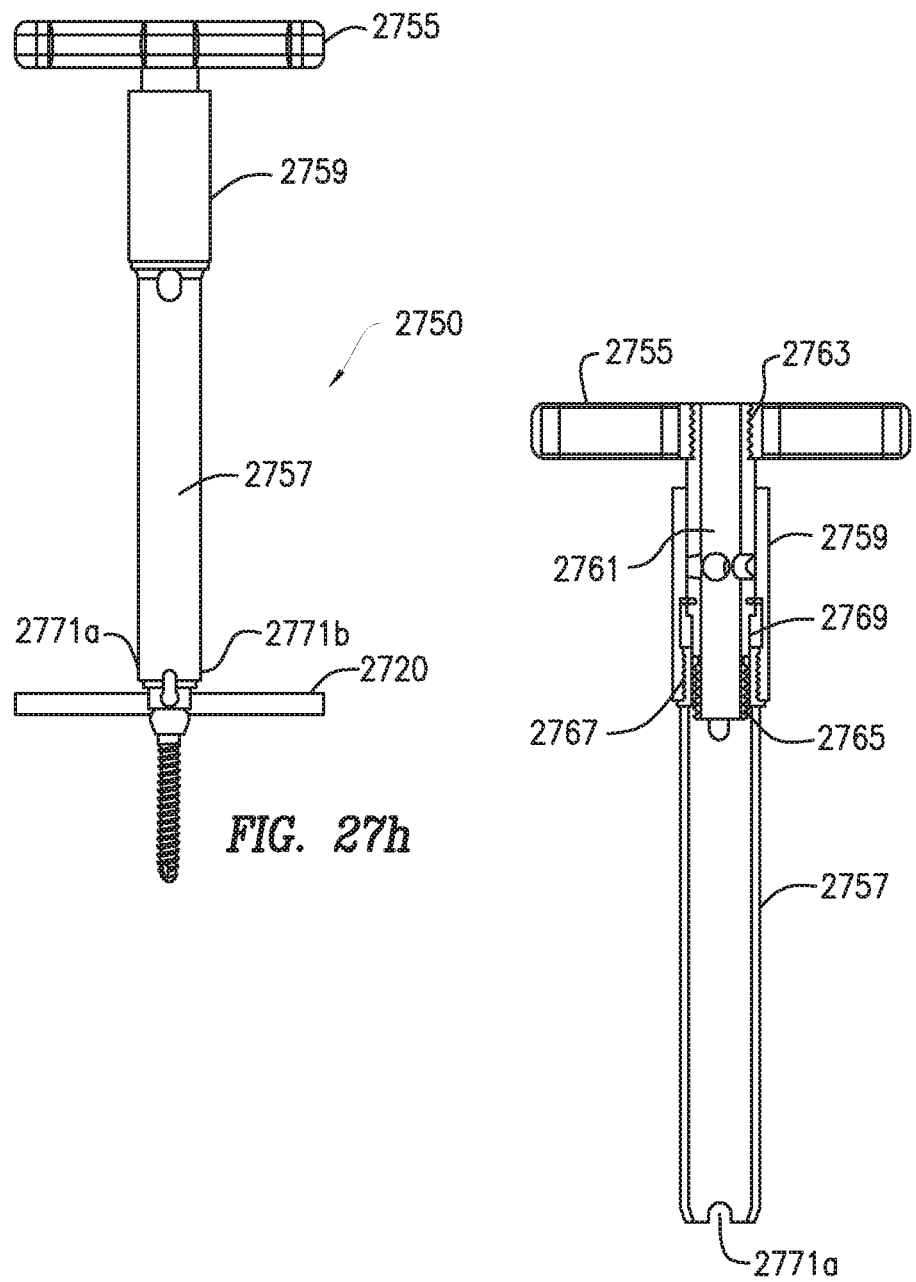

FIGS. 27h-i illustrate an alternate embodiment of a rod reducer tool 2750, according to some embodiments of the present invention. The rod reducer tool 2750 is configured to be similar to the rod reducer tool 2700. The tool 2750 includes a handle 2755, a main shaft 2757, and a collar 2759 disposed between the handle 2755 and the main shaft 2757. The handle 2757 includes a handle shaft 2761, a first handle threading 2763 and a second handle threading 2765, wherein the first handle threading 2763 is disposed at the proximate end of the handle shaft 2761 and the second handle threading 2765 is disposed at a distal end of the handle shaft 2761. The first handle threading 2763 is configured to allow spinning of the handle 2755 about the handle shaft 2761 during the translational movement of the tool 2750 along the screw extender tower (not shown in FIGS. 27h-i). The second handle threading 2765 is configured to engage the screw extender tower in similar fashion as discussed above and shown in FIGS. 27a-g. The collar 2759 is configured to include a collar threading 2767 that interacts with a shaft threading 2769 during rod reduction procedure (i.e., translation of the shaft in a downward fashion along the screw extender tower/housing). The collar 2759 allows a user to hold the collar 2759 during the rod reduction procedure and rotate the handle 2755 to force the tool 2750 toward the screw assembly and to thereby push the rod toward the screw assembly. It should be noted that during rod reduction procedures, the main shaft 2757 is static, while handle 2755 and the collar 2759 are configured to rotate independently of one another and the shaft 2757. In some embodiments, the distal tip of the shaft 2757 includes two grooved portions 2771 (a, b) that are configured to accommodate placement of the rod during rod reduction procedures. The grooved portion 2771 allow better stability of the rod reducer tool 2750 during the procedure.

FIGS. 28a-e illustrate another exemplary tool, a screw extender remover tool 2800, according to some embodiments of the present invention. The tool 2800 is configured to be used when it is necessary to remove a screw extender tower/housing that has been attached to a screw assembly. This tool is configured to easily release the screw extender from the screw assembly while localizing and minimizing axial forces on the screw assembly.

Figure 28E:
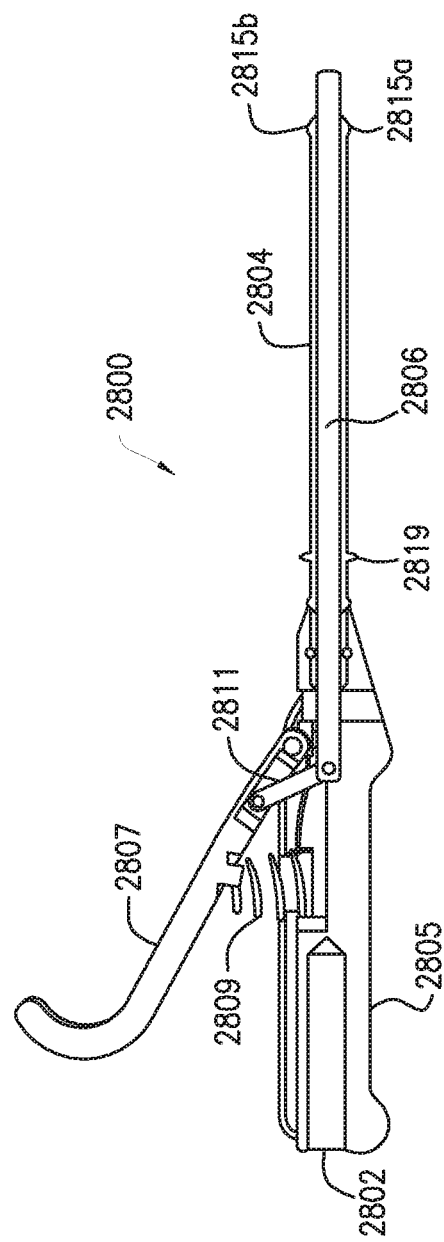

Referring to FIG. 28e, in some embodiments, the tool 2800 includes a handle 2802 coupled to a shaft 2804. The handle 2802 includes a static portion 2805 and a moving portion 2807. The moving portion is resistance-loaded using a spring-like mechanism 2809. The mechanism 2809 allows moving portion 2807 to be pushed toward the static portion 2805 against resistance of the mechanism 2809 and to return portion 2807 to its original state upon its release. The moving portion 2807 is coupled to a lever 2811, which is in turn coupled to an internal shaft 2806 disposed within the shaft 2804. The shaft 2804 is configured to have a smaller diameter than the internal diameter of screw extender housing, which is to be removed from the screw assembly. The lever 2811 is pivotally coupled to both the moving portion 2807 and the internal shaft 2806. Upon squeezing of the portion 2807 of the handle 2802, the pivotal connections of the lever 2811 rotate and push the internal shaft 2806 along the interior of the shaft 2804 and away from the handle 2802. This causes the distal end of the internal shaft 2806 to extend beyond the distal end of the shaft 2804. Upon release of the portion 2807, the internal shaft 2806 returns to its original position within the shaft 2804.

The shaft 2804 further includes protrusions 2815 (a, b) disposed on its outer circumference substantially adjacent the distal end of the shaft 2804. The protrusions 2815 are configured to interact with flexible indentor portions 240 (see, FIG. 2a) upon insertion of the tool 2800 into the screw extender housing 2820, as shown in FIGS. 28a-e. The protrusions 2815 are configured to push apart the flexible indentor portions 240 and thereby free screw extender housing from the locked arrangement with the screw assembly 2830. Thus, to remove the screw extender tower/housing from the screw assembly, the tool 2800 is inserted into the screw extender housing until its distal end is substantially adjacent the setscrew of the screw assembly, the tool 2800 may be rotated so that the protrusions 2815 contact and subsequently push apart (i.e., away from the head of the screw assembly) the flexible indentor portions 240, then the movable portion 2807 of the handle 2802 is squeezed, thereby extending the internal shaft 2806 beyond the distal end of the shaft 2804 and pushing the internal shaft 2806 against the setscrew of the screw assembly and removing the screw extender from the screw assembly, as shown in FIGS. 28a-e. In some embodiments, the shaft 2804 can be configured to include a stopper 2819 that contacts the proximal end of the screw extender housing upon insertion of the tool 2800 and prevents over-insertion of the tool.

Figure 29A:
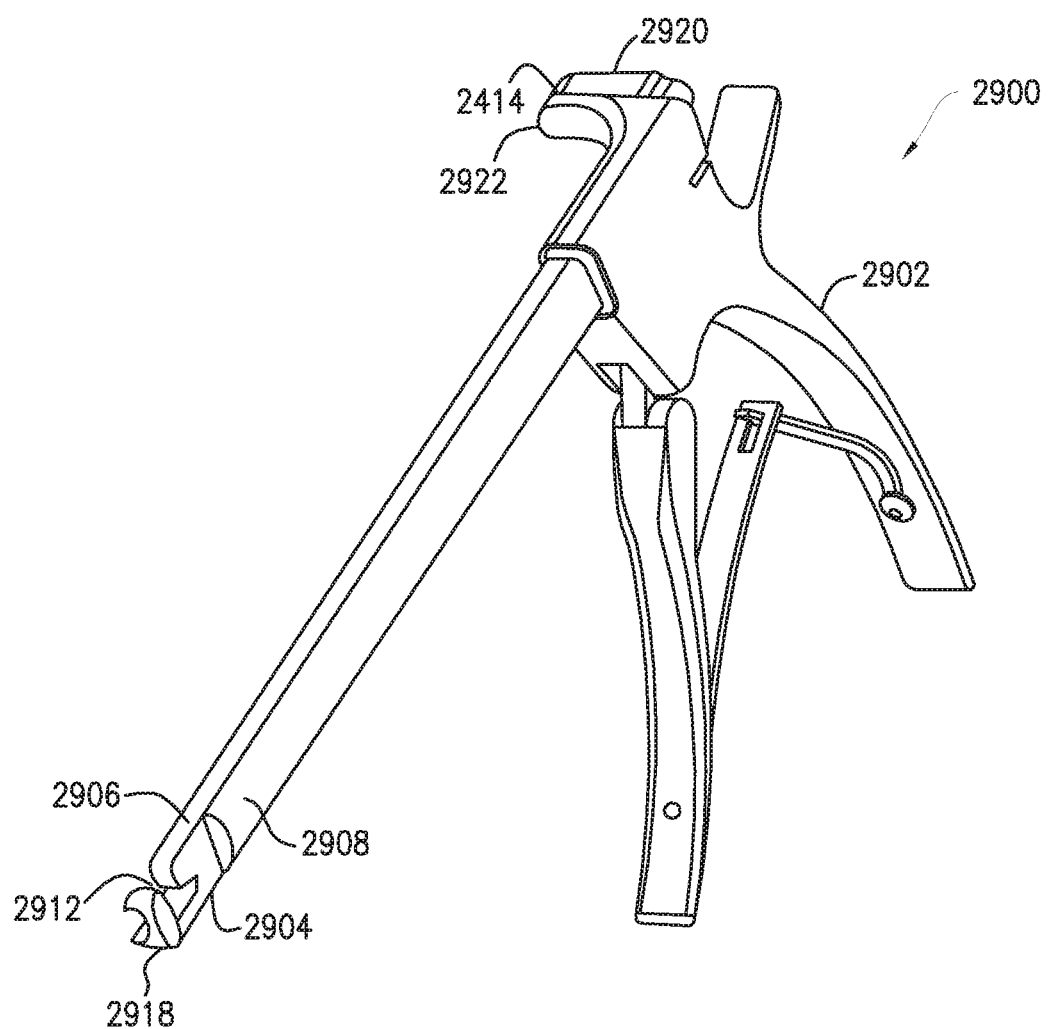
FIGS. 29*a*-*f* illustrate an exemplary rod inserter tool, according to some embodiments of the present invention.
Figure 29B:
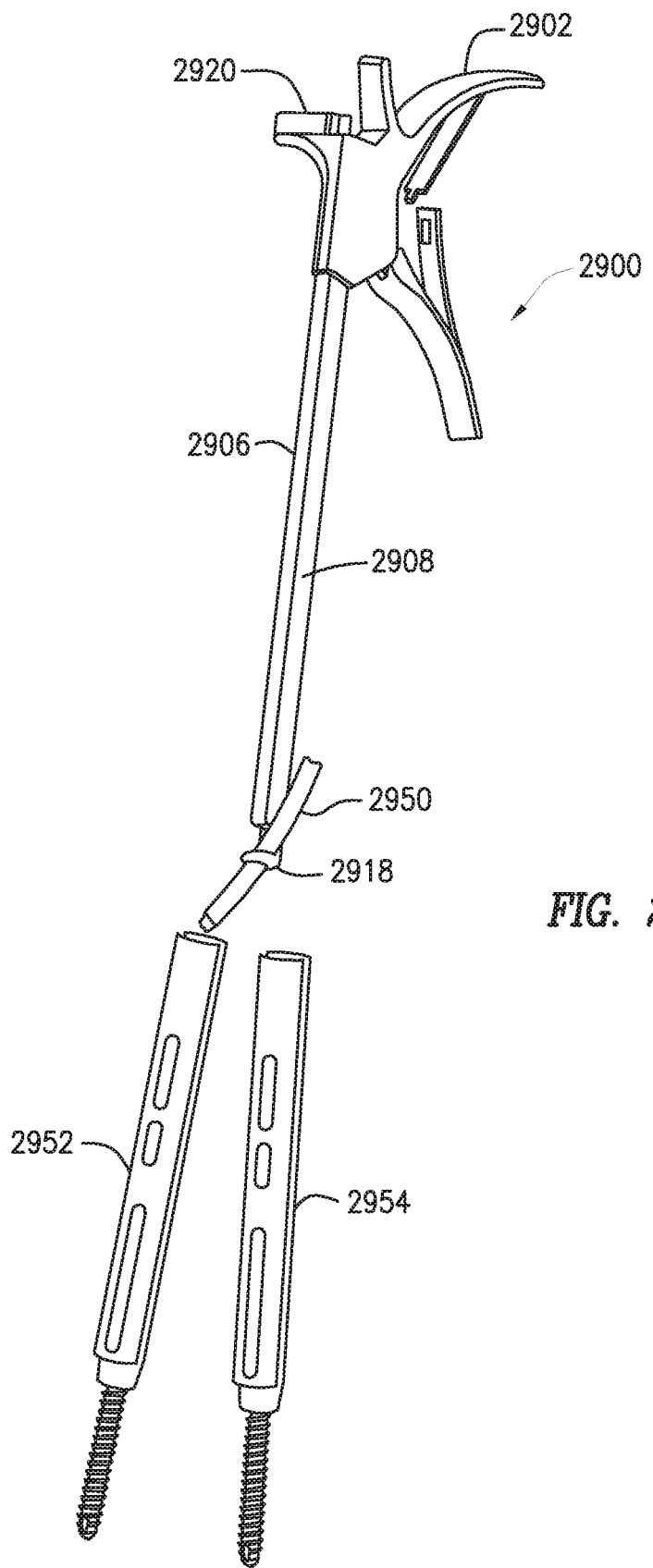
Figure 29C:
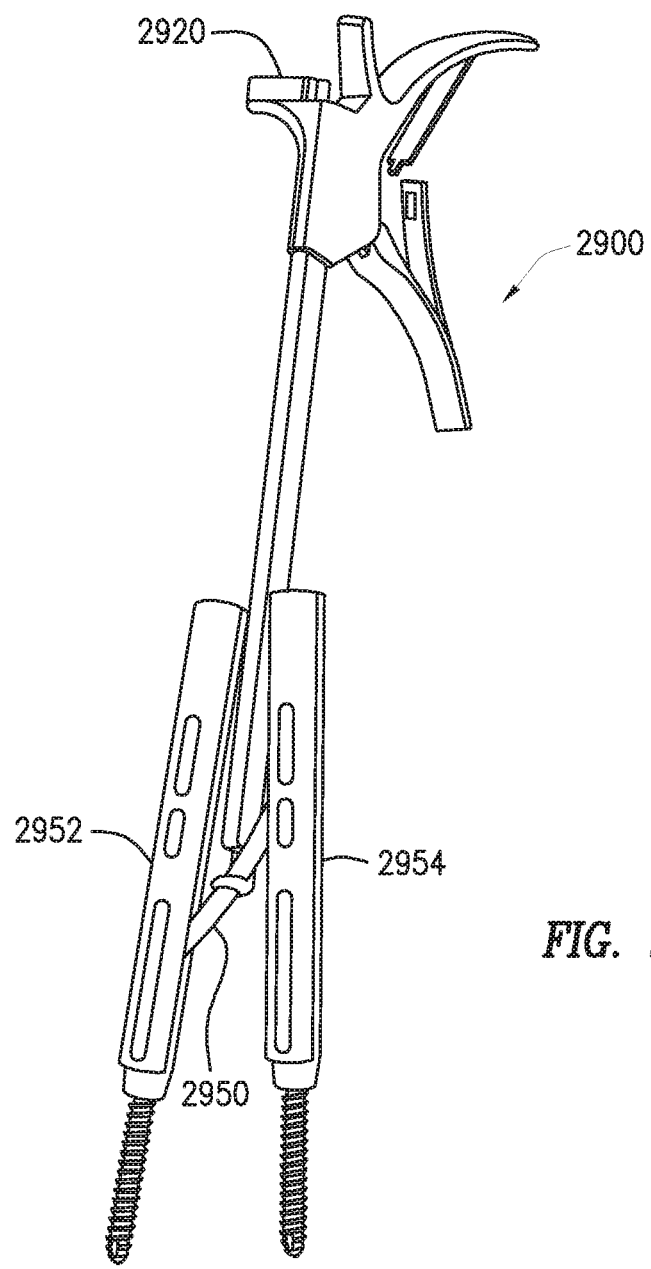
Figure 29D:
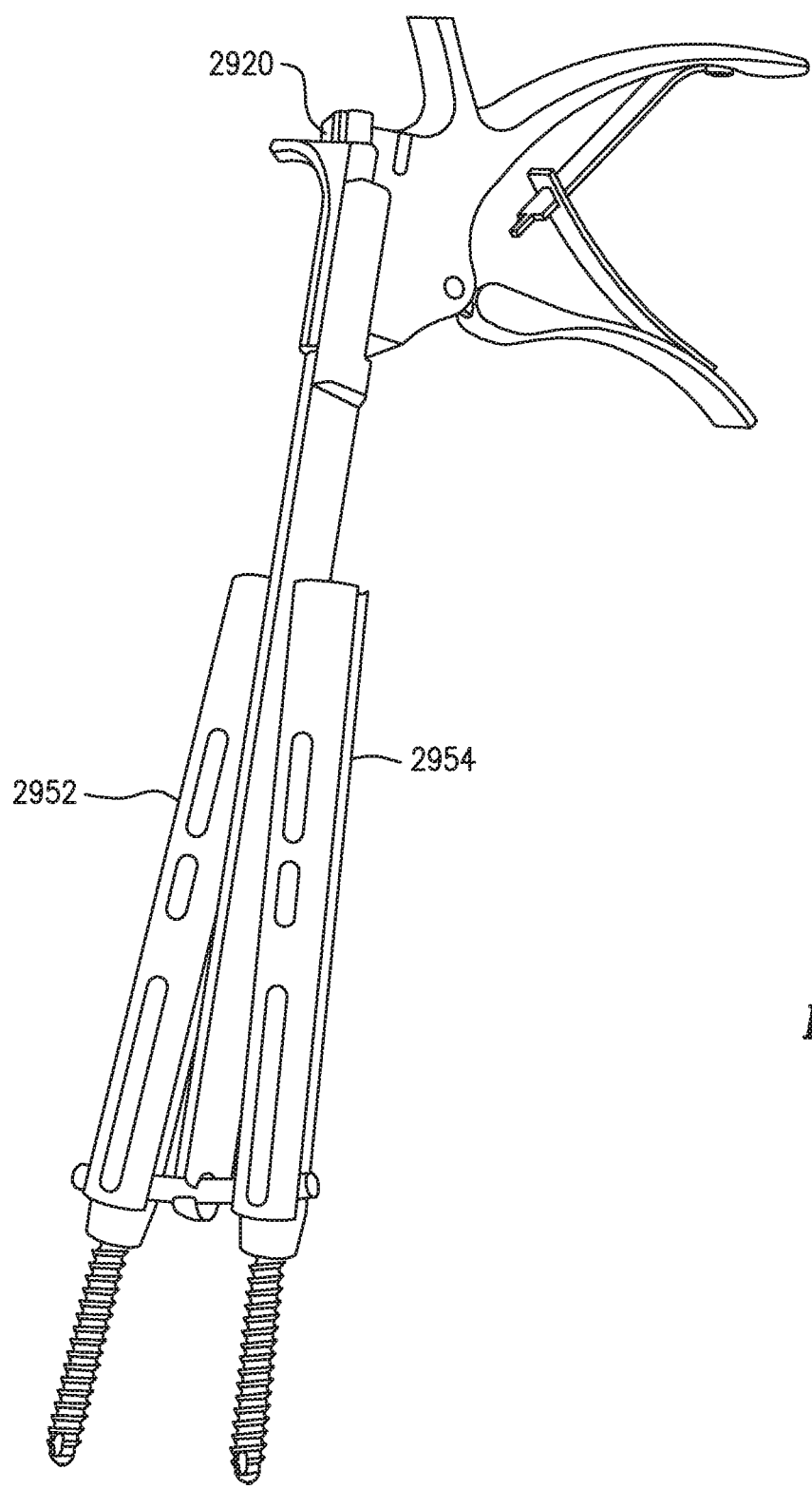

FIGS. 29a-f illustrate an exemplary rod inserter tool 2900 for inserting a connecting element through a diverging exposure of a soft tissue, which is created by the screw extenders, according to some embodiments of the present invention. The tool 2900 includes a handle 2902, a main housing 2904, a secondary housing 2906, a lateral housing 2908, and a switch 2910. The handle 2902 is disposed at the proximal end of the main housing 2904. The tool 2900 further includes a rod holding mechanism (or jaws) 2912 disposed at a distal end of the main housing 2904. The rod holding mechanism 2912 is configured to secure a rod 2950 while it is being inserted between two screw extender housings 2952 and 2954 that are coupled to installed screws, as shown in FIGS. 29b-d. The main housing 2904 is disposed between the handle 2902 and the distal end of the tool 2900. The sub housing 2906 and the lateral housing 2908 are configured to be disposed along the main housing 2904. The tool 2900 further includes a switching mechanism 2914 disposed at the proximal end of the tool 2900 and substantially adjacent to the main housing 2904 and the handle 2902. The switching mechanism 2914 is further illustrated in FIGS. 29e-f. The switching mechanism 2914 is configured to release the rod 2950 once it is installed between two screw extender housings 2952 and 2954.

The rod holding mechanism 2912 is formed using distal ends of the main housing 2904, secondary housing 2906, and the lateral housing 2908. The distal end of the main housing 2904 includes an "L-shaped" gripping feature 2918 that allows placement of the rod in a substantially vertical position with respect to the housings 2904, 2906, 2908, as shown in FIG. 29b. The distal end of the lateral housing 2908 is configured to push on a portion of the rod that is disposed adjacent to the distal end of the lateral housing 2908 in order to rotate the rod into a horizontal position, as shown in FIG. 29d.

Figure 29E:
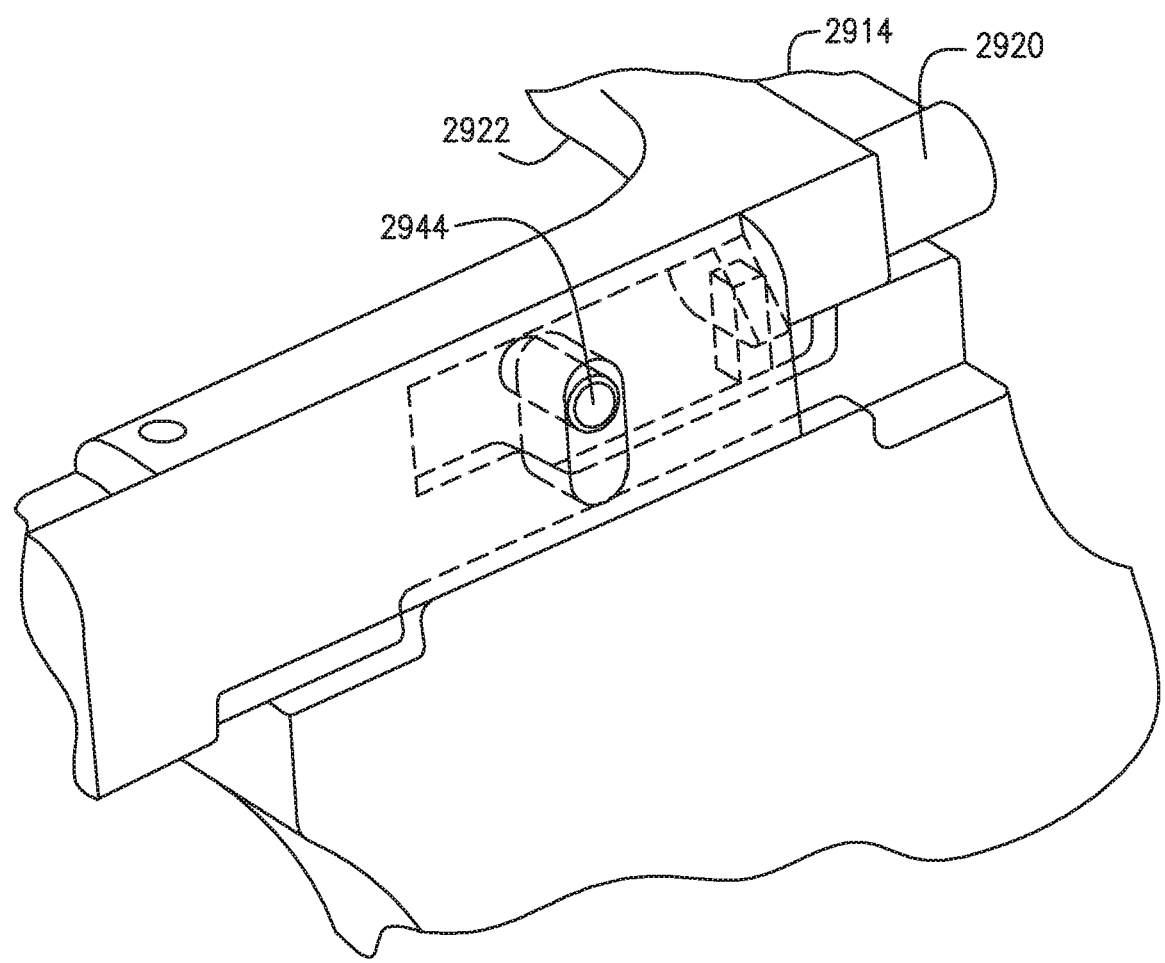
Figure 29F:
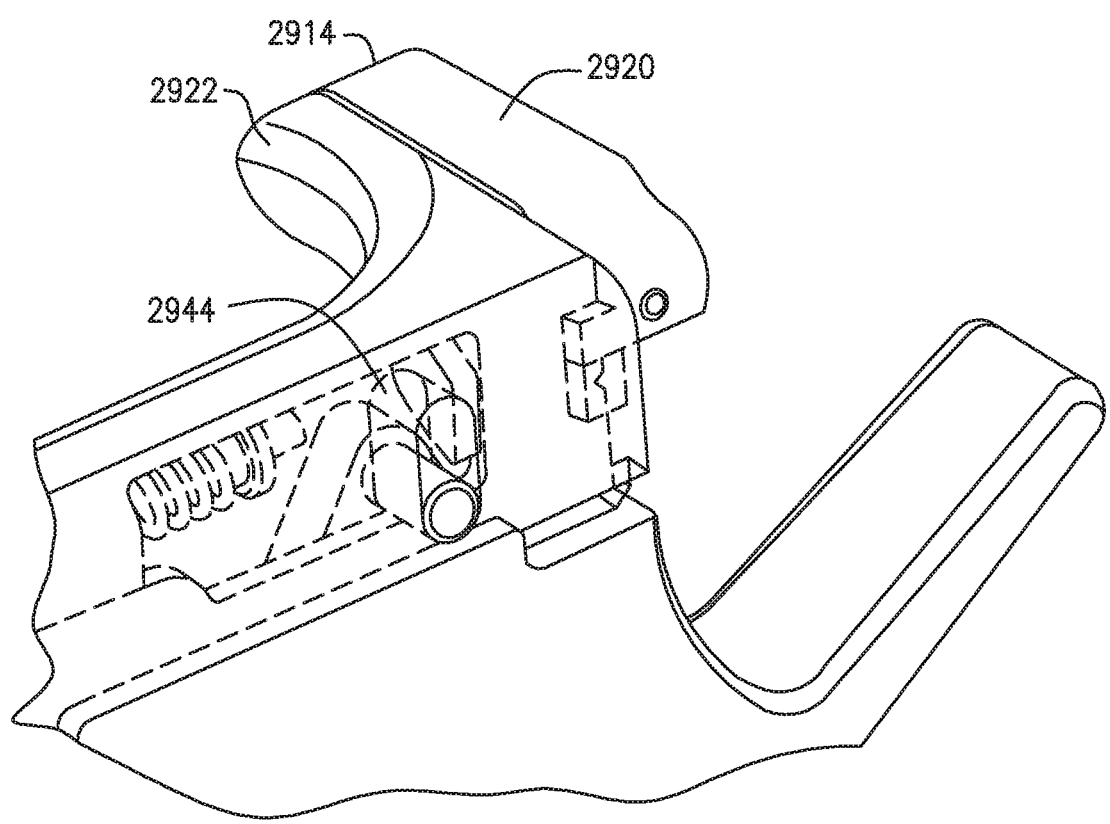

The housings 2904, 2906, and 2908 are configured to be internally coupled to the handle 2902 and the switching mechanism 2914. The handle 2902 is configured to be spring-loaded having a resistance spring that allows return of the handle 2902 into an initial state after the user has squeezed the handle 2902. The switching mechanism 2914 includes a lever 2920 disposed on the handle 2902 substantially adjacent to the proximal end of the main housing 2902. The lever 2920 is further disposed adjacent to a tab 2922. Rotation of the lever 2920 allows release of the rod from the holding mechanism 2912. The lever 2920 is further interconnected with a holding pin 2944, as shown in FIGS. 29e-f. Upon rotation of the lever 2920 in a downward direction, as shown in FIG. 29e, the pin 2944 is configured to be pulled in an upward direction, thereby releasing the housing 2906 from a position, in which it is configured to hold the rod 2950 (see, FIG. 29d). Once the housing 2906 is released, the user can pull on the tab 2922 to release the rod 2950 from the tool 2900 (and vice versa).

The tool 2900 is configured to hold the rod 2950 at an almost vertical position during insertion. The tool 2900 further allows manipulating the rod horizontally once the rod is inserted through a small incision in the skin of the patient to install the rod 2950 between two pedicle screws, as shown in FIGS. 29b-d. The tool 2900 allows its user (a surgeon or any other medical professional) to grip the rod 2950 mid-span without requiring a special feature (e.g., a groove for clamping, etc.) to be placed on the rod. The tool 2900 further allows its user to place the rod 2950 through an incision having a small opening but diverging as the incision deepens. In some embodiments, the tool 2900 is configured to combine two motions in different directions by squeezing the tool 2900, i.e., it allows holding the rod in semi-vertical orientation and then rotating it into a horizontal position for installation between two pedicle screws.

FIGS. 29b-d further illustrate procedure for inserting the rod 2950 using the tool 2900. To install the rod 2950, the user loads the rod 2950 into the tool 2900 by coupling the rod 2950 to the rod holding mechanism 2912 located at the distal end of the tool 2900. To load the rod 2950, the secondary housing 2906 is pulled back using the tab 2922 and the rod 2950 is placed into the L-shaped gripping feature 2918. The secondary housing 2906 is configured to be spring-loaded (e.g., having a spring disposed inside the secondary housing) and is further configured to return to its original position with respect to the main housing and toward the loaded rod 2950. Once the secondary housing 2906 is returned to its original position, the rod 2950 is secured at the distal end of the tool 2900. Thus, the rod 2950 is ready to be placed through the incision.

During insertion of the rod, the user may wish to rotate to rod to place it into a horizontal position to secure it to the pedicle screws. In order to rotate the rod 2950, the user compresses the handle 2902. Handle compression actuates the lateral housing 2908, which causes the lateral housing 2908 to slide along the main housing 2902 toward the secured rod 2950. The distal end of the lateral housing contacts the rod 2950 and forces the rod to rotate into a substantially horizontal position. During the rotation process, the main housing serves as a fulcrum and continues to hold the rod 2950. Further, the secondary housing is configured to be pushed away from the rod and toward the proximal end of the secondary housing upon actuation of the lateral housing and rotation of the rod. Thus, upon fully squeezing the handle 2902, the rod 2950 is configured to rotate to a position that is substantially perpendicular to the axis of the main housing.

Once the rod 2950 is secured to the pedicle screws, the rod is released. To release the rod 2950, the user rotates the switching mechanism from its first position (loading position) to its second position (releasing position), thereby locking the lateral housing 2908 and the secondary body 2906 together. Upon locking the two housings together, the user releases the handle 2902 and the rod 2950 remains in a horizontal position and free from the secondary and lateral housings 2906, 2908. At which point, the inserter tool 2900 can be removed from the incision. To re-grip the rod 2950, the user can squeeze the handle 2902 and rotate the switching mechanism in an opposite direction from its second position to its first position, thereby securing the rod 2950 to the holding mechanism.

In some embodiments, a surgeon can implement one or multiple tools discussed above and shown in FIGS. 1a-29f in connection with a screw extender system and a screw assembly. In an exemplary procedure, a patient can be positioned prone, lying flat on a radiolucent table. Chest rolls may be used, but it is preferable to avoid knee-to chest positions. Adequate clearance may be provided around the surgical table for use of a fluoroscopic C-arm. In some cases, preoperative planning may determine proper pedicle targeting, including an appropriate entry point and trajectory. For pedicle targeting, fluoroscopic imaging can be used to verify anterior-posterior and lateral images of the spine to adequately delineate pedicle morphology and geometry. After identifying pedicle entry point, a targeting needle is used to initiate the entry point. Entry angle and trajectory can be adjusted using fluoroscopic imaging until proper position is obtained. Once the targeting needle is in place, an inner stylet of the needle can be removed. The needle is cannulated to allow for placement of guidewire. The guidewire is inserted through the needle to a desired depth while observing that the guidewire does not cause any damage. Then, after the guidewire is inserted, the needle is removed. For the purposes of spreading apart the tissue and allowing placement of screw extender housing/towers and tools, variable-diameter dilators are advanced along the guidewire. Upon placement of a larger diameter dilator, a smaller diameter dilator is removed and a cannulated awl is placed over the guidewire through the larger diameter dilator to breach the cortex at the pedicle entry point. The pedicle can be tapped using a cannulated tap tool once the cannulated awl is removed. This completes the pedicle preparation stage of the surgical procedure. At this time, the surgeon can begin insertion of the screw. The cannulated tap tool is removed and further larger-diameter dilators are placed over the guidewire. As stated above, the screw extender housing is attached to a cannulated polyaxial screw (or any other type of suitable screw) prior to being installed on the chosen site. In some embodiments, a screw alignment guide tool can be used to attach the screw to the screw extender. Once the screw extender is coupled to the screw, using a screw driver having an axial handle or a T-handle, the combination of the screw extender and the screw are placed over the guidewire and through the attached dilator. The screw is then inserted into the pedicle using the screw driver. After inserting the screw into the pedicle, the screw driver and the dilator are removed. The above procedure can be repeated for any subsequent screws and screw extenders.

Figure 30:
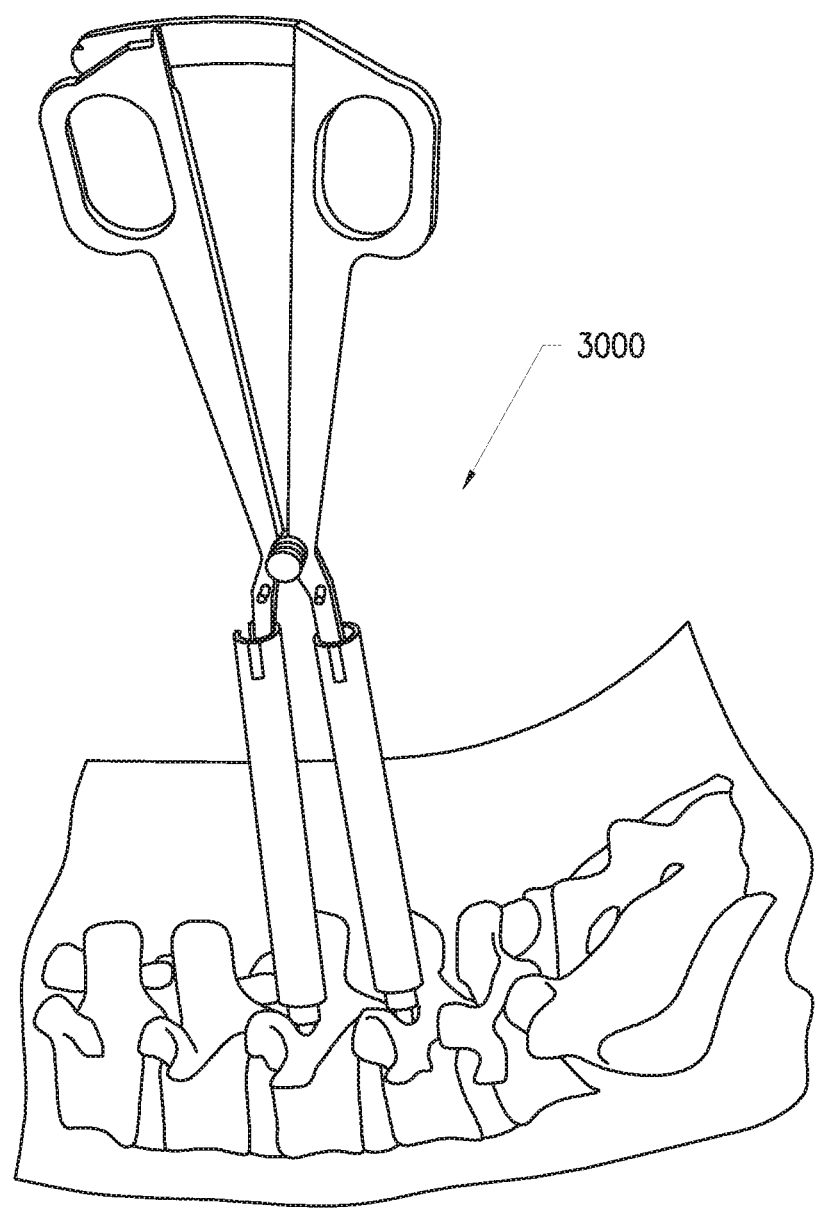
FIG. 30 illustrates a conventional rod caliper tool for measuring length of a rod.

Once the screws with their respective screw extenders are installed at the site, rod insertion procedure can be initiated. Using screw extender calipers 3000 (such as those shown in FIG. 30) or any other suitable tool, length of the rod is determined. If calipers shown in FIG. 30 are used, then rod length can be indicated at the top of the calipers. The rod is then prepared based on these measurements.

A pathway between two installed screws is cleared using a known curved and/or a sharp wand blade. Then, using a rod inserter (FIGS. 22a-b), an end-holding rod inserter (FIGS. 24a-l), the percutaneous end-holding rod inserter (FIGS. 25a-e), a rod inserter (FIGS. 29a-f), or any other rod inserter mechanisms/tools (e.g., FIGS. 19a-20o) are used to advance the rod along screw extenders toward the implanted screws.

In some embodiments, a rod reducer tool (FIGS. 21a-e, 27a-i) can be used to provisionally secure the rod into place. Additionally, compression/distraction tools (FIGS. 13a-14e, 23a-i) can be used to adjust distances/angles between screw extender towers.

Figure 31:
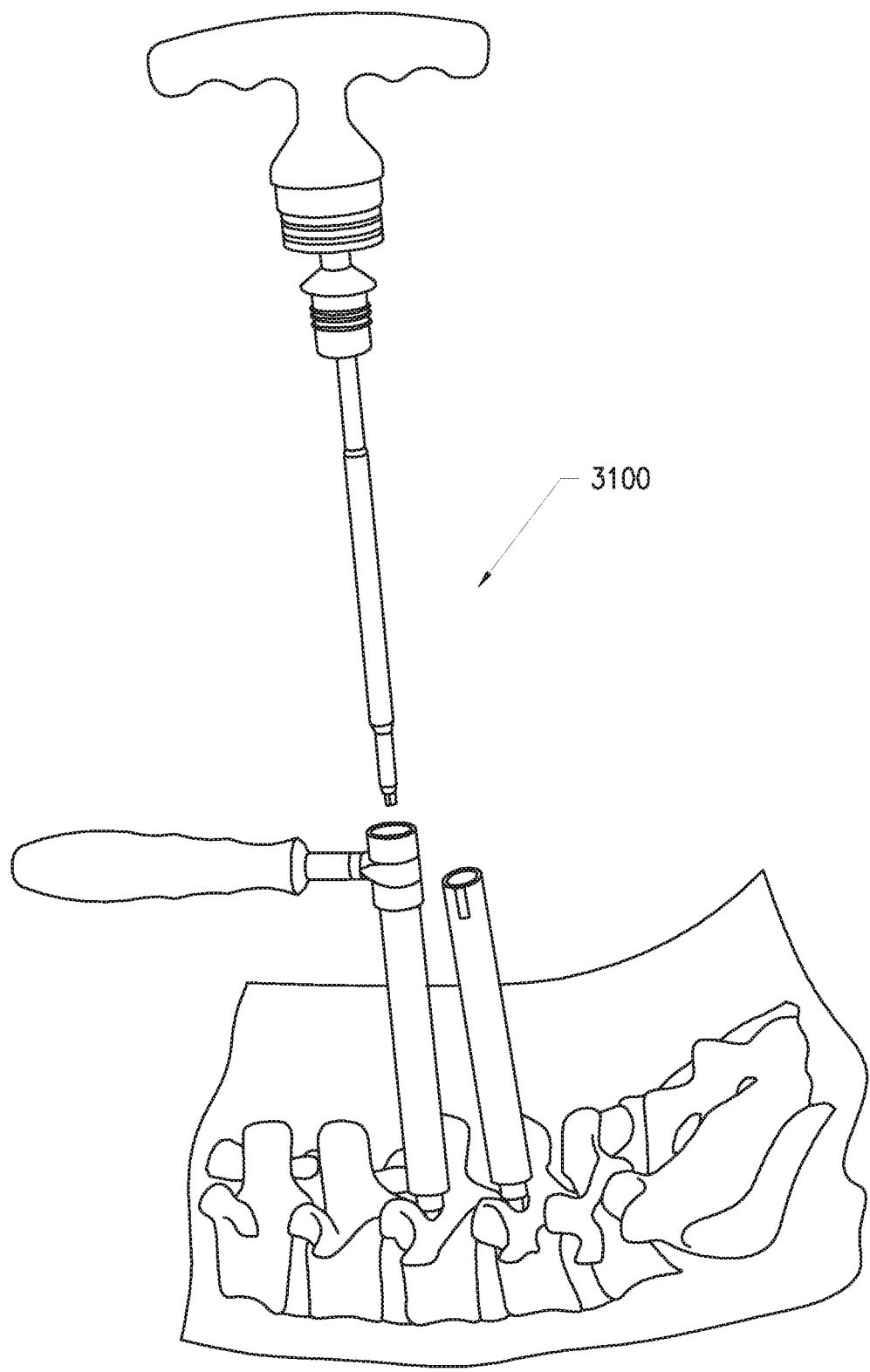
FIG. 31 illustrates a conventional T-handle torque wrench with a torque wrench shaft for final-tightening of a setscrew within a screw assembly.

After the distances/angles are determined, the rod is captured using setscrews that are placed through the screw extender assemblies using a known setscrew inserter tool. The setscrews can be provisionally tightened to secure the rod in place. Then, using a known T-handle torque wrench with a torque wrench shaft and a screw extender anti-torque handle 3100 (e.g., as shown in FIG. 31), the setscrews are finally tightened. The anti-torque handle is coupled to a proximate end of the screw extender housing and the T-handle torque wrench is inserted into the screw extender housing until it contacts the setscrew. Then, the T-handle torque wrench is turned (e.g., clockwise) to secure the setscrew. In some embodiments, an audible indication (e.g., clicking) can alert the surgeon that the setscrews have been finally tightened.

To remove the screw extenders, screw extender remover tools (e.g., FIGS. 18a-c, 28a-e) are used to disengage the screw extender housing from the implanted screw assembly. In some embodiments, an in-situ screw extender re-attachment tool (e.g., FIGS. 26a-k) can be used to re-attach the screw extender housings to the screw assemblies.

In a typical surgery, a plurality of bone screws can be implanted using the methods and tools discussed in connection with and shown in FIGS. 1a-31. In some cases, once an appropriate number of screws have been implanted into the bony matter of a patient, a rod and/or wire can bridge gaps between the screws. Placement and manipulation of screws can be accomplished using the extender devices and various surgical tools, as shown in FIGS. 1a-31. Following that, set screws can be tightened and the guide wire can be removed. Typically, the guide wire is removed prior to use of the caliper tool is used. The extender device and use of surgical tools allows a surgeon (or other medical profession) to perform a minimally invasive surgery of placing various fusion devices, such as in the case of spinal fusion procedures.

Although particular embodiments have been disclosed herein in detail, this has been done by way of example for purposes of illustration only, and is not intended to be limiting with respect to the scope of the appended claims, which follow. In particular, it is contemplated that various substitutions, alterations, and modifications may be made without departing from the spirit and scope of the invention as defined by the claims. Other aspects, advantages, and modifications are considered to be within the scope of the following claims. The claims presented are representative of the inventions disclosed herein. Other, unclaimed inventions are also contemplated. The applicant reserves the right to pursue such inventions in later claims.

What is claimed is:

1. A tool configured to facilitate re-attaching a screw extender to a screw assembly, the screw extender having a screw extender housing with a passageway, and a channel extending along a length of the housing from a proximal end to a distal end of the housing, the channel being open to the passageway, the tool comprising:
   a removable shaft having a distal end configured to engage the screw assembly; and
   a main assembly having a main shaft, a handle and a hollow housing, the main shaft having an interior channel, the handle disposed on a proximal end of the main shaft and the hollow housing disposed on a distal end of the main shaft, the main shaft configured to fit through the channel of the screw extender, and wherein the hollow housing is configured to receive the screw extender housing.

2. The tool as set forth in claim 1, wherein a length of the main shaft between a distal end of the handle and a proximal end of the hollow housing is longer than a length of the screw extender.

3. The tool as set forth in claim 1, wherein the hollow housing includes a pair of grooves disposed at the distal end of the hollow housing, the pair of grooves being open to the distal end of the hollow housing.

4. The tool as set forth in claim 1, wherein the distal end of the removable shaft includes a peg.

5. The tool as set forth in claim 1, wherein the distal end of the removable shaft includes a threaded end.

6. The tool as set forth in claim 5, wherein the proximal end of the removable shaft is configured to removably receive a knob.

7. The tool as set forth in claim 1, wherein the main shaft has a flat surface.

8. The tool as set forth in claim 1, wherein the handle is configured to receive the proximal end of the removable shaft so as to hold the removable shaft in the interior channel of the main shaft and the hollow housing.

9. A surgical kit for spinal procedures using a rod to secure adjacent vertebral bodies to each other, the surgical kit comprising:
   a screw extender, the screw extender having a screw extender housing with a passageway, and a channel extending along a length of the housing from a proximal end to a distal end of the housing, the channel being open to the passageway;
   a screw assembly having a screw and a set screw, the screw having a threaded shaft and a head having a pair of sidewalls spaced apart from each other so as to define a passageway, an interior surface of the pair of sidewalls having threads;
   a first removable shaft having a distal end configured to engage the screw assembly;
   a second removable shaft having a distal end configured to engage the set screw;
   a main assembly having a main shaft, a handle and a hollow housing, the main shaft having an interior channel, the handle disposed on a proximal end of the main shaft and the hollow housing disposed on a distal end of the main shaft, the main shaft configured to fit through the channel of the screw extender, and wherein the hollow housing is configured to receive the screw extender housing.

10. The surgical kit as set forth in claim 9, wherein a length of the main shaft between a distal end of the handle and a proximal end of the hollow housing is longer than a length of the screw extender.

11. The surgical kit as set forth in claim 9, wherein the hollow housing includes a pair of grooves disposed at the distal end of the hollow housing, the pair of grooves being open to the distal end of the hollow housing.

12. The surgical kit as set forth in claim 9, wherein the distal end of the second removable shaft includes a peg.

13. The surgical kit as set forth in claim 9, wherein the distal end of the first removable shaft includes a threaded end configured to engage the threads of the pair of sidewalls.

14. The surgical kit as set forth in claim 9, wherein the proximal end of the first removable shaft and the proximal end of the second removable shaft are both configured to removable receive a knob.

15. The surgical kit as set forth in claim 9, wherein the main shaft has a flat surface.

16. The surgical kit as set forth in claim 9, wherein hollow housing has a diameter that is larger than a diameter of the screw extender.

17. The surgical kit as set forth in claim 9, wherein the screw extender further includes a slot opposite the channel so as to define a passageway for receiving the rod, a distal end of the slot open to the distal end of the housing and a proximal end of the slot closed by the housing.

18. The surgical kit as set forth in claim 9, wherein the hollow housing is dimensioned to fit over the head of the screw.

* * * * *